United States Patent
Adams et al.

(10) Patent No.: US 10,550,102 B2
(45) Date of Patent: Feb. 4, 2020

(54) INDANE AND INDOLINE DERIVATIVES AND THE USE THEREOF AS SOLUBLE GUANYLATE CYCLASE ACTIVATORS

(71) Applicant: NOVARTIS AG, Basel (CH)

(72) Inventors: Christopher M. Adams, Arlington, MA (US); Doug Bevan, Chelmsford, MA (US); Michael Paul Capparelli, Cambridge, MA (US); Takeru Ehara, Arlington, MA (US); Luciana Ferrara, Stoughton, MA (US); Nan Ji, Arlington, MA (US); Erik Meredith, Hudson, MA (US); Muneto Mogi, Waltham, MA (US); James J. Powers, Waltham, MA (US); Ganesh Prasanna, Acton, MA (US); Nello Mainolfi, Belmont, MA (US); Mitsunori Kato, Cambridge, MA (US)

(73) Assignee: NOVARTIS AG, Basel (CH)

(*) Notice: Subject to any disclaimer, the term of this patent is extended or adjusted under 35 U.S.C. 154(b) by 0 days.

(21) Appl. No.: 16/216,420

(22) Filed: Dec. 11, 2018

(65) Prior Publication Data
US 2019/0119254 A1 Apr. 25, 2019

Related U.S. Application Data

(63) Continuation of application No. 15/320,810, filed as application No. PCT/IB2015/055006 on Jul. 2, 2015, now Pat. No. 10,208,018.

(60) Provisional application No. 62/020,166, filed on Jul. 2, 2014, provisional application No. 62/168,627, filed on May 29, 2015.

(51) Int. Cl.
| | |
|---|---|
| C07D 401/14 | (2006.01) |
| C07D 413/14 | (2006.01) |
| C07D 401/10 | (2006.01) |
| C07D 401/12 | (2006.01) |
| A61K 9/00 | (2006.01) |
| A61K 31/4439 | (2006.01) |
| A61K 31/454 | (2006.01) |
| A61K 31/4545 | (2006.01) |
| A61K 31/4725 | (2006.01) |
| C07D 405/14 | (2006.01) |
| C07D 401/04 | (2006.01) |

(52) U.S. Cl.
CPC .......... C07D 401/14 (2013.01); A61K 9/0048 (2013.01); A61K 31/4439 (2013.01); A61K 31/454 (2013.01); A61K 31/4545 (2013.01); A61K 31/4725 (2013.01); C07D 401/10 (2013.01); C07D 401/12 (2013.01); C07D 405/14 (2013.01); C07D 413/14 (2013.01)

(58) Field of Classification Search
CPC ............. C07D 401/04; C07D 401/14

USPC .......................................... 546/194; 514/318
See application file for complete search history.

(56) References Cited

U.S. PATENT DOCUMENTS

| | | |
|---|---|---|
| 6,335,334 B1 | 1/2002 | Schindler et al. |
| 2009/0209556 A1 | 8/2009 | Bittner et al. |
| 2010/0216764 A1 | 8/2010 | Kim et al. |
| 2011/0028493 A1 | 2/2011 | Matsunaga et al. |
| 2013/0158028 A1 | 6/2013 | Stasch et al. |
| 2017/0197940 A1 | 7/2017 | Adams et al. |

FOREIGN PATENT DOCUMENTS

| | | |
|---|---|---|
| EP | 1420023 A1 | 5/2004 |
| EP | 2594270 A2 | 5/2013 |
| WO | 02070462 A1 | 9/2002 |
| WO | 02070510 A2 | 9/2002 |
| WO | 03086407 A1 | 10/2003 |
| WO | 2008073452 A1 | 6/2008 |
| WO | 08119458 A1 | 10/2008 |
| WO | 2009/032248 A1 | 3/2009 |
| WO | 2009032249 A1 | 3/2009 |
| WO | 2009068652 A1 | 6/2009 |
| WO | 2009071504 A1 | 6/2009 |

(Continued)

OTHER PUBLICATIONS

Shie, et al., "Puring derivatives as potent Bruton's tyrosine kinase (BTK) inhibitors for autoimmune diseases", Bioorganic & Medicinal Cemistry Letters, 24(9):2212-2221 (2014).

(Continued)

*Primary Examiner* — Patricia L Morris
(74) *Attorney, Agent, or Firm* — Sophie Binet Cross

(57) ABSTRACT

The present invention provides a compound of formula (I) or a pharmaceutically acceptable salt thereof; a method for manufacturing the compounds of the invention, and its therapeutic uses. The present invention further provides a combination of pharmacologically active agents and a pharmaceutical composition.

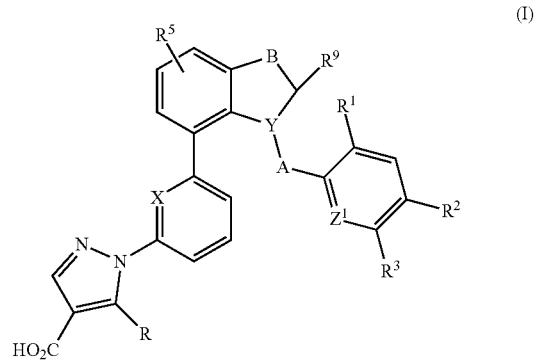

(I)

15 Claims, No Drawings

(56) References Cited

FOREIGN PATENT DOCUMENTS

| WO | 09127338 A1 | 10/2009 |
| WO | 2010/015653 A1 | 2/2010 |
| WO | 10102717 A1 | 9/2010 |
| WO | 2010099054 A2 | 9/2010 |
| WO | 2011051165 A1 | 5/2011 |
| WO | 2011/095534 A1 | 8/2011 |
| WO | 2011/095553 A1 | 8/2011 |
| WO | 2011/147810 A1 | 12/2011 |
| WO | 2011/161099 A1 | 12/2011 |
| WO | 2012058132 A1 | 5/2012 |
| WO | 2012076466 A2 | 6/2012 |
| WO | 2012122340 A1 | 9/2012 |
| WO | 2012139888 A1 | 10/2012 |
| WO | 13025425 A1 | 2/2013 |
| WO | 2014/039434 A1 | 3/2014 |
| WO | 201457740 A1 | 10/2014 |
| WO | 2015011086 A1 | 1/2015 |
| WO | 2015033307 A1 | 3/2015 |
| WO | 2015/095515 A1 | 6/2015 |
| WO | 2016/001876 A1 | 1/2016 |
| WO | 2016/001878 A1 | 1/2016 |

OTHER PUBLICATIONS

Abdel-Rahman, et al., "Synthesis of Novel Fluorine Substituted isolated and Fused Heterobicyckic Nitrogen Systems Bearing 6-(2'-Phosphorylanilido)-1,2,4-Triazin-5-One Moiety as Potential Inhibitor towards HIV-1 Activity", International Journal of Organic Chemistry, 4(4):247-268 (2014).

Stasch, et al., "Renal effects of soluble guanylate cyclase stimunlators and activators: A review of the preclinical evidence", Current Opinion in Pharmacology, 21:95-104 (2015).

INDANE AND INDOLINE DERIVATIVES AND THE USE THEREOF AS SOLUBLE GUANYLATE CYCLASE ACTIVATORS

This application is a continuation application of U.S. application Ser. No. 15/320,810, filed on Dec. 21, 2016, which is a U.S. National Phase filing of International Application No. PCT/IB2015/055006 filed 2 Jul. 2015, which claims priority to U.S. Application No. 62/020,166 filed 2 Jul. 2014, and also claims priority to U.S. Application No. 62/168,627, filed 29 May 2015, the contents' of which are incorporated herein by reference in their entirety.

FIELD OF THE INVENTION

The present invention is related generally to compounds which activate soluble guanylate cyclase (sGC). The invention further relates to the use of said sGC activators in the treatment of glaucoma and in the lowering intraocular pressure (IOP) such as that associated with glaucoma and ocular hypertension.

BACKGROUND OF THE INVENTION

The eye disease glaucoma is characterized by a permanent loss of visual function due to irreversible damage to the optic nerve. The several morphologically or functionally distinct types of glaucoma are typically characterized by an undesirable elevation of IOP, which is considered to be causally related to the pathological course of the disease. Continuously elevated IOP has been associated with the progressive loss of retinal ganglion cells and optic nerve damage ultimately resulting in the loss of visual function. In some cases, ocular hypertension, a condition in which IOP is elevated, can present without apparent loss of visual function. However, patients with ocular hypertension are considered to be at a high risk for eventually developing the visual loss associated with glaucoma. Therefore, lowering IOP is the current treatment objective for the of glaucoma patients and for patients with ocular hypertension in order to decrease the potential for, or severity of, glaucomatous retinopathy. Unfortunately, many individuals do not achieve or maintain desired level of IOP reduction when treated with existing glaucoma therapies.

Patients known as normotensive or low-tension glaucoma patients have relatively low IOP, yet present with glaucomatous visual field loss. These patients may benefit from agents that lower and control IOP, because glaucoma that is detected early and treated promptly may have reduced or delayed loss of visual function. Conventional therapeutic agents that have proven to be effective for the reduction of IOP include both agents that decrease aqueous humor production and agents that increase the outflow facility. Such agents are in general administered by one of two routes; topically by direct application to the eye, or orally. However, many of these agents have associated side effects which may render them undesirable as ocular therapeutic agents.

Soluble guanylate cyclase (sGC) is a receptor enzyme for the second messenger, nitric oxide (NO) in several cell types including muscle, epithelial, neuronal, and endothelial cells. In humans, functional sGC is a heterodimer composed of either an alpha 1 or alpha 2 subunit combined with the beta 1 subunit which has a heme prosthetic group. Under physiological conditions, NO binds to the prosthetic heme of sGC which activates the enzyme to catalyze the conversion of guanosine-5'-triphosphate (GTP) to cyclic guanosine monophosphate (cGMP). cGMP is a second messenger which in turn exerts its effects by activating cGMP dependent protein kinase (PKG) isoforms, phosphodiesterases, and cGMP gated ion channels. In doing so, sGC can thus modulate numerous pathways associated with diseases including hypertension (arterial and pulmonary), heart failure, atherosclerosis, erectile dysfunction, liver cirrhosis, and renal fibrosis. Under aforementioned pathologic conditions, prolonged oxidative stress can cause the oxidation of the heme group of sGC (from ferrous to ferric state) which is incapable of being activated by NO and can contribute to exacerbation of disease processes. As a consequence of sGC oxidation and unresponsiveness to NO, endothelial dysfunction, atherosclerosis, hypertension, stable or unstable angina pectoris, thromboses, myocardial infarction, strokes or erectile dysfunction are worsened. Therefore, pharmacological stimulation or activation of sGC offers a possibility to normalize cGMP production and therefore makes possible the treatment and/or prevention of such disorders.

To this effort, there are two classes of compounds have been identified, including NO-independent/reduced heme-dependent sGC stimulators and NO-independent/heme-independent sGC activators. sGC stimulators are dependent on heme, but they are not active once sGC become oxidized. sGC activators on the other hand can still activate the enzyme to generate cGMP even in the absence of nitric oxide (NO) and/or under oxidative stress induced oxidation of sGC in disease tissue. Thus, the activity of sGC in these situations will be corrected by sGC activators, but not by sGC stimulators, and will have the potential to provide benefit in many diseases caused by defective signaling in the NO pathway especially following oxidative stress.

SUMMARY OF THE INVENTION

The present invention in part relates to new activators of sGC and the use thereof in the treatment of disease. In one aspect the sGC activators provided herein are suitable for use in methods of treating glaucoma in human patients or other mammals. The present invention also relates to methods of lowering or controlling normal or elevated IOP in a human patient or other mammals. In particular, the invention provides methods of treating and/or preventing glaucoma by administration of a sGC activator compound described infra.

In the eye, the trabecular outflow pathway by which 70-80% of aqueous humor would normally leave the anterior chamber of the eye and lower intraocular pressure (IOP), is pathologically compromised in primary open angle glaucoma (POAG). Oxidative stress is thought to be an underlying factor that can adversely affect trabecular meshwork function, resulting from/in IOP elevation in POAG. Reactive oxygen species (ROS) not only decrease the bioavailability of nitric oxide (NO) but also shill the sGC redox equilibrium to its oxidized form, which as mentioned before is unresponsive to NO. Selective activation of the oxidized form of sGC should target only the diseased state of the target enzyme in the putative target tissue, trabecular meshwork/Schlemm's canal tissue, thus offering a highly innovative therapy for glaucoma that should work adjunctively with current therapies.

In one aspect of the invention, sGC activators, and salts thereof, are provided which have the structure of formula (I):

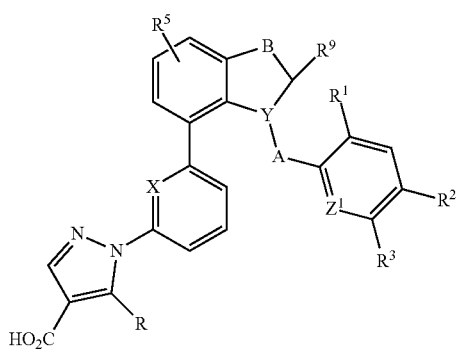

(I)

or a pharmaceutically acceptable salt thereof, wherein the variables are defined infra.

Certain embodiments of the present invention comprise compositions or methods which include or use compounds capable of activating sGC thereby modulating intraocular pressure in the eye. By activating sGC receptor activity, subject compounds according to certain embodiments of the present invention are accordingly useful for lowering and/or controlling IOP associated with normal-tension glaucoma, ocular hypertension, and glaucoma, including primary open-angle glaucoma in humans and other warm-blooded animals. When used in such applications, the compounds may be formulated in pharmaceutical compositions suitable for topical delivery to the eye.

The foregoing brief summary broadly describes the features and technical advantages of certain embodiments of the present invention. Additional features and technical advantages will be described in the detailed description of the invention that follows.

DESCRIPTION OF THE INVENTION

As the term is used herein, a "sGC activator" is a compound capable of modulating sGC activity to generate cGMP signaling which would otherwise be unresponsive to nitric oxide. In contrast, "sGC stimulators" refers to compounds that are capable of synergizing with nitric oxide and can directly stimulate cGMP production so long as the reduced heme domain is present in the enzyme.

In a first embodiment, the invention provides a compound according to Formula (I)

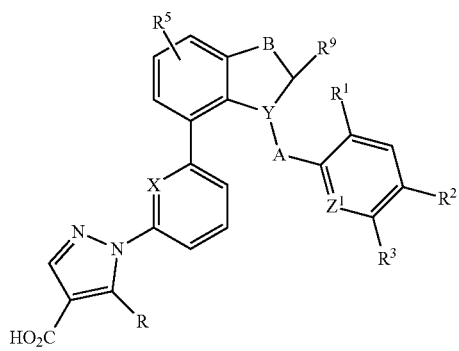

Or a pharmaceutically acceptable salt thereof, wherein
X is N or CH;
Y is CH or N;
A is $CH_2$, O or N(H) when Y is CH, or
A is $CH_2$ when Y is N;
B is O or $CR^7R^8$;
$Z^1$ is $CR^4$ or N;
R is hydrogen, $C_1$-$C_4$alkyl, monofluoromethyl, difluoromethyl or trifluoromethyl;
$R^1$ is hydrogen, halogen, $C_1$-$C_4$alkyl or trifluoromethyl
$R^2$ is piperidinyl which is N-substituted with $C_1$-$C_4$alkyl, $C_3$-$C_6$cycloalkyl, halo$C_1$-$C_4$alkyl, C(O)$C_1$-$C_4$alkyl, $S(O)_2C_1$-$C_4$alkyl, C(O)$C_3$-$C_6$cycloalkyl, C(O)halo$C_1$-$C_4$alkyl, C(O)$C_1$-$C_4$alkoxy, C(O)$C_1$-$C_4$alkenoxy, heteroaryl or $CO(O)_2$benzyl, wherein each cycloalkyl is optionally substituted by hydroxy and each alkyl or alkoxy is optionally substituted by hydroxyl, $C_1$-$C_4$alkoxy or $C_3$-$C_6$cycloalkyl and wherein each heteroaryl has 5 or 6 ring atoms, 1, 2 or 3 ring heteroatoms independently selected from N, O and S and is optionally substituted with 1 or 2 $C_1$-$C_4$alkyl substituents.
$R^3$ is hydrogen, halogen or $C_1$-$C_4$alkyl; or
$R^2$ and $R^3$, taken in combination, form a 5 or 6 member fused saturated azacyclic ring optionally substituted with benzyl or 5 or 6 member heteroarylmethyl, which heteroaryl has 1 or 2 ring heteroatoms independently selected from N, O and S;
$R^4$ is hydrogen or $C_1$-$C_4$alkyl;
$R^5$ is hydrogen, halogen, $C_1$-$C_4$alkyl or $C_3$-$C_6$cycloalkyl;
$R^7$ is hydrogen or $C_1$-$C_4$alkyl; or
$R^7$ and $R^9$, taken in combination with the ring atoms to which they are attached form a carbon-carbon double bond;
$R^8$ is hydrogen or $C_1$-$C_4$alkyl; and
$R^9$ is hydrogen or $C_1$-$C_4$alkyl.

In a second embodiment, the invention provides a compound according to Formula (Ia)

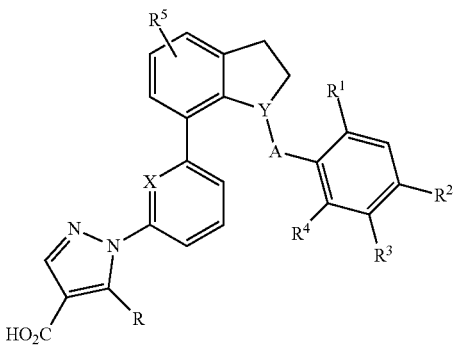

(Ia)

or a pharmaceutically acceptable salt thereof, wherein
X is N or CH;
Y is CH or N;
A is $CH_2$, O or N(H) when Y is CH, or
A is $CH_2$ when Y is N;
R is hydrogen, $C_1$-$C_4$alkyl or trifluoromethyl;
$R^1$ is hydrogen, halogen or $C_1$-$C_4$alkyl;
$R^2$ is piperidinyl which is N-substituted with $C_1$-$C_4$alkyl, $C_3$-$C_6$cycloalkyl, halo$C_1$-$C_4$alkyl, C(O)$C_1$-$C_4$alkyl, C(O)$C_3$-$C_6$cycloalkyl, C(O)halo$C_1$-$C_4$alkyl or C(O)$C_1$-$C_4$alkoxy;
$R^3$ is hydrogen or $C_1$-$C_4$alkyl; or
$R^2$ and $R^3$, taken in combination, form a 5 or 6 member fused saturated azacyclic ring optionally substituted with benzyl or 5 or 6 member heteroarylmethyl, which heteroaryl has 1 or 2 ring heteroatoms independently selected from N, O and S;

$R^4$ is hydrogen or $C_1$-$C_4$alkyl and $R^5$ is hydrogen, halogen, $C_1$-$C_4$alkyl or $C_3$-$C_6$cycloalkyl.

In a third embodiment, the invention provides compounds according to embodiment which are represented by the formula (Ib):

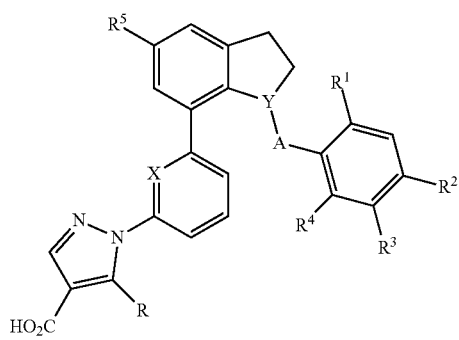

In a fourth embodiment, compounds of any one of embodiments 1 through 3 are provided in which Y is CH and A is O.

In a fifth embodiment, compounds of any one of embodiments 1 through 3 are provided in which Y is CH and A is N(H).

In a sixth embodiment, compounds of any one of embodiments 1 through 3 are provided in which Y is N and A is $CH_2$.

In a seventh embodiment, compounds of any one embodiments 1 to 6 are provided in which $R^2$ is N-substituted piperidin-4-yl wherein the N-substituent is 2,2,2-trifluoroethyl, C(O)cyclopropyl or C(O)$C_1$-$C_4$alkyl.

In an eighth embodiment, compounds of any one embodiments 1 to 7 are provided in which $R^1$ is hydrogen or methyl;

$R^3$ is hydrogen, methyl or ethyl, wherein at least one of $R^1$ or $R^3$ is hydrogen; and $R^4$ is hydrogen.

In a ninth embodiment, compounds of any one embodiments 1 to 8 are provided in which $R^1$ is methyl; and $R^3$ and $R^4$ are hydrogen.

In a tenth embodiment, compounds of any one embodiments 1 to 8 are provided in which $R^1$ and $R^4$ are hydrogen and $R^3$ is ethyl.

In an eleventh embodiment, compounds of any one embodiments 1 to 10 are provided in which R is trifluoromethyl, methyl or ethyl.

In a twelfth embodiment, compounds of any one embodiments 1 to 11 are provided in which R is trifluoromethyl.

In a thirteenth embodiment, compounds of any one embodiments 1 to 12 are provided in which R is methyl or ethyl.

In a fourteenth embodiment, compounds of the first and second embodiment are provided in which the compound of Formula (I) is a compound according to Formula (II):

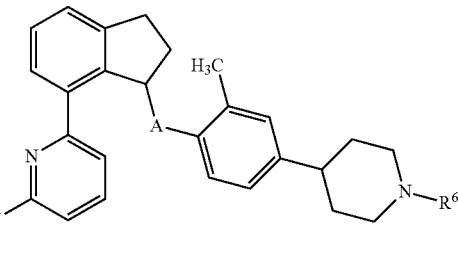

Wherein

A is O, $CH_2$ or NH;

R is methyl, ethyl or trifluoromethyl;

$R^6$ is 2,2,2-trifluoroethyl, C(O)cyclopropyl or C(O)$C_1$-$C_4$alkyl.

In a fifteenth embodiment, compounds of the first or second embodiment are provided in which the compound of Formula (I) is a compound according to Formula (III):

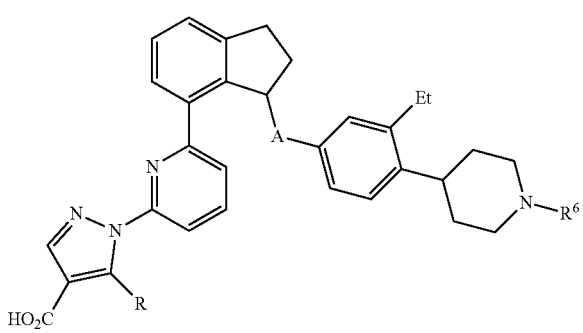

Wherein

A is O, $CH_2$ or NH;

R is methyl, ethyl or trifluoromethyl;

$R^6$ is 2,2,2-trifluoroethyl, C(O)cyclopropyl or C(O)$C_1$-$C_4$alkyl.

In a sixteenth embodiment, compounds of the fourteenth or fifteenth embodiment are provided in which A is NH; R is methyl or ethyl; and $R^6$ is C(O)cyclopropyl or C(O)$C_1$-$C_4$alkyl.

In another aspect of the thirteenth and fifteenth embodiment, compounds are provided in which A is O.

In yet another aspect of the fourteenth or fifteenth embodiment, compounds are provided in which A is NH.

In still another aspect of the fourteenth or fifteenth embodiment, compounds are provided in which A is $CH_2$.

In a seventeenth embodiment, compounds of the first or second embodiment are provided in which the compound of Formula (I) is a compound according to Formula (IV):

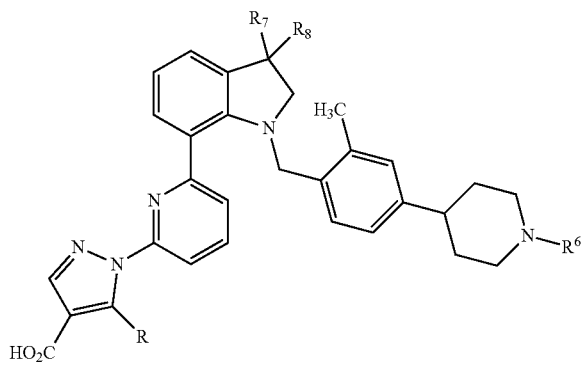

(IV)

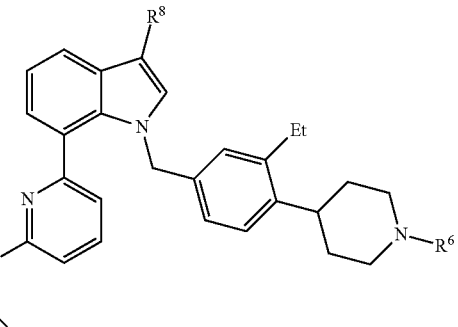

(VI)

Wherein

R is methyl, ethyl or trifluoromethyl;

R⁸ is 2,2,2-trifluoroethyl, C(O)cyclopropyl or C(O)C₁-C₄alkyl; and

Each of R⁷, R⁸ and R⁹ is independently selected from hydrogen and methyl.

In an eighteenth embodiment, compounds of the first or second embodiment are provided in which the compound of Formula (I) is a compound according to Formula (V):

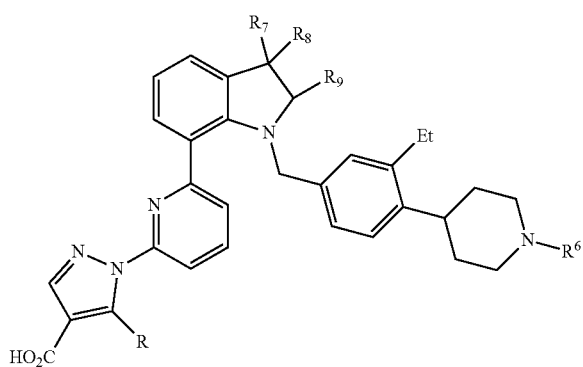

(V)

Wherein

R is methyl, ethyl or trifluoromethyl;

R⁵ is 2,2,2-trifluoroethyl, C(O)cyclopropyl or C(O)C₁-C₄alkyl; and each of R⁷, R⁸ and R⁹ is independently selected from hydrogen and methyl.

In a nineteenth embodiment, compounds of the seventeenth or eighteenth embodiment are provided in which R is methyl or ethyl; and R⁶ is 2,2,2-trifluoroethyl.

In another aspect of any one of the seventeenth to nineteenth embodiments, compounds are provided in which R⁷ and R⁸ are hydrogen and R⁹ is methyl. In certain other compounds of the sixteenth to eighteenth embodiments, R⁷ is hydrogen or methyl, R⁸ is methyl and R⁹ is hydrogen.

In a twentieth embodiment, compounds of the first embodiment are provided in which the compound of Formula (I) is a compound according to Formula (VI):

Wherein

R is methyl, ethyl or trifluoromethyl;

R⁶ is 2,2,2-trifluoroethyl, C(O)cyclopropyl or C(O)C₁-C₄alkyl; and

R⁸ is independently selected from hydrogen and methyl.

In a twenty-first embodiment, compounds of the first embodiment are provided in which the compound of Formula (I) is a compound according to Formula (VII):

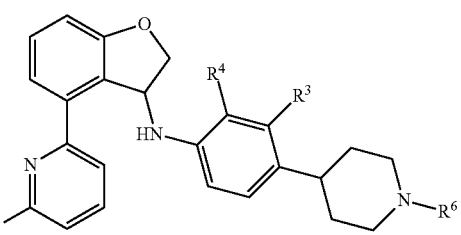

(VII)

Wherein

R is methyl, ethyl or trifluoromethyl;

R³ is hydrogen, methyl or ethyl;

R⁴ is hydrogen or methyl; and

R⁸ is 2,2,2-trifluoroethyl, C(O)cyclopropyl or C(O)C₁-C₄alkyl optionally substituted with hydroxy.

In a twentieth second embodiment of the invention, compounds of the first and second embodiment are provided which are selected from the group consisting of:

(−)-1-(3-(3-(4-(1-(cyclopropanecarbonyl)piperidin-4-yl)-2-methylphenoxy)-2,3-dihydro-1H-inden-4-yl)phenyl)-5-(trifluoromethyl)-1H-pyrazole-4-carboxylic acid;

(+)-1-(3-(3-(4-(1-(cyclopropanecarbonyl)piperidin-4-yl)-2-methylphenoxy)-2,3-dihydro-1H-inden-4-yl)phenyl)-5-(trifluoromethyl)-1H-pyrazole-4-carboxylic acid;

(+)-(S)-1-(3-(3-(4-(1-(cyclopropanecarbonylpiperidin-4-yl)-2-methylphenoxy)-2,3-dihydro-1H-inden-4-yl)phenyl)-5-methyl-1H-pyrazole-4-carboxylic acid;

(−)-1-(6-(3-(4-(1-(cyclopropanecarbonyl)piperidin-4-yl)-2-methylphenoxy)-2,3-dihydro-1H-inden-4-yl)pyridin-2-yl)-5-(trifluoromethyl)-1H-pyrazole-4-carboxylic acid;

(+)-1-(6-(3-(4-(1-(cyclopropanecarbonyl)piperidin-4-yl)-2-methylphenoxy)-2,3-dihydro-1H-inden-4-yl)pyridin-2-yl)-5-(trifluoromethyl)-1H-pyrazole-4-carboxylic acid;

(−)-1-(6-(3-((2-(pyridin-2-ylmethyl)-1,2,3,4-tetrahydroisoquinolin-6-yl)oxy)-2,3-dihydro-1H-inden-4-yl)pyridin-2-yl)-5-(trifluoromethyl)-1H-pyrazole-4-carboxylic acid;

(+)-1-(6-(3-((2-(pyridin-2-ylmethyl)-1,2,3,4-tetrahydroisoquinolin-6-yloxy)-2,3-dihydro-1H-inden-4-yl)pyridin-2-yl)-5-(trifluoromethyl)-1H-pyrazole-4-carboxylic acid;

(±)-1-(6-(6-methyl-3-((2-(pyridin-2-ylmethyl)-1,2,3,4-tetrahydroisoquinolin-6-yl)oxy)-2,3-dihydro-1H-inden-4-yl)pyridin-2-yl)-5-(trifluoromethyl)-1H-pyrazole-4-carboxylic acid;

(±)-1-(6-(3-(4-(1-(cyclopropanecarbonyl)piperidin-4-yl)-2-methylphenoxy)-6-methyl-2,3-dihydro-1H-inden-4-yl)pyridin-2-yl)-5-(trifluoromethyl)-1H-pyrazole-4-carboxylic acid;

(+)-(S)-1-(6-(3-(4-(1-(cyclopropanecarbonyl)piperidin-4-yl)-3-ethylphenoxy)-2,3-dihydro-1H-inden-4-yl)pyridin-2-yl)-5-(trifluoromethyl)-1H-pyrazole-4-carboxylic acid;

(+)-(S)-1-(6-(3-(2-methyl-4-(1-(2,2,2-trifluoroethyl)piperidin-4-yl)phenoxy)-2,3-dihydro-1H-inden-4-yl)pyridin-2-yl)-5-(trifluoromethyl)-1H-pyrazole-4-carboxylic acid;

(+)-(S)-1-(6-(3-(4-(1-(cyclopropanecarbonyl)piperidin-4-yl)-2-methylphenoxy)-2,3-dihydro-1H-inden-4-yl)pyridin-2-yl)-1H-pyrazole-4-carboxylic acid;

(+)-(S)-1-(6-(3-(4-(1-(cyclopropanecarbonyl)piperidin-4-yl)-2-methylphenoxy)-2,3-dihydro-1H-inden-4-yl)pyridin-2-yl)-5-methyl-1H-pyrazole-4-carboxylic acid;

(+)-(S)-1-(6-(3-(4-(1-(cyclopropanecarbonyl)piperidin-4-yl)-2-methylphenoxy)-2,3-dihydro-1H-inden-4-yl)pyridin-2-yl)-5-ethyl-1H-pyrazole-4-carboxylic acid;

(+)-(S)-5-ethyl-1-(6-(3-(2-methyl-4-(1-(2,2,2-trifluoroethyl)piperidin-4-yl)phenoxy)-2,3-dihydro-1H-inden-4-yl)pyridin-2-yl)-1H-pyrazole-4-carboxylic acid;

(+)-(S)-1-(6-(3-(4-(1-(cyclopropanecarbonyl)piperidin-4-yl)-3-ethylphenoxy)-2,3-dihydro-1H-inden-4-yl)pyridin-2-yl)-5-ethyl-1H-pyrazole-4-carboxylic acid;

(+)-1-(3-(3-((4-(1-(cyclopropanecarbonyl)piperidin-4-yl)-2-methylphenyl)amino)-2,3-dihydro-1H-inden-4-yl)phenyl)-5-(trifluoromethyl)-1H-pyrazole-4-carboxylic acid;

(−)-1-(3-(3-((4-(1-(cyclopropanecarbonyl)piperidin-4-yl)-2-methylphenyl)amino)-2,3-dihydro-1H-inden-4-yl)phenyl)-5-(trifluoromethyl)-1H-pyrazole-4-carboxylic acid;

(+)-1-(6-(3-((4-(1-(cyclopropanecarbonyl)piperidin-4-yl)-2-methylphenyl)amino)-2,3-dihydro-1H-inden-4-yl)pyridin-2-yl)-5-methyl-1H-pyrazole-4-carboxylic acid;

(−)-1-(6-(3-((4-(1-(cyclopropanecarbonyl)piperidin-4-yl)-2-methylphenyl)amino)-2,3-dihydro-1H-inden-4-yl)pyridin-2-yl)-5-methyl-1H-pyrazole-4-carboxylic acid;

(−)-1-(6-(3-((4-(1-(cyclopropanecarbonyl)piperidin-4-yl)-2-methylphenyl)amino)-2,3-dihydro-1H-inden-4-yl)pyridin-2-yl)-5-(trifluoromethyl)-1H-pyrazole-4-carboxylic acid;

(+)-1-(6-(3-((4-(1-(cyclopropanecarbonyl)piperidin-4-yl)-2-methylphenyl)amino)-2,3-dihydro-1H-inden-4-yl)pyridin-2-yl)-5-(trifluoromethyl)-1H-pyrazole-4-carboxylic acid;

(−)-1-(6-(3-((4-(1-(cyclopropanecarbonyl)piperidin-4-yl)phenyl)amino)-2,3-dihydro-1H-inden-4-yl)pyridin-2-yl)-5-methy-1H-pyrazole-4-carboxylic acid;

(+)-1-(6-(3-((4-(1-(cyclopropanecarbonyl)piperidin-4-yl)phenylamino)-2,3-dihydro-1H-inden-4-yl)pyridin-2-yl)-5-methyl-1H-pyrazole-4-carboxylic acid;

(−)-1-(6-(3-((4-(1-(cyclopropanecarbonyl)piperidin-4-yl)-2-methylphenyl)amino)-2,3-dihydro-1H-inden-4-yl)pyridin-2-yl)-5-ethyl-1H-pyrazole-4-carboxylic acid;

(+)-1-(6-(3-((4-(1-(cyclopropanecarbonyl)piperidin-4-yl)-2-methylphenyl)amino)-2,3-dihydro-1H-inden-4-yl)pyridin-2-yl)-5-ethyl-1H-pyrazole-4-carboxylic acid;

(±)-1-(6-(3-((4-(1-(cyclopropanecarbonyl)piperidin-4-yl)-2-methylphenyl)amino)-6-methyl-2,3-dihydro-1H-inden-4-yl)pyridin-2-yl)-5-(trifluoromethyl)-1H-pyrazole-4-carboxylic acid;

(±)-1-(6-(3-((4-(1-(cyclopropanecarbonyl)piperidin-4-yl)phenyl)amino)-2,3-dihydro-1H-inden-4-yl)pyridin-2-yl)-5-(trifluoromethyl)-1H-pyrazole-4-carboxylic acid;

(±)-5-ethyl-1-(6-(3-((2-methyl-4-(1-(2,2,2-trifluoroethyl)piperidin-4-yl)phenyl)amino)-2,3-dihydro-1H-inden-4-yl)pyridin-2-yl)-1H-pyrazole-4-carboxylic acid;

(±)-1-(3-(3-((4-(1-(cyclopropanecarbonyl)piperidin-4-yl)-2-methylphenyl)amino)-2,3-dihydro-1H-inden-4-yl)phenyl)-5-methyl-1H-pyrazole-4-carboxylic acid;

1-(6-(1-(4-(1-(cyclopropanecarbonyl)piperidin 4-yl)benzyl)indolin-7-yl)pyridin-2-yl)-5-(trifluoromethyl)-1H-pyrazole-4-carboxylic acid;

1-(6-(1-(4-(1-(cyclopopanecarbonyl)piperidin-4-yl)-3-ethylbenzyl)indolin-7-yl)pyridin-2-yl)-5-(trifluoromethyl)-1H-pyrazole-4-carboxylic acid;

1-(6-(1-(4-(1-(cyclopopanecarbonyl)piperidin-4-yl)-3-ethylbenzyl)indolin-7-yl)pyridin-2-yl)-5-ethyl-1H-pyrazole-4-carboxylic acid;

1-(6-(1-(3-ethyl-4-(1-(2,2,2-trifluoroethyl)piperidin-4-yl)benzyl)indolin-7-yl)pyridin-2-yl)-5-(trifluoromethyl)-1H-pyrazole-4-carboxylic acid;

5-ethyl-1-(6-(1-(3-ethyl-4-(1-(2,2,2-trifluoroethyl)piperidin-4-yl)benzyl)indolin-7-yl)pyridin-2-yl)-1H-pyrazole-4-carboxylic acid;

(+)-(S)-1-(6-(3-(4-(1-(Cyclopropanecarbonyl)piperidin-4-yl)-3-ethylphenoxy)-2,3-dihydro-1H-inden-4-yl)pyridin-2-yl)-5-methyl-1H-pyrazole-4-carboxylic acid;

5-Ethyl-1-(6-(1-(3-ethyl-4-(1-((S)-2-hydroxypropanoyl)piperidin-4-yl)benzyl)-3-methylindolin-7-yl)pyridin-2-yl)-1H-pyrazole-4-carboxylic acid (diastereomer-1);

5-Ethyl-1-(6-(1-(3-ethyl-4-(1-((S)-2-hydroxypropanoyl)piperidin-4-yl)benzyl)-3-methylindolin-7-yl)pyridin-2-yl)-1H-pyrazole-4-carboxylic acid (diastereomer-2);

(S)-5-Ethyl-1-(6-(1-(4-(1-(2-hydroxypropanoyl)piperidin-4-yl)-2-methylbenzyl)indolin-7-yl)pyridin-2-yl)-1H-pyrazole-4-carboxylic acid;

(+)-1-(6-(1-(4-(1-(Cyclopropanecarbonyl)piperidin-4-yl)-3-ethylbenzyl)-3-methylindolin-7-yl)pyridin-2-yl-5-(trifluoromethyl)-1H-pyrazole-4-carboxylic acid;

(−)-1-(6-(1-(4-(1-(Cyclopropanecarbonyl)piperidin-4-yl)-3-ethylbenzyl-3-methylindolin-7-yl)pyridin-2-yl)-5-(trifluoromethyl)-1H-pyrazole-4-carboxylic acid;

(+)-1-(8-(1-(4-(1-(Cyclopropanecarbonyl)piperidin-4-yl)-3-ethylbenzyl)-3-methylindolin-7-yl)pyridin-2-yl)-5-ethyl-1H-pyrazole-4-carboxylic acid;

(−)-1-(6-(1-(4-(1-(Cyclopropanecarbonyl)piperidin-4-yl)-3-ethylbenzyl)-3-methylindolin-7-yl)pyridin-2-yl)-5-ethyl-1H-pyrazole-4-carboxylic acid;

(+)-1-(8-(1-(4-(1-(Cyclopropanecarbonyl)piperidin-4-yl)-2-methylbenzyl)-3-methylindolin-7-yl)pyridin-2-yl)-5-ethyl-1H-pyrazole-4-carboxylic acid;

(−)-1-(6-(1-(4-(1-(Cyclopropanecarbonylpiperidin-4-yl)-2-methylbenzyl)-3-methylindolin-7-yl)pyridin-2-yl)-5-ethyl-1H-pyrazole-4-carboxylic acid;

(+)-1-(8-(1-(4-(1-(Cyclopropanecarbonyl)piperidin-4-yl)-3-ethylbenzyl)-3-methylindolin-7-yl)pyridin-2-yl)-5-methyl-1H-pyrazole-4-carboxylic acid;

(−)-1-(6-(1-(4-(1-(Cyclopropanecarbonyl)piperidin-4-yl)-3-ethylbenzyl)-3-methylindolin-7-yl)pyridin-2-yl)-5-methyl-1H-pyrazole-4-carboxylic acid;

1-(8-(1-(4-(1-(Cyclopropanecarbonyl)piperidin-4-yl)-2-methylbenzyl)indolin-7-yl)pyridin-2-yl-5-methyl-1H-pyrazole-4-carboxylic acid;

1-(6-(1-(4-(1-(Cyclopropanecarbonyl)piperidin-4-yl)-2-methylbenzyl)indolin-7-yl)pyridin-2-yl)-5-ethyl-1H-pyrazole-4-carboxylic acid;

(+)-1-(8-(1-(4-(1-(Cyclopropanecarbonyl)piperidin-4-yl)-3-ethylbenzyl)-2-methylindolin-7-yl)pyridin-2-yl)-5-ethyl-1H-pyrazole-4-carboxylic acid;

(−)-1-(6-(1-(4-(1-(Cyclopropanecarbonyl)piperidin-4-yl)-3-ethylbenzyl)-2-methylindolin-7-yl)pyridin-2-yl)-5-ethyl-1H-pyrazole-4-carboxylic acid;

1-(8-(1-(4-(1-(Cyclopropanecarbonyl)piperidin-4-yl-3-ethylbenzyl)-3,3-dimethylindolin-7-yl)pyridin-2-yl)-5-ethyl-1H-pyrazole-4-carboxylic acid;

1-(6-(1-(4-(1-Cyclopropylpiperidin-4-yl)-2-methylbenzyl)indolin-7-yl)pyridin-2-yl)-5-methyl-1H-pyrazole-4-carboxylic acid;

1-(6-(1-((2-(Pyridin-2-ylmethyl)-1,2,3,4-tetrahydroisoquinolin-6-yl)methyl)indolin-7-yl)pyridin-2-yl)-5-(trifluoromethyl)-1H-pyrazole-4-carboxylic acid;

1-(6-(1-(4-(1-(Cyclopropanecarbonyl)piperidin-4-yl)benzyl)-1H-indol-7-yl)pyridin-2-yl)-5-(trifluoromethyl)-1H-pyrazole-4-carboxylic acid;

1-(6-(1-(4-(1-(Cyclopropanecarbonyl)piperidin-4-yl)-3-ethylbenzyl)-1H-indol-7-yl)pyridin-2-yl)-5-ethyl-1H-pyrazole-4-carboxylic acid;

1-(6-(1-(4-(1-(Cyclopropanecarbonyl)piperidin-4-yl)-3-ethylbenzyl)-3-methyl-1H-indol-7-yl)pyridin-2-yl)-5-(trifluoromethyl)-1H-pyrazole-4-carboxylic acid;

(S)-1-(6-(3-(4-(1-(Ethoxycarbonyl)piperidin-4-yl)-3-ethylphenoxy)-2,3-dihydro-1H-inden-4-yl)pyridin-2-yl)-5-ethyl-1H-pyrazole-4-carboxylic acid;

5-Ethyl-1-(6-((S)-3-(3-ethyl-4-(1-((S)-2-hydroxypropanoyl)piperidin-4-yl)phenoxy)-2,3-dihydro-1H-inden-4-yl)pyridin-2-yl)-1H-pyrazole-4-carboxylic acid;

5-Ethyl-1-(6-((S)-3-(3-ethyl-4-(1-((S)-2-hydroxypentanoyl)piperidin-4-yl)phenoxy)-2,3-dihydro-1H-inden-4-ylpyridin-2-yl)-1H-pyrazole-4-carboxylic acid;

5-Ethyl-1-(8-((S)-3-(3-ethyl-4-(1-((S)-2-hydroxybutanoyl)piperidin-4-yl)phenoxy)-2,3-dihydro-1H-inden-4-yl)pyridin-2-yl-1H-pyrazole-4-carboxylic acid;

5-Ethyl-1-(6-((S)-3-(3-ethyl-4-(1-((S)-3-hydroxy-2-methylpropanoyl)piperidin-4-ylphenoxy)-2,3-dihydro-1H-inden-4-yl)pyridin-2-yl)-1H-pyrazole-4-carboxylic acid;

(S)-5-Ethyl-1-(6-(3-(3-ethyl-4-(1-(1-hydroxycyclobutanecarbonyl)piperidin-4-yl)phenoxy)-2,3-dihydro-1H-inden-4-yl)pyridin-2-yl)-1H-pyrazole-4-carboxylic acid;

5-Ethyl-1-(6-((3S)-3-(3-ethyl-4-(1-(4-hydroxy-2-methylbutanoyl)piperidin-4-yl)phenoxy)-2,3-dihydro-1H-inden-4-yl)pyridin-2-yl)-1H-pyrazole-4-carboxylic acid (diastereomer-1);

5-Ethyl-1-(6-((3S)-3-(3-ethyl-4-(1-(4-hydroxy-2-methylbutanoyl)piperidin-4-yl)phenoxy)-2,3-dihydro-1H-inden-4-ylpyridin-2-yl)-1H-pyrazole-4-carboxylic acid (diastereomer-2);

(S)-5-Ethyl-1-(6-(3-(3-ethyl-4-(1-(1-hydroxycyclopropanecarbonyl)piperidin-4-yl)phenoxy)-2,3-dihydro-1H-inden-4-yl)pyridin-2-yl)-1H-pyrazole-4-carboxylic acid;

(+)-1-(8-(3-((4-(1-(Cyclopropanecarbonyl)piperidin-4-yl)-2-methyl phen yl)amino)-2,3-dihydrobenzofuran-4-yl)pyridin-2-yl)-5-methyl-1H-pyrazole-4-carboxylic acid;

(−)-1-(6-(3-((4-(1-(Cyclopropanecarbonyl)piperidin-4-yl)-2-methylphenyl)amino)-2,3-dihydrobenzofuran-4-yl)pyridin-2-yl)-5-methyl-1H-pyrazole-4-carboxylic acid;

(+)-1-(6-(3-((4-(1-((S)-2-Hydroxypropanoyl)piperidin-4-yl)-2-methylphenyl)amino)-2,3-dihydrobenzofuran-4-yl)pyridin-2-yl)-5-methyl-1H-pyrazole-4-carboxylic acid;

(−)-1-(6-(3-((4-(1-((S)-2-Hydroxypropanoyl)piperidin-4-yl)-2-methylphenyl)amino)-2,3-dihydrobenzofuran-4-yl)pyridin-2-yl)-5-methyl-1H-pyrazole-4-carboxylic acid;

(+)-1-(6-(3-((4-(1-(Cyclopropanecarbonyl)piperidin-4-yl)-3-ethylphenyl)amino)-2,3-dihydrobenzofuran-4-yl)pyridin-2-yl)-5-(trifluoromethyl)-1H-pyrazole-4-carboxylic acid;

(−)-1-(6-(3-((4-(1-(Cyclopropanecarbonyl)piperidin-4-yl)-3-ethylphenylamino)-2,3-dihydrobenzofuran-4-yl)pyridin-2-yl)-5-(trifluoromethyl)-1H-pyrazole-4-carboxylic acid;

(+)-1-(6-(3-((4-(1-(Cyclopropanecarbonyl)piperidin-4-yl)-3-ethylphenyl)amino)-2,3-dihydrobenzofuran-4-yl)pyridin-2-yl-5-ethyl-1H-pyrazole-4-carboxylic acid;

(−)-1-(6-(3-((4-(1-(Cyclopropanecarbonyl)piperidin-4-yl)-3-ethylphenylamino)-2,3-dihydrobenzofuran-4-yl)pyridin-2-yl)-5-ethyl-1H-pyrazole-4-carboxylic acid;

(+)-1-(8-(3-(4-(1-(Cyclopropanecarbonyl)piperidin-4-yl)-2-methylbenzyl)-2,3-dihydro-1H-inden-4-yl)pyridin-2-yl)-5-methy-1H-pyrazole-4-carboxylic acid;

(−)-1-(6-(3-(4-(1-(Cyclopropanecarbonylpiperidin-4-yl)-2-methylbenzyl)-2,3-dihydro-1H-inden-4-yl)pyridin-2-yl)-5-methyl-1H-pyrazole-4-carboxylic acid;

(−)-1-(6-(3-(4-(1-(Cyclopropanecarbonyl)piperidin-4-yl)-3-ethylbenzyl)-2,3-dihydro-1H-inden-4-yl)pyridin-2-yl)-5-ethyl-1H-pyrazole-4-carboxylic acid;

(+)-1-(6-(3-(4-(1-(Cyclopropanecarbonyl)piperidin-4-yl)-3-ethylbenzyl)-2,3-dihydro-1H-inden-4-yl)pyridin-2-yl)-5-ethyl-1H-pyrazole-4-carboxylic acid;

(−)-1-(6-(3-(4-(1-(Cyclopropanecarbonyl)piperidin-4-yl)-3-ethylbenzyl-2,3-dihydro-1H-inden-4-yl)pyridin-2-yl)-5-methyl-1H-pyrazole-4-carboxylic acid;

(+)-1-(8-(3-(4-(1-(Cyclopropanecarbonyl)piperidin-4-yl)-3-ethylbenzyl)-2,3-dihydro-1H-inden-4-yl)pyridin-2-yl)-5-methy-1H-pyrazole-4-carboxylic acid;

(+)-1-(6-(3-(4-(1-(Cyclopropanecarbonyl)piperidin-4-yl)-2-methylbenzyl)-2,3-dihydro-1H-inden-4-yl)pyridin-2-yl)-5-ethyl-1H-pyrazole-4-carboxylic acid;

(−)-1-(6-(3-(4-(1-(Cyclopropanecarbonyl)piperidin-4-yl)-2-methylbenzyl)-2,3-dihydro-1H-inden-4-yl)pyridin-2-yl)-5-ethyl-1H-pyrazole-4-carboxylic acid;

(−)-5-Ethyl-1-(6-(3-(3-ethyl-4-(1-((S)-2-hydroxypropanoyl)piperidin-4-yl)benzyl)-2,3-dihydro-1H-inden-4-yl)pyridin-2-yl)-1H-pyrazole-4-carboxylic acid (diastereomer-1);

(+)-5-Ethyl-1-(6-(3-(3-ethyl-4-(1-((S)-2-hydroxypropanoyl)piperidin-4-yl)benzyl)-2,3-dihydro-1H-inden-4-yl)pyridin-2-yl)-1H-pyrazole-4-carboxylic acid (diastereomer-2);

(−)-5-Ethyl-1-(6-(3-(3-ethyl-4-(1-((S)-2-hydroxypentanoyl)piperidin-4-yl)benzyl)-2,3-dihydro-1H-inden-4-yl)pyridin-2-yl)-1H-pyrazole-4-carboxylic acid (diastereomer-1);

(+)-5-Ethyl-1-(8-(3-(3-ethyl-4-(1-((S)-2-hydroxypentanoyl)piperidin-4-yl)benzyl)-2,3-dihydro-1H-inden-4-yl)pyridin-2-yl)-1H-pyrazole-4-carboxylic acid (diastereomer-2);

(−)-5-Ethyl-1-(6-(3-(4-(1-((S)-2-hydroxypropanoyl)piperidin-4-yl)-2-methylbenzyl)-2,3-dihydro-1H-inden-4-yl)pyridin-2-yl)-1H-pyrazole-4-carboxylic acid (diastereomer-1);

(+)-5-Ethyl-1-(6-(3-(4-(1-((S)-2-hydroxypropanoyl)piperidin-4-yl)-2-methylbenzyl)-2,3-dihydro-1H-inden-4-yl)pyridin-2-yl)-1H-pyrazole-4-carboxylic acid (diastereomer-2);

(−)-5-Ethyl-1-(6-(3-(4-(1-((S)-2-hydroxypentanoyl)piperidin-4-yl)-2-methylbenzyl)-2,3-dihydro-1H-inden-4-yl)pyridin-2-yl)-1H-pyrazole-4-carboxylic acid (diastereomer-1);

(+)-5-Ethyl-1-(6-(3-(4-(1-((S)-2-hydroxypentanoyl)piperidin-4-yl)-2-methylbenzyl)-2,3-dihydro-1H-inden-4-yl)pyridin-2-yl)-1H-pyrazole-4-carboxylic acid (diastereomer-2);

(+)-Ethyl-1-(6-(3-(3-ethyl-4-(1-(methoxycarbonyl)piperidin-4-yl)benzyl)-2,3-dihydro-1H-inden-4-yl)pyridin-2-yl)-1H-pyrazole-4-carboxylic acid;

(−)-Ethyl-1-(6-(3-(3-ethyl-4-(1-(methoxycarbonyl)piperidin-4-yl)benzyl)-2,3-dihydro-1H-inden-4-yl)pyridin-2-yl)-1H-pyrazole-4-carboxylic acid;

(+)-5-Ethyl-1-(8-(3-(4-(1-(methoxycarbonyl)piperidin-4-yl)-2-methylbenzyl)-2,3-dihydro-1H-inden-4-yl)pyridin-2-yl)-1H-pyrazole-4-carboxylic acid;

(−)-5-Ethyl-1-(6-(3-(4-(1-(methoxycarbonyl)piperidin-4-yl)-2-methylbenzyl)-2,3-dihydro-1H-inden-4-yl)pyridin-2-yl)-1H-pyrazole-4-carboxylic acid;

(+)-1-(6-(3-((4-(1-(Cyclopropanecarbonyl)piperidin-4-yl)-2-methylphenyl)amino)-6-methyl-2,3-dihydro-1H-inden-4-yl)pyridin-2-yl)-5-(trifluoromethyl)-1H-pyrazole-4-carboxylic acid;

(−)-1-(6-(3-((4-(1-(Cyclopropanecarbonyl)piperidin-4-yl)-2-methylphenyl)amino)-6-methyl-2,3-dihydro-1H-inden-4-yl)pyridin-2-yl)-5-(trifluoromethyl-1H-pyrazole-4-carboxylic acid;

(+)-1-(3-(3-((4-(1-(cyclopropanecarbonyl)piperidin-4-yl)-2-methylphenyl)amino)-2,3-dihydro-1H-inden-4-yl)phenyl)-5-methyl-1H-pyrazole-4-carboxylic acid;

(−)-1-(3-(3-((4-(1-(cyclopropanecarbonyl)piperidin-4-yl)-2-methylphenylamino)-2,3-dihydro-1H-inden-4-yl)phenyl)-5-methyl-1H-pyrazole-4-carboxylic acid;

(+)-1-(8-(3-((4-(1-(Cyclopropanecarbonyl)piperidin-4-yl)-3-ethylphenyl)amino)-2,3-dihydro-1H-inden-4-yl)pyridin-2-yl)-5-methyl-1H-pyrazole-4-carboxylic acid;

(+)-(6-(3-((4-(1-(Cyclobutanecarbonyl)piperidin-4-yl)-2-methylphenyl)amino)-2,3-dihydro-1H-inden-4-yl)pyridin-2-yl)-5-methyl-1H-pyrazole-4-carboxylic acid;

(−)-(6-(3-((4-(1-(cyclobutanecarbonyl)piperidin-4-yl)-2-methylphenyl)amino)-2,3-dihydro-1H-inden-4-yl)pyridin-2-yl)-5-methyl-1H-pyrazole-4-carboxylic acid;

(+)-1-(6-(3-((4-(1-isobutyrylpiperidin-4-yl)-2-methylphenyl)amino)-2,3-dihydro-1H-inden-4-yl)pyridin-2-yl)-5-methyl-1H-pyrazole-4-carboxylic acid;

(−)-1-(6-(3-((4-(1-isobutyrylpiperidin-4-yl)-2-methylphenyl)amino)-2,3-dihydro-1H-inden-4-yl)pyridin-2-yl)-5-methyl-1H-pyrazole-4-carboxylic acid;

(+)-5-methyl-1-(6-(3-((2-methyl-4-(1-propionylpiperidin-4-yl)phenyl)amino)-2,3-dihydro-1H-inden-4-yl)pyridin-2-yl-1H-pyrazole-4-carboxylic acid;

(−)-5-Methyl-1-(6-(3-((2-methyl-4-(1-propionylpiperidin-4-yl)phenyl)amino)-2,3-dihydro-1H-inden-4-yl)pyridin-2-yl)-1H-pyrazole-4-carboxylic acid;

(+)-1-(8-(3-((4-(1-(2-Cyclopropylacetyl)piperidin-4-yl)-2-methylphenyl)amino)-2,3-dihydro-1H-inden-4-yl)pyridin-2-yl)-5-methyl-1H-pyrazole-4-carboxylic acid;

(−)-1-(6-(3-((4-(1-(2-Cyclopropylacetyl)piperidin-4-yl)-2-methylphenyl)amino)-2,3-dihydro-1H-inden-4-yl)pyridin-2-yl)-5-methyl-1H-pyrazole-4-carboxylic acid;

(+)- or (−)-1-(6-(3-((4-(1-(2-cyclopropylacetyl)piperidin-4-yl)-3-fluoro-2-methylphenyl)amino)-2,3-dihydro-1H-inden-4-yl)pyridin-2-yl)-5-methyl-1H-pyrazole-4-carboxylic acid;

(+)-1-(6-(3-((4-(1-(2-Cyclopropylacetyl)piperidin-4-yl)-5-fluoro-2-methylphenyl)amino)-2,3-dihydro-1H-inden-4-yl)pyridin-2-yl)-5-methyl-1H-pyrazole-4-carboxylic acid;

(−)-1-(6-(3-((4-(1-(2-Cyclopropylacetylpiperidin-4-yl)-5-fluoro-2-methylphenyl)amino)-2,3-dihydro-1H-inden-4-yl)pyridin-2-yl)-5-methyl-1H-pyrazole-4-carboxylic acid;

(+)-1-(8-(3-((4-(1-((S)-2-Hydroxypropanoyl)piperidin-4-yl)-2-methylphenyl)amino)-2,3-dihydro-1H-inden-4-yl)pyridin-2-yl)-5-methyl-1H-pyrazole-4-carboxylic acid (diastereomer-1);

(−)-1-(6-(3-((4-(1-((S)-2-Hydroxypropanoyl)piperidin-4-yl)-2-methylphenyl)amino)-2,3-dihydro-1H-inden-4-yl)pyridin-2-yl)-5-methyl-1H-pyrazole-4-carboxylic acid (diastereomer-2);

(+)-5-Ethyl-1-(6-(3-((3-ethyl-4-(1-((S)-2-hydroxypropanoyl)piperidin-4-yl)phenyl)amino)-2,3-dihydro-1H-inden-4-yl)pyridin-2-yl)-1H-pyrazole-4-carboxylic acid (diastereomer-2);

(−)-5-Ethyl-1-(6-(3-((3-ethyl-4-(1-((S)-2-hydroxypropanoyl)piperidin-4-yl)phenyl)amino)-2,3-dihydro-1H-inden-4-yl)pyridin-2-yl)-1H-pyrazole-4-carboxylic acid (diastereomer-1);

(+)-5-Ethyl-1-(6-(3-((3-ethyl-4-(1-((S)-2-hydroxypentanoyl)piperidin-4-yl)phenyl)amino)-2,3-dihydro-1H-inden-4-yl)pyridin-2-yl)-1H-pyrazole-4-carboxylic acid (diastereomer-2);

(−)-5-Ethyl-1-(6-(3-((3-ethyl-4-(1-((S)-2-hydroxypentanoyl)piperidin-4-yl)phenyl)amino)-2,3-dihydro-1H-inden-4-yl)pyridin-2-yl)-1H-pyrazole-4-carboxylic acid (diastereomer-1);

(+)-5-Ethyl-1-(6-(3-((3-ethyl-4-(1-((S)-2-hydroxybutanoyl)piperidin-4-yl)phenyl)amino)-2,3-dihydro-1H-inden-4-yl)pyridin-2-yl)-1H-pyrazole-4-carboxylic acid (diastereomer-2);

(−)-5-Ethyl-1-(8-(3-((3-ethyl-4-(1-((S)-2-hydroxybutanoyl)piperidin-4-yl)phenyl)amino)-2,3-dihydro-1H-inden-4-yl)pyridin-2-yl)-1H-pyrazole-4-carboxylic acid (diastereomer-1);

(+)-5-Ethyl-1-(6-(3-((3-ethyl-4-(1-(isopropoxycarbonyl)piperidin-4-yl)phenyl)amino)-2,3-dihydro-1H-inden-4-yl)pyridin-2-yl)-1H-pyrazole-4-carboxylic acid;

(−)-Ethyl-1-(6-(3-((3-ethyl-4-(1-(isopropoxycarbonyl)piperidin-4-yl)phenyl)amino)-2,3-dihydro-1H-inden-4-yl)pyridin-2-yl)-1H-pyrazole-4-carboxylic acid;

(−)-1-(6-(3-((4-(1-(Ethoxycarbonyl)piperidin-4-yl)-3-ethylphenyl)amino)-2,3-dihydro-1H-inden-4-yl)pyridin-2-yl)-5-ethyl-1H-pyrazole-4-carboxylic acid;

(+)-1-(8-(3-((4-(1-(Ethoxycarbonyl) piperidin-4-yl)-3-ethylphenyl)amino)-2,3-dihydro-1H-inden-4-yl)pyridin-2-yl)-5-ethyl-1H-pyrazole-4-carboxylic acid;

(−)-5-Ethyl-1-(6-(3-((3-ethyl-4-(1-(methoxycarbonyl)piperidin-4-yl)phenyl)amino)-2,3-dihydro-1H-inden-4-yl)pyridin-2-yl)-1H-pyrazole-4-carboxylic acid;

(+)-5-Ethyl-1-(6-(3-((3-ethyl-4-(1-(methoxycarbonyl)piperidin-4-yl)phenyl)amino)-2,3-dihydro-1H-inden-4-yl)pyridin-2-yl)-1H-pyrazole-4-carboxylic acid;

(−)-1-(6-(3-((4-(1-((Allyloxy)carbonyl)piperidin-4-yl)-3-ethylphenyl)amino)-2,3-dihydro-1H-inden-4-yl)pyridin-2-yl)-5-ethyl-1H-pyrazole-4-carboxylic acid;

(+)-1-(8-(3-((4-(1-((Allyloxy)carbonyl)piperidin-4-yl)-3-ethylphenyl)amino)-2,3-dihydro-1H-Inden-4-yl)pyridin-2-yl)-5-ethyl-1H-pyrazole-4-carboxylic acid;

1-(6-(3-((4-(1-(Ethoxycarbonyl)piperidin-4-yl)-2-methylphenyl)amino)-2,3-dihydro-1H-inden-4-yl)pyridin-2-yl)-5-methyl-1H-pyrazole-4-carboxylic acid;

1-(8-(3-((4-(1-((2-methoxyethoxy)carbonyl)-piperidin-4-yl)-2-methylphenyl)amino)-2,3-dihydro-1H-inden-4-yl)pyridin-2-yl)-5-methyl-1H-pyrazole-4-carboxylic acid;
5-Methyl-1-(6-(3-((2-methyl-4-(1-((prop-1-en-2-yloxy)carbonyl)piperidin-4-yl)phenyl)amino)-2,3-dihydro-1H-inden-4-yl)pyridin-2-yl)-1H-pyrazole-4-carboxylic acid;
(−)-1-(6-(3-((4-(1-(cyclopropanecarbonyl)piperidin-4-yl)-3-ethylphenyl)amino)-2,3-dihydro-1H-inden-4-yl)pyridin-2-yl)-5-ethyl-1H-pyrazole-4-carboxylic acid;
(+)-1-(8-(3-((4-(1-(cyclopropanecarbonyl)piperidin-4-yl)-3-ethylphenyl)amino)-2,3-dihydro-1H-inden-4-yl)pyridin-2-yl)-5-ethyl-1H-pyrazole-4-carboxylic acid;
(−)-1-(6-(3-((4-(1-(2-cyclopropylacetyl)piperidin-4-yl)-3-ethylphenyl)amino)-2,3-dihydro-1H-inden-4-yl)pyridin-2-yl)-5-ethyl-1H-pyrazole-4-carboxylic acid;
(+)-1-(6-(3-((4-(1-(2-cyclopropylacetyl)piperidin-4-yl)-3-ethylphenyl)amino)-2,3-dihydro-1H-inden-4-yl)pyridin-2-yl)-5-ethyl-1H-pyrazole-4-carboxylic acid;
(+)-1-(8-(3-((4-(1-(2-cyclopropylacetyl)piperidin-4-yl)-2-fluor-1-methylphenyl)amino)-2,3-dihydro-1H-inden-4-yl)pyridin-2-yl)-5-methyl-1H-pyrazole-4-carboxylic acid;
(−)-1-(6-(3-((4-(1-(2-cyclopropylacetyl)piperidin-4-yl)-2-fluoro-6-methylphenyl)amino)-2,3-dihydro-1H-inden-4-yl)pyridin-2-yl)-5-methyl-1H-pyrazole-4-carboxylic acid;
(+)-1-(6-(3-((4-(1-(cyclopropanecarbonyl)piperidin-4-yl)-2-methylphenyl)amino)-2,3-dihydro-1H-inden-4-yl)pyridin-2-yl)-5-(difluoromethyl)-1H-pyrazole-4-carboxylic acid;
(−)-1-(6-(3-((4-(1-(cyclopropanecarbonyl)piperidin-4-yl)-2-methylphenyl)amino)-2,3-dihydro-1H-inden-4-yl)pyridin-2-yl)-5-(difluoromethyl)-1H-pyrazole-4-carboxylic acid;
(−)-1-(3-(3-(4-(1-(cyclopropanecarbonyl)piperidin-4-yl)-2-methylbenzyl)-2,3-dihydro-1H-inden-4-yl)phenyl)-5-methyl-1H-pyrazole-4-carboxylic acid;
(+)-1-(3-(3-(4-(1-(cyclopropanecarbonyl)piperidin-4-yl)-2-methylbenzyl)-2,3-dihydro-1H-inden-4-yl)phenyl)-5-methyl-1H-pyrazole-4-carboxylic acid;
(−)-1-(3-(3-(4-(1-(cyclopropanecarbonyl)piperidin-4-yl)-3-ethylbenzyl)-2,3-dihydro-1H-inden-4-yl)phenyl)-5-methyl-1H-pyrazole-4-carboxylic acid;
(+)-1-(3-(3-(4-(1-(cyclopropanecarbonyl)piperidin-4-yl)-3-ethylbenzyl)-2,3-dihydro-1H-inden-4-yl)phenyl)-5-methyl-1H-pyrazole-4-carboxylic acid;
(+)-1-(3-(3-((4-(1-(Cyclopropanecarbonyl)piperidin-4-yl)-2-methylphenyl)amino)-2,3-dihydro-1H-inden-4-yl)phenyl)-5-(difluoromethyl)-1H-pyrazole-4-carboxylic acid;
(+)-1-(3-(3-((4-(1-(2-Hydroxyacetyl)piperidin-4-yl)-2-methylphenyl)amino)-2,3-dihydro-1H-inden-4-yl)phenyl)-5-(trifluoromethyl)-1H-pyrazole-4-carboxylic acid;
(+)-1-(8-(3-((4-(1-(Cyclopropanecarbonyl)piperidin-)-yl)-2-methylphenylamino)-2,3-dihydro-1H-inden-4-yl)pyridin-2-yl)-5-(2,2,2-trifluoroethyl)-1H-pyrazole-4-carboxylic acid;
(−)-5-Methyl-1-(6-(3-((2-methyl-4-(1-(5-methyl-1,3,4-oxadiazol-2-yl)piperidin-4-yl)phenyl)amino)-2,3-dihydro-1H-inden-4-yl)pyridin-2-yl)-1H-pyrazole-4-carboxylic acid;
(+)-5-Methyl-1-(6-(3-((2-methyl-4-(1-(5-methyl-1,3,4-oxadiazol-2-yl)piperidin-4-yl)phenyl)amino)-2,3-dihydro-1H-inden-4-yl)pyridin-2-yl)-1H-pyrazole-4-carboxylic acid;
(±)-5-Methyl-1-(6-(3-((2-methyl-4-(1-(pyridin-2-yl)piperidin-4-yl)phenyl)amino)-2,3-dihydro-1H-inden-4-yl)pyridin-2-yl)-1H-pyrazole-4-carboxylic acid;
(±)-1-(6-(3-((4-(1-Cyclopropylpiperidin-4-yl)-2-methylphenyl)amino)-2,3-dihydro-1H-inden-4-yl)pyridin-2-yl)-5-methyl-1H-pyrazole-4-carboxylic acid;
1-(6-(3-(4-(1-(Cyclopropanecarbonyl)piperidin-4-yl)-2-(trifluoromethyl)phenoxy)-2,3-dihydro-1H-inden-4-yl)pyridin-2-yl)-5-(trifluoromethyl)-1H-pyrazole-4-carboxylic acid (enantiomer-1);
1-(6-(3-(4-(1-(Cyclopropanecarbonyl)piperidin-4-yl)-2-(trifluoromethyl)phenoxy)-2,3-dihydro-1H-inden-4-yl)pyridin-2-yl)-5-(trifluoromethyl)-1H-pyrazole-4-carboxylic acid (enantiomer-2);
(±)-1-(6-(3-((5-(1-(Cyclopropanecarbonyl)piperidin-4-yl)-3-methylpyridin-2-yl)amino)-2,3-dihydro-1H-inden-4-yl)pyridin-2-yl)-5-methyl-1H-pyrazole-4-carboxylic acid;
(+)-1-(6-(3-((5-(1-(Cyclopropanecarbonyl) piperidin-4-yl)-6-ethylpyridin-2-yl)amino)-2,3-dihydro-1H-inden-4-yl)pyridin-2-yl)-5-ethyl-1H-pyrazole-4-carboxylic acid;
(−)-1-(6-(3-((5-(1-(Cyclopropanecarbonyl piperidin-4-yl)-6-ethylpyridin-2-yl)amino)-2,3-dihydro-1H-inden-4-yl)pyridin-2-yl)-5-ethyl-1H-pyrazole-4-carboxylic acid;
(S)-1-(6-(3-(4-(1-((Benzyloxy)carbonyl)piperidin-4-yl)-3-ethylphenoxy)-2,3-dihydro-1H-inden-4-yl)pyridin-2-yl)-5-ethyl-1H-pyrazole-4-carboxylic acid;
(S)-5-Ethyl-1-(6-(3-(3-ethyl-4-(1-(Isobutoxycarbonyl)piperidin-4-yl)phenoxy)-2,3-dihydro-1H-inden-4-yl)pyridin-2-yl)-1H-pyrazole-4-carboxylic acid;
(S)-5-Ethyl-1-(6-(3-(3-ethyl-4-(1-(isopropoxycarbonyl)piperidin-4-yl)phenoxy)-2,3-dihydro-1H-inden-4-yl)pyridin-2-yl)-1H-pyrazole-4-carboxylic acid;
(S)-5-Ethyl-1-(6-(3-(3-ethyl-4-(1-(propoxycarbonyl)piperidin-4-yl)phenoxy)-2,3-dihydro-1H-inden-4-yl)pyridin-2-yl)-1H-pyrazole-4-carboxylic acid;
(S)-1-(6-(3-(4-(1-((Allyloxy)carbonyl)piperidin-4-yl)-3-ethylphenoxy)-2,3-dihydro-1H-inden-4-yl)pyridin-2-yl)-5-ethyl-1H-pyrazole-4-carboxylic acid;
(S)-1-(6-(3-(4-(1-((Cyclopropylmethoxy)carbonyl)piperidin-4-yl)-3-ethylphenoxy)-2,3-dihydro-1H-inden-4-yl)pyridin-2-yl)-5-ethyl-1H-pyrazole-4-carboxylic acid;
(S)-5-Ethyl-1-(6-(3-(3-ethyl-4-(1-(methoxycarbonyl)piperidin-4-yl)phenoxy)-2,3-dihydro-1H-inden-4-yl)pyridin-2-yl)-1H-pyrazole-4-carboxylic acid;
(S)-5-Ethyl-1-(6-(3-(3-ethyl-4-(1-(methylsulfonyl)piperidin-4-yl)phenoxy)-2,3-dihydro-1H-inden-4-yl)pyridin-2-yl)-1H-pyrazole-4-carboxylic acid; and pharmaceutically acceptable salts thereof.

In another aspect of the invention, synthetic intermediates which are suitable for use in the preparation of compounds of embodiments one to twenty two of the invention are provided. In one aspect, intermediates are provided according to the formula:

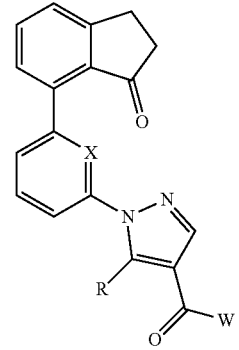

Where X is either CH or N;

R is C1-C4 alkyl, monofluoromethyl, difluoromethyl or trifluoromethyl;

And W is OH or C1-C4alkoxy.

Certain particularly preferred indanone intermediates suitable for use in the preparation of some of the compounds of the invention include, Ethyl 5-methyl-1-(6-(3-oxo-2,3-dihydro-1H-inden-4-yl)pyridin-2-yl)-1H-pyrazole-4-carboxylate;

Ethyl 5-ethyl-1-(6-(3-oxo-2,3-dihydro-1H-inden-4-yl)pyridin-2-yl)-1H-pyrazole-4-carboxylate;

Ethyl 1-(6-(3-oxo-2,3-dihydro-1H-inden-4-yl)pyridin-2-yl)-5-(trifluoromethyl)-1H-pyrazole-4-carboxylate;

Ethyl 5-(difluoromethyl)-1-(6-(3-oxo-2,3-dihydro-1H-inden-4-yl)pyridin-2-yl)-1H-pyrazole-4-carboxylate;

Ethyl 5-methyl-1-(3-(3-oxo-2,3-dihydro-1H-inden-4-yl)phenyl)-1H-pyrazole-4-carboxylate.

In another aspect, synthetic intermediates suitable for use in preparing the compounds of the invention include compounds of the formula:

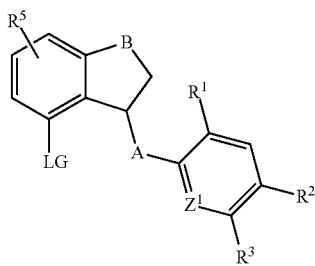

Where A, B, $Z^1$, $R^1$, $R^2$, $R^3$ and $R^5$ are substituents as defined in embodiment one. LG is a moiety suitable for transition metal mediated cross coupling reactions. In preferred intermediates, LG is a sulfonic acid ester (such as triflate ($OSO_2CF_3$), mesylate ($OSO_2CH_3$), or tosylate ($OSO_2CH_2C_6H_4Me$)) or LG is a halide (chloro, bromo or iodo).

Certain preferred synthetic intermediates include those compounds of the formula:

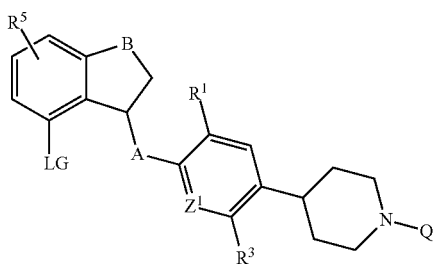

Where A, B, $Z^1$, $R^1$, $R^3$ and $R^5$ are substituents as defined in embodiment 1. Q is $C(O)R^7$ or —$C(O)OR^7$ where $R^7$ is $C_1$-$C_4$alkyl or cyclopropyl. LG is a moiety suitable for transition metal mediated cross coupling reactions. In preferred intermediates, LG is a sulfonic acid ester (such as triflate ($OSO_2CF_3$), mesylate ($OSO_2CH_3$), or tosylate ($OSO_2CH_2C_6H_4Me$)) or LG is a halide (chloro, bromo or iodo).

Certain particularly preferred synthetic intermediates suitable for making compounds of the instant invention include those compounds of the formula:

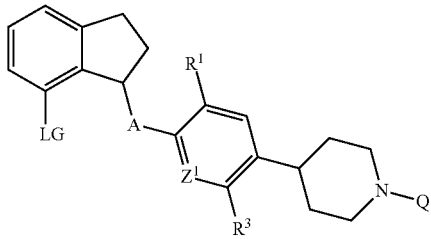

Where A, $Z^1$, $R^1$, and $R^3$ are substituents as defined in embodiment 1. Q is $C(O)R^7$ or —$C(O)OR^7$ where $R^7$ is $C_1$-$C_4$alkyl or cyclopropyl. LG is a moiety suitable for transition metal mediated cross coupling reactions. In preferred intermediates, LG is a sulfonic acid ester (such as triflate ($OSO_2CF_3$), mesylate ($OSO_2CH_3$), or tosylate ($OSO_2CH_2C_6H_4Me$)) or LG is a halide (chloro, bromo or iodo).

Certain particularly preferred intermediates suitable for use in the preparation of some of the compounds of the invention include, (+)-(S)-(4-(4-((7-Bromo-2,3-dihydro-1H-inden-1-yl)oxy)-3-methylphenyl)piperidin-1-yl)(cyclopropyl)methanone (+)-(S)-(4-(4-((7-Bromo-2,3-dihydro-1H-inden-1-yl)oxy)-2-ethylphenyl)piperidin-1-yl)(cyclopropyl)methanone (S)-tert-Butyl 4-(4-((7-bromo-2,3-dihydro-1H-inden-1-yl)oxy)-2-ethylphenyl)piperidine-1-carboxylate (±)-(4-(4-((7-Bromo-2,3-dihydro-1H-inden-1-yl)amino)-3-methylphenyl)piperidin-1-yl)(cyclopropyl)methanone (+)-(4-(4-((7-Bromo-2,3-dihydro-1H-inden-1-yl)amino)-3-methylphenyl)piperidin-1-yl)(cyclopropyl)methanone (±)-(4-(4-((7-bromo-2,3-dihydro-1H-inden-1-yl)amino)phenyl)piperidin-1-yl)(cyclopropyl)methanone (±)-tert-Butyl 4-(4-((7-bromo-2,3-dihydro-1H-inden-1-yl)amino)-3-methylphenyl)piperidine-1-carboxylate (±)-tert-Butyl 4-(4-((7-bromo-2,3-dihydro-1H-inden-1-yl)amino)-2-ethylphenyl)piperidine-1-carboxylate (±)-tert-Butyl 4-(4-((4-bromo-2,3-dihydrobenzofuran-3-yl)amino)-2-ethylphenyl)piperidine-1-carboxylate (±)-tert-Butyl 4-(4-((4-bromo-2,3-dihydrobenzofuran-3-yl)amino)-3-methylphenyl)piperidine-1-carboxylate (±)-tert-Butyl 4-(6-((7-bromo-2,3-dihydro-1H-inden-1-yl)amino)-2-ethylpyridin-3-yl)piperidine-1-carboxylate (±)-3-(4-(1-(Cyclopropanecarbonyl)piperidin-4-yl)-2-methylbenzyl)-2,3-dihydro-1H-inden-4-yl trifluoromethanesulfonate (±)-3-(4-(1-(Cyclopropanecarbonyl)piperidin-4-yl)-3-ethylbenzyl)-2,3-dihydro-1H-inden-4-yl trifluoromethanesulfonate (±)-tert-Butyl 4-(2-ethyl-4-((7-(((trifluoromethyl)sulfonyl)oxy)-2,3-dihydro-1H-inden-1-yl)methyl)phenyl)piperidine-1-carboxylate (±)-tert-Butyl 4-(3-methyl-4-((7-(((trifluoromethyl)sulfonyl)oxy)-2,3-dihydro-1H-inden-1-yl)methyl)phenyl)piperidine-1-carboxylate In a twenty third embodiment, the present invention relates to a method of treating or preventing glaucoma or reducing intraocular pressure comprising administering to a subject in need thereof a sGC activator selected from the compounds of any one of embodiments one to sixteen. The invention has surprisingly shown that administration of sGC activators to a patient in need of therapy has desirable sustained efficacy in reducing IOP and in the treatment of glaucoma.

Unless specified otherwise, the term "compounds of the present invention" refers to compounds of formula (I) and subformulae thereof, and salts thereof, as well as all stereoisomers (including diastereoisomers and enantiomers), rotamers, tautomers and isotopically labeled compounds (including deuterium substitutions), as well as inherently formed moieties.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of formula I in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

In another aspect, the present invention provides (+)-1-(3-(3-((4-(1-(cyclopropanecarbonyl)piperidin-4-yl)-2-methylphenyl)amino)-2,3-dihydro-1H-inden-4-yl)phenyl)-5-(trifluoromethyl)-1H-pyrazole-4-carboxylic acid in sodium, potassium, ammonium, calcium, magnesium, iron, silver, zinc, and copper salt form; particularly suitable inorganic salts include ammonium, potassium, sodium, calcium and magnesium salts. The invention further provides (+)-1-(3-(3-((4-(1-(cyclopropanecarbonyl)piperidin-4-yl)-2-methylphenyl)amino)-2,3-dihydro-1H-inden-4-yl)phenyl)-5-(trifluoromethyl)-1H-pyrazole-4-carboxylic acid in isopropylamine, benzathine, cholinate, diethanolamine, diethylamine, lysine, meglumine, piperazine and tromethamine salt forms. The compound of this embodiment is provided in salt form in racemic or enantiomerically enriched form.

In another aspect, the present invention provides (+)-1-(6-(3-((4-(1-(cyclopropanecarbonyl)piperidin-4-yl)-2-methylphenyl)amino)-2,3-dihydro-1H-inden-4-yl)pyridin-2-yl)-5-methyl-1H-pyrazole-4-carboxylic acid in sodium, potassium, ammonium, calcium, magnesium, iron, silver, zinc, and copper salt form; particularly suitable inorganic salts include ammonium, potassium, sodium, calcium and magnesium salts. The invention further provides (+)-1-(6-(3-((4-(1-(cyclopropanecarbonyl)piperidin-4-yl)-2-methylphenyl)amino)-2,3-dihydro-1H-inden-4-yl)pyridin-2-yl)-5-methyl-1H-pyrazole-4-carboxylic acid in isopropylamine, benzathine, cholinate, diethanolamine, diethylamine, lysine, meglumine, piperazine and tromethamine salt forms. The compound of this embodiment is provided in salt form in racemic or enantiomerically enriched form.

In another aspect, the present invention provides (+)-1-(6-(3-(4-(1-(cyclopropanecarbonyl)piperidin-4-yl)-2-methylphenoxy)-2,3-dihydro-1H-inden-4-yl)pyridin-2-yl)-5-ethyl-1H-pyrazole-4-carboxylic acid in sodium, potassium, ammonium, calcium, magnesium, iron, silver, zinc, and copper salt form; particularly suitable inorganic salts include ammonium, potassium, sodium, calcium and magnesium salts. The invention further provides (+)-1-(6-(3-(4-(1-(cyclopropanecarbonyl)piperidin-4-yl)-2-methylphenoxy)-2,3-dihydro-1H-inden-4-yl)pyridin-2-yl)-5-ethyl-1H-pyrazole-4-carboxylic acid in isopropylamine, benzathine, cholinate, diethanolamine, diethylamine, lysine, meglumine, piperazine and tromethamine salt forms. The compound of this embodiment is provided in salt form in racemic or enantiomerically enriched form.

In another aspect, the present invention provides (+)-(S)-1-(6-(3-(4-(1-(cyclopropanecarbonyl)piperidin-4-yl)-3-ethylphenoxy)-2,3-dihydro-1H-inden-4-yl)pyridin-2-yl)-5-(trifluoromethyl)-1H-pyrazole-4-carboxylic acid in sodium, potassium, ammonium, calcium, magnesium, iron, silver, zinc, and copper salt form; particularly suitable inorganic salts include ammonium, potassium, sodium, calcium and magnesium salts. The invention further provides (+)-(S)-1-(6-(3-(4-(1-(cyclopropanecarbonyl)piperidin-4-yl)-3-ethylphenoxy)-2,3-dihydro-1H-inden-4-yl)pyridin-2-yl)-5-(trifluoromethyl)-1H-pyrazole-4-carboxylic acid in isopropylamine, benzathine, cholinate, diethanolamine, diethylamine, lysine, meglumine, piperazine and tromethamine salt forms. The compound of this embodiment is provided in salt form in racemic or enantiomerically enriched form.

In another aspect, the present invention provides (+)-1-(6-(3-(4-(1-(cyclopropanecarbonyl)piperidin-4-yl)-2-methylbenzyl)-2,3-dihydro-1H-inden-4-yl)pyridin-2-yl)-5-methyl-1H-pyrazole-4-carboxylic acid in sodium, potassium, ammonium, calcium, magnesium, iron, silver, zinc, and copper salt form; particularly suitable inorganic salts include ammonium, potassium, sodium, calcium and magnesium salts. The invention further provides (+)-1-(6-(3-(4-1-(cyclopropanecarbonyl)piperidin-4-yl)-2-methyl-benzyl)-2,3-dihydro-1H-inden-4-yl)pyridin-2-yl)-5-methyl-1H-pyrazole-4-carboxylic acid in isopropylamine, benzathine, cholinate, diethanolamine, diethylamine, lysine, meglumine, piperazine and tromethamine salt forms. The compound of this embodiment is provided in salt form in racemic or enantiomerically enriched form.

In another aspect, the present invention provides 5-Ethyl-1-(6-((S)-3-(3-ethyl-4-(1-((S)-2-hydroxypropanoyl)piperidin-4-yl)phenoxy)-2,3-dihydro-1H-inden-4-yl)pyridin-2-yl)-1H-pyrazole-4-carboxylic acid in sodium, potassium, ammonium, calcium, magnesium, iron, silver, zinc, and copper salt form; particularly suitable inorganic salts include ammonium, potassium, sodium, calcium and magnesium salts. The invention further provides 5-Ethyl-1-(6-((S)-3-(3-ethyl-4-(1-((S)-2-hydroxypropanoyl)piperidin-4-yl)phenoxy)-2,3-dihydro-1H-inden-4-yl)pyridin-2-yl)-1H-pyrazole-4-carboxylic acid in isopropylamine, benzathine, cholinate, diethanolamine, diethylamine, lysine, meglumine, piperazine and tromethamine salt forms. The compound of this embodiment is provided in salt form in racemic or enantiomerically enriched form.

In another aspect, the present invention provides (+)-5-Ethyl-1-(6-(3-((3-ethyl-4-(1-((S)-2-hydroxypropanoyl)piperidin-4-yl)phenyl)amino)-2,3-dihydro-1H-inden-4-yl)pyridin-2-yl)-1H-pyrazole-4-carboxylic acid in sodium, potassium, ammonium, calcium, magnesium, iron, silver, zinc, and copper salt form; particularly suitable inorganic salts include ammonium, potassium, sodium, calcium and magnesium salts. The invention further provides (+)-5-Ethyl-1-(6-(3-((3-ethyl-4-(1-((S)-2-hydroxypropanoyl)piperidin-4-yl)phenyl)amino)-2,3-dihydro-1H-inden-4-yl)pyridin-2-yl)-1H-pyrazole-4-carboxylic acid in isopropylamine, benzathine, cholinate, diethanolamine, diethylamine, lysine, meglumine, piperazine and tromethamine salt forms. The compound of this embodiment is provided in salt form in racemic or enantiomerically enriched form.

In another aspect, the present invention provides (+)-5-ethyl-1-(6-(3-(3-ethyl-4-(1-((S)-2-hydroxypropanoyl)piperidin-4-yl)benzyl)-2,3-dihydro-1H-inden-4-yl)pyridin-2-yl)-1H-pyrazole-4-carboxylic acid in sodium, potassium, ammonium, calcium, magnesium, iron, silver, zinc, and copper salt form; particularly suitable inorganic salts include ammonium, potassium, sodium, calcium and magnesium salts. The invention further provides (+)-5-ethyl-1-(6-(3-(3-ethyl-4-(1-((S)-2-hydroxypropanoyl)piperidin-4-yl)benzyl)-2,3-dihydro-1H-inden-4-yl)pyridin-2-yl)-1H-pyrazole-4-carboxylic acid in isopropylamine, benzathine, cholinate, diethanolamine, diethylamine, lysine, meglumine, piperazine and tromethamine salt forms. The compound of this embodiment is provided in salt form in racemic or enantiomerically enriched form.

In another aspect, the present invention provides 5-Ethyl-1-(6-(1-(3-ethyl-4-(1-((S)-2-hydroxypropanoyl)piperidin-4-yl)benzyl)-3-methylindolin-7-yl)pyridin-2-yl)-1H-pyrazole-4-carboxylic acid (diastereomer-1) in sodium, potassium, ammonium, calcium, magnesium, iron, silver, zinc, and copper salt form; particularly suitable inorganic salts include ammonium, potassium, sodium, calcium and magnesium salts. The invention further provides 5-Ethyl-1-(6-1-(3-ethyl-4-(1-((S)-2-hydroxypropanoyl)piperidin-4-yl)benzyl)-3-methylindolin-7-yl)pyridin-2-yl)-1H-pyrazole-4-carboxylic acid (diastereomer-1) in isopropylamine, benzathine, cholinate, diethanolamine, diethylamine, lysine, meglumine, piperazine and tromethamine salt forms. The compound of this embodiment is provided in salt form in racemic or enantiomerically enriched form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{123}I$, $^{124}I$, $^{125}I$ respectively. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, activation of soluble guanylate cyclase activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by activation of sGC, or (ii) associated with decreased sGC activity, or (iii) characterized by activity (normal or abnormal) of sGC. In another non-limiting embodiment, the term "a therapeutically effective amount" refers to the amount of the compound of the present invention that, when administered to a cell, or a tissue, or a non-cellular biological material, or a medium, is effective to at least partially increasing the activity of sGC.

As used herein, the term "subject" refers to an animal. Typically the animal is a mammal. A subject also refers to for example, primates (e.g., humans, male or female), cows, sheep, goats, horses, dogs, cats, rabbits, rats, mice and the like. In certain embodiments, the subject is a primate. In yet other embodiments, the subject is a human. In yet other embodiments, the subject is a human. In certain other embodiments, the compounds of the invention may be suitable for use in the treatment of glaucoma or reduction of IOP in dogs.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "activate", "activation" or "activating" refers to the significant increase in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, 'treat', "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis- (Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

Typically, the compounds of formula (I) can be prepared according to the Schemes provided infra General Synthetic Aspects Typically, the compounds of Formula (I) can be prepared according to the Schemes provided below. The following Examples serve to illustrate the invention without limiting the scope thereof.

Compounds such as 1-3; wherein $R^a$ is $C_1$-$C_4$ alkyl (preferably methyl or ethyl), $R^b$ is $R^a$ or trifluoromethyl, $W^a$ is CH or N, and $X^a$ is Cl or Br; can be prepared according to Scheme 1.

Scheme 1

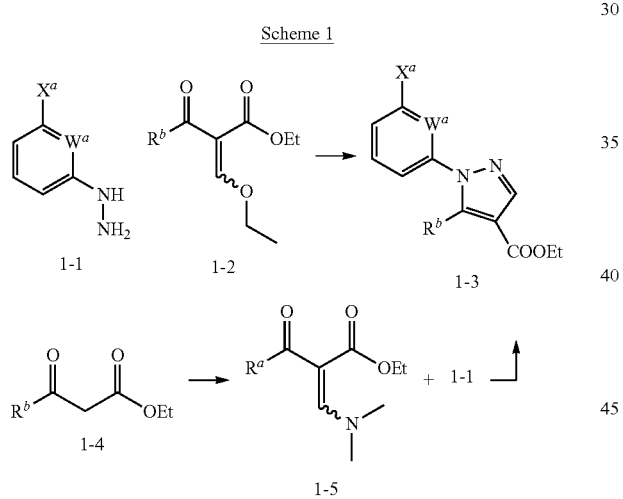

Aryl hydrazines 1-1 and beta-ketoester derivatives 1-2 can be reacted in an alcoholic solvent such as EtOH at temperatures between room temperature and at reflux to provide the pyrazole derivatives 1-3. Alternatively, the beta-ketoester derivatives 1-5 can be prepared by a reaction of the corresponding beta-ketoesters 1-4 with dimethylformamide dimethyl acetal at room temperature. Reaction of 1-1 with 1-6 to afford 1-3 can be achieved by applying similar conditions described above for the reaction with 1-2.

Compounds such as 2a-4 or 2b-2; wherein $R^{c-1}$ is H, F, $R^a$, $C_1$-$C_4$ alkoxy, or hydroxymethyl; $R^{c-2}$ is $R^b$, hydrogen, $C_1$-$C_4$ alkoxy, or fluorine; and $R^d$ is hydrogen or methyl; $R^e$ is Boc, C(O)-Et, —C(O)-cPr, or $CH_2CF_3$; $R^w$ is C(O)-Et, —C(O)-cPr, or $CH_2CF_3$, and $R^f$ is benzyl or 5 or 6 membered heteroarylmethyl can be synthesized according to Scheme 2a and Scheme 2b.

Scheme 2a

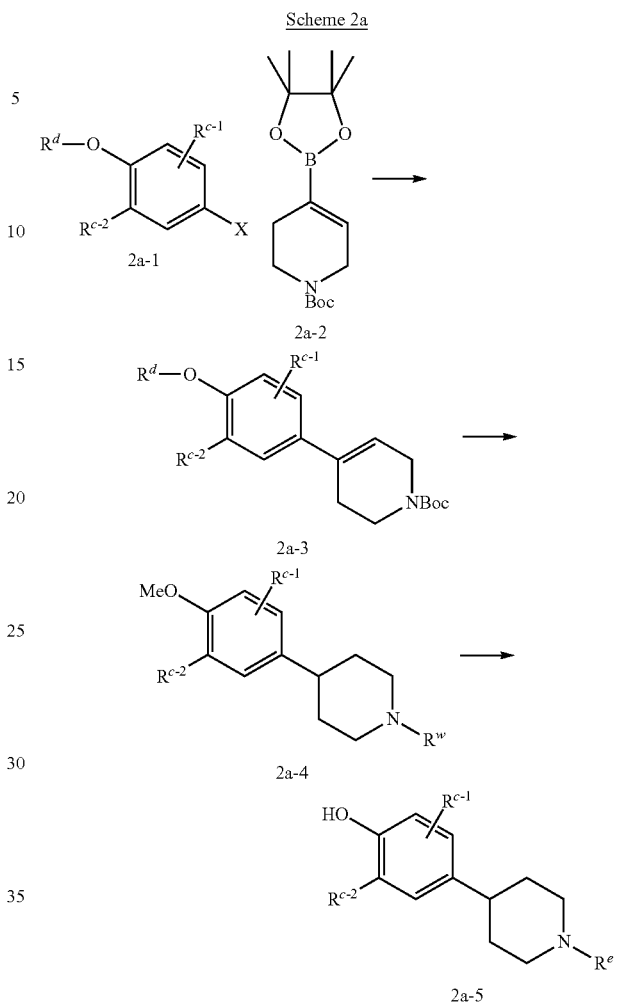

2a-1 can be transformed to 2a-3 utilizing a Suzuki-type coupling with boronate 2a-2. 2a-3, when $R^d$=Me, can be transformed into 2a-4 via hydrogenation over catalysts such as Pd/C or platinum oxide, followed by treating with an acid such as TFA in an appropriate solvent such as $CH_2Cl_2$ and subsequent reaction with an acid anhydride such as propionic anhydride or an acid chloride such as cyclopropylcarbonyl chloride along with a trialkylamine base (e.g., trimethylamine), or reacted with alkyl halides or reagents such as 2,2,2-trifluoroethyl trifluoromethanesulfonate in an appropriate solvent such as DMF in the presence of $K_2CO_3$. 2a-4 can be transformed into 2a-6 via treatment with boron tribromide in the appropriate solvent such as dichloromethane at low temperatures. Alternatively 2a-3 when $R^d$=H can be directly converted to 2a-5 ($R^e$=Boc) by hydrogenation over catalysts such as Pd/C or platinum oxide, or 2a-3 when $R^d$=H can be directly converted to 2a-5 ($R^e$=$R^w$) by treating with an acid such as TFA in an appropriate solvent such as $CH_2Cl_2$ and subsequent reaction with an acid anhydride such as propionic anhydride or an acid chloride such as cyclopropylcarbonyl chloride along with a trialkylamine base (e.g., trimethylamine) followed by treatment with MeOH in the presence of $K_2CO_3$.

Scheme 2b

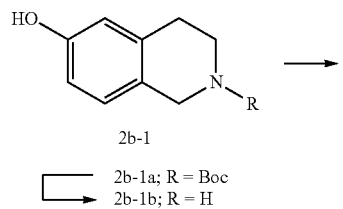
2b-1

2b-1a; R = Boc
2b-1b; R = H

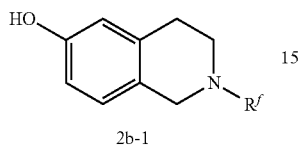
2b-1

Treatment of 2b-1a with acid such as TFA in an appropriate solvent such as CH$_2$Cl$_2$ affords 2b-1b. 2b-1b can then be reacted with arylmethyl halide such as benzyl bromide or (2-bromomethyl)pyridine in the presence of a suitable base such as triethylamine in an acceptable solvent such as DCM can provide 2b-2.

Compounds such as 3-3 can be prepared according to Scheme 3.

Scheme 3

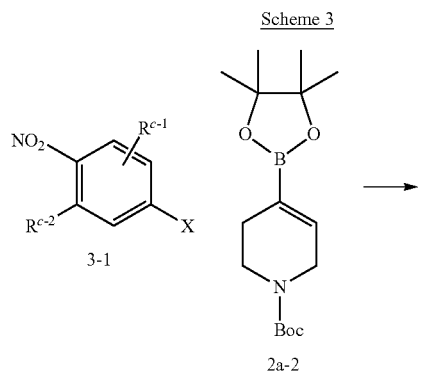
3-1                2a-2

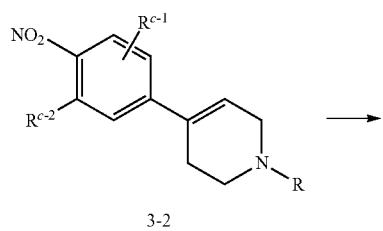
3-2

3-2a; R = Boc
3-2b; R = H
3-2c; R = R$^e$

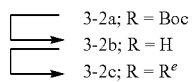
3-3

Transformation of 3-1 to 3-2 can be accomplished employing similar methods as described in Scheme 2a (i.e., 2a-1→2a-3). When necessary 3-2a to 3-2c can be accomplished by treating with an acid such as TFA in an appropriate solvent such as CH$_2$Cl$_2$ and subsequent reaction with an acid anhydride such as propionic anhydride or an acid chloride such as cyclopropylcarbonyl chloride along with a trialkylamine base (e.g., trimethylamine), or reacted with alkyl halides or reagents such as 2,2,2-trifluoroethyl trifluoromethanesulfonate in an appropriate solvent such as DMF in the presence of K$_2$CO$_3$. Subsequent catalytic hydrogenation of 3-2 over Pd/C in appropriate solvents such as EtOH can furnish 3-3.

Compounds such as 4a-4 and 4a-6 wherein R$^g$ is H or C$_1$-C$_4$ alkyl, preferably H or Me; wherein X$^b$ is —OTf, or —Br can be prepared according to Scheme 4a.

Scheme 4a

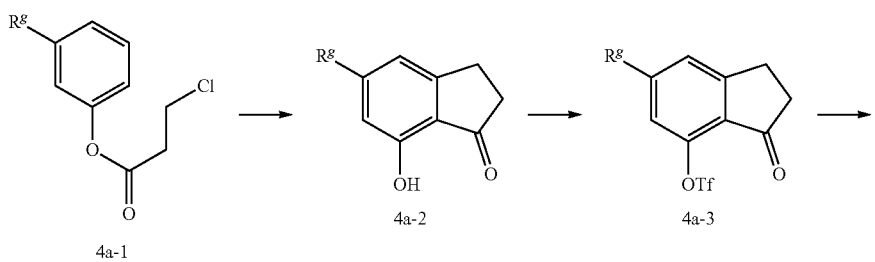
4a-1          4a-2          4a-3

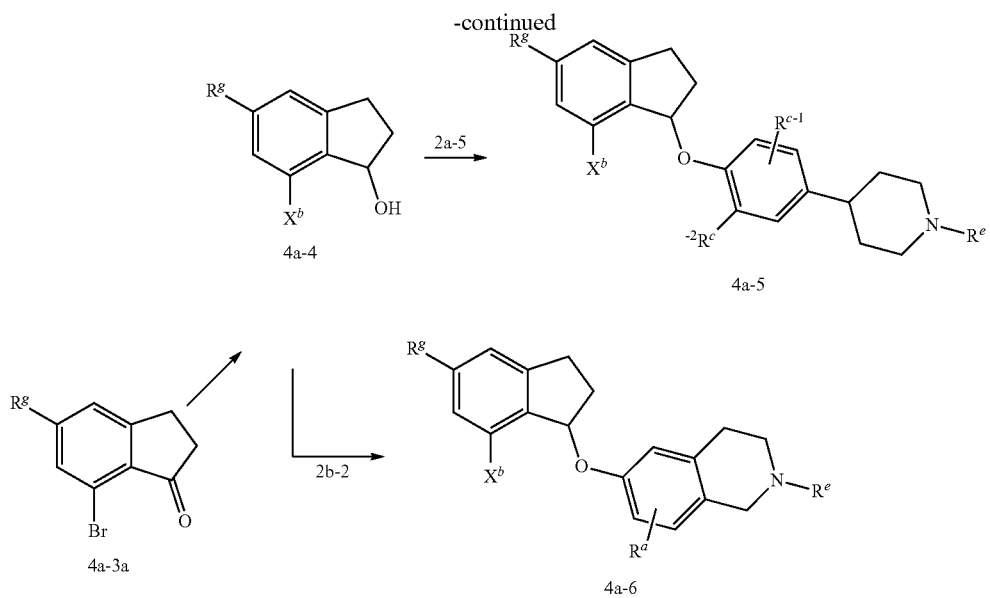

Heating an intimate mixture of 4-1 and AlCl₃ at temperatures between 100° C. and 180° C. room can afford 4a-2 (as in *Heterocycles*, 407-421, 1988). 4-2 can then be converted to trifluoromethanesulfonate 4a-3 by treatment with a triflating agent such as trifluoromethanesulfonic anhydride in an appropriate solvent such as CH₂Cl₂ in the presence of an appropriate base such as pyridine. The ketone 4a-3 can then be reduced by a reducing agent such as NaBH₄ in a suitable solvent such as MeOH at temperatures between 0° C. and room temperature to generate alcohol 4a-4 where $X^b$ is OTf. Alternatively, alcohol 4a-4 where $X^b$ is Br, can be generated by reduction of ketone 4a-3a under similar reducing conditions (ie. 4a-3→4a-4). The alcohol 4a-4 can then be reacted with a wide variety of phenol derivatives such as 2a-6 or 2b-2 by employing triaryl- or trialkyl-phosphines such as triphenylphosphine and an azodicarboxylate such as DIAD in suitable solvents such as THF at temperatures between 0° C. to room temperature to afford 4a-5 or 4a-6 respectively.

Compounds such as 4b-1 can be prepared according to Scheme 4b.

Scheme 4b

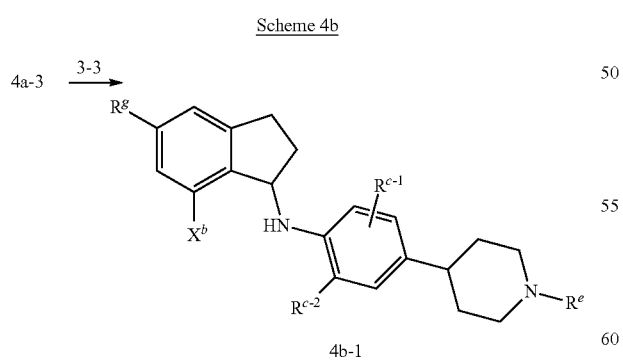

Ketones of type 4a-3 can be reacted with and the anilines such as 3-3 in the presence of suitable reducing agent such as NaB(OAc)₃H in solvents such as AcOH at temperatures between room temperature and 50° C. can furnish 4b-1. Alternatively, reaction of Ketones of type 4a-3 with anilines such as 3-3 in the presence of acid such as TsOH, in solvents such as toluene or a solvent mixture of toluene and dimethylacetamide under the reflux conditions with a Dean-Stark trap can provide corresponding imine. The subsequent imine reduction can be achieved by reagents such as NaB(OAc)₃H the presence of an appropriate acid such as AcOH in solvents such as CH₂Cl₂ or mixture of CH₂Cl₂ and alcoholic solvents at temperatures between 0° C. and room temperature.

Compounds such as 5-1 and 5-2 can be prepared according to Scheme 5.

Scheme 5

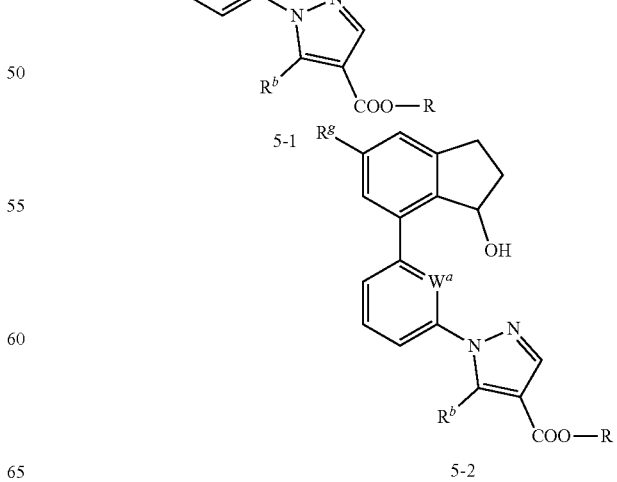

A Miyaura-type borylation of 1-3 with bis(pinacolato) diboron employing conditions such as Pd(OAc)$_2$, 2,2-dicyclohexylphosphino-2',4',6'-triisopropylbiphenyl and potassium acetate in dioxane at temperatures between 60° C. and 120° C. can provide the corresponding boronic ester, which can then be reacted directly with 4a-3 or 4a-3a by a Suzuki-type reaction utilizing conditions such as Pd(dppf)Cl$_2$ in the presence of a suitable aqueous base such as aqueous sodium carbonate in dioxane at temperatures between 80° C. to 110° C. to afford 5-1. The ketone 5-1 can then be reduced using a reductive agent such as NaBH$_4$ in a suitable solvent such as EtOH to provide 5-2.

Compounds such as 6a-1, 6a-2, 6b-1, and 6b-2 can be prepared according to Scheme 6a and Scheme 6b.

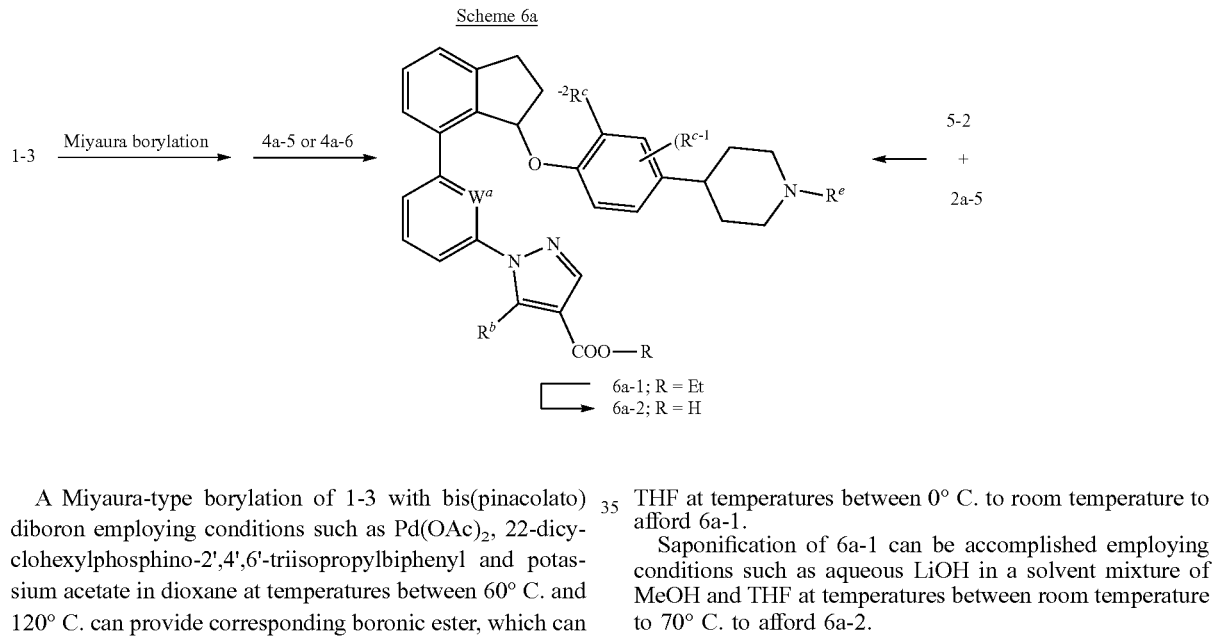

A Miyaura-type borylation of 1-3 with bis(pinacolato) diboron employing conditions such as Pd(OAc)$_2$, 22-dicyclohexylphosphino-2',4',6'-triisopropylbiphenyl and potassium acetate in dioxane at temperatures between 60° C. and 120° C. can provide corresponding boronic ester, which can then be reacted directly with 4a-5 or 4a-6 by a Suzuki-type reaction utilizing conditions such as Pd(dppf)Cl$_2$ in the presence of a suitable aqueous base such as aqueous sodium carbonate in dioxane at temperatures between 80° C. to 110° C. to afford 6a-1.

Alternatively, 5-2 can be reacted with a wide variety of phenol derivatives such as 2a-5 by employing triaryl- or trialkyl-phosphines such as triphenylphosphine and an azodicarboxylate such as DIAD in suitable solvent such as THF at temperatures between 0° C. to room temperature to afford 6a-1.

Saponification of 6a-1 can be accomplished employing conditions such as aqueous LiOH in a solvent mixture of MeOH and THF at temperatures between room temperature to 70° C. to afford 6a-2.

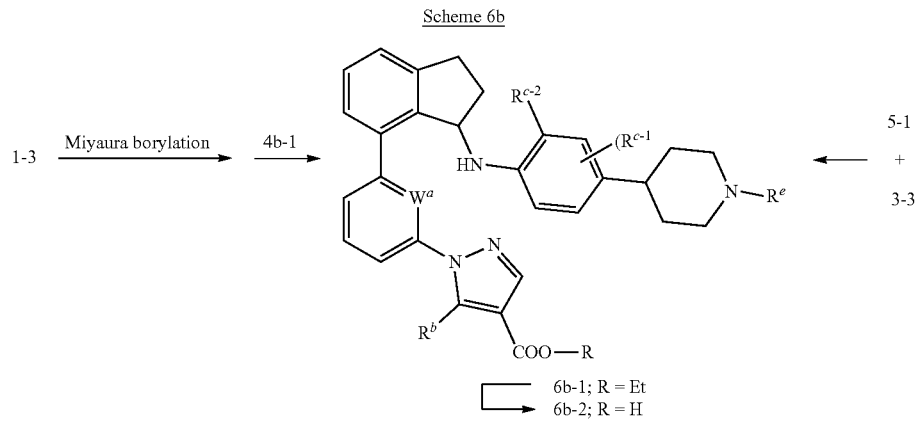

A Miyaura-type borylation of 1-3 with bis(pinacolato) diboron employing conditions such as Pd(OAc)$_2$, 2,2-dicyclohexylphosphino-2',4',6'-triisopropylbiphenyl and potassium acetate in dioxane at temperatures between 60° C. and 120° C. can provide corresponding boronic ester, which can then be reacted directly with one of 4b-1 by a Suzuki-type reaction utilizing conditions such as Pd(dppf)Cl$_2$ in the presence of a suitable aqueous base such as aqueous sodium carbonate in dioxane at temperatures between 80° C. to 110° C. to afford 6b-1.

Alternatively compounds such as 6b can be accessed via ketone 5-1 by treatment with anilines such as 3-3 in refluxing toluene in the presence of catalytic acid such as TsOH, followed by treatment with a reducing agent such as $NaBH_4$ in a suitable solvent such as EtOH to afford 6b-1. Saponification of 6b-1 can be accomplished employing conditions such as aqueous LiOH in a solvent mixture of MeOH and THF at temperatures between room temperature to 70° C. to afford 6b-2.

Compounds such as 6c-3, wherein $R^{e-1}$=C(O)—$C_1$-$C_4$ alkyl or C(O)-cycloalkyl, can be prepared according to Scheme 6c.

Scheme 6c 6b-1 ⟶

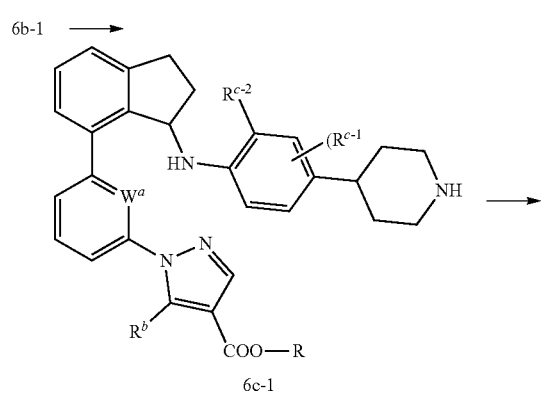

6c-1

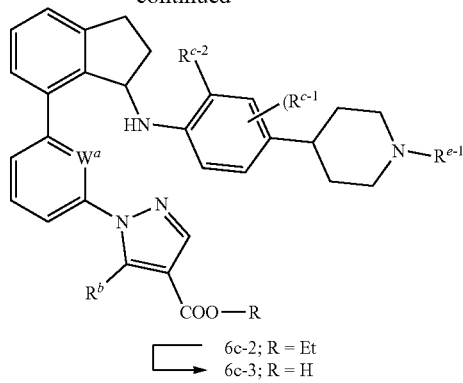

6c-2; R = Et
6c-3; R = H

Treatment of 6b-1 ($R^e$=Boc) with suitable acids such as anhydrous HCl (e.g., a solution of HCl in 1,4-dioxane or in THF) in solvents such as $CH_2Cl_2$ at temperatures between 0° C. to room temperature can provide 6c-1 which can then be transformed to compounds of type 6c-2 ($R^{e-1}$=C(O)—$C_1$-$C_4$ alkyl or C(O)-cycloalkyl) by reactions with acyl chlorides such as cyclopropanecarbonyl chloride, or acid anhydrides such as propionic anhydride, or carboxylic acids, such as 2-cyclopropylacetic acid, under peptide coupling conditions (e.g., HATU and DIPEA).

Saponification of 6c-2 can be accomplished employing conditions such as aqueous LiOH in a solvent mixture of MeOH and THF at temperatures between room temperature to 70° C. to afford 6c-3.

Compound such as 74 can be prepared according to scheme 7.

Scheme 7

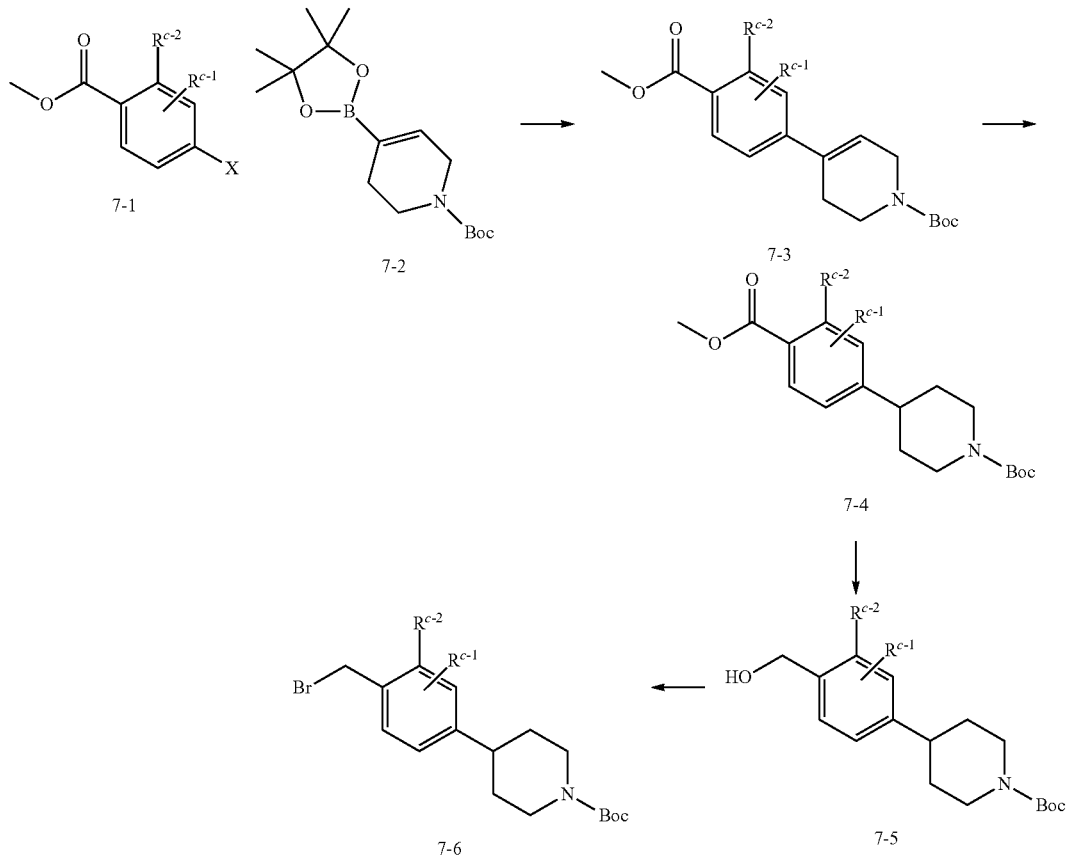

Transformation of 7-1 to 7-3 can be accomplished in accordance with the route described in Scheme 2a. (i.e. 2a-1→2a-3). 7-3 can undergo hydrogenation over catalysts such as Pd/C or platinum oxide to furnish 7-4. The ester 7-4 can then be reduced by reagents such as LiAlH$_4$ in solvent such as THF preferably at 0° C. to afford 7-6. Lastly, treatment of 7-6 with reagents such as triphenylphosphine and carbon tetrabromide in solvents such as dichloromethane at temperatures between 0° C. and room temperature can afford 7-6.

Compound such as 8-4, where $R^{f-1}$ and $R^{f-2}$ are independently selected from hydrogen or C1-C4 alkyl, can be synthesized according to Scheme 8.

Scheme 8

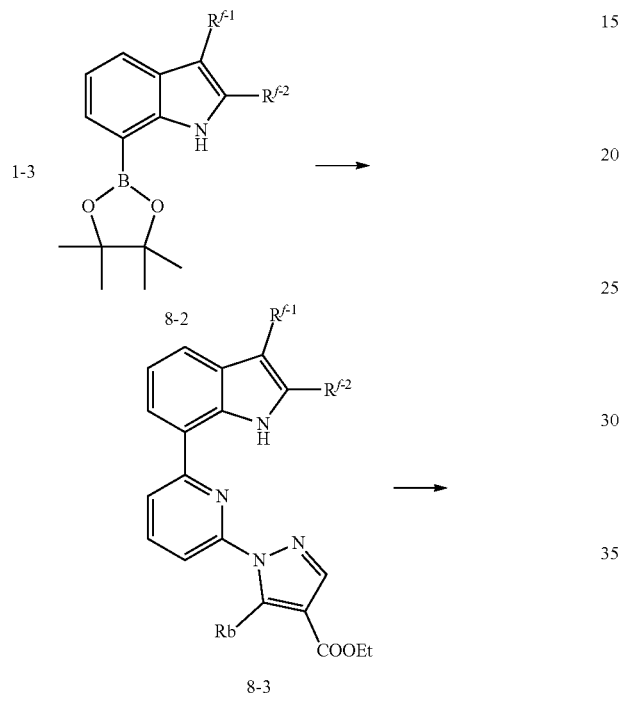

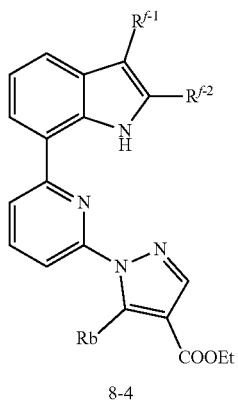

Transformation of 1-3 ($W^a$=N) to 8-3 can be achieved utilizing a Suzuki-type coupling with an appropriate boronate such as 7-(4,4,5,5-tetramethyl-1,3,2-dioxaborolan-2-yl)-1H-indole, 8-2. Reduction of the indole 8-3 to corresponding indoline 8-4 can them be accomplished by reaction with triethylsilane in the presence of TFA in dichloromethane at room temperature.

Compound such as 9-2b, 9-3b, and 9-4b can be synthesized according to Scheme 9 where $R^{e-2}$=$R^{e-3}$=$C_1$-$C_4$alkyl or cycloalkyl, and $R^{e-4}$=$C_1$-$C_4$alkyl, $C_3$-$C_6$cycloalkyl, halo$C_1$-$C_4$alkyl Scheme 9

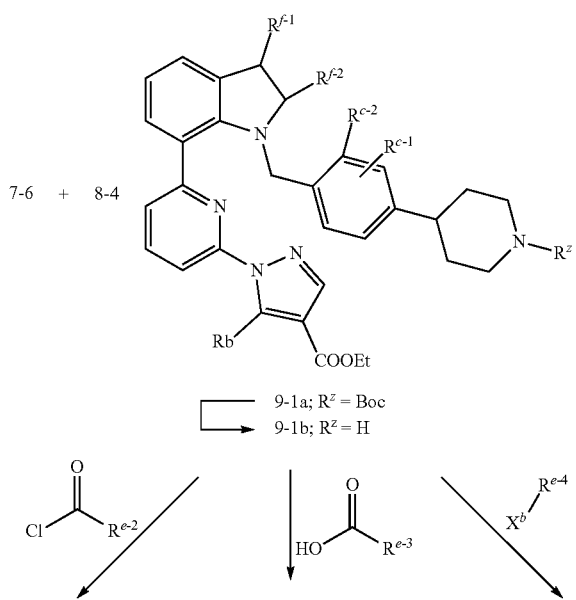

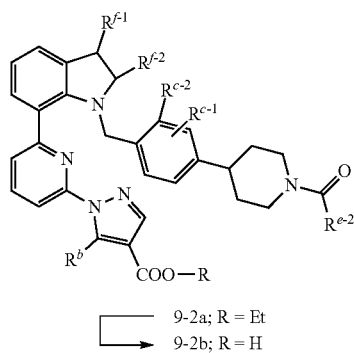
9-2a; R = Et
9-2b; R = H

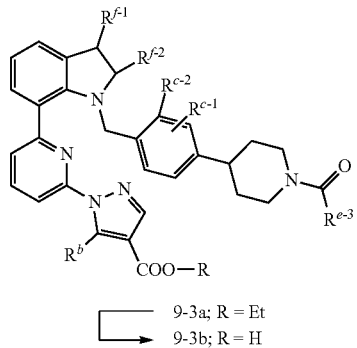
9-3a; R = Et
9-3b; R = H

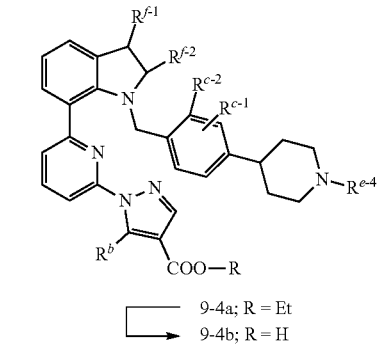
9-4a; R = Et
9-4b; R = H

Reaction of compound 7-6 with indoline 84 can be achieved by employing bases such as potassium carbonate in solvents such as DMF at temperatures between 0° C. to 80° C. to afford 9-1a. Treatment of 9-1a with suitable acids such as TFA in $CH_2Cl_2$ or HCl in dioxane at temperatures between 0° C. to room temperature can provide 9-1b, which can then be further functionalized to 9-2a 9-3a in accordance with Scheme 5c (i.e. 6c-1→6c-2). Alternatively, the amine 9-1b can be alkylated with electrophiles such as 2,2,2-trifluoroethyl trifluoromethanesulfonate in the presence of bases such as $K_2CO_3$ in solvents such as DMF at temperatures between room temperature to 100° C. to furnish 9-4a. Lastly, saponification of 9-2a, 9-3a or 9-4a can be accomplished employing conditions such as aqueous LiOH in a solvent mixture of MeOH and THF at temperatures between room temperature to 70° C. to afford 9-2b, 9-3b or 9-4b respectively.

Compound such as 10-1b, could be synthesized according to Scheme 10.

Scheme 10

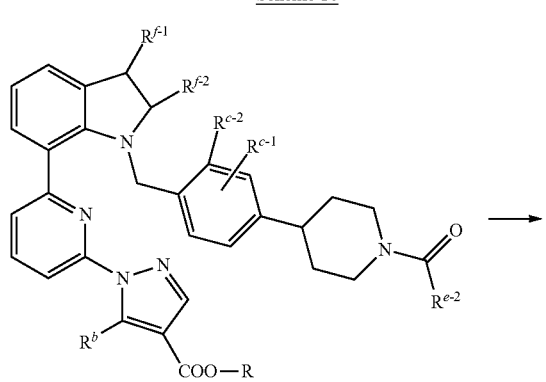
9-2a, 9-3a,
9-2b, 9-3b,

-continued

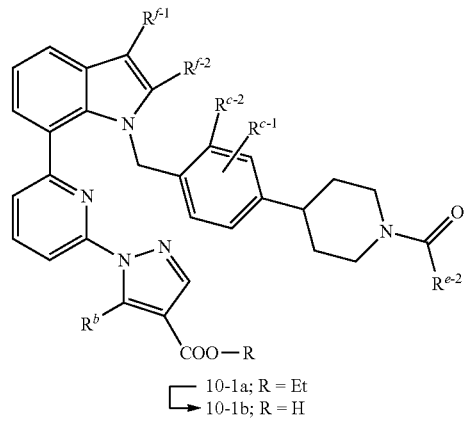
10-1a; R = Et
10-1b; R = H

Treatment of compounds type 9-2a. 9-2b. 9-3a, and 9-3b with oxidizing reagents such as o-chloranil in suitable solvents such as cyclopentylmethyl ether at room temperature could afford compounds type 10-1a and 10-1b. For compound type 10-1a, saponification by methods as outlined above can furnish Compound type 10-1b.

Compound such as 11c-3, 11d-3, 11d-5, and 11d-7, could be synthesized according to Scheme 11.

Scheme 11a

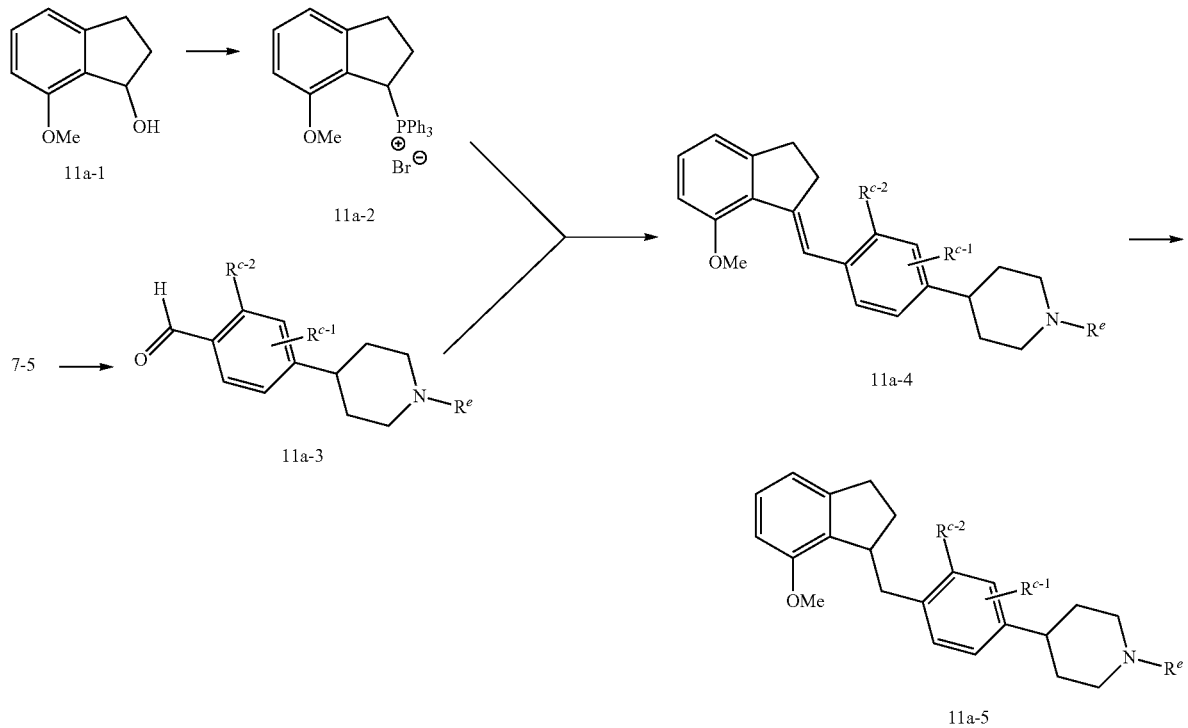

Compounds such as 11a-5 can be prepared starting from 7-methoxy-2,3-dihydro-1H-inden-1-ol (CAS #34985-44-9), 11a-1. 11a-1 can be reacted with triphenylphosphine hydrobromide in toluene at elevated temperatures, preferably 90° C., to afford salt 11a-2. Salt 11a-2 can undergo a Wittig-like coupling with aldehydes of type 11a-3 (prepared via oxidation of 7-8) by reacting with a strong base, such as potassium tert-butoxide, in solvents such as THF at elevated temperatures, preferably at 70° C. to furnish olefins of type 11a-4 Compounds of type 11a-4 can undergo palladium mediated hydrogenation to provide compounds such as type 11a-5.

Scheme 11b

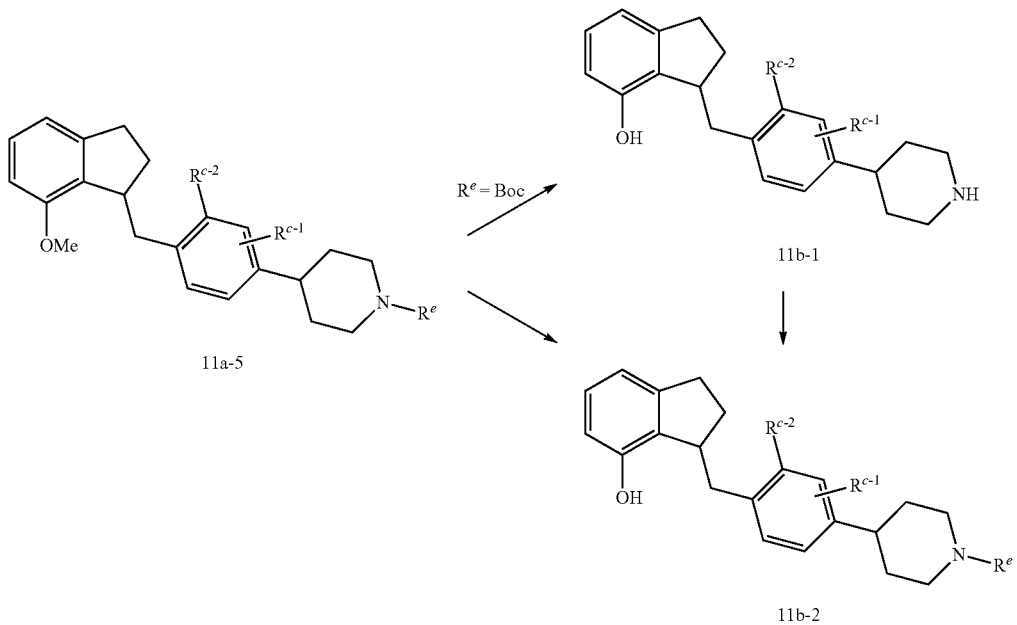

Compounds such as 11a-5 when $R^e$=Boc can be treated with a strong Lewis acid such as $BBr_3$ at low temperatures, preferably 0° C., to afford phenols of type 11b-1. 11b-1 can then be converted into 11b-2, by reaction with acyl chlorides such as cyclopropanecarbonyl chloride, or acid anhydrides such as propionic anhydride, or carboxylic acids under peptide coupling conditions. 11b-1 can also be reacted with di-tert-butyl dicarbonate to furnish 11b-2, where $R^e$=Boc. Alternatively when 11a-5 employs $R^e$ as an Lewis acid stable moiety these compounds can be treated with $BBr_3$ at low temperatures, preferably −78° C. to furnish 11 b-2 directly.

Scheme 11c

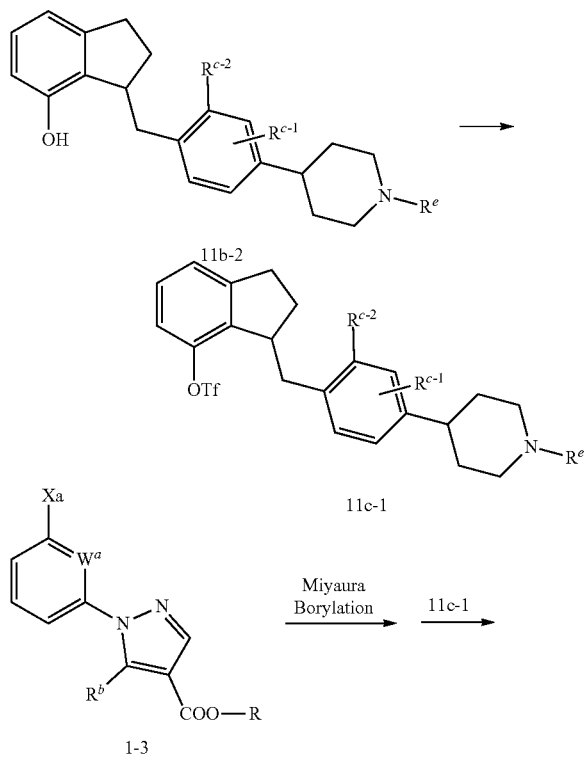

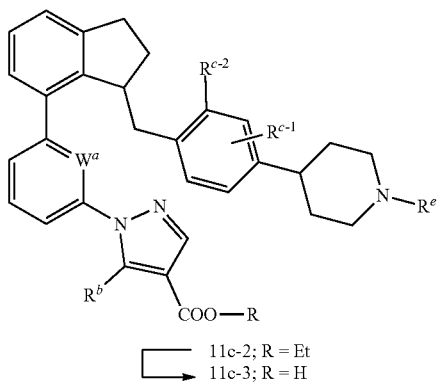

Phenols of type 11 b-2 can be converted to trifluoromethanesulfonates of type 11c-1 by treatment with a triflating agent such as trifluoromethanesulfonic anhydride in an appropriate solvent such as $CH_2Cl_2$ in the presence of an appropriate base such as pyridine. A Miyaura-type borylation of 1-3 with bis(pinacolato)diboron employing conditions such as $Pd(OAc)_2$. 2,2-dicyclohexylphosphino-2',4',6'-triisopropylbiphenyl and potassium acetate in dioxane at temperatures between 60° C. and 120° C. can provide corresponding boronic ester, which can then be reacted directly with compounds of type 11c-1 by a Suzuki-type reaction utilizing conditions such as $Pd(dppf)C_1$ in the presence of a suitable aqueous base such as aqueous sodium carbonate in dioxane at temperatures between 80° C. to 110° C. to afford esters of type 11c-2. Saponification of esters of type 11c-2 can then be accomplished by employing conditions such as aqueous LiOH in a solvent mixture of MeOH and THF at temperatures between room temperature to 70° C. to furnish acids of type 11c-3

Scheme 11d

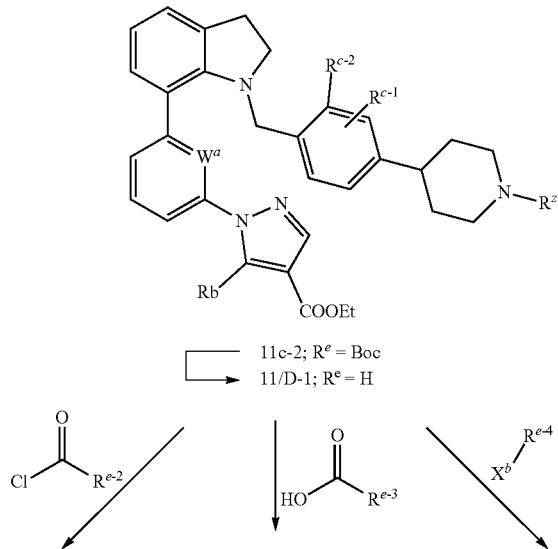

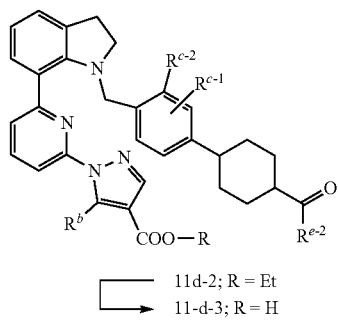 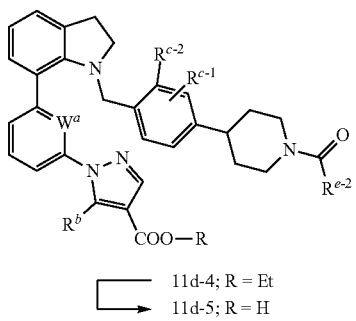 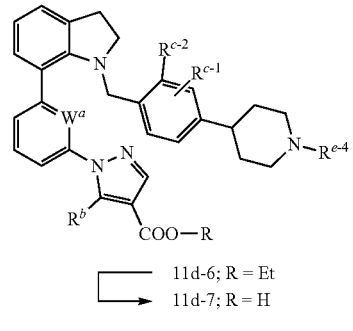

11d-2; R = Et
11-d-3; R = H 11d-4; R = Et
11d-5; R = H 11d-6; R = Et
11d-7; R = H

Alternatively, compounds of type 11c-2 where $R^e$=Boc can be treated with suitable acids such as TFA in $CH_2Cl_2$ or HCl in dioxane at temperatures between 0° C. to room temperature to provide 11d-1, which can then be further functionalized to 11d-2 and 11d-4, in accordance with Scheme 6c (i.e. 6c-1→6c-2). Alternatively, the amine 11d-2 can be alkylated with electrophiles such as 2,2,2-trifluoroethyl trifluoromethanesulfonate in the presence of bases such as $K_2CO_3$ in solvents such as DMF at temperatures between room temperature to 100° C. to furnish compounds of type 11d-6.

Lastly, saponification of 11d-2, 11d-4 and 11d-6 can be accomplished employing conditions such as aqueous LiOH in a solvent mixture of MeOH and THF at temperatures between room temperature to 70° C. to afford 11d-3, 11d-5 and 11d-7 respectively.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc. Typically, the pharmaceutical compositions are tablets or gelatin capsules comprising the active ingredient together with one or more of a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Compositions of the present invention may be utilized in various dosage regimens known to those of skill in the art. Such dosing frequency is maintained for a varying duration of time depending on the therapeutic regimen. The duration of a particular therapeutic regimen may vary from one-time dosing to a maintenance regimen that extends for a month, year or more. One of ordinary skill in the art would be familiar with determining a therapeutic regimen for a specific indication. Preferred dosage regimens of the present invention include, but are not limited to, once a day dosing and twice a day dosing.

In the methods for the treatment of ocular disease and particularly for the treatment of glaucoma, set forth herein, administration to a subject of a composition of the present invention may be by various methods known to those of skill in the art, including, but not limited to, topical, subconjunctival, periocular, retrobulbar, subtenon, intraocular, subretinal, posterior juxtascleral, or suprachoroidal administration. In preferred embodiments, administration of a composition of the present invention is by topical administration to the ocular surface.

It is contemplated that the concentration of the sGC activator in the compositions of the present invention can vary, but is preferably 0.01 to 3.0 w/v % and more preferably 0.05-1.0 w/v %. The most preferred concentration range is from 0.05-0.5 w/v % and the most preferred concentration is about 0.1 w/v % The sGC activators of the present invention comprise the pharmaceutically useful hydrates and salts of such compounds and stereoisomers (where applicable), and may be formulated with a pharmaceutically acceptable vehicle.

The methods of treating glaucoma may include administering the sGC activator compound by a technique selected from the group consisting of: topical ocular administration, periocular injection, sub-conjunctival injection, sub-tenon injection, intracameral injection, intravitreal injection, intracanalicular injection, implanting delivery device in the cul-de-sac, implanting delivery device adjacent to the sclera, implanting delivery device within the eye, oral administration, intravenous administration, subcutaneous administration, intramuscular administration, parenteral administration, dermal administration, and nasal administration.

In certain aspects of the invention, compounds of the invention may be formulated in either fixed and unfixed combinations of two therapeutic agents effective in the treatment of glaucoma wherein one therapeutic agent is sGC activator disclosed supra and the second therapeutic agent is an efficacious glaucoma drug. In other embodiments, a pharmaceutical composition of the invention comprising a sGC activator can be administered to a patient alone or in combination with other IOP-lowering agents to increase the potency, efficacy and/or duration of the IOP reduction. In certain preferred combinations, the second IOP-lowering agent is selected from carbonic anhydrase inhibitors, beta-blockers, prostaglandins, alpha-2 agonists, serotonin-2 agonists, alpha-1 antagonists, dopamine agonists, Rho kinase inhibitors, myosin-II Ca2+ATPase, inhibitors, matrix metalloproteinase activators, activator protein-1 (AP-1) activators, natriuretic peptide receptor-B agonists, phosphodiesterase inhibitors, K+-channel blockers and maxi-K-channel activators. The combination therapy of the invention provides the benefit of lowering IOP by two mechanisms, including inducing uveoscleral outflow of aqueous humor and inhibiting aqueous humor inflow, which can allow for reduced dosages of the compounds thereby lowering the risk of side effects.

Pharmaceutical compositions of the invention can also be advantageously combined with suitable neuroprotective agents such as memantine, eliprodil, Ca2+-channel blockers, and betaxolol.

In a further aspect of the invention, the sGC activator may be administered alone or in combination with a second therapeutic agent which is suitable for the treatment of glaucoma. Certain preferred second therapeutic agents include beta-blockers, prostaglandin analogs, carbonic anhydrase inhibitors, α2 agonists, miotics, PDE-V inhibitors, Rho kinase inhibitors and neuroprotectants. In one preferred combination, a prostaglandin F2α analogue selected from the group consisting of Latanaprost and Travoprost is administered in combination with sGC activator of Formula (I) or subformulae thereof. In another preferred combination, a PDE-V inhibitor selected from the group consisting of Sildenafil, Tadalafil, Vardenafil, Udenafil, Avanafil, Lodenafil and Mirodenafil is administered in combination with a sGC activator of Formula (I) or subformulae thereof. In yet another preferred combination, a sGC activator of Formula (I) or subformulae thereof is administered in combination with a sGC stimulator (such as Riociguat) or a NO precursor (such as sodium nitroprusside or nitroglycerine). In another preferred combination, a sGC activator of Formula (I) or subformulae thereof is administered in combination with a Rho-kinase inhibitor (such as AR-13324 alone or combination of AR-13324 and Latanaprost).

In a further embodiment of the invention, a sGC activator of Formula (I) is administered in combination with a carbonic anhydrase inhibitor (such as Brinzolamide) for the treatment of glaucoma or to reduce IOP. In another embodiment, a sGC activator of Formula (I) is administered in combination with a α2 adrenergic agonist (such as Brimonidine) for the treatment of glaucoma or to reduce IOP. In a particularly preferred combination therapy, a sGC activator of Formula (I) is administered in combination with a fixed combination of Brimonidine and Brinzolamide (such as SIMBRINZA™ from by Alcon, Fort Worth, Tex.) for the treatment of glaucoma or to reduce IOP.

In certain embodiments, a sGC activator and the second pharmaceutical agent are administered concurrently in separate pharmaceutical compositions. In other embodiments, a sGC activator and the second pharmaceutical agent are administered formulated together in a pharmaceutical composition. In yet other embodiments, the sGC activator and the second pharmaceutical agent are administered sequentially in separate pharmaceutical compositions.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (II) by the physician themselves (or under the guidance of the physician) shortly before administration; (iii) in the patient themselves, e.g. during sequential administration of the compound of the invention and the other therapeutic agent.

In addition to a sGC activator, the compositions of the present invention optionally comprise one or more excipients. Excipients commonly used In pharmaceutical compositions include, but are not limited to, tonicity agents, preservatives, chelating agents, buffering agents, surfactants and antioxidants. Other excipients comprise solubilizing agents, stabilizing agents, comfort-enhancing agents, polymers, emollients, pH-adjusting agents and/or lubricants. Any of a variety of excipients may be used in compositions of the present invention including water, mixtures of water and water-miscible solvents, such as C1-C7-alkanols, vegetable oils or mineral oils comprising from 0.5 to 5% non-toxic water-soluble polymers, natural products, such as alginates, pectins, tragacanth, karaya gum, xanthan gum, carrageenin, agar and acacia, starch derivatives, such as starch acetate and hydroxypropyl cellulose or starch, and also other synthetic products such as polyvinyl alcohol, polyvinylpyrrolidone, polyvinyl methyl ether, polyethylene oxide, preferably cross-linked polyacrylic acid and mixtures of those products. The concentration of the excipient is, typically, from 1 to 100,000 times the concentration of the sGC activator. In preferred embodiments, excipients are selected on the basis of their inertness towards the sGC activator.

Relative to ophthalmic formulations, suitable tonicity-adjusting agents include, but are not limited to, mannitol, sodium chloride, glycerin, sorbitol and the like. Suitable buffering agents include, but are not limited to, phosphates, borates, acetates and the like. Suitable surfactants include, but are not limited to, ionic and nonionic surfactants (though nonionic surfactants are preferred), RLM 100, POE 20 cetylstearyl ethers such as Procol® CS20 and poloxamers such as Pluronic® F68. Suitable antioxidants include, but are not limited to, sulfites, ascorbates, butylated hydroxyanisole (BHA) and butylated hydroxytoluene (BHT).

The compositions set forth herein may comprise one or more preservatives. Examples of such preservatives include p-hydroxybenzoic acid ester, sodium chlorite, benzalkonium chloride, parabens such as methylparaben or propylparaben, alcohols such as chlorobutanol, benzyl alcohol or phenyl ethanol, guanidine derivatives such as polyhexamethylene biguanide, polymeric quaternary ammonium compounds such as Onamer M and Polyquaterium-1 (POLYQUAD® from Alcon), sodium perborate, or sorbic acid. In certain embodiments, the composition may be self-preserved that no preservation agent is required.

In preferred compositions a sGC activator of the present invention will be formulated for topical application to the eye in aqueous solution in the form of drops. The term "aqueous" typically denotes an aqueous composition wherein the composition is >50%, more preferably >75% and in particular >90% by weight water. These drops may be delivered from a single dose ampoule which may preferably be sterile and thus render bacteriostatic components of the composition unnecessary. Alternatively, the drops may be delivered from a multi-dose bottle which may preferably comprise a device which extracts any preservative from the composition as it is delivered, such devices being known in the art.

In other aspects, components of the invention may be delivered to the eye as a concentrated gel or a similar vehicle, or as dissolvable inserts that are placed beneath the eyelids. In yet other aspects, components of the invention may be delivered to the eye as ointments, water-in-oil and oil-in-water emulsions, solutions, or suspensions.

The compositions of the present invention, and particularly the topical compositions, are preferably isotonic or slightly hypotonic in order to combat any hypertonicity of tears caused by evaporation and/or disease. This may require a tonicity agent to bring the osmolality of the composition to a level at or near 210-320 milliosmoles per kilogram (mOsm/kg). The compositions of the present invention generally have an osmolality in the range of 220-320 mOsm/kg, and preferably have an osmolality in the range of 235-300 mOsm/kg. The ophthalmic compositions will generally be formulated as sterile aqueous solutions.

In certain embodiments, a sGC activator of the present invention is formulated in a composition that comprises one or more tear substitutes. A variety of tear substitutes are known in the art and include, but are not limited to: monomeric polyols, such as, glycerol, propylene glycol, and ethylene glycol; polymeric polyols such as polyethylene glycol; cellulose esters such hydroxypropylmethyl cellulose, carboxy methylcellulose sodium and hydroxy propylcellulose; dextrans such as dextran 70; vinyl polymers, such as polyvinyl alcohol; guars, such as HP-guar and other guar derivatives, and carbomers, such as carbomer 934P, carbomer 941, carbomer 940 and carbomer 974P. Certain compositions of the present invention may be used with contact lenses or other ophthalmic products.

In certain embodiments, the compositions set forth herein have a viscosity of 0.5-100 cps, preferably 0.5-50 cps, and most preferably 1-20 cps. These viscosities insure that the product is comfortable, does not cause blurring, and is easily processed during manufacturing, transfer and filling operations.

Preferred compositions are prepared using a buffering system that maintains the composition at a pH of about 3 to a pH of about 8.0, preferably 5.5-7.5, and most preferably 6.0-7.4. Topical compositions (particularly topical ophthalmic compositions) are preferred which have a physiological pH matching the tissue to which the composition will be applied or dispensed.

The following examples are presented to further illustrate selected embodiments of the present invention.

Topical Ocular Formulation Example

| Ingredient | Concentration (w/v %) |
|---|---|
| sGC activator | 0.1% |
| Dibasic Sodium Phosphate | 0.2% |
| Sodium Chloride | 0.75% |
| Disodium EDTA | 0.01% |
| Polysorbate 80 | 0.05% |
| Benzalkonium Chloride Solution | 0.01% |
| Hydroxypropyl Methylcellulose | 0.5% |

The compounds of formula I in free form or in pharmaceutically acceptable salt form, exhibit valuable pharmacological properties, e.g. sGC modulating properties, e.g. as indicated in vitro and in vivo tests as provided in the next sections, and are therefore indicated for therapy or for use as research chemicals, e.g. as tool compounds. More particularly, the compounds of formula I, in free form or in pharmaceutically acceptable salt form, activate sGC which is suitable for use in treatment of disease.

In one preferred use, the compounds of Formula I are suitable for use in lowering intra-ocular pressure (IOP) and in the treatment of glaucoma. The compounds of the invention may be used alone or in combination with a second therapeutic agent for the treatment of glaucoma. The embodiment further provides methods of treating glaucoma or reducing intraocular pressure in a subject, the method comprising administering a compound of Formula I alone or in combination with a second therapeutic agent. In certain aspects, the method contemplates to topical ocular administration of the compound of Formula I to the subject in need of such therapy. In preferred aspects, the method comprises administration of the compound of Formula I as a mono-therapy. In certain other aspects, the method comprises the co-administration (either concomitantly or sequentially) of a compound of Formula I and a PDE-V inhibitor.

Compounds of the invention may also be useful in the treatment of an indication selected from: kidney disease, urologic disorders hypertension, atherosclerosis, peripheral artery disease, restenosis, stroke, heart failure, coronary vasospasm, cerebral vasospasm, ischemia/reperfusion injury, thromboembolic pulmonary hypertension, pulmonary arterial hypertension, stable and unstable angina, thromboembolic disorders. In addition, the compounds of the invention have the potential to treat renal disease, diabetes, fibrotic disorders (including those of the liver, kidney and lungs), urologic disorders (including overactive bladder), benign prostatic hyperplasia, erectile dysfunction, neuropathic pain and neurological disorders (Including Alzheimer's disease and Parkinson's disease). Treatment with an sGC activator of the invention may further provide benefit in the treatment of inflammatory disorder such as psoriasis, multiple sclerosis, arthritis, asthma and chronic obstructive pulmonary disease.

Thus, as a further embodiment, the present invention provides the use of a compound of formula (I) in therapy. In a further embodiment, the therapy is selected from a disease which may be treated by activation of sGC. In a preferred application, the disease is selected from the afore-mentioned list, suitably glaucoma.

In another embodiment, the invention provides a method of treating a disease which is treated by activation of sGC comprising administration of a therapeutically acceptable amount of a compound of formula (I) or a salt thereof. In a further embodiment, the disease is selected from the afore-mentioned list, suitably glaucoma.

In a particularly preferred use, (+)-1-(3-(3-((4-(1-(cyclopropanecarbonyl)piperidin-4-yl)-2-methylphenyl)amino)-2,3-dihydro-1H-inden-4-yl)phenyl)-5-(trifluoromethyl)-1H-pyrazole-4-carboxylic acid, (+)-1-(6-(3-((4-(1-(cyclopropanecarbonyl)piperidin-4-yl)-2-methylphenyl)amino)-2,3-dihydro-1H-inden-4-yl)pyridin-2-yl)-5-methyl-1H-pyrazole-4-carboxylic acid, (+)-1-(6-(3-(4-(1-(cyclopropanecarbonyl)piperidin-4-yl)-2-methylphenoxy)-2,3-dihydro-1H-inden-4-yl)pyridin-2-yl)-5-ethyl-1H-pyrazole-4-carboxylic acid or (+)-(S)-1-(6-(3-(4-(1-(cyclopropanecarbonyl)piperidin-4-yl)-3-ethylphenoxy)-2,3-dihydro-1H-inden-4-yl)pyridin-2-yl)-5-(trifluoromethyl)-1H-pyrazole-4-carboxylic acid or a pharmaceutically acceptable salt thereof are suitable for use in lowering intra-ocular pressure (IOP) and in the treatment of glaucoma. (+)-1-(3-(3-((4-(1-(cyclopropanecarbonyl)piperidin-4-yl)-2-methylphenyl)amino)-2,3-dihydro-1H-inden-4-yl)phenyl)-5-(trifluoromethyl)-1H-pyrazole-4-carboxylic acid, (+)-1-(6-(3-((4-(1-(cyclopropanecarbonyl)piperidin-4-yl)-2-methylphenyl)amino)-2,3-dihydro-1H-inden-4-yl)pyridin-2-yl)-5-methyl-1H-pyrazole-4-carboxylic acid, (+)-1-(6-(3-(4-(1-(cyclopropanecarbonyl)piperidin-4-yl)-2-methylphenoxy)-2,3-dihydro-1H-inden-4-yl)pyridin-2-yl)-5-ethyl-1H-pyrazole-4-carboxylic acid or (+)-(S)-1-(6-(3-(4-(1-(cyclopropanecarbonyl)piperidin-4-yl)-3-ethylphenoxy)-2,3-dihydro-1H-inden-4-yl)pyridin-2-yl)-5-(trifluoromethyl)-1H-pyrazole-4-carboxylic acid or a pharmaceutically acceptable salt thereof may be used alone or in combination with a second therapeutic agent for the treatment of glaucoma. The embodiment further provides methods of treating glaucoma or reducing intraocular pressure in a subject, the method comprising administering one of the specific compounds listed supra alone or in combination with a second therapeutic agent. In certain aspects, the method contemplates topical ocular administration of one of the specific compounds listed supra to the subject in need of such therapy. In preferred aspects, the method comprises administration of one of these specific compounds as a mono-therapy. In certain other aspects, the method comprises the co-administration (either concomitantly or sequentially) of a compound of Formula I and a PDE-V inhibitor. (+)-1-(3-(3-((4-(1-(Cyclopropanecarbonyl)piperidin-4-yl)-2-methylphenyl)amino)-2,3-dihydro-1H-inden-4-yl)phenyl)-5-(trifluoromethyl)-1H-pyrazole-4-carboxylic acid, (+)-1-(6-(3-((4-(1-(cyclopropanecarbonyl)piperidin-4-yl)-2-methylphenyl)amino)-2,3-dihydro-1H-inden-4-yl)pyridin-2-yl)-5-methyl-1H-pyrazole-4-carboxylic acid, (+)-1-(6-(3-(4-(1-(cyclopropanecarbonyl)piperidin-4-yl)-2-methylphenoxy)-2,3-dihydro-1H-inden-4-yl)pyridin-2-yl)-5-ethyl-1H-pyrazole-4-carboxylic acid or (+)-(S)-1-(6-(3-(4-(1-(cyclopropanecarbonyl)piperidin-4-yl)-3-ethylphenoxy)-2,3-dihydro-1H-inden-4-yl)pyridin-2-yl)-5-(trifluoromethyl)-1H-pyrazole-4-carboxylic acid may be used in the treatment of glaucoma or reducing intraocular pressure in racemic or enantiomerically enriched form.

Thus, as a further embodiment, the present invention provides the use of a compound of formula (I) or subformulae thereof for the manufacture of a medicament. In a further embodiment, the medicament is for treatment of a disease which may be treated by activation of sGC. In another embodiment, the disease is selected from the afore-mentioned list, suitably glaucoma.

For systemic administration, the administered pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro & in vivo methods.

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art. Further, the compounds of the present invention can be produced by organic synthesis methods known to one of ordinary skill in the art as shown in the following examples.

Abbreviations

Ac acetyl
AcOH acetic acid
AIBN azobisisobutyronitrile
App apparent
aq. aqueous
atm atmosphere
Bis(pinacolato)diboron 4,4,4',4',5,5,5',5'-Octamethyl-2,2'-bi-1,3,2-dioxaborolane
Boc tertiary butyl carboxy
Boc-anhydride di-tert-butyl dicarbonate
(Boc)$_2$O di-tert-butyl dicarbonate
br. broad
BSA bovine serum albumin
BuOH butanol
calcd. calculated
CHAPS 3-[(3-cholamidopropyl)dimethylammonio]-1-propanesulfonate
CH$_3$CN acetonitrile
Cs$_2$CO$_3$ cesium carbonate
d doublet
DBU 1,8-diazabicyclo[5.4.0]undec-7-ene
dd doublet of doublets
DCE 1,2-dichloroethane
DCM dichloromethane
DEA diethylamine
DEAD diethyl azodicarboxylate
DIAD diisopropyl azodicarboxylate
DIPEA N,N-diisopropylethylamine
DIBAL-H diisobutylaluminum hydride
DIPEA N,N-diisopropylethylamine
DMAP 4,4-dimethylaminopyridine
DME 1,4-dimethoxyethane
DMF N,N-dimethylformamide
Dess-Martin Periodinane Dess-Martin reagent; 1,1,1-Triacetoxy-1,1-dihydro-1,2-benziodoxol-3(1H)-one (CAS #87413-09-0)
DMSO dimethylsulfoxide
EDCl N$^1$-((ethylimino)methylene)-N$^2$,N$^2$-dimethylethane-1,2-diamine
ESI electrospray ionization
EtOAc, AcOEt ethyl acetate
Et ethyl
EtOH ethanol
FCC flash column chromatography
g grams
h hour(s)
HATU 2-(1H-7-azabenzotriazol-1-yl)-1,1,3,3-tetramethyl uronium hexafluorophosphate methanaminium
HBSS Hank's Balanced Salt Solution
HBTU O-benzotriazole-N,N,N',N'-tetramethyl-uronium-hexafluorophosphate
HC HPLC condition
HEPES 4-(2-hydroxyethyl)-1-piperazineethanesulfonic acid
HFIP 1,1,1,3,3,3-hexafluoro-2-propanol
HPLC high performance liquid chromatography
IBMX 1-methyl-3-(2-methylpropyl)-7H-purine-2,6-dione
IPA 2-propanol
IR infrared spectroscopy
L liter(s)
LDA lithium diisopropyl amide
LHMDS lithium bis(trimethylsilyl)amide
M molar
MHz mega Hertz
m multiplet
m-CPBA meta-chloroperoxybenzoic acid
Me methyl
MeCN acetonitrile
MeI iodomethane
MeOH methanol
mg milligram(s)
mm millimeter(s)
min minutes
mL milliliter(s)
mmol millimoles
MP melting point
MS mass spectrometry
MsCl methanesulfonyl chloride
Ms$_2$O methanesulfonyl anhydride
MsOH methanesulfonic acid
MTBE methyl tert-butylether
m/z mass to charge ratio
N normal
NaBH$_4$ sodium borohydride
Na(AcO)$_3$BH sodium triacetoxyborohydride NBS N-bromosuccinimide
NCS N-chlorosuccinimide
NH$_4$Cl ammonium chloride
NMR nuclear magnetic resonance
PBS phosphate buffered saline
ODQ 1H-[1,2,4]Oxadiazolo[4,3-a]quinoxalin-1-one (CAS #41443-28-1)
Pd/C palladium on carbon
Pd(dppf)Cl$_2$ 1,1'-bis(diphenylphosphino)ferrocene-palladium(II)dichloride
Pd(dppf)Cl$_2$.CH$_2$Cl$_2$ adduct 1,1'-bis(diphenylphosphino)ferrocene-palladium(II)dichloride dichloromethane complex
Pd(PPh$_3$)$_4$ tetrakis(triphenylphosphine)palladium(0)
Ph phenyl
ppm parts per million
PyBOP benzotriazol-1-yloxytripyrrolidinophosphonium hexafluorophosphate
rac racemic
RP reverse phase
rt room temperature
s singlet
sat. saturated
SFC Supercritical Fluid Chromatography
t triplet
t$_r$ retention time
T3P propylphosphonic anhydride
TBAF tetra-n-butylammonium fluoride
TBAT tetrabutylammonium difluorotriphenylsilicate
TBSCl tert-butyldimethylsilyl chloride
TEA, Et$_3$N triethylamine
tert- tertiary
TFA trifluoroacetic acid
THF tetrahydrofuran
TLC Thin Layer Chromatography
TMP 2,2',6,6'-tetramethylpiperidine, 2,2',6,6'-tetramethylpiperidyl
TMSCF$_3$ trifluoromethyltrimethylsilane
TMS trimethylsilyl
TMSOTf trimethylsilyl trifluoromethanesulfonate
Ts p-toluenesulfonyl
Tsdpen N-(2-amino-1,2-diphenylethyl)-4-methylbenzenesulfonamide
TsOH p-toluenesulfonic acid
UPLC ultra performance liquid chromatography
v/v volume per volume
w/v weight per volume
w/w weight per weight The following examples are intended to illustrate the invention and are not to be construed as being limitations thereon. Unless otherwise stated, one or more tautomeric forms of compounds of the examples described hereinafter may be prepared In situ and/or isolated. All tautomeric forms of compounds of the examples described hereafter should be considered to be disclosed. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme. Volume 21). Further, the compounds of the present invention can be produced by organic synthesis methods known to one of ordinary skill in the art as shown in the following examples.

All reactions are carried out under nitrogen or argon unless otherwise stated. Optical rotations were measured in MeOH, using D line of a sodium lamp.

Proton NMR ($^1$H NMR) is conducted in deuterated solvent. In certain compounds disclosed herein, one or more $^1$H shifts overlap with residual proteo solvent signals; these signals have not been reported in the experimental provided hereinafter.

Multiple parent ion masses are reported for mass spectroscopy data when the compound of the invention contains one or more bromine atoms. Bromine exists as an approximately 1:1 molar ratio of $^{79}$Br:$^{81}$Br. Thus, a compound with a single bromine atom will exhibit two parent mass ions having a difference of 2 amu. The smaller mass is reported in the Experimental infra.

Following preparation methods were used for reverse phase HPLC (RP-HPLC).

HC-A:
Stationary phase: Waters SunFire™ Prep C$_{18}$ OBD™ 5 µm, 30×100 mm
Mobile phase: gradient, water with 0.1% TFA/acetonitrile HC-B
Stationary phase: Gemini® NX 5µ C$_{18}$ $_{110}$A 100×30 mm
Mobile phase: gradient, water with 0.1% (28% ammonium hydroxide)/acetonitrile HC-C
Stationary phase: X-Bridge® BEH C$_{18}$ OBD Prep 5 µm, 30 mm×50 mm
Mobile phase: gradient, water with 0.1% (28% ammonium hydroxide)/acetonitrile Absolute stereochemistry and/or optical rotations are provided for the embodiments of the invention where applicable. The invention contemplates all stereochemical forms of the compounds provided herein. Where absolute stereochemistry is provided the assessment was made via X-ray diffraction, and/or chemical correlation, and/or at least one chiral center was from a purchased commercial enantiopure (>15:1 er) starting material In the case of racemic samples, including intermediates, enantiomers are separated by chromatography using a chiral stationary phase and are identified/differentiated either by HPLC retention time employing a chiral stationary phase and the monikers "enantiomer-1" or "enantiomer-2", and/or by a specific "+" or "−" sign referring to the rotation of polarized light when this data is available.

In some instances examples possess an acidic functional group as such during final purification procedures samples may contain an undetermined mixture of the free acid along with potassium and/or lithium salts of the titled compound. Small changes in the amount of salt present may change the observed chemical shift or intensity for some peaks in the $^1$H NMR spectra.

Intermediate 1-1. Ethyl 1-(6-bromopyridin-2-yl)-5-(trifluoromethyl)-1H-pyrazole-4-carboxylate

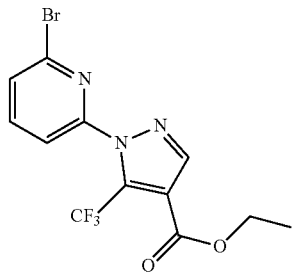 [SMILES: CCOC(=O)c1cnn(-c2cccc(Br)n2)c1C(F)(F)F]

A solution of 2-bromo-6-hydrazinylpyridine (CAS #26944-71-8; 12.63 g, 67 mmol) in THF (350 mL) was cooled in an acetone/dry ice bath, and then ethyl 2-(ethoxymethylene)-4,4,4-trifluoro-3-oxobutyrate (CAS #571-55-1, 13.72 mL, 71 mmol) was added dropwise. Once the addition was complete, the reaction mixture was gradually allowed to warm to room temperature over 2 h. The reaction mixture was then concentrated, and dissolved in EtOAc. The organic layer was then washed successively with sat. aq. $NaHCO_3$ and brine, dried over $MgSO_4$, filtered, and then concentrated. The resulting residue was purified by silica gel flash column chromatography (10% EtOAc in hexane) to afford the title compound. $^1$H NMR (400 MHz, Methanol-$d_4$) δ 8.19 (s, 1H), 7.96 (t, J=7.82 Hz, 1H), 7.74-7.80 (m, 2H), 4.37 (q, J=7.13 Hz, 2H), 1.38 (t, J=7.15 Hz, 3H).

Intermediate 1-2

The following compounds were prepared using similar methods as described above for Intermediate 1-1 using the appropriate hydrazines denoted below as starting materials.

| intermediate | Structure/Chemical Name | Starting materials | Analytical data |
| --- | --- | --- | --- |
| 1-2-1 | Ethyl 1-(6-chloropyridin-2-yl)-5-(trifluoromethyl)-1H-pyrazole-4-carboxylate | 2-chloro-6-hydrazinylpyridine (CAS# 5193-03-3) and ethyl 2-(ethoxymethylene)-4,4,4-trifluoro-3-oxobutyrate (CAS# 571-55-1) | $^1$H NMR (400 MHz, DMSO-$d_6$) δ 8.38 (s, 1H), 8.22 (dd, J = 7.8, 7.9 Hz, 1H), 7.86 (dd, J = 0.63, 8.0 Hz, 1H), 7.81 (dd, J = 0.63, 8.0 Hz, 1H), 4.33 (q, J = 7.15 Hz, 2H), 1.31 (t, J = 7.15 Hz, 3H) |
| 1-2-2 | Ethyl 1-(3-bromophenyl)-5-(trifluoromethyl)-1H-pyrazole-4-carboxylate | (3-bromophenyl) hydrazine hydrochloride (CAS# 27246-81-7) and ethyl 2-(ethoxymethylene)-4,4,4-trifluoro-3-oxobutyrate (the reaction was carried in the presence of 1 equivalent of $Et_3N$) | MS (ESI+) m/z 362.9 (M + H) |

Intermediate 1-3. Ethyl 1-(6-bromopyridin-2-yl)-5-methyl-1H-pyrazole-4-carboxylate

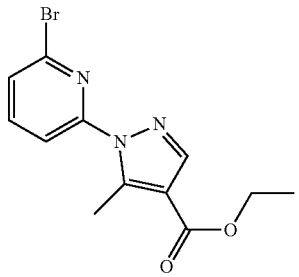 [SMILES: CCOC(=O)c1cnn(-c2cccc(Br)n2)c1C]

A mixture of 2-bromo-6-hydrazinylpyridine (5.04 g, 26.8 mmol) and ethyl 2-acetyl-3-(dimethylamino)acrylate (CAS #51145-57-4; 4.96 g, 26.8 mmol) in EtOH (81 ml) was heated to 70° C. for 1.5 h. The reaction mixture was then allowed to cool to room temperature and a precipitate formed. Water (80 mL) was then added to the mixture and the resulting heterogeneous mixture was filtered. The filter cake was washed with water and dried under reduced pressure to yield the title compound. MS (ESI+) m/z 310.1 (M+H).

Intermediate 1.4

The following compounds were prepared using similar methods as described above for Intermediate 1-3 using the appropriate starting materials as denoted below.

| Intermediate | Structure/Chemical Name | Starting materials | Analytical data |
|---|---|---|---|
| 1-4-1 | Ethyl 1-(6-chloropyridin-2-yl)-5-methyl-1H-pyrazole-4-carboxylate | 2-Chloro-6-hydrazinylpyridine (CAS# 5193-03-3) and ethyl 2-((dimethylamino)methylene)-3-oxobutanoate (CAS#; 51145-57-4) | $^1$H NMR (400 MHz, CDCl$_3$) δ 8.02 (S, 1H), 7.86-7.76 (m, 2H), 7.30 (dd, J = 6.4, 2.1 Hz, 1H), 4.33 (q, J = 7.1 Hz, 2H), 2.97 (s, 3H), 1.38 (t, J = 7.1 Hz, 3H). |
| 1-4-2 | Ethyl 1-(6-bromopyridin-2-yl)-5-ethyl-1H-pyrazole-4-carboxylate | 2-Bromo-6-hydrazinylpyridine and ethyl 2-((dimethylamino)methylene)-3-oxopentanoate (CAS# 89193-23-7) | MS (ESI+) m/z 324.1(M + H) |
| 1-4-3 | Ethyl 1-(3-bromophenyl)-5-methyl-1H-pyrazole-4-carboxylate | (3-Bromophenyl)hydrazine hydrochloride (CAS# 27246-81-7) and ethyl 2-acetyl-3-(dimethylamino)acrylate (CAS# 51145-57-4). (the reaction was carried in the presence of 1 equivalent of Et$_3$N) | MS (ESI+) m/z 309.3 (M + H) |

-continued

| Intermediate | Structure/Chemical Name | Starting materials | Analytical data |
|---|---|---|---|
| 1-4-4 | Ethyl 1-(6-bromopyridin-2-yl)-1H-pyrazole-4-carboxylate | 2-Bromo-6-hydrazinylpyridine and ethyl 3-(dimethylamino)-2-formylacrylate (CAS # 92385-43-8) | MS (ESI+) m/z 296.1 (M + H) |
| 1-4-5 | Ethyl 1-(6-bromopyridin-2-yl)-5-(difluoromethyl)-1H-pyrazole-4-carboxylate | 2-Bromo-6-hydrazinylpyridine and ethyl 2-(ethoxymethylene)-4,4-difluoro-3-oxobutanoate (CAS# 176969-33-8) | MS (ESI+) m/z 346.1 (M + H) |
| 1-4-6 | Ethyl 1-(3-bromophenyl)-5-(difluoromethyl)-1H-pyrazole-4-carboxylate | (3-Bromophenyl) hydrazine hydrochloride (CAS# 27246-81-7) and ethyl 2-(ethoxymethylene)-4,4-difluoro-3-oxobutanoate (CAS# 176964-33-8) (the reaction was carried in the presence of 1 equivalent of Et$_3$N) | MS (ESI+) m/z 345.1 (M + H) |
| 1-4-7 | Ethyl 1-(6-bromopyridin-2-yl)-5-isopropyl-1H-pyrazole-4-carboxylate | 2-Bromo-6-hydrazinylpyridine and ethyl 2-((dimethylamino)methylene)-4-methyl-3-oxopentanoate (CAS# 116344-09-3) | MS (ESI+) m/z 338.1 (M + H) |

Intermediate 1-5. Ethyl 5-methyl-1-(3-(4,4,5,5-tetramethyl-1,3,2-dioxaborolan-2-yl)phenyl)-1H-pyrazole-4-carboxylate

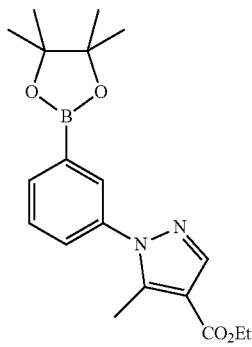 [SMILES: CCOC(=O)c1cnn(-c2cccc(B3OC(C)(C)C(C)(C)O3)c2)c1C]

Chloro(2-dicyclohexylphosphino-2',6'-dimethoxy-1,1'-biphenyl)[2-(2-aminoethylphenyl)]palladium(II)-methyl-t-butyl ether adduct (CAS #1028206-58-7; 0.125 g, 0.186 mmol) was added to a solution of Intermediate 1-4-3 (1.15 g, 3.72 mmol), bis(pinacolato)diboron (1.039 g, 4.09 mmol), KOAc (0.730 g, 7.44 mmol) in dioxane (19 mL) and the head space purged with nitrogen. The reaction mixture was heated at 100° C. for 90 minutes. After the reaction mixture was cooled to room temperature, Celite® was added and the mixture was concentrated. The residue was purified by flash column chromatography to provide the title compound. $^1$H NMR (400 MHz, Chloroform-d) δ 8.02 (s, 1H), 7.89-7.84 (m, 2H), 7.51-7.48 (m, 2H), 4.33 (q, J=7.1 Hz, 2H), 2.56 (s, 3H), 1.38 (t, J=7.1 Hz, 3H), 1.34 (s, 12H).

Intermediate 1-6

The following compound was prepared using similar methods as described above for Intermediate 1-6 using the appropriate starting materials.

Intermediate 1-8

Intermediate 1-8-A. Ethyl 2-((dimethylamino)methylene)-6,5,5-trifluoro-3-oxopentanoate

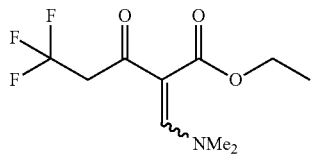 [SMILES: CCOC(=O)C(=CN(C)C)C(=O)CC(F)(F)F]

A mixture of 1,1-dimethoxy-N,N-dimethylmethanamine (0.713 mL, 5.05 mmol) and ethyl 5,5,5-trifluoro-3-oxopentanoate (CAS #127146-29-6; 1 g, 5.05 mmol) was stirred at room temperature for 18 hr. The reaction mixture was concentrated to furnish the title compound. $^1$H NMR (400 MHz, Chloroform-d) δ 7.84 (s, 1H), 4.24 (q, J=7.1 Hz, 2H), 3.72 (q, J=10.9 Hz, 2H), 3.38-3.28 (m, 3H), 2.92-2.82 (m, 3H), 1.34 (t, J=7.1 Hz, 3H).

Intermediate 1-8. Ethyl 1-(6-bromopyridin-2-yl)-5-2,2,2-trifluoroethyl)-1H-pyrazole-4-carboxylate

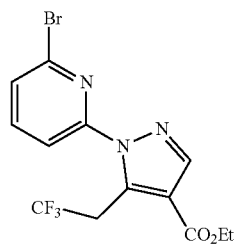 [SMILES: CCOC(=O)c1cnn(-c2cccc(Br)n2)c1CC(F)(F)F]

2-Bromo-6-hydrazinylpyridine (0.933 g, 4.96 mmol) was added to Intermediate 1-8-A (1.256 g, 4.96 mmol) in EtOH (17 mL) and the reaction mixture was heated to 75° C. for 3 h. The reaction mixture was cooled to room temperature

| Intermediate | Structure/Chemical Name | Starting materials | Analytical data |
|---|---|---|---|
| 1-6-1 | 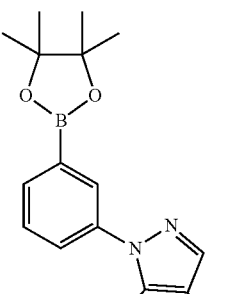<br>Ethyl 1-(3-(4,4,5,5-tetramethyl-1,3,2-dioxaborolan-2-yl)phenyl)-5-(trifluoromethyl)-1H-pyrazole-4-carboxylate | Intermediate 1-2-2 | $^1$H NMR (400 MHz, Chloroform-d) δ 8.13 (d, J = 0.8 Hz, 1H), 7.98-7.93 (m, 1H), 7.90-7.87 (m, 1H), 7.58-7.45 (m, 2H), 4.40 (q, J = 7.1 Hz, 2H), 1.41 (t, J = 7.1 Hz, 3H), 1.37 (s, 12H). | and poured into water (150 mL) to afford a precipitate. The mixture was filtered and the solid was washed with water to provide the title compound. MS (ESI+) m/z 378.1 (M+H).

Intermediate 2-1

Intermediate 2-1-A. tert-Butyl 4-(4-hydroxy-3-methylphenyl)-8,6-dihydropyridine-1(2H)-carboxylate

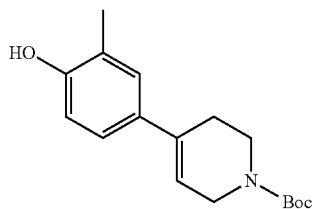 [SMILES: Cc1cc(C2CCN(C(=O)OC(C)(C)C)CC2)ccc1O]

To a suspension of 4-bromo-2-methyl phenol (CAS #2362-12-1, 5 g, 26.7 mmol), tert-butyl 4-(4,4,5,5-tetramethyl-1,3,2-dioxaborolan-2-yl)-5,6-dihydropyridine-1 (2H)-carboxylate (CAS #286961-14-6, 8.27 g, 26.7 mmol), and K$_3$PO$_4$ (2M in H$_2$O, 26.7 mL, 53.5 mmol) in acetonitrile (54 mL) was added Pd(dppf)Cl$_2$·CH$_2$Cl$_2$ adduct (1.09 g, 1.33 mmol). The mixture was then stirred at 80° C. for 3 h, and then cooled to room temperature. The reaction mixture was added to Celite®, and then concentrated. The resulting residue was purified by silica gel flash column chromatography (heptane/EtOAc=1/0 to 1/1) to afford the title compound. MS (ESI+) m/z 290.1 (M+H).

Intermediate 2-1. tert-Butyl 4-(4-hydroxy-3-methylphenyl)piperidine-1-carboxylate

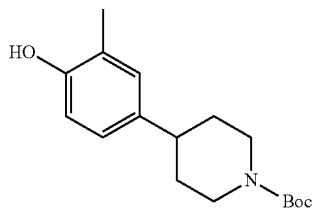

A mixture of Intermediate 2-1-A (4.4 g, 15.21 mmol) and Pd/C (5%, 0.8 g) in MeOH (50 mL) was stirred under H$_2$ atmosphere at room temperature for 2 h. The reaction mixture was then filtered through a plug of Celite®. The filtrate was then concentrated to furnish the title compound directly. MS (ESI−) m/z 290.2 (M−H).

Intermediate 2-2

Intermediate 2-2-A. tert-Butyl 4-(2-ethyl-4-hydroxyphenyl)-5,6-dihydropyridine-1(2H)-carboxylate

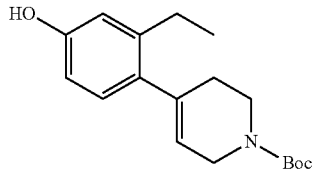

To a mixture of 4-chloro-3-ethylphenol (3 g, 19.16 mmol), tert-butyl 4-(4,4,5,5-tetramethyl-1,3,2-dioxaborolan-2-yl)-5,6-dihydropyridine-1(2H)-carboxylate (CAS #286961-14-6, 7.70 g, 24.90 mmol), chloro(2-dicyclohexylphosphino-2',6'-dimethoxy-1,1'-biphenyl)[2-(2-aminoethylphenyl)]palladium(II) methyl-t-butylether adduct (CAS #1028206-58-7, 0.644 g, 0.958 mmol) in DMF (96 mL) was added 2 M aq. potassium phosphate (28.7 mL, 57.5 mmol). The mixture was stirred at 110° C. for 1 h, and then cooled to room temperature. The reaction mixture was diluted with EtOAc and H$_2$O. The organic layer was then separated, and dried over Na$_2$SO$_4$, filtered, and then concentrated. The resulting residue was purified by silica gel flash column chromatography (heptane/EtOAc=1/0 to 6/4) to afford the title compounds. MS (ESI+) m/z 248.2 (M−tBu+2H).

Intermediate 2-2. tert-Butyl 4-(2-ethyl-4-hydroxyphenyl)piperidine-1-carboxylate

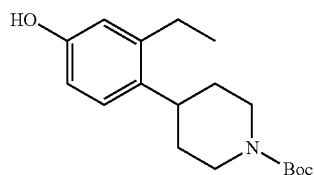 [SMILES: CCc1cc(O)ccc1C1CCN(C(=O)OC(C)(C)C)CC1]

A mixture of Intermediate 2-2-A (5.4 g, 17.80 mmol) and 10% Pd/C (1.894 g) in MeOH (250 mL) was stirred under an H$_2$ atmosphere at room temperature for 1 h. The reaction mixture was then filtered through a plug of Celite® which was then washed with MeOH. The filtrate was then concentrated to furnish the title compound directly. MS (ESI−) m/z 304.1 (M−H).

Intermediate 2-3

Intermediate 2-3-A. 2-Methyl-4-piperidin-4-yl)phenol

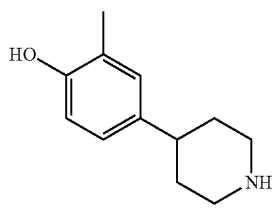

To a solution of Intermediate 2-1 (3.98 g, 13.66 mmol) in CH$_2$Cl$_2$ (137 mL) at 0° C. was added TFA (12.63 mL, 164 mmol). The mixture was then stirred for 1.5 h, and then concentrated to furnish the title compound as the TFA salt. MS (ESI+) n/z 192.1 (M+H).

Intermediate 2-3. Cyclopropyl(4-(4-hydroxy-3-methylphenyl)piperidin-1-yl)methanone

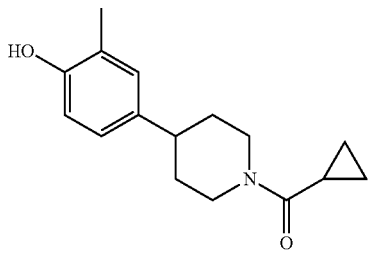 [SMILES: Cc1cc(C2CCN(C(=O)C3CC3)CC2)ccc1O]

To a solution of Intermediate 2-3-A (2.6 g, 13.59 mmol) in CH$_2$Cl$_2$ (68 mL) at 0° C. was added DIPEA (9.5 mL, 54.4 mmol), followed by cyclopropanecarbonyl chloride (2.47 mL, 27.2 mmol). The mixture was then stirred at 0° C. for 1 h, and then quenched with H$_2$O. The mixture was then extracted with CH$_2$Cl$_2$. The organic layer was then concentrated. The resulting residue was diluted with MeOH (68 mL) and charged with K$_2$CO$_3$ (9.39 g, 68 mmol) and placed at room temperature. The mixture was stirred for 2 h, and then diluted with CH$_2$Cl$_2$ and H$_2$O. The mixture was then passed through an ISOLUTE® Phase Separator. The resulting organic layer was then concentrated to furnish the title compound. MS (ESI+) m/z 260.1 (M+H).

Intermediate 2.4

The following compounds were prepared using similar methods as described above for Intermediate 2-3 using the appropriate starting materials as denoted below.

| Intermediate | Structure/Chemical Name | Starting material(s) | MS or NMR data |
|---|---|---|---|
| 2-4-1 | 1-(4-(4-Hydroxyphenyl)piperidin-1-yl)propan-1-one | tert-Butyl 4-(4-hydroxyphenyl)piperidine-1-carboxylate (CAS# 149377-19-5) and propionyl chloride | MS (ESI+) m/z 234.0 |
| 2-4-2 | Cyclopropyl(4-(4-hydroxy-3-(trifluoromethyl)phenyl)piperidin-1-yl)methanone | 4-bromo-2-(trifluoromethyl)phenol (CAS# 50824-04-9) and cyclopropanecarbonyl chloride | MS (ESI+) m/z 314.3 |
| 2-4-5 | Cyclopropyl(4-(2-ethyl-4-hydroxyphenyl)piperidin-1-yl)methanone | Intermediate 2-2 and cyclopropanecarbonyl chloride | MS (ESI+) m/z 274.3 (M + H) |

Intermediate 2-5

Intermediate 2-4-A. 1-Benzyl-4-methoxy-3-methylphenyl)piperidin-4-ol

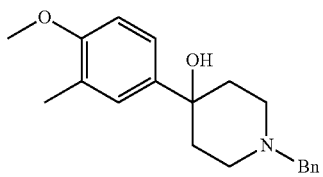 [SMILES: COc1ccc(C2(O)CCN(Cc3ccccc3)CC2)cc1C]

Magnesium turnings (3.63 g, 149.2 mmol) and a catalytic amount of iodine were suspended in THF (20 mL), 4-bromo-1-methoxy-2-methylbenzene (CAS #14804-31-0, 30.0 g, 149.2 mmol) in THF (140 mL) was added dropwise over 60 min. The mixture was refluxed for 1 h. After the reaction mixture was cooled to room temperature a solution of N-benzyl-4-piperidone (CAS #3612-20-2, 31.06 g, 164 mmol) in THF (100 mL) was then added dropwise over 50 min and then the mixture was stirred at reflux for 20 min. The mixture was cooled to room temperature and quenched with sat. aq. NH$_4$Cl and diluted with EtOAc. The organic layer was then separated. The aqueous phase was extracted twice with EtOAc. The combined organic layers were dried over MgSO$_4$, filtered and concentrated. The resulting residue was purified by silica gel flash column chromatography (hexane/EtOAc=5/1 to 3/1) to afford the title compound. MS (ESI+) m/z 312.3 (M+H).

Intermediate 2-5-B. 1-Benzyl-4-(4-methoxy-3-methylphenyl)-1,2,3,6-tetrahydropyridine

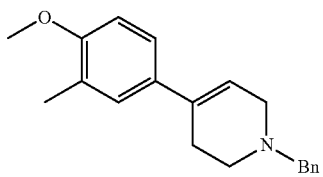 [SMILES: COc1ccc(C2=CCN(Cc3ccccc3)CC2)cc1C]

A mixture of Intermediate 2-5-A (29.3 g, 94.1 mmol) and 6M aq. HCl (100 mL) in dioxane (50 mL) was stirred under the reflux conditions for 3.5 h, and then concentrated. The resulting residue was triturated with diethyl ether. The resulting solid was collected by filtration to afford the title compound as an HCl salt. MS (ESI+) m/z 294.3 (M+H).

Intermediate 2-5-C. 4-(4-Methoxy-3-methylphenyl)piperidine

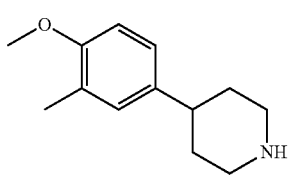

To a degassed solution of Intermediate 2-5-B (32.0 g, 97.1 mmol) in MeOH/H$_2$O (80 mL/40 mL) was added Pd/C (10%, 30 mg), and then the mixture was then stirred under H$_2$ atmosphere at 50° C. for 16 h. The H$_2$ atmosphere was then replaced with N$_2$, and then the additional Pd/C (10%, 30 mg) was added to the mixture. The mixture was then placed back under a H$_2$ atmosphere and stirred at 50° C. for 16 h. The mixture was then filtered through a plug of Celite® which was rinsed with MeOH. The filtrate was then concentrated and the resulting residue was suspended in diethyl ether, and then the resulting precipitate was collected by filtration to afford the title compound as the HCl salt. MS (ESI+) m/z 206.0 (M+H).

Intermediate 2-5-D. 1-(4-(4-Methoxy-3-methylphenyl)piperidin-1-yl)propan-1-one

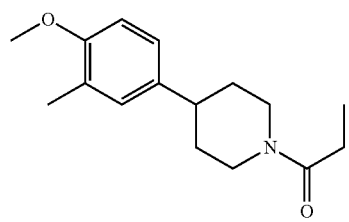 [SMILES: CCC(=O)N1CCC(c2ccc(OC)c(C)c2)CC1]

To a solution of Intermediate 2-5-C (6.3 g, 26 mmol) and triethylamine (9.09 mL, 65 mmol) in CH$_2$Cl$_2$ (63 mL) at 0° C. was added propionic anhydride (3.67 mL, 29 mmol) dropwise. The mixture was stirred at room temperature for 2 h and then quenched with H$_2$O. The mixture was then washed with H$_2$O, dried over MgSO$_4$, filtered and concentrated to furnish the title compound. MS (ESI+) m/z 261.9 (M+H).

Intermediate 2-5. 1-(4-(4-Hydroxy-3-methylphenyl)piperidin-1-yl)propan-1-one

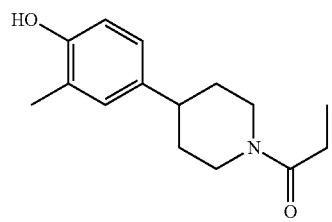 [SMILES: CCC(=O)N1CCC(c2ccc(O)c(C)c2)CC1]

To a solution of Intermediate 2-5-D (6.4 g, 25 mmol) in CH$_2$Cl$_2$ (32 mL) at −78° C. was added a solution of boron tribromide (1M in CH$_2$Cl$_2$, 61 mL, 61 mmol). The mixture was stirred at −78° C. for 1.5 h, and then stirred at room temperature for 16 h. The reaction was then quenched with 1M solution of NaHCO$_3$ until the pH=~9. Then the mixture was washed with H$_2$O, dried over Na$_2$SO$_4$, filtered, and concentrated. The resulting solid was triturated with i-PrOH to afford the title compound. MS (ESI+) m/z 248.1 (M+H).

Intermediate 2-6. 2-Pyridin-2-ylmethyl)-1,2,3,4-tetrahydroisoquinolin-6-ol

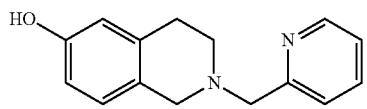 [SMILES: Oc1ccc2c(c1)CCN(Cc1ccccn1)C2]

2-(Bromomethyl)pyridine hydrobromide (CAS #31106-82-8) (2.42 g, 9.56 mmol) was added to a mixture of 1,2,3,4-tetrahydroisoquinolin-6-ol hydrobromide (CAS #59839-23-5; 2 g, 8.69 mmol) and TEA (4.85 mL, 34.8 mmol) in DCM (87 mL) at 0° C. in four portions (30 min apart). The reaction mixture was allowed to warm to room temperature over 1 h. The reaction mixture was then partitioned between half saturated aq. NaHCO$_3$ and DCM. The mixture was passed through an ISOLUTE® Phase Separator and the organic phase was concentrated. The resulting residue was purified by silica gel flash column chromatography (acetone/heptane, 0-50% gradient) to give the title compound. MS (ESI+) m/z 241.1 (M+H).

Intermediate 2-7

Intermediate 2-7-A. tert-Butyl 4-(4-(benzyloxy)-3-methylphenyl)piperidine-1-carboxylate

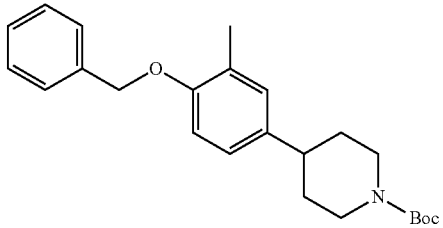 [SMILES: Cc1cc(C2CCN(C(=O)OC(C)(C)C)CC2)ccc1OCc1ccccc1]

To a suspension of Intermediate 2-1 (10 g, 34.3 mmol) and K$_2$CO$_3$ (10 g, 72.4 mmol) in DMF (100 mL) was added benzyl bromide (5 mL, 42.1 mmol). The mixture was then stirred at room temperature for 67 h. The reaction was then quenched with N,N-dimethylaminoethylenediamine. The mixture was then stirred for 3 h. and then diluted with H$_2$O/sat. aq. KHSO$_4$ (ca. 3/1). The mixture was then extracted with EtOAc. The organic layer was then washed successively with H$_2$O and brine, dried over Na$_2$SO$_4$, filtered, and then concentrated to furnish the title compound. MS (ESI+) m/z 326.3 (M-tBu+2H)

Intermediate 2-7-B.
4-(4-(Benzyloxy)-3-methylphenyl)piperidine

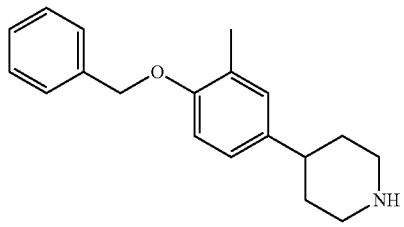 [SMILES: Cc1cc(C2CCNCC2)ccc1OCc1ccccc1]

The title compound was synthesized analogously to the preparation of Intermediate 2-3-A using tert-butyl 4-(4-(benzyloxy)-3-methylphenyl)piperidine-1-carboxylate. MS (ESI+) m/z 282.0 (M+H).

Intermediate 2-7-C. 4-(4-(Benzyloxy)-3-methylphenyl)-1-(2,2,24-trifluoroethyl)piperidine

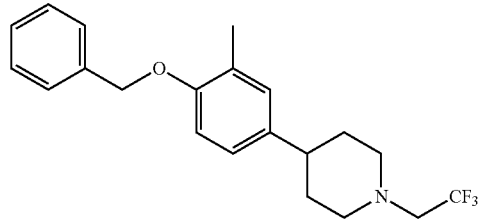 [SMILES: Cc1cc(C2CCN(CC(F)(F)F)CC2)ccc1OCc1ccccc1]

To a suspension of Intermediate 2-7-B (5 g, 17.77 mmol) and K$_2$CO$_3$ (5 g, 36.2 mmol) in DMF (40 mL) was added 2,2,2-trifluoroethyl trifluoromethanesulfonate (CAS #6226-25-1) (4 mL, 27.8 mmol). The mixture was then stirred at 40° C. for 23 h. The reaction was then quenched with H$_2$O. The mixture was then stirred at room temperature for 3 h. The mixture was then extracted with EtOAc. The organic layer was then washed successively with H$_2$O and brine, dried over Na$_2$SO$_4$, filtered, and then concentrated. The resulting residue was purified by silica gel flash column chromatography (heptane/EtOAc=1/0 to 4/1) to afford the title compound. MS (ESI+) m/z 364.0 (M+H).

Intermediate 2-7. 2-Methyl-4-(2,2,2-trifluoroethyl)piperidin-4-yl)phenol

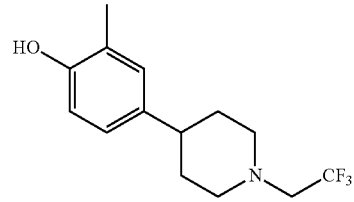 [SMILES: Cc1cc(C2CCN(CC(F)(F)F)CC2)ccc1O]

A mixture of Intermediate 2-7-C (4.9 g, 13.48 mmol) and Pd/C (10%) (500 mg, 13.48 mmol) in MeOH (100 mL) was stirred under H$_2$ atmosphere for 12 h. The mixture was then filtered through a plug of Celite®, which was rinsed with a mixture of EtOAc/MeOH (ca. 2/1). The filtrate was then concentrated to furnish the title compound. MS (ESI+) m/z 274.3 (M+H).

Intermediate 2-8

Intermediate 2-8-A. tert-Butyl 4-(3-methyl-4-nitrophenyl)-6,6-dihydropyridine-1(2H)-carboxylate

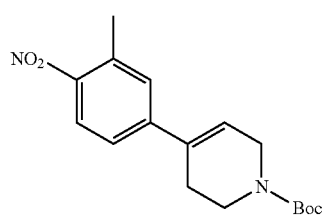 [SMILES: Cc1cc(C2=CCN(C(=O)OC(C)(C)C)CC2)ccc1[N+](=O)[O-]]

The title compound was synthesized analogously to the preparation of Intermediate 2-1-A using 4-bromo-2-methyl-1-nitrobenzene (CAS #52414-98-9) and tert-butyl 4-(4,4,5,5-tetramethyl-1,3,2-dioxaborolan-2-yl)-5,6-dihydropyridine-1(2H)-carboxylate. MS (ESI−) m/z 317.2 (M−H).

Intermediate 2-8-B. Cyclopropyl(4-(3-methyl-4-nitrophenyl)-5,6-dihydropyridin-1(2H)-yl)methanone

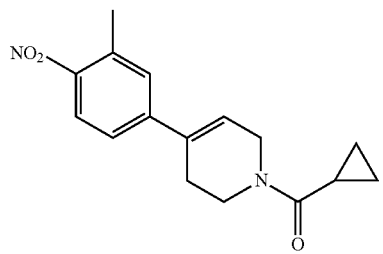 [SMILES: Cc1cc(C2=CCN(C(=O)C3CC3)CC2)ccc1[N+](=O)[O-]]

The title compound was synthesized from Intermediate 2-8-A in a similar manner as described for the synthesis of Intermediate 2-3. MS (ESI+) m/287.2 (M+H).

Intermediate 2-8. (4-(4-Amino-3-methylphenyl)piperidin-1-yl)(cyclopropyl)methanone

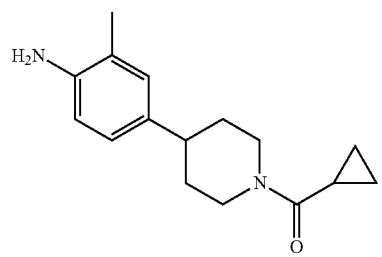 [SMILES: Cc1cc(C2CCN(C(=O)C3CC3)CC2)ccc1N]

A mixture of Intermediate 2-8-8 (5.98 g, 20.89 mmol) and Pd/C (10%) (1.11 g) in EtOH (104 mL) was stirred under $H_2$ atmosphere at room temperature for 8 h. The mixture was filtered through a plug of Celite®, which was rinsed with EtOH. The filtrate was concentrated. The resulting residue was resubjected to the same reaction conditions for 8 h, and the mixture was filtered through a plug of Celite®, which was rinsed with EtOH. The filtrate was concentrated and the resulting residue was purified by silica gel flash column chromatography (0.2% $Et_3N$ in heptane/EtOAc=1/0 to 0/1) to afford the title compound. MS (ESI+) m/z 259.3 (M+H).

Intermediate 2-9. (4-(4-Aminophenyl)piperidin-1-yl)(cyclopropyl)methanone

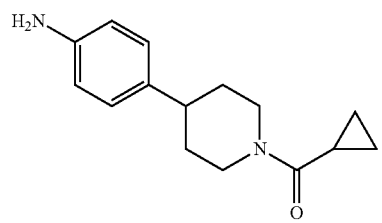 [SMILES: Nc1ccc(C2CCN(C(=O)C3CC3)CC2)cc1]

The title compound was synthesized starting from 4-bromo-1-nitrobenzene (CAS #586-78-7). Reaction of 4-bromo-1-nitrobenzene with tert-butyl 4-(4,4,5,5-tetramethyl-1,3,2-dioxaborolan-2-yl)-5,6-dihydropyridine-1 (2H)-carboxylate (CAS #286961-14-6), in a fashion analogous to Intermediate 2-1-A, afforded the Boc protected amine which was deprotected analogous to the transformation outlined in Intermediate 2-3-A. The resulting TFA salt of the amine was then reacted with cyclopropanecarbonyl chloride analogously to the procedure as described in Intermediate 2460. The resulting product underwent concomitant hydrogenation and nitro reduction in a similar manner as described for the synthesis of Intermediate 2-1 to furnish (4-(4-aminophenyl)piperidin-1-yl)(cyclopropyl)methanone. MS (ESI+) m/z 245.1 (M+H).

Intermediate 2-10

Intermediate 2-10-A. tert-Butyl 4-(4-amino-2-ethylphenyl)-5,6-dihydropyridine-1(2H)-carboxylate

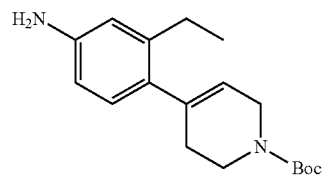 [SMILES: CCc1cc(N)ccc1C1=CCN(C(=O)OC(C)(C)C)CC1]

To a mixture of 4-bromo-3-ethylaniline (CAS #52121-42-3, 5 g, 24.99 mmol), 2-(3,6-dihydro-2H-pyran-4-yl)-4,4,5,5-tetramethyl-1,3,2-dioxaborolane (9.66 g, 31.2 mmol), and Pd(dppf)$Cl_2$.$CH_2Cl_2$ adduct (1.02 g, 1.25 mmol) in DMF (100 mL) was added 2 M aq. potassium phosphate (37.5 mL, 75.0 mmol). The mixture was then stirred at 110° C. for 50 minutes, cooled to room temperature, and diluted with EtOAc. The organic layer was then separated from the aqueous layer, dried over $Na_2SO_4$, filtered, and then concentrated. The resulting residue was purified by silica gel flash column chromatography (heptane/EtOAc=1/0 to 4/6) to afford the title compound. MS (ESI+) m/z 303.1 (M+H).

Intermediate 2-10. tert-Butyl 4-(4-amino-2-ethylphenyl)piperidine-1-carboxylate

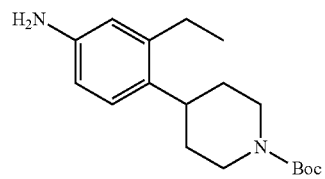

To a solution of Intermediate 2-10-A (8.34 g, 27.6 mmol) in MeOH (276 ml) was added Pd/C (10% wet; 2.93 g, 2.76 mmol) and the mixture was degassed and back filled with hydrogen from a balloon (3 times). The reaction mixture was filtered after 2 hours and the filtrate was concentrated to obtain the title compound. MS (ESI+) m/z 249.3 (M-tBu+2H).

Intermediate 2-11. 2-methyl-4-(1-(2,2,2-trifluoroethyl)piperidin-4-yl)aniline

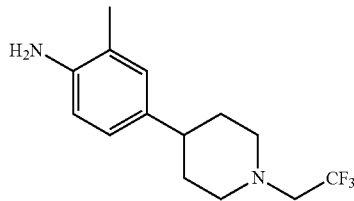 [SMILES: Cc1cc(C2CCN(CC(F)(F)F)CC2)ccc1N]

The title compound was synthesized starting from Intermediate 2-8-A. Deprotection of Intermediate 28-A with TFA, in a fashion analogous to the procedure described for Intermediate 2-3-A, afforded the TFA salt of the amine which was reacted with 2,2,2-trifluoroethyl trifluoromethanesulfonate analogously to the procedure described in Intermediate 2-7-C. The resulting product was hydrogenated analogous to the transformation outlined in Intermediate 2-8 to furnish the title compound. MS (ESI+) m/z 273.3 (M+H).

Intermediate 2-12

The following compounds were prepared by coupling the appropriate bromo aniline starting material as denoted in the table and 2-(3,6-dihydro-2H-pyran-4-yl)-4,4,5,5-tetramethyl-1,3,2-dioxaborolane as described in Intermediate 2-10-A, followed by palladium catalyzed hydrogenation analogous to Intermediate 2-10.

| Intermediate | Structure/Chemical Name | Starting material | MS or NMR data |
|---|---|---|---|
| 2-12-1 | 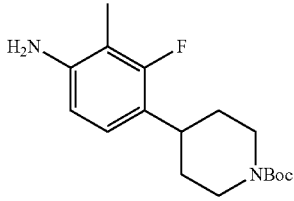 [SMILES: Cc1c(N)ccc(C2CCN(C(=O)OC(C)(C)C)CC2)c1F]<br>tert-Butyl 4-(4-amino-2-fluoro-3-methylphenyl)piperidine-1-carboxylate | 4-bromo-3-fluoro-2-methylaniline (CAS# 127408-03-1) | MS (ESI+) m/z 309.3 (M + H) |
| 2-12-2 | 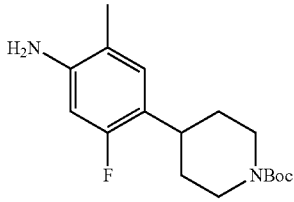<br>tert-Butyl 4-(4-amino-2-fluoro-5-methylphenyl)piperidine-1-carboxylate | 4-bromo-5-fluoro-2-methylaniline (CAS# 52723-82-7) | MS (ESI+) m/z 253.2 (M − t-Bu + 2H) |
| 2-12-3 | 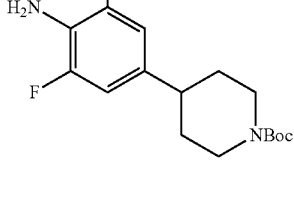<br>tert-Butyl 4-(4-amino-3-fluoro-5-methylphenyl)piperidine-1-carboxylate | 4-bromo-2-fluoro-6-methylaniline (CAS# 429683-46-5) | MS (ESI+) m/z 253.2 (M − t-Bu + 2H) |

Intermediate 2-13. tert-Butyl 4-(4-amino-3-methylphenyl)piperidine-1-carboxylate

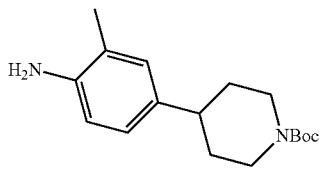 [SMILES: Cc1cc(C2CCN(C(=O)OC(C)(C)C)CC2)ccc1N]

Pd/C (10% wet) (0.251 g, 2.356 mmol) was added to a solution of Intermediate 2-8-A (1.5 g, 4.71 mmol) in EtOH (23.5 mL). The atmosphere of the flask was purged and backfilled with $H_2$ and the reaction mixture was stirred under an $H_2$ atmosphere at room temperature for 3 h. About 5 g of Celite® and 20 µL of saturated aqueous $NH_4Cl$ were added to the reaction mixture. The mixture was filtered through a plug of Celite®, which was rinsed with MeOH. The filtrate was concentrated to provide the title compound, which was used without further purification. $^1H$ NMR (400 MHz, Methanol-$d_4$) δ 6.87-6.85 (m, 1H), 6.82 (dd, J=8.0, 2.1 Hz, 1H), 6.66 (d, J=8.0 Hz, 1H), 4.16 (dt, J=13.4, 2.4 Hz, 2H), 2.82 (br.s, 2H), 2.54 (tt, J=12.1, 3.6 Hz, 1H), 2.14 (s, 3H), 1.74 (ddd, J=14.0, 3.2, 1.8 Hz, 2H), 1.56-1.51 (m, 2H), 1.47 (s, 9H).

Intermediate 3-1

Intermediate 3-1-A. 7-Hydroxy-2,3-dihydro-1H-inden-1-one

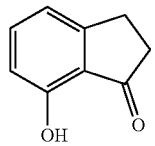 [SMILES: O=C1CCc2cccc(O)c21]

As described in *Heterocycles*, 27(2), 407-21; 1988, a mixture of phenyl 3-chloropropanoate (CAS #24552-27-0, 7 g, 37.9 mmol) and $AlCl_3$ (20.22 g, 152 mmol) was heated at 100° C. for 1 h, then at 180° C. for 2 h, and subsequently cooled to room temperature. The excess $AlCl_3$ was then quenched with 1N HCl. The resulting mixture was extracted with DCM. The combined organic layers were washed with water, passed through an ISOLUTE® phase separator. The filtrate was concentrated to give 7-hydroxy-2,3-dihydro-1H-inden-1-one. $^1H$ NMR (400 MHz, Chloroform-d) δ 9.07 (s, 1H), 7.47 (t, J=7.8 Hz, 1H), 6.97-6.92 (m, 1H), 6.78-6.74 (m, 1H), 3.16-3.06 (m, 2H), 2.78-2.68 (m, 2H).

Intermediate 3-1-B. 3-Oxo-2,3-dihydro-1H-inden-4-yl trifluoromethanesulfonate

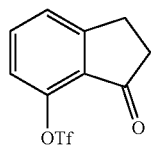 [SMILES: O=C1CCc2cccc(OS(=O)(=O)C(F)(F)F)c21]

Trifluoromethanesulfonic anhydride (800 µl, 4.74 mmol) was added dropwise to a solution of Intermediate 3-1-A (500 mg, 3.37 mmol) and pyridine (820 µl, 10.14 mmol) in DCM (7 mL) at 0° C. The resulting suspension was stirred at 0° C. for 60 min. The reaction mixture was quenched with water, followed by 1N HCl (5 mL). The resulting mixture was passed through an ISOLUTE® Phase Separator and the organic phase was concentrated to provide the title compound. MS (ESI+) m/z 281.0 (M+H).

Intermediate 3-1-C. (±)-3-Hydroxy-2,3-dihydro-1H-inden-yl trifluoromethanesulfonate

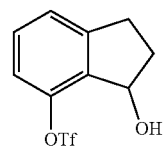

Sodium borohydride (126 mg, 3.33 mmol) was added to a solution of Intermediate 3-1-B (932.1 mg, 3.33 mmol) in MeOH (20 mL) at 0° C. The mixture was stirred at 0° C. for 1 h and was then partitioned between water and DCM. The mixture was passed through an ISOLUTE® Phase Separator. The organic layer was concentrated to furnish the title compound. $^1H$ NMR (400 MHz, Chloroform-d) δ 7.34 (t, J=7.8 Hz, 1H), 7.28 (dd, J=7.5, 1.1 Hz, 1H), 7.10 (d, J=8.0 Hz, 1H), 5.57-5.45 (m, 1H), 3.26-3.13 (m, 1H), 2.96-2.84 (m, 1H), 2.45-2.32 (m, 1H), 2.18 (d, J=5.1 Hz, 1H), 2.17-2.07 (m, 1H).

Intermediate 3-1. (±)-3-((2-(Pyridin-2-ylmethyl)-1,2,3,4-tetrahydroisoquinolin-6-yl)oxy)-2,3-dihydro-1H-inden-4-yl trifluoromethanesulfonate

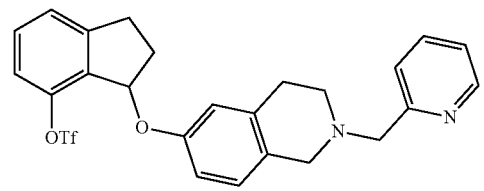 [SMILES: O=S(=O)(Oc1cccc2c1C(Oc1ccc3c(c1)CCN(Cc1ccccn1)C3)CC2)C(F)(F)F]

DIAD (150 µl, 0.771 mmol) was added to a mixture of Intermediate 3-1-C (164 mg, 0.581 mmol), Intermediate 2-6 (130 mg, 0.541 mmol), and tri-n-butylphosphine (200 µl, 0.770 mmol) in DCM (6 mL) at room temperature under nitrogen. The reaction mixture was stirred for 1 h. and then was partitioned between DCM and half saturated brine. The mixture was passed through an ISOLUTE® Phase Separator and the organic layer was concentrated. The resulting residue was purified by flash column chromatography to provide title compound. MS (ESI+) m/Z 505.1 (M+H).

Intermediate 3-1-D. 7-hydroxy-1-methyl-2,3-dihydro-1H-inden-1-one

Intermediate 3-1-D was synthesized using the same procedure as Intermediate 3-1-A, starting with m-tolyl 3-chloropropanoate (CAS #158304-80-4). $^1$H NMR (400 MHz, Chloroform-d) δ 8.95 (s, 1H), 6.80-6.72 (m, 1H), 6.64-6.52 (m, 1H), 3.08-3.03 (m, 2H), 2.71-2.67 (m, 2H), 2.38 (s, 3H).

Intermediate 3-1-E. 6-methyl-3-oxo-2,3-dihydro-1H-Inden-4-yl trifluoromethanesulfonate

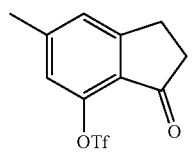 [SMILES: Cc1cc2c(c(OS(=O)(=O)C(F)(F)F)c1)C(=O)CC2]

Intermediate 3-1-E was synthesized using the same procedure as Intermediate 3-1-B starting with Intermediate 3-1-D. $^1$H NMR (400 MHz. Chloroform-d) δ 7.25-7.21 (m, 1H), 6.90 (s, 1H), 3.11-3.02 (m, 2H), 2.70-2.63 (m, 2H), 2.41 (s, 3H).

Intermediate 3-1-F. 3-hydroxy-methyl-2,3-dihydro-1H-inden-4-yl trifluoromethanesulfonate Intermediate 3-1-F was reduced using the same procedure as Intermediate 3-1-C, starting with Intermediate 3-1-E. $^1$H NMR (400 MHz, Chloroform-d) δ 7.09 (s, 1H), 6.89 (s, 1H), 5.47-5.42 (m, 1H), 3.22-3.11 (m, 1H), 2.89-2.78 (m, 1H), 2.50-2.40 (m, 1H), 2.38 (s, 3H), 2.15-2.06 (m, 1H).

Intermediate 3-2

The following compounds were prepared using similar methods as described above for Intermediate 3-1 using the appropriate starting materials as denoted below.

| Intermediate | Structure/Chemical Name | Starting material(s) | MS or NMR data |
|---|---|---|---|
| 3-2-1 | (±)-6-Methyl-3-((2-(pyridin-2-ylmethyl)-1,2,3,4-tetrahydroisoquinolin-6-yl)oxy)-2,3-dihydro-1H-inden-4-yl trifluoromethanesulfonate | Intermediate 3-1-F and Intermediate 2-6 | MS (ESI+) m/z 518.5 (M + H) |
| 3-2-2 | (±)-3-(4-(1-(Cyclopropanecarbonyl)piperidin-4-yl)-2-methylphenoxy)-6-methyl-2,3-dihydro-1H-inden-4-yl trifluoromethanesulfonate | Intermediate 3-1-F and Intermediate 2-3 | MS (ESI+) m/z 538.3 (M + H) |

| Intermediate | Structure/Chemical Name | Starting material(s) | MS or NMR data |
|---|---|---|---|
| 3-2-3 | 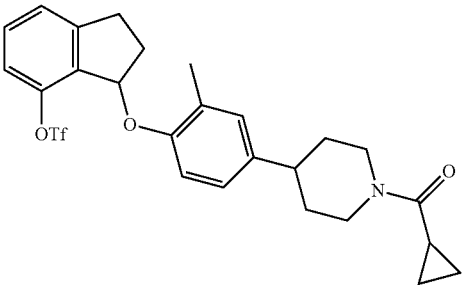 [SMILES: Cc1cc(C2CCN(C(=O)C3CC3)CC2)ccc1OC1CCc2cccc(OS(=O)(=O)C(F)(F)F)c21]<br>(±)-3-(4-(1-(Cyclopropaneearbonyl)piperidin-4-yl)-2-methylphenoxy)-2,3-dihydro-1H-inden-4-yl trifluoromethanesulfanate | Intermediate 3-1-C and Intermediate 2-3 | MS (ESI+) m/z 524.2 (M + H) |

Intermediate 3-3

Intermediate 3-3-A. (±)-7-Bromo-2,3-dihydro-1H-inden-1-ol

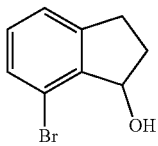

Sodium borohydride (0.090 g, 2.369 mmol) was added to a solution of 7-bromo-2,3-dihydro-1H-inden-1-one (CAS #125114-77-4; 0.5 g, 2.37 mmol) in MeOH (24 mL) at 0° C. The mixture was stirred at 0° C. for 1 h then let warm to room temperature. After 2 h the reaction mixture was diluted with water and DCM, and then saturated aqueous ammonium chloride was added. The mixture was then passed through an ISOLUTE® Phase Separator and the organic phase was concentrated to give (±)-7-bromo-2,3-dihydro-1H-inden-1-ol. $^1$H NMR (400 MHz, Chloroform-d) δ 7.41-7.33 (m, 1H), 7.25-7.20 (m, 1H), 7.15 (t, J=7.6 Hz, 1H), 5.41-5.34 (m, 1H), 3.30-3.17 (m, 1H), 2.97-2.84 (m, 1H), 2.51-2.35 (m, 1H), 2.20-2.09 (m, 1H).

Intermediate 3-3-B. (−)-R-7-bromo-2,3-dihydro-1H-inden-1-ol

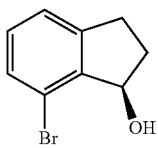

Triethylamine (1.45 mL, 10.42 mmol) was added dropwise to a 40 mL vial with formic acid (1.018 mL, 26.5 mmol) and a stir bar at room temperature. The temperature of the reaction mixture was maintained under 45° C. by controlling the rate of the addition. After the addition was completed, the reaction mixture was cooled to 0° C. in an ice bath and stirred for 30 min. The mixture was then warmed to room temperature and stirred for 1 h. To this solution was added DMF (7 mL) followed by 7-bromo-2,3-dihydro-1H-inden-1-one (4 g, 18.95 mmol) and RuCl[(R,R)-Tsdpen](p-cymene) (CAS #192139-92-7) (0.013 g, 0.021 mmol). The reaction mixture was stirred at room temperature for 40 h before being heated to 60° C. for a further 24 h. The reaction mixture was cooled to room temperature and partitioned between EtOAc and half saturated brine. The layers were separated and the aqueous layer was extracted with EtOAc. The combined organic layers were concentrated. The residue was absorbed onto silica and purified by flash column chromatography with 100% DCM to provide (−)-7-bromo-2,3-dihydro-1H-inden-1-ol (>98% e.e.). $^1$H NMR (400 MHz, Chloroform-d) δ 7.41-7.33 (m, 1H), 7.25-7.20 (m, 1H), 7.15 (t, J=7.6 Hz, 1H), 5.41-5.34 (m, 1H), 3.30-3.17 (m, 1H), 2.97-2.84 (m, 1H), 2.51-2.35 (m, 1H), 2.20-2.09 (m, 1H). Absolute stereochemistry of (−)-R-7-bromo-2,3-dihydro-1H-inden-1-ol was confirmed by X-ray single crystal diffraction.

Enantiomeric excess of 7-bromo-2,3-dihydro-1H-inden-1-ol was determined by chiral SFC using CHIRALPAK® OD-H, 10% IPA in $CO_2$; (−)-7-bromo-2,3-dihydro-1H-inden-1-ol ($t_r$=4.87 min) and (+)-7-bromo-2,3-dihydro-1H-inden-1-ol ($t_r$=5.58 min).

Intermediate 3-3. a). (±)-(4-(4-((7-Bromo-2,3-dihydro-1H-inden-1-yl)oxy)-3-methylphenyl)piperidin-1-yl)(cyclopropyl)methanone

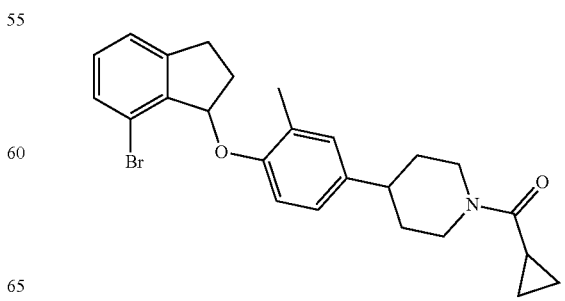

Azodicarboxylic dimorpholide (CAS #10465-82-4; 502 mg, 1.960 mmol) was added to a solution of Intermediate 3-3-A (348 mg, 1.633 mmol), Intermediate 2-3 (508 mg, 1.960 mmol), and tri-n-butylphosphine (509 µl, 1.960 mmol) in THF (6.5 mL) at room temperature. The mixture was stirred at room temperature for 16 h. The reaction mixture was partitioned between DCM and water, and then passed through an ISOLUTE® Phase Separator. Celite® was added to the organic layer and the resulting mixture was concentrated. The resulting residue was purified by silica flash column chromatography to provide the title compound. MS (ESI+) m/z 454.2 (M+H).

Intermediate 3-3. b). (+)-(S)-(4-(4-((7-Bromo-2,3-dihydro-1H-inden-1-yl)oxy)-3-methylphenyl)piperidin-1-yl)(cyclopropyl)methanone

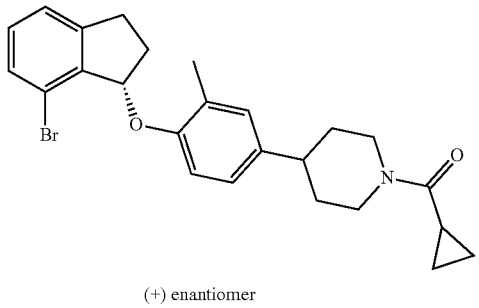 [SMILES: Cc1cc(C2CCN(C(=O)C3CC3)CC2)ccc1O[C@H]1CCc2cccc(Br)c21]

(+) enantiomer

Intermediate 3-3-B underwent reaction with Intermediate 2-3 under the conditions described for Intermediate 3-3. a) to provide the title compound in >97% e.e. MS (ESI+) m/z 454.3 (M+H).

Enantiomeric excess of (4-(4-((7-bromo-2,3-dihydro-1H-inden-1-yl)oxy)-3-methylphenyl)piperidin-1-yl)(cyclopropyl)methanone was determined by chiral SFC using CHIRALPAK® OJ-H 5-55% IPA gradient in $CO_2$, 5 mL/min; (+)-(4-(4-((7-bromo-2,3-dihydro-1H-inden-1-yl)oxy)-3-methylphenyl)piperidin-1-yl)(cyclopropyl)methanone ($t_r$=2.38 min) and (−)-(4-(4-((7-bromo-2,3-dihydro-1H-inden-1-yl)oxy)-3-methylphenyl)piperidin-1-yl)(cyclopropyl)methanone ($t_r$=2.70 min).

Intermediate 3-4

The following compounds were prepared using either Intermediate 3-3-A (racemate) or Intermediate 3-3-B (>98% e.e.) employing similar methods as described above for Intermediate 3-3. a) using the appropriate starting materials as denoted below.

| Intermediate | Structure/Chemical Name | Starting material(s) | MS or NMR data |
|---|---|---|---|
| 3-4-1 | (±)-6-((7-Bromo-2,3-dihydro-1H-inden-1-yl)oxy)-2-(pyridin-2-ylmethyl)-1,2,3,4-tetrahydroisoquinoline | Intermediate 2-6 and Intermediate 3-3-A | MS (ESI+) m/z 435.2 (M + H) |
| 3-4-2 | (±)-(S)-6-((7-Bromo-2,3-dihydro-1H-inden-1-yl)oxy)-2-(pyridin-2-ylmethyl)-1,2,3,4-tetrahydroisoquinoline | Intermediate 2-6 and Intermediate 3-3-B | MS (ESI+) m/z 435.1 (M + H) |

| Inter-mediate | Structure/Chemical Name | Starting material(s) | MS or NMR data |
|---|---|---|---|
| 3-4-3 | 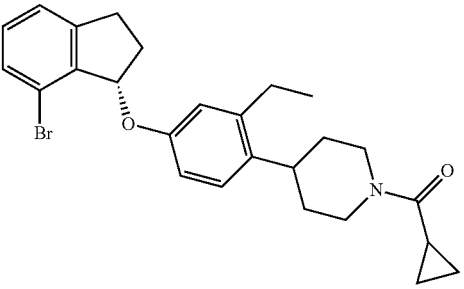 [SMILES: CCc1cc(O[C@H]2CCc3cccc(Br)c32)ccc1C1CCN(C(=O)C2CC2)CC1]<br>(±)-(S)-(4-(4-((7-Bromo-2,3-dihydro-1H-inden-1-yl)oxy)-2-ethylphenyl)piperidin-1-yl)(cyclopropyl)methanone | Intermediate 2-4-5 and Intermediate 3-3-B | MS (ESI+) m/z 468.2 (M + H) |
| 3-4-4 | 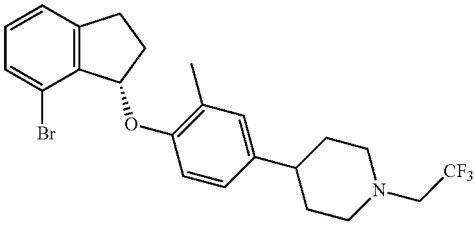 [SMILES: Cc1cc(C2CCN(CC(F)(F)F)CC2)ccc1O[C@H]1CCc2cccc(Br)c21]<br>(±)-(S)-4-(4-((7-Bromo-2,3-dihydro-1H-inden-1-yl)oxy)-3-methylphenyl)-1-(2,2,2-trifluoroethyl)piperidine | Intermediate 2-7 and Intermediate 3-3-B | MS (ESI+) m/z 468.6 (M + H) |
| 3-4-5 | 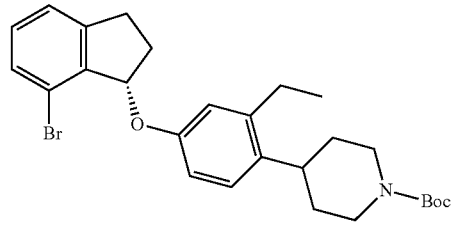 [SMILES: CCc1cc(O[C@H]2CCc3cccc(Br)c32)ccc1C1CCN(C(=O)OC(C)(C)C)CC1]<br>(S)-tert-Butyl 4-(4-((7-bromo-2,3-dihydro-1H-inden-1-yl)oxy)-2-ethylphenyl)piperidine-1-carboxylate | Intermediate 2-2 and Intermediate 3-3-B | MS (ESI+) m/z 500.2 (M + H) |
| 3-4-6 | 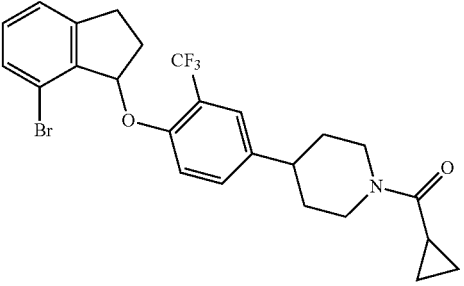 [SMILES: O=C(C1CC1)N1CCC(c2ccc(OC3CCc4cccc(Br)c43)c(C(F)(F)F)c2)CC1]<br>(±)-(4-(4-((7-Bromo-2,3-dihydro-1H-inden-1-yl)oxy)-3-(trifluoromethyl)phenyl)piperidin-1-yl)(cyclopropyl)methanone | Intermediate 2-4-2 and Intermediate 3-3-A | MS (ESI+) m/z 508.2 (M + H) |

Intermediate 3-5-A. a). (±)-(4-(4-((7-Bromo-2,3-dihydro-1H-inden-1-yl)amino)-3-methylphenyl)piperidin-1-yl)(cyclopropyl)methanone

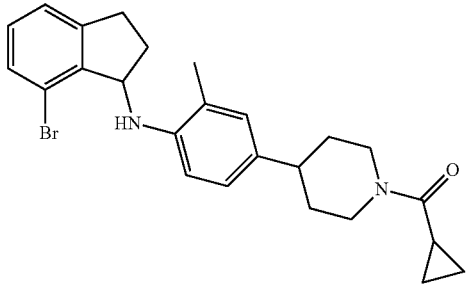 [SMILES: Cc1cc(C2CCN(C(=O)C3CC3)CC2)ccc1NC1CCc2cccc(Br)c21]

A solution of 7-bromo-2,3-dihydro-1H-inden-1-one (160 mg, 0.759 mmol) and Intermediate 2-8 (196 mg, 0.759 mmol) in glacial acetic acid (3 mL) was stirred at room temperature for 30 min. Sodium triacetoxyborohydride (161 mg, 0.759 mmol) was then added at room temperature and the reaction mixture was stirred at room temperature for 1 h. Another portion of sodium triacetoxyborohydride (161 mg, 0.759 mmol) was added and the mixture was stirred for 16 h. Another portion of sodium triacetoxyborohydride (161 mg, 0.759 mmol) was added, and then the mixture was stirred for an additional 2 h. The reaction mixture was poured into water (10 mL) and the pH of the mixture was adjusted by addition of 33% NH$_4$OH to ~11. The resulting mixture was then extracted twice with EtOAc. The combined organic layers were concentrated. The resulting residue was purified by flash column chromatography (0-40% EtOAc/heptane gradient) to give title compound. MS (ESI+) m/z 453.2 (M+H).

Intermediate 3-5-A. b). (+)-(4-(4-((7-Bromo-2,3-dihydro-1H-inden-1-yl)amino)-3-methylphenyl)piperidin-1-yl)(cyclopropyl)methanone and (−)-(4-(4-((7-bromo-2,3-dihydro-1H-inden-1-yl)amino)-3-methylphenyl)piperidin-1-yl)cyclopropyl)methanone Resolution of the enantiomers of (+)-(4-(4-((7-bromo-2,3-dihydro-1H-inden-1-yl)amino)-3-methylphenyl)piperidin-1-yl)(cyclopropyl)methanone was achieved by chiral SFC using CHIRALCEL® OJ-H column with 25% MeOH in CO$_2$ to give (+)-(4-(4-((7-bromo-2,3-dihydro-1H-inden-1-yl)amino)-3-methylphenyl)piperidin-1-yl)(cyclopropyl) methanone (t$_r$=2.93 min) and (−)-(4-(4-((7-bromo-2,3-dihydro-1H-inden-1-yl)amino)-3-methylphenyl)piperidin-1-yl)(cyclopropyl)methanone (t$_r$=3.58 min).

Intermediate 3-5-B. (±)-(4-(4-((7-bromo-2,3-dihydro-1H-inden-1-yl)amino)phenyl)piperidin-1-yl)(cyclopropyl)methanone

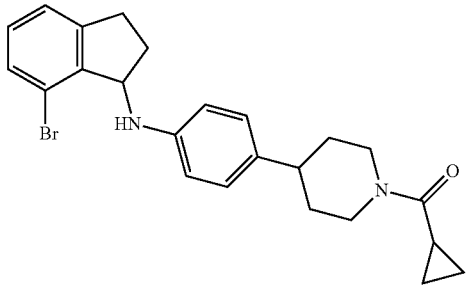 [SMILES: O=C(C1CC1)N1CCC(c2ccc(NC3CCc4cccc(Br)c43)cc2)CC1]

The title compound was prepared using a similar procedure to that described in Intermediate 3-5-A. a) starting with Intermediate 2-9. MS (ESI+) m/z 439.2 (M+H).

Intermediate 3-5-C. (±)-tert-Butyl 4-(4-((7-bromo-2,3-dihydro-1H-inden-1-yl)amino)-3-methylphenyl)piperidine-1-carboxylate

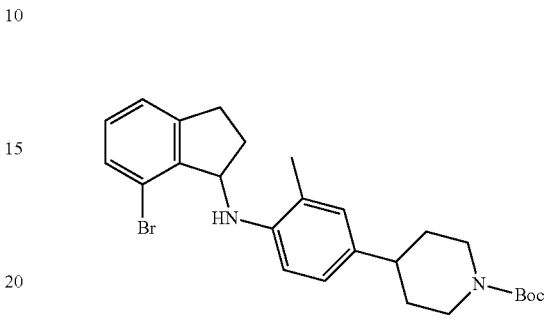

A mixture of 7-bromo-2,3-dihydro-1H-inden-1-one (400 mg, 2.00 mmol), tert-butyl 4-(4-amino-3-methylphenyl)piperidine-1-carboxylate (Intermediate 2-13) (600 mg, 2.07 mmol), and TsOH.H$_2$O (50 mg, 0.263 mmol) in toluene/dimethylacetamide (20 mL/5 mL) was stirred under the reflux condition for 19 h, and then cooled to 0° C., and then diluted with CH$_2$Cl$_2$ (10 mL). To the reaction mixture was then added NaB(OAc)$_3$H (1 g, 4.72 mmol), followed by AcOH (2 mL). The mixture was then stirred at 0° C. for 2 h, and then poured into H$_2$O. The mixture was then extracted with EtOAc. The organic extracts were washed successively with 5% aq. NaHCO$_3$, H$_2$O, and brine, dried over Na$_2$SO$_4$, filtered, and then concentrated. The resulting residue was purified by silica gel flash column chromatography (heptane/EtOAc=1/0 to 85/15) to afford the title compound. MS (ESI+) m/z 485.3 (M+H).

Intermediate 3-5-D. (±)-tert-Butyl 4-(4-(7-bromo-2,3-dihydro-1H-inden-1-yl)amino)-2-ethylphenyl)piperidine-1-carboxylate

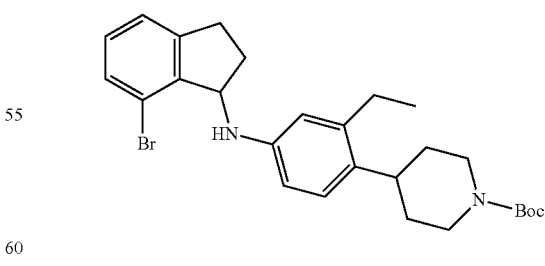

The title compound was prepared by a reaction of 7-bromo-2,3-dihydro-1H-inden-1-one with tert-butyl 4-(4-amino-2-ethylphenyl)piperidine-1-carboxylate (Intermediate 2-10) by the similar procedure as described in the synthesis of Intermediate 3-5-C. MS (ESI+) m/z 499.3 (M+H).

Intermediate 3-6. Ethyl 1-(3-(3-oxo-2,3-dihydro-1H-inden-4-yl)phenyl)-6-(trifluoromethyl)-1H-pyrazole-4-carboxylate

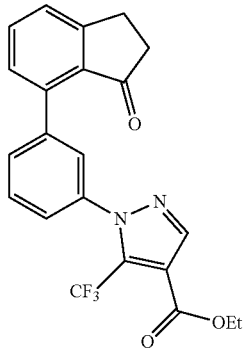 [SMILES: CCOC(=O)c1cnn(-c2cccc(-c3cccc4c3C(=O)CC4)c2)c1C(F)(F)F]

Pd(dppf)Cl$_2$.CH$_2$Cl$_2$ adduct (87 mg, 0.107 mmol) was added to a mixture of 7-bromo-2,3-dihydro-1H-inden-1-one (225 mg, 1.066 mmol) and Intermediate 1-6-1 (481 mg, 1.173 mmol) in dioxane (5 mL) and 2M aqueous K$_3$PO$_4$ (1.1 mL, 2.132 mmol). The reaction mixture was stirred at 80° C. under a nitrogen atmosphere for 3 hour. The reaction mixture was then cooled to room temperature and Celite® was added. The resulting mixture was concentrated and the residue was purified by flash column chromatography using silica gel with a gradient of 0-50% EtOAc/heptane to provide the title compound. $^1$H NMR (400 MHz, Methanol-d4) δ 8.16 (d, J=0.8 Hz, 1H), 7.69 (t, J=7.6 Hz, 1H), 7.66-7.62 (m, 1H), 7.61-7.55 (m, 2H), 7.53-7.50 (m, 1H), 7.50-7.45 (m, 1H), 7.33-7.29 (m, 1H), 4.36 (q, J=7.1 Hz, 2H), 3.23-3.17 (m, 2H), 2.72-2.66 (m, 2H), 1.37 (t, J=7.1 Hz, 3H).

Intermediate 3-7. Ethyl 5-methyl-1-(6-(3-oxo-2,3-dihydro-1H-inden-4-yl)pyridin-2-yl)-1H-pyrazole-4-carboxylate

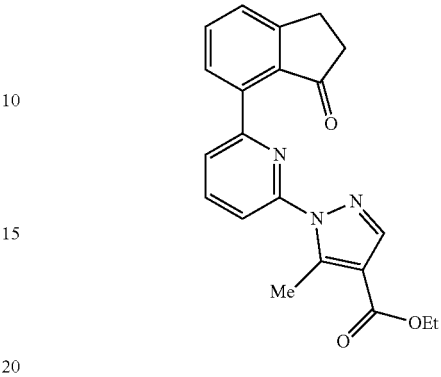

To a mixture of Intermediate 1-3 (1.03 g, 3.31 mmol), bis(pinacolato)diboron (0.84 g, 3.31 mmol), KOAc (0.65 g, 6.61 mmol) in dioxane (11 mL) was added chloro(2-dicyclohexylphosphino-2',6'-dimethoxy-1,1'-biphenyl)[2-(2-aminoethylphenyl)]palladium(II)-methyl-t-butyl ether adduct (CAS #1028206-58-7; 0.11 g, 0.165 mmol). The mixture was then stirred at 120° C. under the microwave irradiation for 45 minutes. To the mixture was then added a solution of 7-bromo-2,3-dihydro-1H-inden-1-one (0.66 g, 3.14 mmol) in dioxane (11 mL), followed by sodium carbonate (1M in water; 8.3 mL, 8.27 mmol) and Pd(dppf)Cl$_2$.CH$_2$Cl$_2$ adduct (CAS #95464-05-4; 0.14 g, 0.165 mmol). The whole mixture was then stirred under microwave irradiation for 30 min at 110° C. Celite® was added to the reaction mixture and the mixture was concentrated. The residue was purified by flash column chromatography (0-50% EtOAc/heptane) to yield the title compound. MS (ESI+) m/z 362.3 (M+H).

Intermediate 3-8

The following compounds were prepared using similar methods as described above for Intermediate 3-7 using the appropriate starting materials.

| Intermediate | Structure/Chemical Name | Starting material(s) | MS or NMR data |
|---|---|---|---|
| 3-8-1 | Ethyl 5-ethyl-1-(6-(3-oxo-2,3-dihydro-1H-inden-4-yl)pyridin-2-yl)-1H-pyrazole-4-carboxylate | Intermediate 1-4-2 and 7-bromo-2,3-dihydro-1H-inden-1-one | MS (ESI+) m/z 376.3 (M + H). |

-continued

| Intermediate | Structure/Chemical Name | Starting material(s) | MS or NMR data |
|---|---|---|---|
| 3-8-2 | Ethyl 1-(6-(3-oxo-2,3-dihydro-1H-inden-4-yl)pyridin-2-yl)-5-(trifluoromethyl)-1H-pyrazole-4-carboxylate | Intermediate 1-2-1 and 7-bromo-2,3-dihydro-1H-inden-1-one | MS (ESI+) m/z 416.2 (M + H). |
| 3-8-3 | Ethyl 1-(6-(6-methyl-3-oxo-2,3-dihydro-1H-inden-4-yl)pyridin-2-yl)-5-(trifluoromethyl)-1H-pyrazole-4-carboxylate | Intermediate 1-2-1 and Intermediate 3-1-E | MS (ESI+) m/z 430.3 (M + H). |
| 3-8-4 | Ethyl 5-(difluoromethyl)-1-(6-(3-oxo-2,3-dihydro-1H-inden-4-yl)pyridin-2-yl)-1H-pyrazole-4-carboxylate | Intermediate 1-4-6 and 7-bromo-2,3-dihydro-1H-inden-1-one | MS (ESI+) m/z 398.3 (M + H). |

| Intermediate | Structure/Chemical Name | Starting material(s) | MS or NMR data |
|---|---|---|---|
| 3-8-5 | 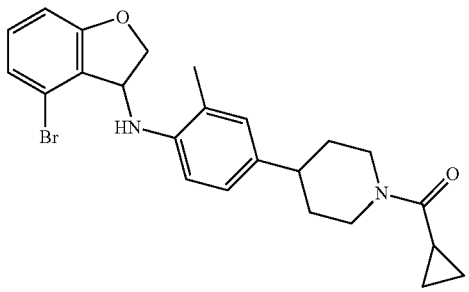<br>Ethyl 5-methyl-1-(3-(3-oxo-2,3-dihydro-1H-inden-4-yl)phenyl)-1H-pyrazole-4-carboxylate | Intermediate 1-5 and 7-bromo-2,3-dihydro-1H-inden-1-one | MS (ESI+) m/z 361.3 (M + H). |

Intermediate 3-9. (±)-4-(4-((4-bromo-2,3-dihydrobenzofuran-3-yl)amino)-3-methylphenyl)piperidin-1-yl)(cyclopropyl)methanone

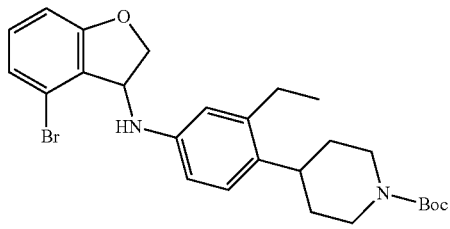 [SMILES: CCc1cc(NC2COc3cccc(Br)c32)ccc1C1CCN(C(=O)OC(C)(C)C)CC1]

Sodium cyanoborohydride (377 mg, 6.00 mmol) was added to a solution of Intermediate 2-8 (776 mg, 3.00 mmol), 4-bromobenzofuran-3(2H)-one (CAS #1020966-78-2; 640 mg, 3.00 mmol), and AcOH (860 µl, 15.00 mmol) in MeOH (15 mL) at room temperature. The reaction mixture was stirred at room temperature for 6 hours before another portion of sodium cyanoborohydride (377 mg, 6.00 mmol) was added. After a total of 24 hours stirring, the reaction mixture was partitioned between $CH_2Cl_2$ and saturated aq. sodium bicarbonate. The organic layer was passed through a phase separator and the filtrate was concentrated onto Celite®. The residue was purified by silica gel flash chromatography to afford the title compound. MS (ESI+) m/z 457.3 (M+H).

Intermediate 3-10. (±)-tert-Butyl 4-(4-((4-bromo-2,3-dihydrobenzofuran-3-yl)amino)-2-ethylphenyl)piperidine-1-carboxylate The title compound was synthesized starting from 4-bromo-benzofuran-1-one and tert-butyl 4-(4-amino-2-ethylphenyl)piperidine-1-carboxylate (Intermediate 2-10) by a similar method described for the synthesis of Intermediate 3-5-C but using $NaCNBH_3$ in the place of $NaB(OAc)_3H$. $^1H$ NMR (400 MHz. $CDCl_3$): δ 7.15-7.03 (m, 3H), 6.82 (d, J=8.4 Hz, 1H), 6.46-6.44 (m, 2H), 5.07-5.06 (m, 1H), 4.67-4.63 (m, 1H), 4.58-4.55 (m, 1H), 4.24 (br.s, 2H), 3.93 (br.s, 1H), 2.78-2.70 (m, 3H), 2.62 (q, J=7.6, 15.2 Hz, 2H), 1.72-1.58 (m, 4H), 1.49 (s, 9H), 1.26 (t, J=7.2 Hz, 3H).

Intermediate 3-11. (±)-tert-Butyl 4-(4-(4-bromo-2,3-dihydrobenzofuran-3-yl)amino)-3-methylphenyl)piperidine-1-carboxylate

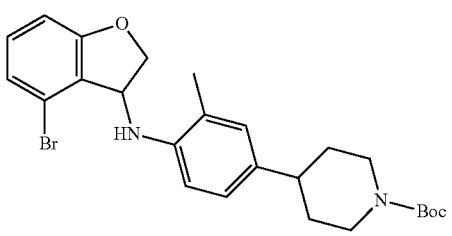 [SMILES: Cc1cc(C2CCN(C(=O)OC(C)(C)C)CC2)ccc1NC1COc2cccc(Br)c21]

The title compound was synthesized starting from 4-bromo-benzofuran-1-one and tert-butyl 4-(4-amino-3-methylphenyl)piperidine-1-carboxylate (Intermediate 2-13) by a similar method described for the synthesis of Intermediate 3-5-C but using $NaCNBH_3$ in the place of $NaB(OAc)_3H$. $^1H$ NMR (400 MHz, $CDCl_3$): δ 7.17-7.08 (m, 2H), 6.99-6.95 (m, 2H), 6.84 (d, J=7.6 Hz, 1H), 6.45 (d, J=8.4 Hz, 1H), 5.07 (d, J=3.2 Hz, 1H), 4.71 (dd, J=6.8, 9.2 Hz, 1H), 4.55 (dd, J=2.8, 9.6 Hz, 1H), 4.22 (br.s, 2H), 3.85 (s, 1H), 2.78 (br.s, 2H), 2.57-2.51 (m, 1H), 2.12 (s, 3H), 1.79 (d, J=12.8 Hz, 2H), 1.63-1.59 (m, 2H), 1.48 (s, 9H).

Intermediate 3-12

Intermediate 3-12-A. tert-Butyl 2-chloro-5',6'-dihydro-[3,4'-bipyridine]-1'(2'H)-carboxylate

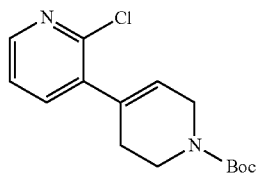 [SMILES: CC(C)(C)OC(=O)N1CC=C(c2cccnc2Cl)CC1]

To a solution of 3-bromo-2-chloropyridine (CAS #52200-48-3, 2.89 g, 15 mmol) and tert-butyl 4-(4,4,5,5-tetramethyl-1,3,2-dioxaborolan-2-yl)-5,6-dihydropyridine-1 (2H)-carboxylate (CAS #286961-14-6, 4.87 g, 15.75 mmol) in toluene (100 mL)/ethanol (15 mL) were added 2N $Na_2CO_3$ solution (22.5 mL, 45.0 mmol) and $Pd(PPh_3)_4$ (0.87 g, 0.75 mmol). The mixture was then stirred at 120° C. for 2 h and then cooled to room temperature. The reaction mixture was diluted with brine and extracted three times with EtOAc. The combined organic layers were washed with brine and dried over $Na_2SO_4$, filtered, and then concentrated. The resulting residue was purified by silica gel flash column chromatography (heptane/EtOAc=1/0 to 1/2) to afford the title compound. MS (ESI+) m/z 295.1, 297.1 (M+H).

Intermediate 3-12-B. tert-Butyl 2-ethyl-5',6'-dihydro-[3,4'-bipyridine]-1'(2'H)-carboxylate

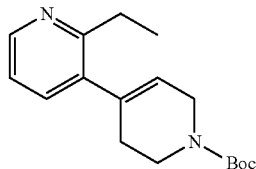 [SMILES: CCc1ncccc1C1=CCN(C(=O)OC(C)(C)C)CC1]

To a solution of tert-butyl 2-chloro-5',6'-dihydro-[3,4'-bipyridine]-1'(2'H)-carboxylate (1 g, 3.39 mmol) in THF (20 mL) were added $Pd(dppf)Cl_2 \cdot CH_2Cl_2$ adduct (0.208 g, 0.254 mmol) and $K_2CO_3$ solid (1.407 g, 10.18 mmol), followed by diethylzinc (15% w/w in toluene, 10.68 mL). The mixture was then stirred at room temperature for 1 h, and then at 50° C. for 3 h. The reaction at 0° C. was quenched with sat. aq. $NH_4Cl$. The mixture was then extracted three times with EtOAc. The combined organic layers were dried over $Na_2SO_4$, filtered, and then concentrated. The resulting residue was purified by silica gel flash column chromatography (heptane/EtOAc=1/0 to 0/1) to afford the title compound. MS (ESI+) m/z 289.6 (M+H).

Intermediate 3-12-C. tert-Butyl 4-(2-ethylpyridin-3-yl)piperidine-1-carboxylate

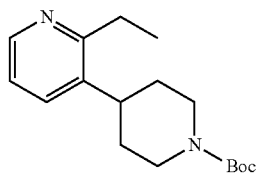 [SMILES: CCc1ncccc1C1CCN(C(=O)OC(C)(C)C)CC1]

A mixture of tert-butyl 2-ethyl-5',6'-dihydro-[3,4'-bipyridine]-1'(2'H)-carboxylate (810 mg, 2.81 mmol) and Pd/C 10% wet (299 mg, 0.281 mmol) in MeOH (20 mL) was stirred at room temperature under hydrogen atmosphere for 0.5 h. The reaction mixture was then filtered through a plug of Celite®, which was rinsed with MeOH. The filtrate was concentrated to afford the title compound. MS (ESI+) m/z 291.4 (M+H).

Intermediate 3-12-D. 3-(1-(tert-Butoxycarbonyl)piperidin-4-yl)-2-ethylpyridine 1-oxide

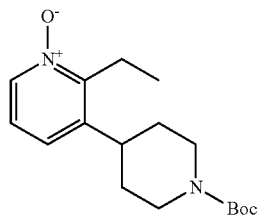 [SMILES: CCc1c(C2CCN(C(=O)OC(C)(C)C)CC2)ccc[n+]1[O-]]

To a solution of tert-butyl 4-(2-ethylpyridin-3-yl)piperidine-1-carboxylate (350 mg, 1.2 mmol) in chloroform (15 mL) was added m-CPBA (77% purity, 520 mg, 3.0 mmol). The reaction mixture was then stirred at room temperature for 0.5 h. The reaction was then quenched with 1N $Na_2S_2O_3$, and a saturated $NaHCO_3$ aqueous solution. To the mixture was then added sat. aq. $NaHCO_3$. The reaction mixture was then extracted three times with EtOAc. The combined organic layers were washed with brine and dried over $Na_2SO_4$, filtered, and then concentrated. The resulting residue was absorbed onto silica gel, which was purified by silica gel flash column chromatography (0 to 15% MeOH in $CH_2Cl_2$) to afford the title compound. MS (ESI+) m/z 307.2 (M+H).

Intermediate 3-12. (±)-tert-Butyl 4-(6-((7-bromo-2,3-dihydro-1H-inden-1-yl)amino)-2-ethylpyridin-3-yl)piperidine-1-carboxylate

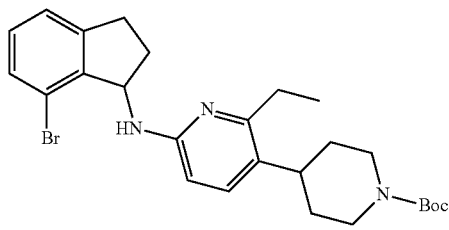 [SMILES: CCc1nc(NC2CCc3cccc(Br)c32)ccc1C1CCN(C(=O)OC(C)(C)C)CC1]

To a solution of 7-bromo-2,3-dihydro-1H-inden-1-amine (*ACS Med. Chem. Lett.* 2011, 2, 565-570) (346 mg, 1.63 mmol) and 3-(1-(tert-butoxycarbonyl)piperidin-4-yl)-2-ethylpyridine 1-oxide (250 mg, 0.816 mmol) and DIPEA (143 μL, 0.816 mmol) in $CH_2Cl_2$ (5 mL), was added PyBrOP (761 mg, 1.632 mmol). The reaction was stirred at room temperature for 76 h. The reaction was quenched with 1N citric acid solution. The bi-layer was then separated. The aqueous layer was extracted twice with $CH_2Cl_2$. The combined organic layers were washed with brine and dried over $Na_2SO_4$, filtered, and then concentrated. The resulting residue was absorbed onto silica gel, and purified by silica gel flash column chromatography (0 to 60% EtOAc in CH$_2$Cl$_2$) to afford the title compound. MS (ESI+) m/z 499.9 (M+H).

Intermediate 4-1

Intermediate 4-1-A. Ethyl 1-(6-(1H-indol-7-yl)pyridin-2-yl)-5-(trifluoromethyl)-1H-pyrazole-4-carboxylate

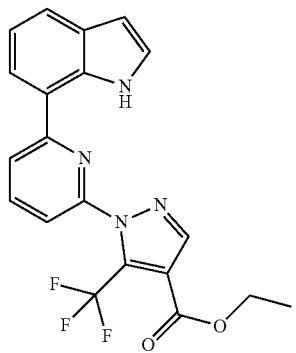 [SMILES: CCOC(=O)c1cnn(-c2cccc(-c3cccc4cc[nH]c34)n2)c1C(F)(F)F]

Bis(triphenylphosphine) palladium(II) dichloride (CAS #13965-03-2, 46.2 mg, 0.066 mmol) was added to a solution of 7-(4,4,5,5-tetramethyl-1,3,2-dioxaborolan-2-yl)-1H-indole (CAS #642494-37-9; 448 mg, 1.842 mmol) and Intermediate 1-1 (600 mg, 1.648 mmol) in acetonitrile (8.0 mL) and 1.0 M Na$_2$CO$_3$ (5.27 mL, 5.27 mmol). The reaction mixture was sealed and stirred at 70° C. for 16 h, after which it was cooled to room temperature. The reaction mixture was then filtered through a plug of Celite®. The filtrate was diluted with EtOAc and the organic layer was washed successively with H$_2$O and brine. The organic layer was dried over Na$_2$SO$_4$, filtered, and then concentrated. The resulting residue was purified by flash column chromatography on silica gel (heptane/EtOAc=100/0 to 50/50) to afford the title compound. MS (ESI+) m/z 401.1 (M+H).

Intermediate 4-1. Ethyl 1-(6-(indolin-7-yl)pyridin-2-yl)-5-(trifluoromethyl)-1H-pyrazole-4-carboxylate

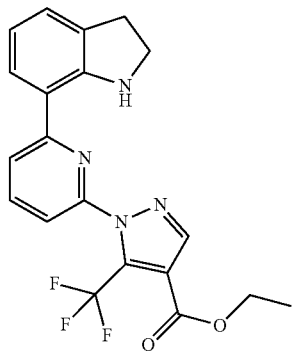 [SMILES: CCOC(=O)c1cnn(-c2cccc(-c3cccc4c3NCC4)n2)c1C(F)(F)F]

Triethylsilane (CAS #617-86-7; 1.08 g, 9.24 mmol) and TFA (1.05 g, 9.24 mmol) were added to a solution of Intermediate 4-1-A (370 mg, 0.924 mmol) in dichloromethane (5 mL). The reaction mixture was stirred at room temperature for 24 h, and then concentrated. The resulting residue was partitioned between EtOAc and saturated NaHCO$_3$. The isolated organic layer was washed with brine, dried over Na$_2$SO$_4$, filtered, and then concentrated. The resulting residue was purified by flash column chromatography on silica gel (heptane/EtOAc=100/0 to 50/50) to afford the title compound. $^1$H NMR (400 MHz, CDCl$_3$) δ 8.15 (s, 1H) 7.80-8.02 (m, 2H) 7.51 (d, J=8.08 Hz, 1H) 7.40 (d, J=7.45 Hz, 1H) 7.14 (d, J=7.20 Hz, 1H) 6.71 (t, J=7.58 Hz, 1H) 4.40 (q, J=7.07 Hz, 2H) 3.67 (t, J=8.46 Hz, 2H) 3.07 (t, J=8.40 Hz, 2H) 1.40 (t, J=7.14 Hz, 3H).

Intermediate 4-2

Intermediate 4-2-A. Ethyl 1-(6-(1H-indol-7-yl)pyridin-2-yl)-5-ethyl-1H-pyrazole-4-carboxylate

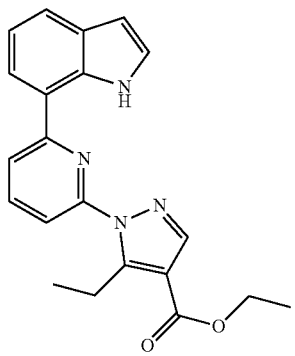 [SMILES: CCOC(=O)c1cnn(-c2cccc(-c3cccc4cc[nH]c34)n2)c1CC]

Bis(triphenylphosphine)palladium(II) dichloride (0.11 g, 0.154 mmol) was added to a solution of 7-(4,4,5,5-tetramethyl-1,3,2-dioxaborolan-2-yl)-1H-indole (0.84 g, 3.45 mmol) and Intermediate 1-4-2 (1 g, 3.08 mmol) in acetonitrile (16 mL) and 1.0 M Na$_2$CO$_3$ (9.25 mL, 9.25 mmol). The reaction mixture was sealed and stirred at 70° C. for 16 h. The mixture was then cooled to room temperature, and then filtered through a plug of Celite®. The filtrate was diluted with EtOAc and the organic layer was washed successively with H$_2$O and brine. The organic layer was dried over Na$_2$SO$_4$, filtered, and then concentrated. The resulting residue was purified by flash column chromatography on silica gel (0-50% EtOAc/heptane gradient) to afford the title compound. MS (ESI+) m/z 361.3 (M+H).

Intermediate 4-2. Ethyl 5-ethyl-1-(6-(indolin-7-yl)pyridin-2-yl)-1H-pyrazole-4-carboxylate

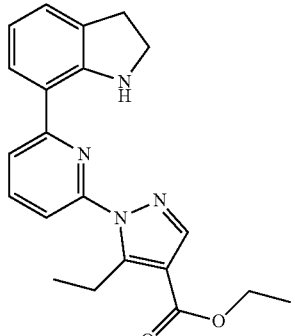

Triethylsilane (2.7 mL, 17 mmol) and TFA (1.3 mL, 17 mmol) were added to a solution of Intermediate 4-2-A (611 mg, 1.7 mmol) in dichloromethane (10 mL). The mixture was stirred at room temperature for 24 h, and then concentrated. The resulting residue was partitioned between EtOAc and saturated NaHCO$_3$. The isolated organic layer was washed with brine, dried over Na$_2$SO$_4$, filtered, and then concentrated. The resulting residue was purified by silica gel flash column chromatography (0-50% EtOAc/heptane gradient) to afford the title compound. MS (ESI+) m/z 363.3 (M+H).

Intermediate 5-1

Intermediate 5-1-A. tert-Butyl 4-(2-ethyl-4-(methoxycarbonyl)phenyl)-6,6-dihydropyridine-1(2H)-carboxylate

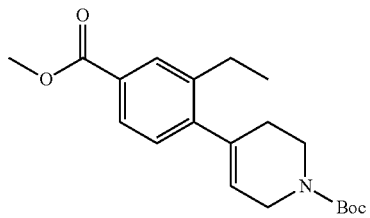 [SMILES: CCc1cc(C(=O)OC)ccc1C1=CCN(C(=O)OC(C)(C)C)CC1]

To a mixture of methyl 4-bromo-3-ethylbenzoate (CAS #1008769-90-1) (1.4 g, 5.76 mmol) and tert-butyl 4-(4,4,5,5-tetramethyl-1,3,2-dioxaborolan-2-yl)-5,6-dihydropyridine-1(2H)-carboxylate (CAS #286961-14-6, 2.32 g, 7.49 mmol) in DMF (20 mL) was added 2.0 M aq. potassium phosphate (8.64 mL, 17.28 mmol), followed by Pd(dppf)Cl$_2$.CH$_2$Cl$_2$ adduct (260 mg, 0.317 mmol). The mixture was stirred at 110° C. for 2.0 h, and then cooled to room temperature. The reaction mixture was filtered through a plug of Celite®. The filtrate was diluted with EtOAc. The organic layer was then washed with H$_2$O, dried over Na$_2$SO$_4$, filtered, and then concentrated. The resulting residue was purified by silica gel flash column chromatography (0-50% EtOAc/heptane gradient) to afford the title compound. $^1$H NMR (400 MHz, Chloroform-d) δ 7.90 (s, 1H) 7.81 (dd, J=7.96, 1.52 Hz, 1H) 7.12 (d, J=7.96 Hz, 1H) 5.57 (br. s., 1H) 4.04 (br., 2H) 3.91 (s, 3H) 3.63 (t, J=5.49 Hz, 2H) 2.65 (q, J=7.58 Hz, 2H) 2.34 (br. s., 2H) 1.51 (s, 9H) 122 (t, J=7.58 Hz, 3H).

Intermediate 5-1-8. tert-Butyl 4-(2-ethyl-4-(methoxycarbonyl)phenyl)piperidine-1-carboxylate

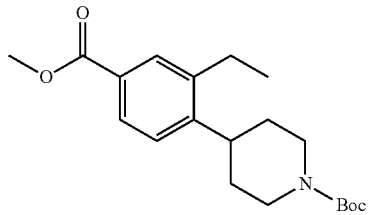 [SMILES: CCc1cc(C(=O)OC)ccc1C1CCN(C(=O)OC(C)(C)C)CC1]

A mixture of Intermediate 5-1-A (1.75 g, 5.07 mmol) and 10% Pd/C (175 mg) in EtOH (200 mL) was stirred under H$_2$ atmosphere at room temperature for 2 h. The reaction mixture was then filtered through a plug of Celite® which was then rinsed with EtOH. The filtrate was then concentrated to furnish the title compound directly. $^1$H NMR (400 MHz, Chloroform-d) δ 7.81-7.88 (m, 2H) 7.23-7.26 (m, 1H) 4.27 (br. s., 2H) 3.90 (s, 3H) 2.88-2.99 (m, 1H) 2.82 (t, J=11.75 Hz, 2H) 2.73 (q, J=7.49 Hz, 2H) 1.59-1.78 (m, 4H) 1.49 (s, 9H) 1.23-1.27 (t, J=8.0 Hz, 3H).

Intermediate 5-1. tert-Butyl 4-(2-ethyl-4-(hydroxymethyl)phenyl)piperidine-1-carboxylate

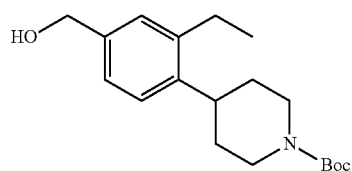 [SMILES: CCc1cc(CO)ccc1C1CCN(C(=O)OC(C)(C)C)CC1]

To a solution of Intermediate 6-1-B (1.3 g, 3.74 mmol) in THF (16 mL) was added a solution of 1.0M lithium aluminum hydride in THF (4.5 mL, 4.5 mmol) dropwise. The mixture was then stirred at 0° C. for 1 h. The reaction was quenched with 0.5 M NaOH solution, and then diluted with H$_2$O and EtOAc. The mixture was then filtered through a plug of Celite®. The organic phase was then separated. The organic phase was washed with brine, dried over Na$_2$SO$_4$ and concentrated. The resulting residue was purified by silica gel flash column chromatography (0-50% EtOAc/heptane gradient) to afford the title compound. $^1$H NMR (400 MHz, DMSO-d$_6$) δ 6.98-7.19 (m, 3H) 5.02 (t, J=5.68 Hz, 1H) 4.41 (d, J=5.68 Hz, 2H) 4.07 (d, J=12.00 Hz, 2H) 2.77-2.96 (m, 3H) 2.64 (q, J=7.49 Hz, 2H) 1.58-1.68 (m, 2H) 1.45-1.55 (m, 2H) 1.37-1.44 (m, 9H) 1.15 (t, J=7.52 Hz, 3H).

Intermediate 65-2. tert-Butyl 4-(4-(bromomethyl)-2-ethylphenyl)piperidine-1-carboxylate

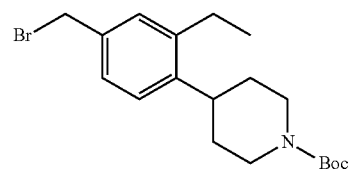 [SMILES: CCc1cc(CBr)ccc1C1CCN(C(=O)OC(C)(C)C)CC1]

Triphenylphosphine (723 mg, 2.76 mmol) and CBr$_4$ (916 mg, 2.76 mmol) were added to a solution of Intermediate 5-1 (840 mg, 2.63 mmol) in dichloromethane (14 mL). The mixture was then stirred at room temperature for 16 h. and then concentrated. The resulting residue was purified by flash column chromatography (0-20% EtOAc/heptane gradient) to afford the title compound. MS (ESI+) m/z 326.2 (M-tBu+2H).

Intermediate 5-3

Intermediate 5-3-A. Methyl 3-ethyl-4-(piperidin-4-yl)benzoate

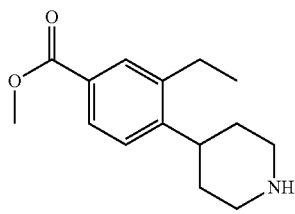 [SMILES: CCc1cc(C(=O)OC)ccc1C1CCNCC1]

A mixture of Intermediate 5-1-B (3.5 g, 10.1 mmol) and TFA (10 mL) in CH$_2$Cl$_2$ (100 mL) was stirred at room temperature for 0.5 h, and then concentrated. The resulting residue was dissolved in CH$_2$Cl$_2$, which was then washed successively with satd. NaHCO$_3$ and brine, dried over Na$_2$SO$_4$, filtered, and then concentrated to furnish the title compound. MS (ESI+) m/z 248.3 (M+H).

Intermediate 5-3-8. Methyl 4-(1-(cyclopropanecarbonyl)piperidin-4-yl)-3-ethylbenzoate

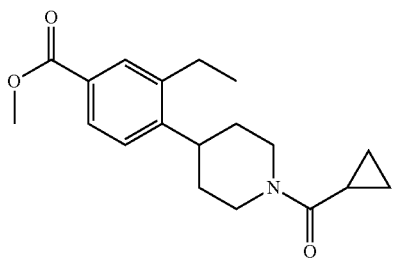 [SMILES: CCc1cc(C(=O)OC)ccc1C1CCN(C(=O)C2CC2)CC1]

To a solution of Intermediate 5-3-A (2.23 g, 9.02 mmol) and triethylamine (1.89 mL, 13.5 mmol) in CH$_2$Cl$_2$ (50 mL) at 0° C. was added cyclopropanecarbonyl chloride (1.13 g, 10.8 mmol). The mixture was then stirred at room temperature for 1.5 h. The reaction was quenched with sat. aq. NaHCO$_3$. The mixture was then extracted twice with CH$_2$Cl$_2$. The combined organic layers were then dried over Na$_2$SO$_4$, filtered, and then concentrated. The resulting residue was purified by silica gel flash column chromatography (heptane/EtOAc=1/0 to 0/1) to afford the title compound. MS (ESI+) m/z 316.4 (M+H).

Intermediate 5-3-C. Cyclopropyl(4-(2-ethyl-4-(hydroxymethyl)phenyl)piperidin-1-yl)methanone

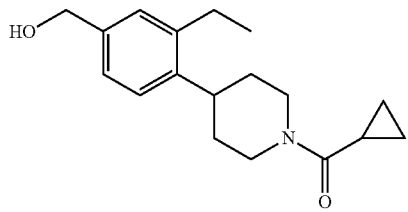 [SMILES: CCc1cc(CO)ccc1C1CCN(C(=O)C2CC2)CC1]

To a solution of Intermediate 5-3-B (4.2 g, 13.3 mmol) in THF (50 mL) at 0° C. was added LiBH$_4$ (2M in THF, 20 ml, 40 mmol), followed by MeOH (3.2 mL). The mixture was then stirred at room temperature for 2 h and then 60° C. for 2 h. The reaction was quenched with sat. aq. NH$_4$Cl at 0° C. The mixture was concentrated, and then diluted with brine, and then extracted three times with EtOAc. The combined organic extracts were dried over Na$_2$SO$_4$, filtered, and then concentrated. The resulting residue was purified by silica gel flash column chromatography (heptane/EtOAc=1/0 to 0/1) to afford the title compound. MS (ESI+) m/z 288.3 (M+H).

Intermediate 5-3. (4-(4-(Bromomethyl)-2-ethylphenyl)piperidin-1-yl)(cyclopropyl)methanone

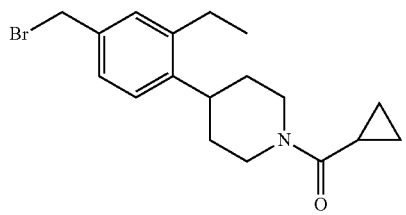 [SMILES: CCc1cc(CBr)ccc1C1CCN(C(=O)C2CC2)CC1]

To a solution of Intermediate 5-3-C (600 mg, 2.09 mmol) in CHCl$_2$ (20 mL) was added CBr$_4$ (1.04 g, 3.13 mmol), followed by PPh$_3$ (0.82 g, 3.13 mmol). The mixture was then stirred at room temperature for 24 h. The mixture was diluted with CH$_2$Cl$_2$, and then washed twice with brine, dried over MgSO$_4$, filtered, and then concentrated. The resulting residue was purified by silica gel flash column chromatography (heptane/EtOAc) to afford the title compound. MS (ESI+) m/z 350.3, 352.1 (M+H).

Intermediate 54. tert-Butyl 4-(4-(hydroxymethyl)-3-methylphenyl)piperidine-1-carboxylate

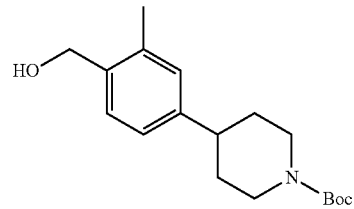 [SMILES: Cc1cc(C2CCN(C(=O)OC(C)(C)C)CC2)ccc1CO]

The title compound was synthesized starting from methyl 4-bromo-2-methylbenzoate (CAS #148547-19-7) as outlined in the synthesis of Intermediate 5-1. MS (ESI+) m/z 306.2 (M+H).

Intermediate 5-5. tert-Butyl 4-(4-(bromomethyl)-3-methylphenyl)piperidine-1-carboxylate

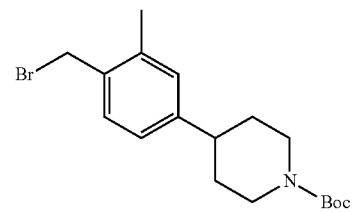 [SMILES: Cc1cc(C2CCN(C(=O)OC(C)(C)C)CC2)ccc1CBr]

The title compound was synthesized starting from Intermediate 5-4 by the method described for the synthesis of Intermediate 5-2. MS (ESI+) m/368.3 (M+H).

Intermediate 5-6. (4-(4-(Bromomethyl)-3-methylphenyl)piperidin-1-yl)(cyclopropyl)methanone

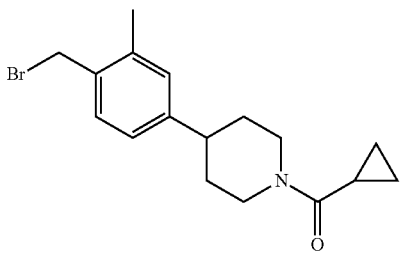 [SMILES: Cc1cc(C2CCN(C(=O)C3CC3)CC2)ccc1CBr]

The title compound was synthesized starting from methyl 4-bromo-2-methylbenzoate as outlined in the synthesis of Intermediate 5-3. MS (ESI+) m/z 336.1 (M+H).

Intermediate 6-1

Intermediate 6-1-A. tert-Butyl 4-(4-formyl-3-methylphenyl)piperidine-1-carboxylate

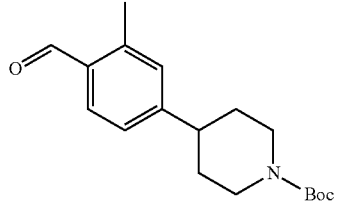 [SMILES: Cc1cc(C2CCN(C(=O)OC(C)(C)C)CC2)ccc1C=O]

To a mixture of tert-butyl 4-(4-(hydroxymethyl)-3-methylphenyl)piperidine-1-carboxylate, Intermediate 5-4, (1.04 g, 3.41 mmol) and H$_2$O (0.06 mL, 3.41 mmol) in CH$_2$Cl$_2$ (34 mL) was added Dess-Martin periodinane (1.59 g, 3.75 mmol). The mixture was then stirred at room temperature for 1.5 h. The reaction mixture was diluted with 1N NaOH (15 mL), and then extracted with CH$_2$Cl$_2$. The organic layer was passed through an ISOLUTE® phase separator, and then concentrated. The resulting residue was purified by silica gel flash chromatography to afford the title compound. $^1$H NMR (400 MHz, CDCl$_3$) δ 10.24 (s, 1H), 7.77 (d, J=7.9 Hz, 1H), 7.22 (dd, J=7.9, 1.7 Hz, 1H), 7.15-7.08 (m, 1H), 4.36-4.22 (m, 2H), 2.89-2.76 (m, 2H), 2.76-2.62 (m, 4H), 1.89-1.78 (m, 2H), 1.71-1.60 (m, 2H), 1.51 (s, 9H).

Intermediate 6-1-B. (7-Methoxy-2,3-dihydro-1H-inden-1-yl)triphenylphosphonium bromide

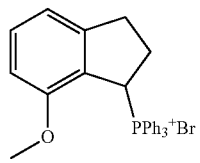

A mixture of 7-methoxyindan-1-ol (CAS #34985-44-9) (0.86 g, 5.23 mmol) and triphenylphosphine hydrobromide (1.85 g, 5.23 mmol) in toluene (10.5 ml) was stirred at 90° C. for 16 h, and then cooled to room temperature. The solvent from the resulting heterogeneous mixture was decanted, and then diethyl ether was added to the mixture, which was then stirred for 0.5 h at room temperature. The resulting solid was collected by filtration, and then washed with diethyl ether to furnish the title compound. MS (ESI+) m/z 409.3 (M-Br).

Intermediate 6-1-C. tert-Butyl 4-(4-((7-methoxy-2,3-dihydro-1H-inden-1-ylidene)methyl)-3-methylphenyl)piperidine-1-carboxylate

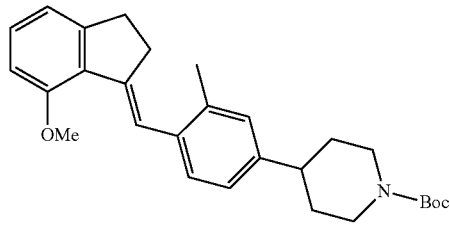 [SMILES: COc1cccc2c1/C(=C/c1ccc(C3CCN(C(=O)OC(C)(C)C)CC3)cc1C)CC2]

To a solution of (7-methoxy-2,3-dihydro-1H-inden-1-yl)triphenylphosphonium bromide (1.22 g, 2.50 mmol) in THF (12.5 mL) at room temperature was added potassium tert-butoxide (1M in THF) (2.74 mL, 2.74 mmol). The mixture was stirred at room temperature for 0.5 h. To the reaction mixture was then added a solution of tert-butyl 4-(4-formyl-3-methylphenyl)piperidine-1-carboxylate (0.75 g, 2.49 mmol) in THF (12.5 mL). The mixture was then stirred at 70° C. for 16 h. The reaction mixture was then diluted with CH$_2$Cl$_2$, and then washed with half saturated NH$_4$Cl. The organic layer was passed through an ISOLUTE® phase separator, and then concentrated. The resulting residue was purified by silica gel flash chromatography to afford the title compound. MS (ESI+) m/z 434.3 (M+H).

Intermediate 6-1-D. (±)-tert-Butyl 4-(4-((7-methoxy-2,3-dihydro-1H-inden-1-yl)methyl)-3-methylphenyl)piperidine-1-carboxylate

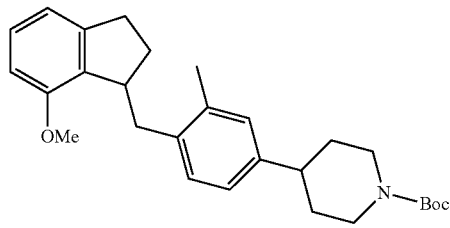 [SMILES: COc1cccc2c1C(Cc1ccc(C3CCN(C(=O)OC(C)(C)C)CC3)cc1C)CC2]

A mixture of tert-butyl 4-(4-methoxy-2,3-dihydro-1 inden-1-ylidene)methyl)-3-methylphenyl)piperidine-1-carboxylate (0.72 g, 1.67 mmol) and Pd/C (10%, 0.09 g, 0.83 mmol) in MeOH/EtOAc (20 mL/2 mL) was stirred at room temperature under H$_2$ atmosphere for 3 h. The reaction mixture was filtered through a plug of Celite®, which was rinsed with MeOH. The filtrate was concentrated to afford the title compound. MS (ESI+) m/z 380.3 (M-tBu+2H).

Intermediate 6-1-E. (±)-4-(7-Methoxy-2,3-dihydro-1H-inden-1-yl)methyl)-3-methylphenyl)piperidine

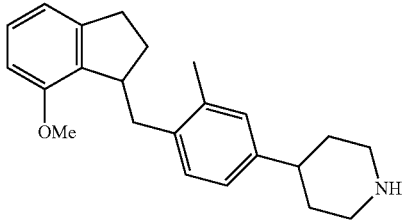 [SMILES: COc1cccc2c1C(Cc1ccc(C3CCNCC3)cc1C)CC2]

To a solution of tert-butyl 4-(4-((7-methoxy-1H-inden-1-yl)methyl)-3-methylphenyl)piperidine-1-carboxylate (0.3 mg, 0.68 mmol) in MeOH (2 mL) at 0° C. was added 4M HCl in dioxane) (0.34 mL, 1.37 mmol). The mixture was then stirred at room temperature for h. The reaction was quenched with 1M aq. Na₂CO₃ (ca. 1.5 mL). The mixture was then extracted twice with CH₂Cl₂. The combine organic layers were passed through an ISOLUTE® phase separator, and then concentrated to furnish the title compound. MS (ESI+) m/z 336.3 (M+H).

Intermediate 6-1-F. (±)-Cyclopropyl(4-(4-((7-methoxy-2,3-dihydro-1H-inden-1-yl)methyl)-3-methylphenyl)piperidin-1-yl)methanone

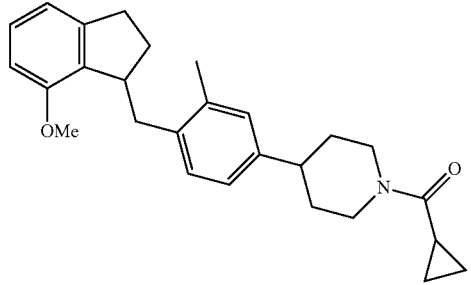 [SMILES: COc1cccc2c1C(Cc1ccc(C3CCN(C(=O)C4CC4)CC3)cc1C)CC2]

To a solution of 4-(4-((7-methoxy-2,3-dihydro-1H-inden-1-yl)methyl)-3-methylphenyl)piperidine (79 mg, 0.235 mmol) and DIPEA (82 µL, 0.471 mmol) in CH₂Cl₂ (2.4 mL) at 0° C. was added cyclopropanecarbonyl chloride (23.5 µL, 0.259 mmol). The mixture was stirred at 0° C. for 2 h, and then diluted with CH₂Cl₂. The organic layer was then washed with H₂O, and passed through a phase separator, and then concentrated to furnish the title compound. MS (ESI+) m/z 404.3 (M+H).

Intermediate 6-1-G. (±)-Cyclopropyl(4-(4-((7-hydroxy-2,3-dihydro-1H-inden-1-yl)methyl)-3-methylphenyl)piperidin-1-yl)methanone

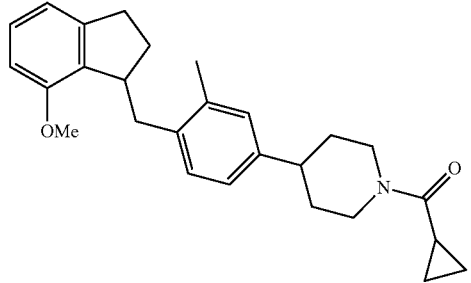 [SMILES: Cc1cc(C2CCN(C(=O)C3CC3)CC2)ccc1CC1CCc2cccc(OS(=O)(=O)C(F)(F)F)c21]

To a solution of cyclopropyl(4-(4-((7-methoxy-2,3-dihydro-1H-inden-1-yl)methyl)-3-methylphenyl)piperidin-1-yl)methanone (270 mg, 0.67 mmol) in CH₂Cl₂ (6.7 mL) at −78° C. was added a solution of BBr₃ in CH₂Cl₂ (1.34 mL, 1.34 mmol). The mixture was then stirred at 0° C. for 1 h. The reaction was quenched with a mixture of CH₂Cl₂ and satd. aq. NaHCO₃. The organic layer was passed through an ISOLUTE® phase separator, and then concentrated to furnish the title compound. MS (ESI+) m/z 390.3 (M+H).

Intermediate 6-1. (±)-3-(4-(1-(Cyclopropanecarbonyl)piperidin-4-yl)-2-methylbenzyl)-2,3-dihydro-1H-inden-4-yl trifluoromethanesulfonate

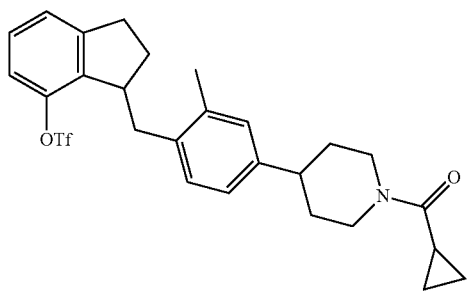

To an solution of cyclopropyl(4-(4-((7-hydroxy-2,3-dihydro-1H-inden-1-yl)methyl)-3-methylphenyl)piperidin-1-yl)methanone (156 mg, 0.40 mmol) and pyridine (97 µL, 1.20 mmol) in CH₂Cl₂ (4.0 mL) at 0° C. was added Tf₂O (95 µL, 0.56 mmol). The mixture was then stirred at 0° C. for 1.5 h. The reaction was quenched with a mixture of 1N HCl and CH₂Cl₂. The organic layer was washed with satd. aq. NaHCO₃, and then passed through an ISOLUTE® phase separator, and concentrated to furnish the title compound. MS (ESI+) m/z 522.3 (M+H).

Intermediate 6-2

Intermediate 6-2-A (±)-tert-Butyl 4-(2-ethyl-4-((7-methoxy-2,3-dihydro-1H-inden-1-yl)methyl)phenyl)piperidin-1-carboxylate

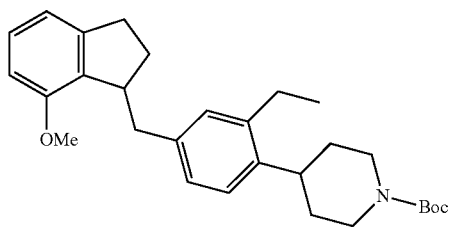 [SMILES: CCc1cc(CC2CCc3cccc(OC)c32)ccc1C1CCN(C(=O)OC(C)(C)C)CC1]

The title compound was synthesized by the similar method as outlined in the synthesis of Intermediate 6-1 (i.e. 6-1-A→6-1-B→6-1-C→6-1-D) but using tert-butyl 4-(2-ethyl-4-(hydroxymethyl)phenyl)piperidine-1-carboxylate (Intermediate 5-1) in the place of Intermediate 5-4. MS (ESI+) m/z 450.3 (M+H).

Intermediate 6-2 (±)-3-(4-(1-(Cyclopropanecarbonyl)piperidin-4-yl)-3-ethylbenzyl)-2,3-dihydro-1H-inden-4-yl trifluoromethanesulfonate

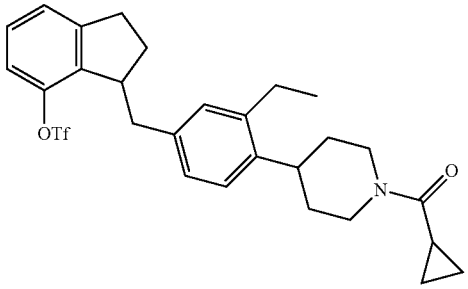 [SMILES: CCc1cc(CC2CCc3cccc(OS(=O)(=O)C(F)(F)F)c32)ccc1C1CCN(C(=O)C2CC2)CC1]

The title compound was synthesized by the similar method as outlined for the synthesis of Intermediate 6-1 (i.e. 6-1-D→6-1-E→6-1-F→6-1-G→6-1) starting with (±)-tert-Butyl 4-(2-ethyl-4-(((7-methoxy-2,3-dihydro-1H-inden-1-yl)methyl)phenyl)piperidine-1-carboxylate, Intermediate 6-2-A. MS (ESI+) m/z 536.2 (M+H).

Intermediate 6-3

Intermediate 6-3-A. (±)-3-(3-Ethyl-4-(piperidin-4-yl)benzyl)-2,3-dihydro-1H-inden-4-ol

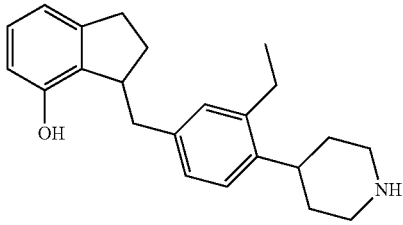 [SMILES: CCc1cc(CC2CCc3cccc(O)c32)ccc1C1CCNCC1]

To a solution of tert-butyl 4-(2-ethyl-4-((7-methoxy-2,3-dihydro-1H-inden-1-yl)methyl)phenyl)piperidine-1-carboxylate, Intermediate 6-2-A, (1.52 g, 3.38 mmol) in CH$_2$Cl$_2$ (34 mL) at −78° C. was added a solution of BBr$_3$ in CH$_2$Cl$_2$ (1M, 10 mL, 10 mmol). The mixture was stirred at 0° C. for 1 h, and then diluted with CH$_2$Cl$_2$. The reaction was then carefully quenched with satd. aq. NaHCO$_3$. The organic layer was washed successively with H$_2$O and brine, and then was passed through an ISOLUTE® Phase Separator. The organic layer was concentrated to furnish the title compound. MS (ESI+) m/z 336.5 (M+H).

Intermediate 6-3-B. (±)-tert-Butyl 4-2-ethyl-4-((7-hydroxy-2,3-dihydro-1H-inden-1-yl)methyl)phenyl)piperidine-1-carboxylate

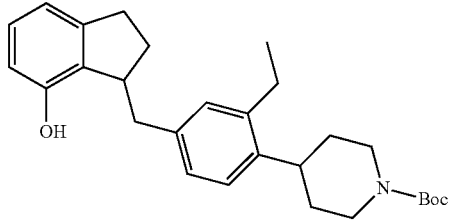 [SMILES: CCc1cc(CC2CCc3cccc(O)c32)ccc1C1CCN(C(=O)OC(C)(C)C)CC1]

To a solution of (±)-3-(3-ethyl-4-(piperidin-4-yl)benzyl)-2,3-dihydro-1H-inden-4-ol (1.14 g, 3.40 mmol) and Boc$_2$O (0.89 g, 4.08 mmol) in THF (17 mL) at 0° C. was added triethylamine (0.71 mL, 5.1 mmol). The mixture was stirred for 0.5 h, and then diluted with EtOAc. The mixture was then washed with satd. aq. NaHCO$_3$. The aqueous layer was extracted with EtOAc. The combined organic layers were washed with brine, and then passed through a phase separator and concentrated. The resulting residue was purified by silica gel flash column chromatography to afford the title compound. MS (ESI+) m/z 380.2 (M-tBu+2H).

Intermediate 6-3. (±)-tert-Butyl 4-(2-ethyl-4-((7-(((trifluoromethyl)sulfonyl)oxy)-2,3-dihydro-1H-inden-1-yl)methyl)phenyl)piperidine-1-carboxylate

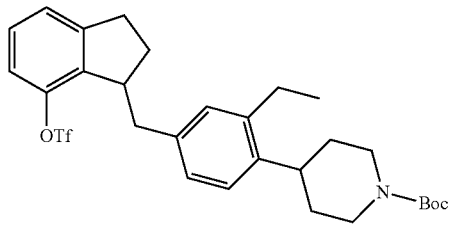 [SMILES: CCc1cc(CC2CCc3cccc(OS(=O)(=O)C(F)(F)F)c32)ccc1C1CCN(C(=O)OC(C)(C)C)CC1]

To a solution of (±)-tert-butyl 4-(2-ethyl-4-((7-hydroxy-2,3-dihydro-1H-inden-1-yl)methyl)phenyl)piperidine-1-carboxylate (540 mg, 1.24 mmol) and pyridine (0.30 mL, 3.72 mmol) in CH$_2$Cl$_2$ (12.4 mL) at 0° C. was added Tf$_2$O (0.29 mL, 1.73 mmol) dropwise. The mixture was stirring at the same temperature for 1 h. The reaction mixture was diluted with CH$_2$Cl$_2$, and then washed successively with 1N HCl, and satd. NaHCO$_3$. The organic layer was then passed through an ISOLUTE® Phase Separator and concentrated to furnish the title compound. MS (ESI+) m/z 512.2 (M-tBu+2H).

Intermediate 6-4. (±)-tert-Butyl 4-(3-methyl-4-((7-((trifluoromethyl)sulfonyl)oxy)-2,3-dihydro-1H-inden-1-yl)methyl)phenyl)piperidine-1-carboxylate

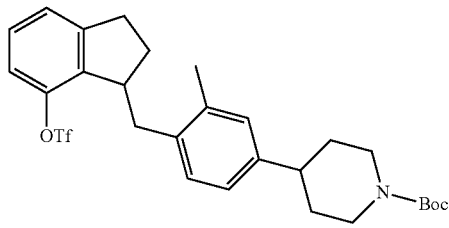 [SMILES: Cc1cc(C2CCN(C(=O)OC(C)(C)C)CC2)ccc1CC1CCc2cccc(OS(=O)(=O)C(F)(F)F)c21]

The title compound was synthesized by the similar method as outlined in the synthesis of Intermediate 6-3 but using (±)-tert-Butyl 4-(4-((7-methoxy-2,3-dihydro-1H-inden-1-yl)methyl)-3-methylphenyl)piperidine-1-carboxylate (Intermediate 6-1-D). MS (ESI+) m/z 554.2 (M+H).

Example 1

Example 1-A. (±)-Ethyl 1-(3-(3-(4-(1-(cyclopropanecarbonyl)piperidin-4-yl)-2-methylphenoxy)-2,3-dihydro-1H-inden-4-yl)phenyl)-5-(trifluoromethyl)-1H-pyrazole-4-carboxylate

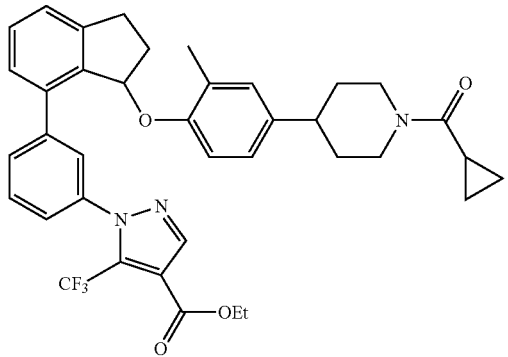 [SMILES: Cc1cc(C2CCN(C(=O)C3CC3)CC2)ccc1OC1CCc2cccc(-c3cccc(-n4ncc(C(=O)O)c4C(F)(F)F)c3)c21]

Pd(dppf)C$_2$·CH$_2$Cl$_2$ adduct (17.79 mg, 0.022 mmol) was added to a mixture of Intermediate 3-3. a) (99 mg, 0.218 mmol) and Intermediate 1-6-1 (98 mg, 0.240 mmol) in dioxane (1.0 mL) and K$_3$PO$_4$ (2M in water; 218 µl, 0.436 mmol). The reaction mixture was stirred at 80° C. under a nitrogen atmosphere for 1 h and then cooled to room temperature. Celite® was added and the resulting mixture was concentrated. The residue was purified by flash column chromatography using silica gel with a gradient of 0-50% EtOAc/heptane to provide the title compound. MS (ESI+) m/z 658.4 (M+H).

Example 1. a). (±)-1-(3-(3-(4-(1-(Cyclopropanecarbonyl)piperidin-4-yl)-2-methylphenoxy)-2,3-dihydro-1H-inden-4-yl)phenyl)-6-(trifluoromethyl)-1H-pyrazole-4-carboxylic Acid

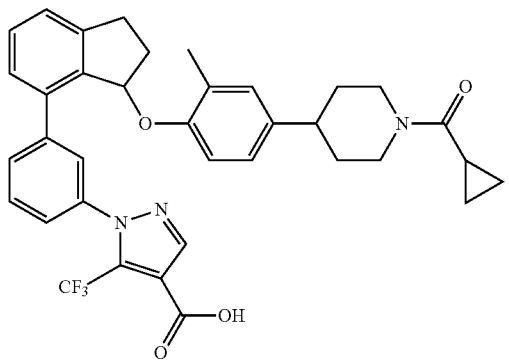

LiOH (1M in water; 0.785 mL, 0.785 mmol) was added dropwise to a solution of Example 1-A (1032 mg, 0.157 mmol) in MeOH (0.78 mL) and THF (0.78 mL) and the resulting mixture was stirred for 3 h at room temperature. 1N HCl (0.79 mL) was added to quench the excess base and the resulting mixture was then partitioned between water and EtOAc. The aqueous layer was extracted with EtOAc. The combined organic layers were concentrated. The resulting residue was purified by reverse phase HPLC (HC-B) to provide the title compound. $^1$H NMR (400 MHz, Methanol-d4) δ 7.95 (s, 1H), 7.73-7.87 (m, 2H), 7.52 (t, J=7.8 Hz, 1H), 7.49-7.43 (m, 1H), 7.42-7.32 (m, 3H), 6.92-6.86 (m, 1H), 6.86-6.82 (m, 1H), 6.74 (d, J=8.4 Hz, 1H), 5.59 (d, J=4.9 Hz, 1H), 4.64 (d, J=13.1 Hz, 1H), 4.45 (d, J=13.5 Hz, 1H), 3.25-3.16 (m, 2H), 3.00-2.91 (m, 1H), 2.78-2.63 (m, 2H), 2.34-2.21 (m, 2H), 2.05-1.96 (m, 1H), 1.96-1.88 (m, 4H), 1.88-1.79 (m, 1H), 1.67-1.41 (m, 2H), 0.94-0.86 (m, 2H), 0.86-0.79 (m, 2H). HRMS; calcd. for C$_{36}$H$_{35}$F$_3$N$_3$O$_4$(M+H) 630.2580, found 630.2615.

Example 1. b). (+)-1-(3-(3-(4-(1-Cyclopropanecarbonyl)piperidin-4-yl)-2-methylphenoxy)-2,3-dihydro-1H-inden-4-yl)phenyl)-5-(trifluoromethyl)-1H-pyrazole-4-carboxylic acid and (−)-1-(3-(3-(4-(1-(Cyclopropanecarbonyl)piperidin-4-yl)-2-methylphenoxy)-2,3-dihydro-1H-inden-4-yl)phenyl)-6-(trifluoromethyl)-1H-pyrazole-4-carboxylic Acid Resolution of the enantiomers of (±)-1-(3-(3-(4-(1-(cyclopropanecarbonyl)piperidin-4-yl)-2-methylphenoxy)-2,3-dihydro-1H-inden-4-yl)phenyl)-5-(trifluoromethyl)-1H-pyrazole-4-carboxylic acid was achieved by chiral SFC using CHIRALPAK® AD-H column with 20% (5 mM NH$_4$OH in 2-propanol) in CO$_2$ to afford (+)-1-(3-(3-(4-(1-(cyclopropanecarbonyl)piperidin-4-yl)-2-methylphenoxy)-2,3-dihydro-1H-inden-4-yl)phenyl)-5-(trifluoromethyl)-1H-pyrazole-4-carboxylic acid (t$_r$=5.85 min) and (−)-1-(3-(3-(4-(1-(cyclopropanecarbonyl)piperidin-4-yl)-2-methylphenoxy)-2,3-dihydro-1H-inden-4-yl)phenyl)-5-(trifluoromethyl)-1H-pyrazole-4-carboxylic acid (t$_r$=6.95 min).

Example 2

Example 2-A. (+)-(S)-Ethyl-1-(3-(3-(4-(1-(cyclopropanecarbonyl)piperidin-4-yl)-2-methylphenoxy)-2,3-dihydro-1H-inden-4-yl)phenyl)-6-methyl-1H-pyrazole-4-carboxylate

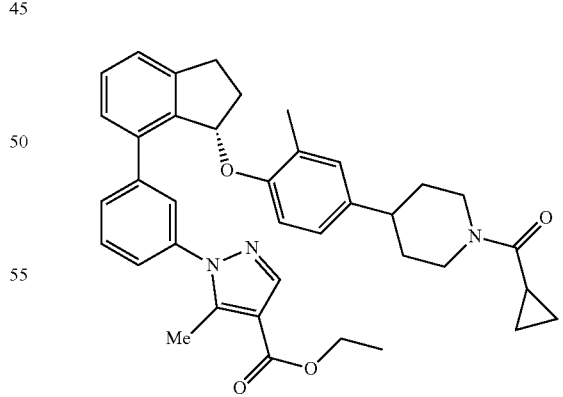

Example 2-A was prepared as described in Example 1-A using Intermediate 3-3. b) and Intermediate 1-6 to provide (+)-ethyl-1-(3-(3-(4-(1-(cyclopropanecarbonyl)piperidin-4-yl)-2-methylphenoxy)-2,3-dihydro-1H-inden-4-yl)phenyl)-5-methyl-1H-pyrazole-4-carboxylate. MS (ESI+) m/z 604.4 (M+H).

Example 2. (+)-(S)-1-(3-(3-(4-(1-(Cyclopropanecarbonyl)piperidin-4-yl)-2-methylphenoxy)-2,3-dihydro-1H-inden-4-yl)phenyl)-6-methyl-1H-pyrazole-4-carboxylic Acid

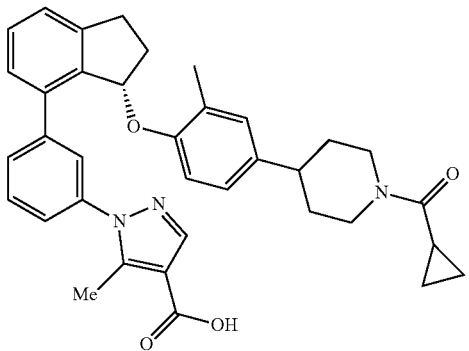 [SMILES: Cc1cc(C2CCN(C(=O)C3CC3)CC2)ccc1O[C@H]1CCc2cccc(-c3cccc(-n4ncc(C(=O)O)c4C)c3)c21]

LiOH (2M in water; 760 µl, 1.52 mmol) was added dropwise to a solution of Example 2-A (92 mg, 0.152 mmol) in MeOH (1.5 mL) and THF (1.5 mL) at room temperature and then heated to 50° C. for 6 h. The reaction mixture was cooled to room temperature and 1.55 ml 1N HCl was added and the mixture was partitioned between EtOAc and water. The aqueous layer was extracted with EtOAc and the combined organic layers were concentrated. The residue was purified by reverse phase HPLC (HC-B) to provide the title compound. $^1$H NMR (400 MHz, Methanol-d4) δ 7.85 (s, 1H), 7.64-7.59 (m, 2H), 7.52 (t, J=7.8 Hz, 1H), 7.45 (t, J=7.5 Hz, 1H), 7.41-7.37 (m, 1H), 7.36-7.30 (m, 2H), 6.91-6.86 (m, 1H), 6.85-6.83 (m, 1H), 6.75 (d, J=8.4 Hz, 1H), 5.72-5.67 (m, 1H), 4.64 (d, J=12.1 Hz, 1H), 4.45 (d, J=13.3 Hz, 1H), 3.23 (d, J=8.6 Hz, 2H), 3.01-2.92 (m, 1H), 2.79-2.64 (m, 2H), 2.44-2.33 (m, 1H), 2.23-2.16 (m, 1H), 2.15 (s, 3H), 2.05-1.97 (m, 1H), 1.97-1.77 (m, 5H), 1.67-1.43 (m, 2H), 0.93-0.85 (m, 2H), 0.85-0.79 (m, 2H). HRMS; calcd. for $C_{35}H_{38}N_3O_4$(M+H) 576.2862, found 576.2864.

Example 3

Example 3-A. a). (±)-Ethyl 1-(6-(3-(4-(1-(cyclopropanecarbonyl)piperidin-4-yl)-2-methylphenoxy)-2,3-dihydro-1H-inden-4-yl)pyridin-2-yl)-5-(trifluoromethyl)-1H-pyrazole-4-carboxylate

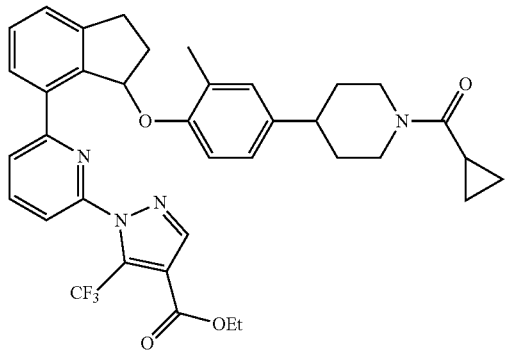 [SMILES: Cc1cc(C2CCN(C(=O)C3CC3)CC2)ccc1OC1CCc2cccc(-c3cccc(-n4ncc(C(=O)O)c4C(F)(F)F)n3)c21]

Chloro(2-dicyclohexylphosphino-2',6'-dimethoxy-1,1'-biphenyl)[2-(2-aminoethylphenyl)]paladium(II)-methyl-t-butyl ether adduct (CAS #1028206-58-7; 4.37 mg, 6.49 µmol) was added to Intermediate 1-2-1 (62.3 mg, 0.195 mmol), bis(pinacolato)diboron (49.5 mg, 0.195 mmol), and KOAc (38.2 mg, 0.390 mmol) in dioxane (0.65 mL) and the head space was purged with $N_2$. The reaction mixture was heated at 120° C. under microwave irradiation for 45 minutes. The reaction mixture was cooled to room temperature and a solution of Intermediate 3-3. a) (59 mg, 0.130 mmol) in dioxane (0.65 mL) was added, followed by sodium carbonate (1M in water; 195 µl, 0.195 mmol) and chloro(2-dicyclohexylphosphino-2',6'-dimethoxy-1,1'-biphenyl)[2-(2-aminoethylphenyl)]palladium(II)-methyl-t-butyl ether adduct (CAS #1028206-58-7; 4.37 mg, 6.49 µmol). The reaction mixture was heated to 110° C. under microwave irradiation for 30 min. Celite® was added to the reaction mixture and the mixture was concentrated. The resulting residue was purified with flash column chromatography (0-50% EtOAc/heptane gradient) to yield the title compound MS (ESI+) m/z 659.4 (M+H).

Example 3-A. b). (+)-Ethyl 1-(6-(3-(4-(1-(cycloopanecarbonyl)piperidin-4-yl)-2-methylphenoxy)-2,3-dihydro-1H-inden-4-yl)pyridin-2-yl)-6-(trifluoromethyl)-1H-pyrazole-4-carboxylate and (−)-Ethyl 1-(6-(3-(4-1-cyclopropanecarbonyl)piperidin-4-yl)-2-methylphenoxy)-2,3-dihydro-1H-inden-4-yl)pyridin-2-yl)-8-(trifluoromethyl)-1H-pyrazole-4-carboxylate

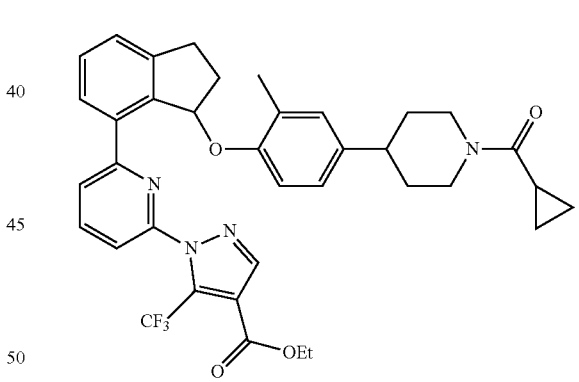

Resolution of the enantiomers of (±)-ethyl 1-(6-(3-(4-(1-(cyclopropanecarbonyl)piperidin-4-yl)-2-methylphenoxy)-2,3-dihydro-1H-inden-4-yl)pyridin-2-yl)-5-(trifluoromethyl)-1H-pyrazole-4-carboxylate was achieved by chiral SFC using CHIRALPAK® OJ-H column with 5% to 55% MeOH gradient in $CO_2$ to give (+)-ethyl 1-(6-(3-(4-(1-(cyclopropanecarbonyl)piperidin-4-yl)-2-methylphenoxy)-2,3-dihydro-1H-inden-4-yl)pyridin-2-yl)-5-(trifluoromethyl)-1H-pyrazole-4-carboxylate ($t_r$=2.02 min) and (−)-ethyl 1-(6-(3-(4-(1-(cyclopropanecarbonyl)piperidin-4-yl)-2-methylphenoxy)-2,3-dihydro-1H-inden-4-yl)pyridin-2-yl)-5-(trifluoromethyl)-1H-pyrazole-4-carboxylate ($t_r$=2.19 min).

Example 3a. (+)-1-(6-(3-(4-(1-(cyclopropanecarbonyl)piperidin-4-yl)-2-methylphenoxy)-2,3-dihydro-1H-inden-4-yl)pyridin-2-yl)-5-(trifluoromethyl)-1H-pyrazole-4-carboxylic Acid

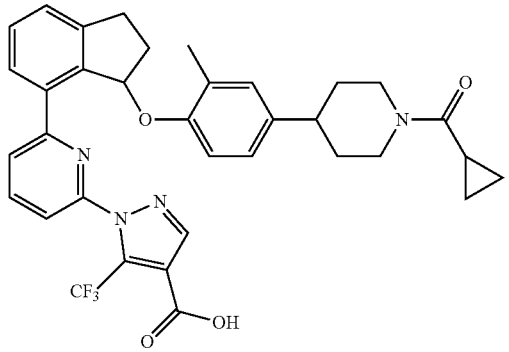

LiOH (1M aq, 660 µL, 0.660 mmol) was added to a solution of Example 3-A. b) ((+)-isomer, $t_r$=2.02 min) (87 mg, 0.132 mmol) in MeOH (1.3 mL) and THF (1.3 mL) at room temperature and the reaction mixture was stirred for 4 h at room temperature. HCl (1M aq, 660 µL, 0.66 mmol) was added to the reaction mixture, and the resulting suspension was extracted twice with EtOAc. The combined organic layers were concentrated. The resulting residue was purified by RP-HPLC (HC-B) to afford the title compound. $^1$H NMR (400 MHz. Methanol-d4) δ 7.97 (s, 1H), 7.93 (t, J=7.9 Hz, 1H), 7.82-7.78 (m, 1H), 7.68-7.63 (m, 1H), 7.55-7.51 (m, 1H), 7.47 (t, J=7.5 Hz, 1H), 7.45-7.41 (m, 1H), 6.82-6.75 (m, 2H), 6.69 (d, J=8.2 Hz, 1H), 6.39-6.34 (m, 1H), 4.64 (d, J=13.0 Hz, 1H), 4.45 (d, J=13.6 Hz, 1H), 3.24-3.16 (m, 2H), 3.05-2.95 (m, 1H), 2.78-2.64 (m, 2H), 2.59-2.47 (m, 1H), 2.18-2.08 (m, 1H), 2.05-1.97 (m, 1H), 1.92 (d, J=13.1 Hz, 1H), 1.84 (d, J=13.5 Hz, 1H), 1.63 (s, 3H), 1.61-1.44 (m, 2H), 0.93-0.86 (m, 2H), 0.86-0.78 (m, 2H). HRMS; calcd. for $C_{35}H_{34}F_3N_4O_4$(M+H) 631.2532. found 631.2572.

Example 3b. (−)-1-(6-(3-(4-(1-Cyclopropanecarbonyl)piperidin-4-yl)-2-methylphenoxy)-2,3-dihydro-1H-inden-4-yl)pyridin-2-yl)-6-(trifluoromethyl)-1H-pyrazole-4-carboxylic Acid (−)-Isomer in Example 3-A. b) ($t_r$=2.19 min) was saponified as described in Example 1. a) and then purified by reverse phase HPLC (HC-B) to afford the title compound. $^1$H NMR and HRMS data were substantially identical to Example 3a.

Example 4

Example 4-A. a). (±)-Ethyl 1-(6-(3-((2-(pyridin-2-ylmethyl)-1,2,3,4-tetrahydroisoquinolin-1-yl)oxy)-2,3-dihydro-1H-inden-4-yl)pyridin-2-yl)-5-(trifluoromethyl)-1H-pyrazole-4-carboxylate

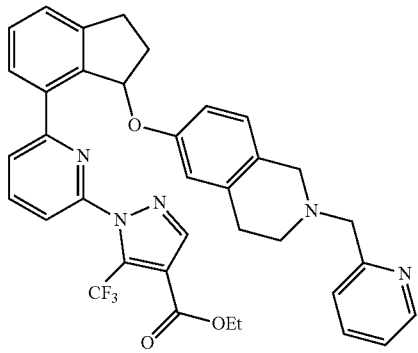 [SMILES: CCOC(=O)c1cnn(-c2cccc(-c3cccc4c3C(Oc3ccc5c(c3)CCN(Cc3ccccn3)C5)CC4)n2)c1C(F)(F)F]

Example 4-A. a) was prepared as described in Example 3-A using Intermediate 1-2-1 and Intermediate 3-1 to provide the title compound. MS (ESI+) m/z 640.2 (M+H).

Example 4-A. b). (+)-Ethyl 1-(6-(3-((2-(pyridin-2-ylmethyl)-1,2,3,4-tetrahydroisoquinolin-1-yl)oxy)-2,3-dihydro-1H-inden-4-yl)pyridin-2-yl)-5-(trifluoromethyl)-1H-pyrazole-4-carboxylate and (−)-Ethyl 1-(6-(3-((2-(pyridin-2-ylmethyl)-1,2,3,4-tetrahydroisoquinolin-1-yl)oxy)-2,3-dihydro-1H-Inden-4-yl)pyridin-2-yl)-5-(trifluoromethyl)-1H-pyrazole-4-carboxylate

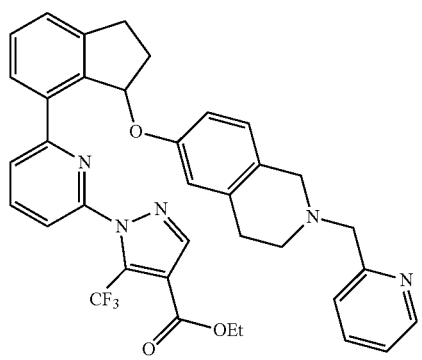 [SMILES: CCOC(=O)c1cnn(-c2cccc(-c3cccc4c3C(Oc3ccc5c(c3)CCN(Cc3ccccn3)C5)CC4)n2)c1C(F)(F)F]

Resolution of the enantiomers of (±)-ethyl 1-6-3-((2-(pyridin-2-ylmethyl)-1,2,3,4-tetrahydroisoquinolin-6-yl)oxy)-2,3-dihydro-1H-inden-4-yl)pyridin-2-yl)-5-(trifluoromethyl)-1H-pyrazole-4-carboxylate was achieved by chiral SFC using CHIRALPAK® AD-H column with 5% to 55% IPA gradient in $CO_2$ to give (−)-ethyl 1-(6-(3-((2-(pyridin-2-ylmethyl)-1,2,3,4-tetrahydroisoquinolin-6-yl)oxy)-2,3-dihydro-1H-inden-4-yl)pyridin-2-yl)-5-(trifluoromethyl)-1H-pyrazole-4-carboxylate ($t_r$=3.01 min) and (+)-ethyl 1-(6-(3-((2-pyridin-2-ylmethyl)-1,2,3,4-tetrahydroisoquinolin-6-yl)oxy)-2,3-dihydro-1H-inden-4-yl)pyridin-2-yl)-5-(trifluoromethyl)-1H-pyrazole-4-carboxylate ($t_r$=3.42 min).

Example 4a. (+)-1-(6-(3-((2-(pyridin-2-ylmethyl)-1,2,3,4-tetrahydroisoquinolin-6-yl)oxy)-2,3-dihydro-1H-inden-4-yl)pyridin-2-yl)-5-(trifluoromethyl)-1H-pyrazole-4-carboxylic Acid

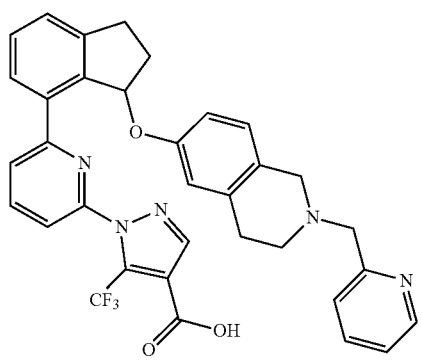 [SMILES: O=C(O)c1cnn(-c2cccc(-c3cccc4c3C(Oc3ccc5c(c3)CCN(Cc3ccccn3)C5)CC4)n2)c1C(F)(F)F]

LiOH (aq) (457 µL, 0.915 mmol) was added dropwise to a solution of Example 4-A. b) ((+)-isomer, $t_r$=3.42 min) (117 mg, 0.183 mmol) in THF (0.9 mL) at 0° C. The mixture was stirred for 1 h at 0° C. MeOH (0.9 mL) was added to the mixture, and then the mixture was warmed to room temperature and stirred for 1 h. 1N HCl (0.92 mL) was added to the reaction mixture and the resulting suspension was extracted twice with EtOAc. The combined organic layers were concentrated. The resulting residue was purified by RP-HPLC (HC-B) to afford the title compound. $^1$H NMR (400 MHz, Methanol-d4) δ 8.61-8.54 (m, 1H), 7.96-7.85 (m, 2H), 7.82-7.77 (m, 2H), 7.70-7.60 (m, 2H), 7.52-7.37 (m, 4H), 6.76 (d, J=8.4 Hz, 1H), 6.48 (d, J=2.5 Hz, 1H), 6.45-6.40 (m, 1H), 6.37-6.32 (m, 1H), 4.12 (s, 2H), 3.86 (s, 2H), 3.19 (dd, J=16.0, 8.0 Hz, 1H), 3.10-3.02 (m, 2H), 3.02-2.93 (m, 1H), 2.93-2.86 (m, 2H), 2.52-2.38 (m, 1H), 2.22-2.12 (m, 1H). HRMS; calcd. for $C_{34}H_{29}F_3N_5O_3$ (M+H) 612.2222, found 612.2199.

Example 4b. (−)-1-(6-(3-((2-(Pyridin-2-ylmethyl)-1,2,3,4-tetrahydroisoquinolin-6-yl)oxy)-2,3-dihydro-1H-inden-4-yl)pyridin-2-yl)-6-(trifluoromethyl)-1H-pyrazole-4-carboxylic Acid The (−)-isomer in Example 4-A. b) ($t_r$=3.01 min) was saponified as described in Example 4a and purified by reverse phase HPLC (HC-B) to afford the title compound. $^1$H NMR and HRMS data were substantially identical to Example 4a.

Example 5

The following compounds were prepared using similar methods as described above in Example 3 and/or Example 4 using the appropriate starting materials.

| Example | Structure/Chemical Name | Starting material(s) | MS or NMR data |
| --- | --- | --- | --- |
| 5-1 | 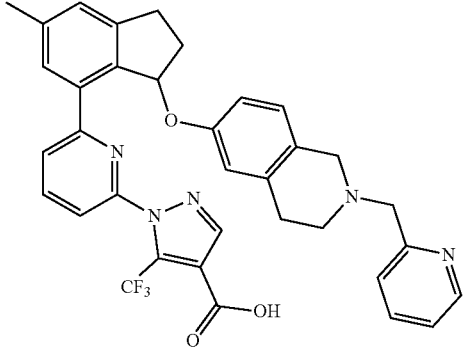<br>(±)-1-(6-(6-Methyl-3-((2-(pyridin-2-ylmethyl)-1,2,3,4-tetrahydroisoquinolin-6-yl)oxy)-2,3-dihydro-1H-inden-4-yl)pyridin-2-yl)-5-(trifluoromethyl)-1H-pyrazole-4-carboxylic acid | Intermediate 1-2-1 and Intermediate 3-2-1 | $^1$H NMR (400 MHz, DMSO-$d_6$) δ 8.49-8.54 (m, 1H), 7.93-8.05 (m, 2H), 7.83 (d, J = 7.7 Hz, 1H), 7.75-7.81 (m, 1H), 7.60 (d, J = 7.7 Hz, 1H), 7.46-7.52 (m, 2H), 7.24-7.30 (m, 2H), 6.77 (d, J = 8.2 Hz, 1H), 6.40-6.48 (m, 2H), 6.13-6.18 (m, 1H), 3.76 (s, 2H), 3.50 (s, 2H), 3.03-3.11 (m, 1H), 2.83-2.94 (m, 1H), 2.64-2.74 (m, 4H), 2.44-2.57 (m, 1H), 2.40 (s, 3H), 2.30-2.38 (m, 1H), 2.01-2.11 (m, 1H). HRMS; calcd. for $C_{35}H_{31}F_3N_5O_3$ (M + H) 626.2379, found 626.2415. |
| 5-2 | 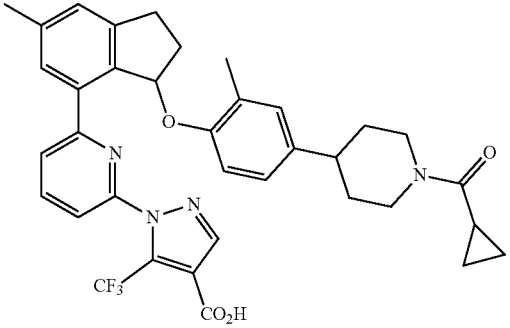<br>(±)-1-(6-(3-(4-(1-(Cyclopropanecarbonyl)piperidin-4-yl)-2-methylphenoxy)-6-methyl-2,3-dihydro-1H-inden-4-yl)pyridin-2-yl)-5-(trifluoromethyl)-1H-pyrazole-4-carboxylic acid | Intermediate 1-2-1 and Intermediate 3-2-2 | $^1$H NMR (400 MHz, Methanol-$d_4$) δ 7.92 (s, 1H), 7.88 (t, J = 7.9 Hz, 1H), 7.77-7.73 (m, 1H), 7.53-7.48 (m, 2H), 7.25 (s, 1H), 6.82-6.78 (m, 2H), 6.70 (d, J = 9.0 Hz, 1H), 6.30-6.27 (m, 1H), 4.64 (d, J = 12.7 Hz, 1H), 4.45 (d, J = 13.3 Hz, 1H), 3.23-3.14 (m, 2H), 2.99-2.89 (m, 1H), 2.78-2.64 (m, 2H), 2.54-2.46 (m, 1H), 2.45 (s, 3H), 2.18-2.09 (m, 1H), 2.05-1.97 (m, 1H), 1.92 (d, J = 13.1 Hz, 1H), 1.83 (d, J = 13.1 Hz, 1H), 1.67 (s, 3H), 1.64-1.43 (m, 2H), 0.93-0.79 (m, 4H). HRMS; calcd. for $C_{36}H_{36}F_3N_4O_4$ (M + H) 645.2689, found 645.2698. |

-continued

| Example | Structure/Chemical Name | Starting material(s) | MS or NMR data |
|---|---|---|---|
| 5-3 | (+)-(S)-1-(6-(3-(4-(1-(Cyclopropanecarbonyl)piperidin-4-yl)-3-ethylphenoxy)-2,3-dihydro-1H-inden-4-yl)pyridin-2-yl)-5-(trifluoromethyl)-1H-pyrazole-4-carboxylic acid | Intermediate 1-2-1 and Intermediate 3-4-3 | $^1$H NMR (400 MHz, Methanol-$d_4$) δ 7.92-7.86 (m, 2H), 7.81-7.76 (m, 1H), 7.67-7.63 (m, 1H), 7.56-7.52 (m, 1H), 7.46 (t, J = 7.5 Hz, 1H), 7.44-7.41 (m, 1H), 6.96 (d, J = 8.5 Hz, 1H), 6.59-6.51 (m, 1H), 6.48 (d, J = 9.5 Hz, 1H), 6.27 (d, J = 6.0 Hz, 1H), 4.71-4.61 (m, 1H), 4.52-4.42 (m, 1H), 3.24-3.15 (m, 2H), 3.05-2.92 (m, 2H), 2.75 (t, J = 12.7 Hz, 1H), 2.67-2.54 (m, 2H), 2.48-2.36 (m, 1H), 2.25-2.16 (m, 1H), 2.07-1.97 (m, 1H), 1.89-1.80 (m, 1H), 1.78-1.49 (m, 3H), 1.15 (t, J = 7.5 Hz, 3H), 0.95-0.78 (m, 4H). HRMS calculated for $C_{36}H_{36}F_3N_4O_4$ (M + H) 645.2689, found 645.2744. |
| 5-4 | (+)-(S)-1-(6-(3-(2-Methyl-4-(1-(2,2,2-trifluoroethyl)-piperidin-4-yl)phenoxy)-2,3-dihydro-1H-inden-4-yl)-pyridin-2-yl)-5-(trifluoromethyl)-1H-pyrazole-4-carboxylic acid | Intermediate 1-2-1 and Intermediate 3-4-4 | $^1$H NMR (400 MHz, Methanol-$d_4$) δ 7.92 (s, 1H), 7.89 (dd, J = 7.8, 8.0 Hz, 1H), 7.76 (d, J = 7.8 Hz, 1H), 7.63-7.67 (m, 1H), 7.53 (dd, J = 0.7, 8.0 Hz, 1H), 7.41-7.50 (m, 2H), 6.78-6.82 (m, 2H), 6.68-6.72 (m, 1H), 6.34 (dd, J = 2.8, 6.4 Hz, 1H), 3.16-3.25 (m, 1H), 3.04-3.14 (m, 4H), 2.95-3.04 (m, 1H), 2.42-2.56 (m, 3H), 2.31-2.41 (m, 1H), 2.08-2.18 (m, 1H), 1.67-1.80 (m, 4H), 1.65 (s, 3H). HRMS; calcd. for $C_{33}H_{31}F_6N_4O_3$ (M + H) 645.2300, found 645.2324. |
| 5-5 | (+)-(S)-1-(6-(3-(4-(1-(Cyclopropanecarbonyl)piperidin-4-yl)-2-methylphenoxy)-2,3-dihydro-1H-inden-4-yl)-pyridin-2-yl)-1H-pyrazole-4-carboxylic acid | Intermediate 1-4-4 and Intermediate 3-3. b) | $^1$H NMR (400 MHz, Methanol-$d_4$) δ 8.60 (d, J = 0.6 Hz, 1H), 7.87-7.94 (m, 2H), 7.74 (d, J = 7.6 Hz, 1H), 7.57-7.63 (m, 2H), 7.41-7.51 (m, 2H), 6.92 (d, J = 8.4 Hz, 1H), 6.77 (dd, J = 1.7, 8.2 Hz, 1H), 6.56-6.62 (m, 2H), 4.54-4.63 (m, 1H), 4.36-4.44 (m, 1H), 3.17-3.26 (m, 2H), 3.02-3.12 (m, 1H), 2.79-2.90 (m, 1H), 2.62-2.72 (m, 1H), 2.47-2.58 (m, 1H), 2.12-2.23 (m, 1H), 1.95-2.03 (m, 1H), 1.64-1.82 (m, 2H), 1.33-1.54 (m, 5H), 0.77-0.94 (m, 4H). HRMS; calcd. for $C_{34}H_{35}N_4O_4$ (M + H) 563.2658, found 563.2669. |

| Example | Structure/Chemical Name | Starting material(s) | MS or NMR data |
|---|---|---|---|
| 5-6 | (+)-(S)-1-(6-(3-(4-(1-(Cyclopropanecarbonyl)piperidin-4-yl)-2-methylphenoxy)-2,3-dihydro-1H-inden-4-yl)-pyridin-2-yl)-5-methyl-1H-pyrazole-4-carboxylic acid | Intermediate 1-3 and Intermediate 3-3. b) | $^1$H NMR (400 MHz, Methanol-$d_4$) δ 7.91-7.85 (m, 2H), 7.68-7.64 (m, 1H), 7.63-7.56 (m, 2H), 7.47 (t, J = 7.5 Hz, 1H), 7.45-7.41 (m, 1H), 6.80-6.72 (m, 3H), 6.36-6.31 (m, 1H), 4.62 (d, J = 13.1 Hz, 1H), 4.42 (d, J = 12.1 Hz, 1H), 3.27-3.17 (m, 2H), 3.06-2.96 (m, 1H), 2.76-2.66 (m, 4H), 2.66-2.53 (m, 2H), 2.19-2.09 (m, 1H), 2.04-1.96 (m, 1H), 1.88 (d, J = 13.4 Hz, 1H), 1.80 (d, J = 13.6 Hz, 1H), 1.62 (s, 3H), 1.60-1.39 (m, 2H), 0.92-0.78 (m, 4H). HRMS; calcd. for $C_{35}H_{37}N_4O_4$ (M + H) 577.2815, found 577.2859. |
| 5-7 | (+)-(S)-1-(6-(3-(4-(1-(Cyclopropanecarbonyl)piperidin-4-yl)-2-methylphenoxy)-2,3-dihydro-1H-inden-4-yl)-pyridin-2-yl)-5-ethyl-1H-pyrazole-4-carboxylic acid | Intermediate 1-4-2 and Intermediate 3-3. b) | $^1$H NMR (400 MHz, Methanol-$d_4$) δ 7.93 (s, 1H), 7.84 (t, J = 7.9 Hz, 1H), 7.66-7.62 (m, 1H), 7.61-7.55 (m, 2H), 7.47 (t, J = 7.4 Hz, 1H), 7.45-7.41 (m, 1H), 6.85-6.81 (m, 2H), 6.76 (d, J = 9.0 Hz, 1H), 6.28-6.23 (m, 1H), 4.62 (d, J = 13.3 Hz, 1H), 4.44 (d, J = 13.7 Hz, 1H), 3.40-3.34 (m, 2H), 3.25-3.19 (m, 2H), 3.05-2.96 (m, 1H), 2.77-2.62 (m, 2H), 2.58-2.47 (m, 1H), 2.24-2.14 (m, 1H), 2.05-1.96 (m, 1H), 1.88 (d, J = 13.0 Hz, 1H), 1.80 (d, J = 13.5 Hz, 1H), 1.71 (s, 3H), 1.66-1.41 (m, 2H), 1.12 (t, J = 7.3 Hz, 3H), 0.93-0.79 (m, 4H). HRMS; calcd. for $C_{35}H_{39}N_4O_4$ (M + H) 591.2971, found 591.2981. |
| 5-8 | (+)-(S)-5-Ethyl-1-(6-(3-(2-methyl-4-(1-(2,2,2-trifluoroethyl)-piperidin-4-yl)phenoxy)-2,3-dihydro-1H-inden-4-yl)pyridin-2-yl)-1H-pyrazole-4-carboxylic acid | Intermediate 1-3 and Intermediate 3-4-4 | $^1$H NMR (400 MHz, Chloroform-d) δ 7.98 (s, 1H), 7.68-7.53 (m, 4H), 7.41-7.28 (m, 2H), 6.87-6.78 (m, 2H), 6.74-6.65 (m, 1H), 5.95-5.86 (m, 1H), 3.45-3.26 (m, 2H), 3.18 (dt, J = 15.8, 7.8 Hz, 1H), 3.02-2.97 (m, 2H), 2.97 (s, 2H), 2.89-2.82 (m, 1H), 2.43-2.35 (m, 2H), 2.33-2.25 (m, 2H), 2.23-2.14 (m, 1H), 1.78 (s, 3H), 1.73-1.64 (m, 4H), 1.17 (t, J = 7.3 Hz, 4H). HRMS; calcd. for $C_{37}H_{41}N_4O_4$ (M + H) 605.2661, found 605.2735. |

| Example | Structure/Chemical Name | Starting material(s) | MS or NMR data |
|---|---|---|---|
| 5-9 | (+)-(S)-1-(6-(3-(4-(1-(Cyclopropanecarbonyl)piperidin-4-yl)-3-ethylphenoxy)-2,3-dihydro-1H-inden-4-yl)pyridin-2-yl)-5-ethyl-1H-pyrazole-4-carboxylic acid | Intermediate 1-4-2 and Intermediate 3-4-3 | $^1$H NMR (400 MHz, Methanol-$d_4$) δ 7.93 (s, 1H), 7.89 (t, J = 7.9 Hz, 1H), 7.72 (dd, J = 7.7, 0.9 Hz, 1H), 7.62-7.57 (m, 2H), 7.47 (t, J = 7.5 Hz, 1H), 7.43 (dd, J = 7.5, 1.3 Hz, 1H), 6.96 (d, J = 8.5 Hz, 1H), 6.58-6.51 (m, 1H), 6.51-6.46 (m, 1H), 6.18 (dd, J = 6.2, 2.4 Hz, 1H), 4.65 (d, J = 13.2 Hz, 1H), 4.46 (d, J = 13.4 Hz, 1H), 3.29-3.15 (m, 4H), 3.04-2.93 (m, 2H), 2.74 (t, J = 12.6 Hz, 1H), 2.63-2.54 (m, 2H), 2.50-2.39 (m, 1H), 2.26-2.17 (m, 1H), 2.05-1.96 (m, 1H), 1.81 (d, J = 13.4 Hz, 1H), 1.72 (d, J = 13.6 Hz, 1H), 1.68-1.48 (m, 2H), 1.16-1.08 (m, 6H), 0.94-0.86 (m, 2H), 0.86-0.78 (m, 2H). HRMS; calcd. for $C_{37}H_{40}N_4O_4$ (M + H) 605.3050, found 605.3146. |
| 5-10 | (+)-(S)-1-(6-(3-(4-(1-(Cyclopropanecarbonyl)piperidin-4-yl)-3-ethylphenoxy)-2,3-dihydro-1H-inden-4-yl)pyridin-2-yl)-5-methyl-1H-pyrazole-4-carboxylic acid | Intermediate 1-3 and Intermediate 3-4-3 | $^1$H NMR (400 MHz, Methanol-$d_4$) δ 7.94-7.86 (m, 2H), 7.68 (dd, J = 7.8, 0.8 Hz, 1H), 7.62-7.56 (m, 2H), 7.47 (t, J = 7.5 Hz, 1H), 7.42 (dd, J = 7.6, 1.2 Hz, 1H), 6.92 (d, J = 8.8 Hz, 1H), 6.54-6.41 (m, 2H), 6.25 (dd, J = 6.4, 2.8 Hz, 1H), 4.65 (d, J = 13.1 Hz, 1H), 4.46 (d, J = 13.4 Hz, 1H), 3.27-3.15 (m, 2H), 3.05-2.90 (m, 2H), 2.78-2.67 (m, 4H), 2.61-2.52 (m, 2H), 2.52-2.44 (m, 1H), 2.24-2.14 (m, 1H), 2.06-1.96 (m, 1H), 1.80 (d, J = 13.1 Hz, 1H), 1.72 (d, J = 13.4 Hz, 1H), 1.66-1.45 (m, 2H), 1.12 (t, J = 7.5 Hz, 3H), 0.95-0.86 (m, 2H), 0.86-0.77 (m, 2H). HRMS; calcd. for C36H39N4O4 (M + H) 591.2971, found 591.2953. |

Example 6

Example 6-A. (±)-Ethyl 1-(3-(3-((4-(1-(cyclopropanecarbonyl)piperidin-4-yl)-2-methylphenyl)amino)-2,3-dihydro-1H-inden-4-yl)phenyl)-5-trifluoromethyl)-1H-pyrazole-4-carboxylate

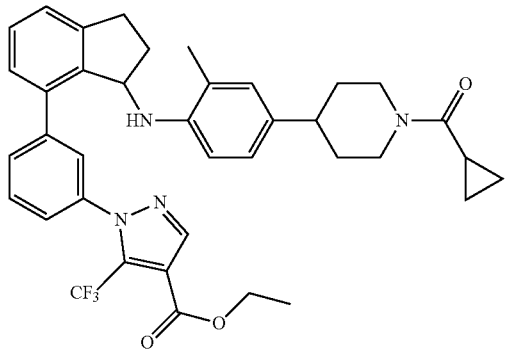 [SMILES: CCOC(=O)c1cnn(-c2cccc(-c3cccc4c3C(Nc3ccc(C5CCN(C(=O)C6CC6)CC5)cc3C)CC4)c2)c1C(F)(F)F]

A mixture of Intermediate 3-5-A. a) (150 mg, 0.232 mmol) and Intermediate 1-6-1 (95 mg, 0.232 mmol) in CH$_3$CN (1.2 mL) and aqueous K$_3$PO$_4$ (2M in water, 232 µl, 0.463 mmol) was degassed using a slow stream of nitrogen gas for 5 minutes. Pd(dppf)Cl$_2$.CH$_2$Cl$_2$ adduct (18.9 mg, 0.023 mmol) was then added to the solution and the reaction mixture was heated at 80° C. under a nitrogen atmosphere for 3 hours. The reaction mixture was filtered and the eluent was directly purified by reverse phase HPLC to provide the title compound. MS (ESI+) m/z 657.3 (M+H).

Example 6. a). (±)-1-(3-(3-((4-(1-(cyclopropanecarbonyl)piperidin-4-yl)-2-methylphenyl)amino)-2,3-dihydro-1H-inden-4-yl)phenyl)-6-trifluoromethyl)-1H-pyrazole-4-carboxylic Acid

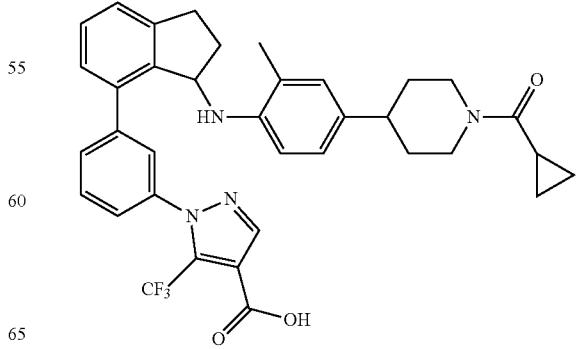

Example 6-A (195 mg, 0.297 mmol) was dissolved in MeOH (3.0 mL) and THF (3.0 mL) and then LiOH (2M aq) (1.485 mL, 1.485 mmol) was added dropwise at room temperature and stirred at room temperature for 3 hrs. 1N HCl (1.5 mL) was added and the mixture was partitioned between EtOAc and water. The aqueous layer was extracted with EtOAc and the combined organic layers were concentrated to provide the title compound, which was purified by reverse phase HPLC (HC-B). $^1$H NMR (400 MHz, Methanol-$d_4$) δ 7.97 (d, J=0.8 Hz, 1H), 7.76 (t, J=1.9 Hz, 1H), 7.72-7.67 (m, 1H), 7.47 (t, J=7.9 Hz, 1H), 7.43-7.38 (m, 1H), 7.38-7.30 (m, 3H), 6.84-6.79 (m, 1H), 6.75-6.73 (m, 1H), 6.50 (d, J=8.2 Hz, 1H), 5.05-4.99 (m, 1H), 4.62 (d, J=12.9 Hz, 1H), 4.43 (d, J=13.5 Hz, 1H), 3.26-3.18 (m, 2H), 2.99-2.88 (m, 1H), 2.77-2.58 (m, 2H), 2.40-2.28 (m, 1H), 2.14-2.05 (m, 1H), 2.04-1.96 (m, 1H), 1.89 (d, J=13.3 Hz, 1H), 1.84-1.76 (m, 4H), 1.65-1.40 (m, 2H), 0.94-0.77 (m, 4H). HRMS; calcd. for $C_{36}H_{36}F_3N_4O_3$ (M+H) 629.2740, found 629.2668.

Example 6. b). (+)-1-(3-(3-((4-(1-Cyclopropanecarbonyl)piperidin-4-yl)-2-methylphenyl)amino)-2,3-dihydro-1H-inden-4-yl)phenyl)-6-(trifluoromethyl)-1H-pyrazole-4-carboxylic acid and (−)-1-(3-(3-((4-(1-(cyclopropanecarbonyl)piperidin-4-yl)-2-methylphenyl)amino)-2,3-dihydro-1H-inden-4-yl)phenyl)-6-(trifluoromethyl)-1H-pyrazole-4-carboxylic Acid

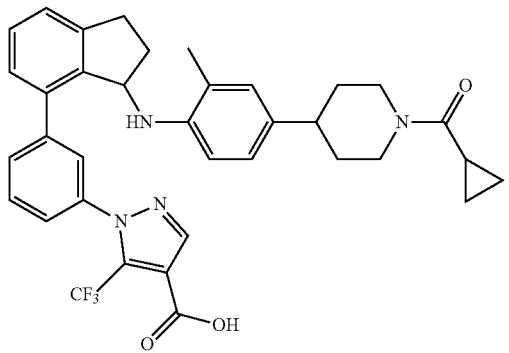 [SMILES: Cc1cc(C2CCN(C(=O)C3CC3)CC2)ccc1NC1CCc2cccc(-c3cccc(-n4ncc(C(=O)O)c4C(F)(F)F)c3)c21]

Resolution of enantiomers of (±)-1-(3-(3-((4-(1-cyclopropanecarbonyl)piperidin-4-yl)-2-methylphenyl)amino)-2,3-dihydro-1H-inden-4-yl)phenyl)-5-(trifluoromethyl)-1H-pyrazole-4-carboxylic acid was achieved by chiral SFC using CHIRALPAK® AD-H column with 25% MeOH in $CO_2$ to give (−)-1-(3-(3-((4-(1-cyclopropanecarbonyl)piperidin-4-yl)-2-methylphenyl)amino)-2,3-dihydro-1H-inden-4-yl)phenyl)-5-(trifluoromethyl)-1H-pyrazole-4-carboxylic acid ($t_r$=2.30 min) and (+)-1-(3-(3-((4-(1-cyclopropanecarbonyl)piperidin-4-yl)-2-methylphenyl)amino)-2,3-dihydro-1H-inden-4-yl)phenyl)-5-(trifluoromethyl)-1H-pyrazole-4-carboxylic acid ($t_r$=3.05 min).

Example 7

Example 7-A. a). (±)-Ethyl 1-(6-(3-(4-(1-(cyclopropanecarbonyl)piperidin-4-yl)-2-methylphenyl)amino)-2,3-dihydro-1H-inden-4-yl)pyridin-2-yl)-5-methyl-1H-pyrazole-4-carboxylate

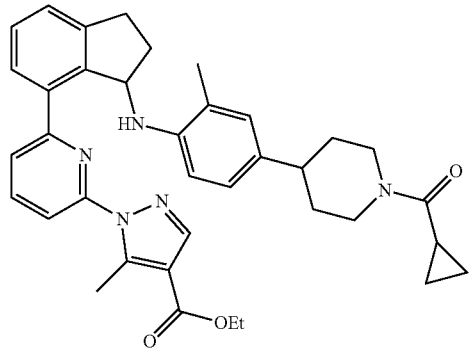 [SMILES: CCOC(=O)c1cnn(-c2cccc(-c3cccc4c3C(Nc3ccc(C5CCN(C(=O)C6CC6)CC5)cc3C)CC4)n2)c1C]

A Dean-Stark trap was fitted to a flask containing a solution of Intermediate 2-8 (286 mg, 1.107 mmol), Intermediate 3-7 (400 mg, 1.107 mmol), and TsOH (21 mg, 0.111 mmol) in anhydrous toluene (12 mL). The reaction mixture was heated at 130° C. for 22 hours, at which point the mixture was concentrated. The crude residue was re-dissolved in anhydrous EtOH (12 mL) and cooled to 0° C. Sodium borohydride (42 mg, 1.107 mmol) was added to the cooled solution and the reaction mixture was stirred at 0° C. for 1.5 h. The reaction mixture was quenched with water and saturated aq. ammonium chloride. The aqueous layer was extracted twice with $CH_2Cl_2$. Celite® was added to the combined organic layers and the mixture was concentrated. The resulting residue was purified by flash column chromatography (0-50% EtOAc/heptane gradient) to give the title compound. MS (ESI+) m/z 604.4 (M+H).

Example 7-A. b). (+)-Ethyl 1-(6-(3-((4-(1-(cyclopropanecarbonyl)piperidin-4-yl)-2-methylphenyl)amino)-2,3-dihydro-1H-inden-4-yl)pyridin-2-yl)-5-methyl-1H-pyrazole-4-carboxylate and (−)-ethyl 1-(6-(3-((4-(1-(cyclopropanecarbonyl)piperidin-4-yl)-2-methylphenyl)amino)-2,3-dihydro-1H-inden-4-yl)pyridin-2-yl)-5-methyl-1H-pyrazole-4-carboxylate

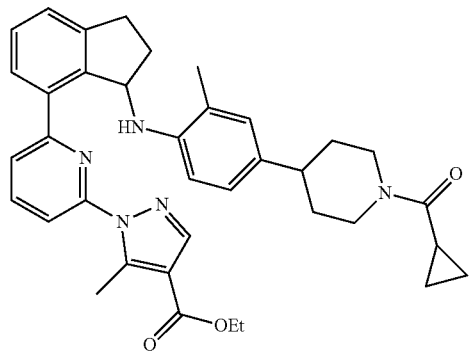 [SMILES: CCOC(=O)c1cnn(-c2cccc(-c3cccc4c3C(Nc3ccc(C5CCN(C(=O)C6CC6)CC5)cc3C)CC4)n2)c1C]

Resolution of enantiomers of (+)-ethyl 1-(6-(3-((4-(1-(cyclopropanecarbonyl)piperidin-4-yl)-2-methylphenyl)amino)-2,3-dihydro-1H-inden-4-yl)pyridin-2-yl)-5-methyl-1H-pyrazole-4-carboxylate was achieved by chiral SFC using CHIRALPAK® AD-H column with 5% to 55% IPA gradient in CO$_2$ to give (+)-ethyl 1-(6-(3-((4-(1-(cyclopropenecarbonyl)piperidin-4-yl)-2-methylphenyl)amino)-2,3-dihydro-1H-inden-4-yl)pyridin-2-yl)-5-methyl-1H-pyrazole-4-carboxylate (t$_r$=4.24 min) and (−)-ethyl 1-(6-(3-((4-(1-(cyclopropanecarbonyl)piperidin-4-yl)-2-methylphenyl)amino)-2,3-dihydro-1H-inden-4-yl)pyridin-2-yl)-5-methyl-1H-pyrazole-4-carboxylate (t$_r$=4.55 min).

Example 7a. (+)-1-((4-(1-(cyclopropanecarbonyl)piperidin-4-yl)-2-methylphenyl)amino)-2,3-dihydro-1H-inden-4-yl)pyridin-2-yl)-5-methyl-1H-pyrazole-4-carboxylic Acid

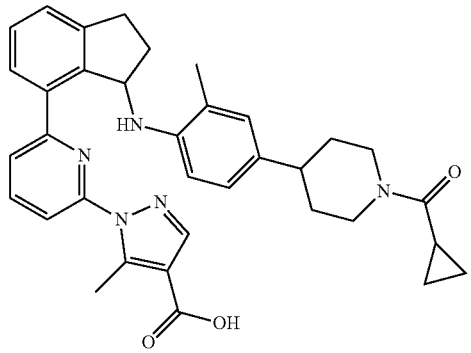 [SMILES: Cc1cc(C2CCN(C(=O)C3CC3)CC2)ccc1NC1CCc2cccc(-c3cccc(-n4ncc(C(=O)O)c4C)n3)c21]

LiOH (1M aq; 2.8 mL, 2.8 mmol) was added dropwise to a solution of Example 7-A. b) ((+)-isomer, t$_r$=4.24 min) (168 mg, 0.278 mmol) in MeOH (2.8 mL) and THF (2.8 mL) at room temperature and the reaction mixture was heated to 50° C. for 2 h. Upon completion, the reaction mixture was cooled to room temperature and 2.9 mL 1M HCl was added. The resulting mixture was extracted with EtOAc and the combined organic layers were concentrated to provide the title compound after purification by reverse phase HPLC (HC-B). $^1$H NMR (400 MHz, Methanol-d$_4$) δ 7.89 (s, 1H), 7.82 (t, J=7.9 Hz, 1H), 7.69-7.65 (m, 1H), 7.58-7.54 (m, 1H), 7.53-7.50 (m, 1H), 7.44-7.37 (m, 2H), 6.83-6.79 (m, 1H), 6.74-6.71 (m, 1H), 6.56 (d, J=8.2 Hz, 1H), 5.38 (s, 1H), 4.61 (d, J=12.9 Hz, 1H), 4.43 (d, J=13.2 Hz, 1H), 3.24-3.15 (m, 2H), 3.02-2.93 (m, 1H), 2.75-2.59 (m, 5H), 2.54-2.43 (m, 1H), 2.13-2.04 (m, 1H), 2.03-1.96 (m, 1H), 1.90 (d, J=13.1 Hz, 1H), 1.80 (d, J=13.4 Hz, 1H), 1.67 (s, 3H), 1.64-1.41 (m, 2H), 0.92-0.78 (m, 4H). HRMS; calcd. for C$_{35}$H$_{38}$N$_5$O$_3$ (M+H) 576.2975, found 576.3015. Absolute stereochemistry of (+)-1-(6-(3-((4-(1-(cyclopropanecarbonyl)piperidin-4-yl)-2-methylphenyl)amino)-2,3-dihydro-1H-inden-4-yl)pyridin-2-yl)-5-methyl-1H-pyrazole-4-carboxylic acid was confirmed by X-ray single crystal diffraction Example 7b. (−)-1-(6-(3-((4-(1-(Cyclopropanecarbonyl)piperidin-4-yl)-2-methylphenyl)amino)-2,3-dihydro-1H-inden-4-yl)pyridin-2-yl)-5-methyl-1H-pyrazole-4-carboxylic Acid Example 7-A. b) ((−)-isomer, t$_r$=4.55 min) was saponified as described in Example 7a to provide the title compound after purification by reverse phase HPLC (HC-B). $^1$H NMR and HRMS data were substantially identical to Example 7a.

Example 8

Example 8-A. (±)-Ethyl 1-(6-(3-((4-(1-(cyclopropanecarbonyl)piperidin-4-yl)-2-methylphenyl)amino)-2,3-dihydro-1H-inden-4-yl)pyridin-2-yl)-5-(trifluoromethyl)-1H-pyrazole-4-carboxylate

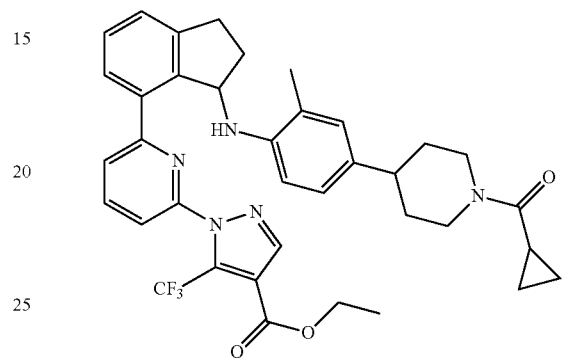

The reductive amination between Intermediate 2-8 and Intermediate 3-8-2 was performed as described in Example 7-A. a) to provide the title compound. MS (ESI+) m/h 658.5 (M+H).

Example 8. a). (±)-1-(6-(3-((4-(1-(cyclopropanecarbonyl)piperidin-4-yl)-2-methylphenyl)amino)-2,3-dihydro-1H-inden-4-yl)pyridin-2-yl)-5-(trifluoromethyl)-1H-pyrazole-4-carboxylic Acid

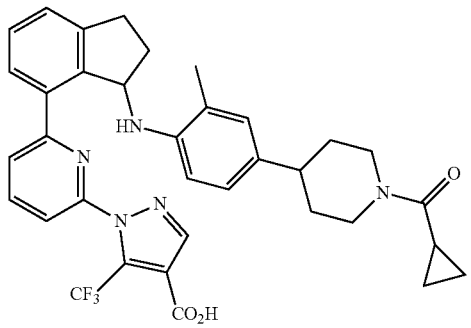 [SMILES: Cc1cc(C2CCN(C(=O)C3CC3)CC2)ccc1NC1CCc2cccc(-c3cccc(-n4ncc(C(=O)O)c4C(F)(F)F)n3)c21]

Example 8-A was saponified as described in Example 1. a) to provide the title compound after purification by reverse phase HPLC (HC-B). $^1$H NMR (400 MHz, Methanol-d$_4$) δ 7.98-7.91 (m, 2H), 7.91-7.87 (m, 1H), 7.67-7.61 (m, 1H), 7.51-7.47 (m, 1H), 7.43 (d, J=5.9 Hz, 2H), 6.85-6.80 (m, 1H), 6.74-6.71 (m, 1H), 6.55 (d, J=8.2 Hz, 1H), 5.24 (s, 1H), 4.63 (d, J=13.0 Hz, 1H), 4.45 (d, J=13.3 Hz, 1H), 3.26-3.16 (m, 2H), 2.98-2.89 (m, 1H), 2.79-2.61 (m, 2H), 2.42-2.31 (m, 1H), 2.16-2.07 (m, 1H), 2.05-1.97 (m, 1H), 1.93 (d, J=13.2 Hz, 1H), 1.84 (d, J=12.9 Hz, 1H), 1.70 (s, 3H), 1.67-1.45 (m, 2H), 0.93-0.78 (m, 4H). HRMS; calcd. for CH$_{35}$H$_{35}$F$_3$N$_5$O$_3$(M+H) 630.2692, found 630.2451.

Example 8. b). (+)-1-(6-(3-((4-(1-(cyclopropanecarbonyl)piperidin-4-yl)-2-methylphenyl)amino)-2,3-dihydro-1H-inden-4-yl)pyridin-2-yl)-5-(trifluoromethyl)-1H-pyrazole-4-carboxylic acid and (−)-1-(6-(3-((4-(1-(cyclopropanecarbonyl)piperidin-4-yl)-2-methylphenyl)amino)-2,3-dihydro-1H-inden-4-yl)pyridin-2-yl)-5-(trifluoromethyl)-1H-pyrazole-4-carboxylic Acid Resolution of the enantiomers of (+)-1-(6-(3-((4-(1-(cyclopropanecarbonyl)piperidin-4-yl)-2-methylphenyl)amino)-2,3-dihydro-1H-inden-4-yl)pyridin-2-yl)-5-(trifluoromethyl)-1H-pyrazole-4-carboxylic acid was achieved by chiral SFC using CHIRALPAK® OJ-H column with 20% (5 mM NH$_4$OH in MeOH) in CO$_2$ to give (+)-1-(6-(3-((4-(1-(cyclopropanecarbonyl)piperidin-4-yl)-2-methylphenyl)amino)-2,3-dihydro-1H-inden-4-yl)pyridin-2-yl)-5-(trifluoromethyl)-1H-pyrazole-4-carboxylic acid (t$_r$=3.10 min) and (−)-1-(6-(3-((4-(1-(cyclopropanecarbonyl)piperidin-4-yl)-2-methylphenyl)amino)-2,3-dihydro-1H-inden-4-yl)pyridin-2-yl)-5-(trifluoromethyl)-1H-pyrazole-4-carboxylic acid (t$_r$=4.40 min).

Example 9

Example 9-A. (±)-Ethyl 1-(6-(3-((4-(1-(cyclopropanecarbonyl)piperidin-4-yl)phenyl)amino)-2,3-dihydro-1H-inden-4-yl)pyridin-2-yl)-6-methyl-1H-pyrazole-4-carboxylate

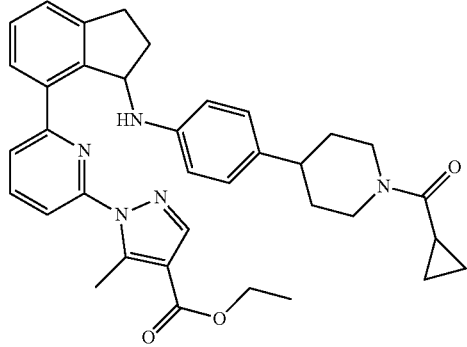 [SMILES: CCOC(=O)c1cnn(-c2cccc(-c3cccc4c3C(Nc3ccc(C5CCN(C(=O)C6CC6)CC5)cc3)CC4)n2)c1C]

The reductive amination between Intermediate 3-7 and Intermediate 2-9 was performed as described in Example 7-A to provide the title compound. MS (ESI+) m/z 590.5 (M+H).

Example 9. a). (±)-1-(6-(3-((4-(1-(cyclopropanecarbonyl)piperidin-4-yl)phenyl)amino)-2,3-dihydro-1H-inden-4-yl)pyridin-2-yl)-6-methyl-1H-pyrazole-4-carboxylic Acid

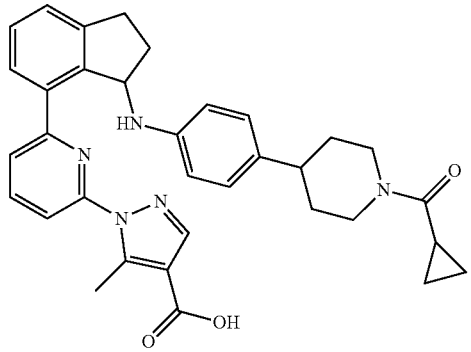 [SMILES: Cc1c(C(=O)O)cnn1-c1cccc(-c2cccc3c2C(Nc2ccc(C4CCN(C(=O)C5CC5)CC4)cc2)CC3)n1]

Example 9-A was saponified as described in Example 2 to provide the title compound after purification by reverse phase HPLC. $^1$H NMR (400 MHz, Methanol-d$_4$) δ 7.94 (s, 1H), 7.91 (t, J=7.9 Hz, 1H), 7.85-7.80 (m, 1H), 7.60-7.54 (m, 2H), 7.43-7.38 (m, 2H), 6.87-6.82 (m, 2H), 6.44-6.38 (m, 2H), 5.25-5.21 (m, 1H), 4.62 (d, J=13.2 Hz, 1H), 4.43 (d, J=132 Hz, 1H), 3.23-3.15 (m, 2H), 2.97-2.88 (m, 1H), 2.77-2.59 (m, 5H), 2.38-2.26 (m, 1H), 2.17-2.08 (m, 1H), 2.04-1.96 (m, 1H), 1.89 (d, J=13.3 Hz, 1H), 1.80 (d, J=13.3 Hz, 1H), 1.64-1.41 (m, 2H), 0.93-0.78 (m, 4H). HRMS; calcd. for C$_{34}$H$_{36}$N$_5$O$_3$ (M+H) 562.2818, found 562.2833.

Example 9. b). (+)-1-(6-(3-(4-(1-(cyclopropanecarbonyl)piperidin-4-yl)phenyl)amino)-2,3-dihydro-1H-inden-4-yl)pyridin-2-yl)-5-methyl-1H-pyrazole-4-carboxylic acid and (−)-1-(6-(3-((4-(1-(cyclopropanecarbonyl)piperidin-4-yl)phenyl)amino)-2,3-dihydro-1H-inden-4-yl)pyridin-2-yl)-5-methyl-1H-pyrazole-4-carboxylic Acid

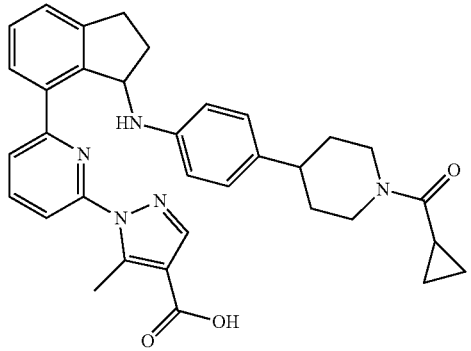 [SMILES: Cc1c(C(=O)O)cnn1-c1cccc(-c2cccc3c2C(Nc2ccc(C4CCN(C(=O)C5CC5)CC4)cc2)CC3)n1]

Resolution of the enantiomers of (±)-1-(6-(3-((4-(1-(cyclopropanecarbonyl)piperidin-4-yl)phenyl)amino)-2,3-dihydro-1H-inden-4-yl)pyridin-2-yl)-5-methyl-1H-pyrazole-4-carboxylic acid was achieved by chiral SFC using CHIRALPAK® AD-H column with 5-55% (5 mM NH$_4$OH in MeOH) gradient in CO$_2$ to give (−)-1-(6-(3-((4-(1-(cyclopropanecarbonyl)piperidin-4-yl)phenyl)amino)-2,3-dihydro-1H-inden-4-yl)pyridin-2-yl)-5-methyl-1H-pyrazole-4-carboxylic acid (t$_r$=3.68 min) and (+)-1-(6-(3-((4-(1-(cyclopropanecarbonyl)piperidin-4-yl)phenyl)amino)-2,3-dihydro-1H-inden-4-yl)pyridin-2-yl)-5-methyl-1H-pyrazole-4-carboxylic acid (t$_r$=4.10 min).

Example 10

Example 10-A. a). (±)-Ethyl 1-(6-(3-((4-(1-cyclo-propanecarbonyl)piperidin-4-yl)-2-methylphenyl)amino)-2,3-dihydro-1H-inden-4-yl)pyridin-2-yl)-5-ethyl-1H-pyrazole-4-carboxylate

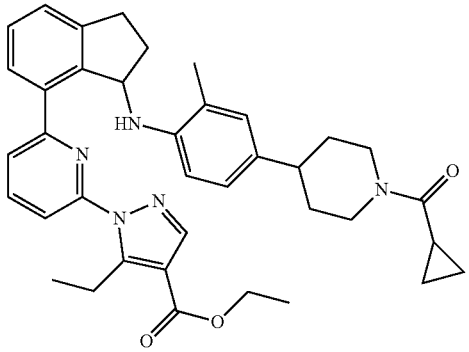 [SMILES: CCOC(=O)c1cnn(-c2cccc(-c3cccc4c3C(Nc3ccc(C5CCN(C(=O)C6CC6)CC5)cc3C)CC4)n2)c1CC]

The reductive amination between Intermediate 2-8 and Intermediate 3-8-1 was performed as described in Example 7-A. a) to provide the title compound. MS (ESI+) m/z 618.4 (M+H).

Example 10-A. b). (+)-Ethyl 1-(6-(3-((4-(1-cyclo-propanecarbonyl)piperidin-4-yl)-2-methylphenyl)amino)-2,3-dihydro-1H-inden-4-yl)pyridin-2-yl)-5-ethyl-1H-pyrazole-4-carboxylate and (−)-Ethyl 1-(6-(3-((4-(1-cyclopropanecarbonyl)piperidin-4-yl)-2-methylphenyl)amino)-2,3-dihydro-1H-inden-4-yl)pyridin-2-yl)-5-ethyl-1H-pyrazole-4-carboxylate

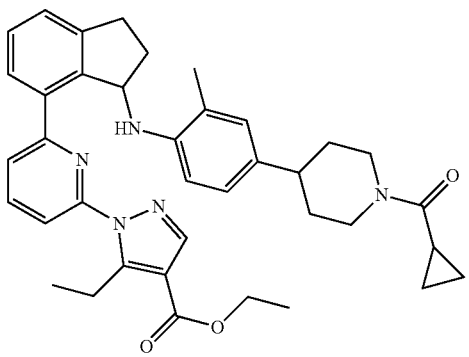 [SMILES: CCOC(=O)c1cnn(-c2cccc(-c3cccc4c3C(Nc3ccc(C5CCN(C(=O)C6CC6)CC5)cc3C)CC4)n2)c1CC]

Resolution of the enantiomers of (+)-ethyl 1-(6-(3-((4-(1-(cyclopropanecarbonyl)piperidin-4-yl)-2-methylphenyl)amino)-2,3-dihydro-1H-inden-4-yl)pyridin-2-yl)-5-ethyl-1H-pyrazole-4-carboxylate was achieved by chiral SFC using CHIRALPAK® OJ-H column with 30% to 45% IPA gradient in $CO_2$ to give (+)-ethyl 1-(6-(3-((4-(1-cyclopropanecarbonyl)piperidin-4-yl)-2-methylphenyl)amino)-2,3-dihydro-1H-inden-4-yl)pyridin-2-yl)-5-ethyl-1H-pyrazole-4-carboxylate ($t_r$=3.77 min) and (−)-ethyl 1-(6-(3-((4-(1-(cyclopropanecarbonyl)piperidin-4-yl)-2-methylphenyl)amino)-2,3-dihydro-1H-inden-4-yl)pyridin-2-yl)-5-ethyl-1H-pyrazole-4-carboxylate ($t_r$=5.85 min).

Example 10a. (+)-1-(6-(3-(4-(1-(cyclopropanecarbonyl)piperidin-4-yl)-2-methylphenyl)amino)-2,3-dihydro-1H-inden-4-yl)pyridin-2-yl)-5-ethyl-1H-pyrazole-4-carboxylic Acid

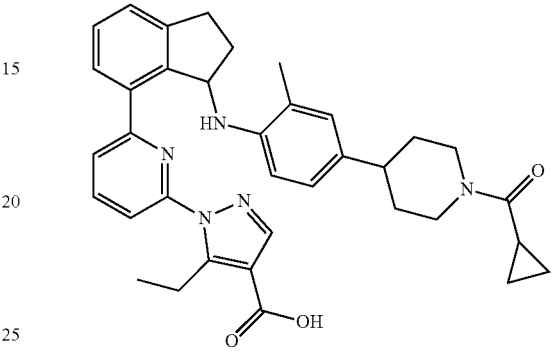

LiOH (1M aq.) (1.20 mL, 1.20 mmol) was added dropwise at room temperature to a solution of Example 10-A. b) ((+)-isomer, $t_r$=3.77 min) (74.6 mg, 0.121 mmol) in MeOH (1.2 mL) and THF (1.2 mL). The mixture was stirred at 50° C. for 5 h. The reaction mixture was cooled to room temperature and 1N HCl (aq. 1.3 mL) was added. The resulting suspension was extract twice with EtOAc. The combined organic layers were concentrated. The resulting residue was purified by reverse phase HPLC (HC-B) to afford the title compound. $^1$H NMR (400 MHz, Methanol-$d_4$) δ 7.92 (s, 1H), 7.88 (t, J=7.9 Hz, 1H), 7.78-7.74 (m, 1H), 7.58-7.52 (m, 2H), 7.43-7.40 (m, 2H), 6.84-6.80 (m, 1H), 6.74-6.72 (m, 1H), 6.56 (d, J=8.2 Hz, 1H), 5.33-5.28 (m, 1H), 4.62 (d, J=12.9 Hz, 1H), 4.43 (d, J=13.5 Hz, 1H), 3.21-3.15 (m, 3H), 3.11-3.04 (m, 1H), 3.01-2.92 (m, 1H), 2.77-2.58 (m, 2H), 2.50-2.40 (m, 1H), 2.16-2.06 (m, 1H), 2.04-1.96 (m, 1H), 1.88 (d, J=13.6 Hz, 1H), 1.81 (d, J=13.6 Hz, 1H), 1.69 (s, 3H), 1.64-1.42 (m, 2H), 1.08 (t, J=7.4 Hz, 3H), 0.91-0.80 (m, 4H). HRMS; calcd. for $C_{36}H_{40}N_5O_3$ (M+H) 590.3131, found 590.3145.

Example 10b. (−)-1-(6-(3-((4-(1-(Cyclopropanecarbonyl)piperidin-4-yl)-2-methylphenyl)amino)-2,3-dihydro-1H-inden-4-yl)pyridin-2-yl)-5-ethyl-1H-pyrazole-4-carboxylic Acid The (−)-isomer in Example 10-A. b) ($t_r$=5.85 min) was saponified as described in Example 10a and then purified by reverse phase HPLC (HC-B) to afford the title compound. $^1$H NMR and HRMS data were substantially identical to Example 10a.

Example 11

The following compounds were prepared using similar methods as described above for Example 7-A. a) using the appropriate starting

| Example | Structure/Chemical Name | Starting material(s) | HRMS and NMR data |
|---|---|---|---|
| 11-1 | (±)-1-(6-(3-((4-(1-(cyclopropanecarbonyl)piperidin-4-yl)-2-methylphenyl)amino-6-methyl-2,3-dihydro-1H-inden-4-yl)pyridin-2-yl)-5-(trifluoromethyl)-1H-pyrazole-4-carboxylic acid | Intermediate 2-8 and Intermediate 3-8-3 | $^1$H NMR (400 MHz, Methanol-$d_4$) δ 7.94-7.89 (m, 2H), 7.89-7.85 (m, 1H), 7.49-7.45 (m, 2H), 7.25-7.23 (m, 1H), 6.84-6.81 (m, 1H), 6.75-6.71 (m, 1H), 6.55 (d, J = 8.2 Hz, 1H), 5.20-5.16 (m, 1H), 4.63 (d, J = 13.1 Hz, 1H), 4.43 (d, J = 13.1 Hz, 1H), 3.28-3.21 (m, 1H), 3.19-3.12 (m, 1H), 2.93-2.84 (m, 1H), 2.77-2.61 (m, 2H), 2.43 (s, 3H), 2.39-2.28 (m, 1H), 2.15-2.06 (m, 1H), 2.05-1.96 (m, 1H), 1.96-1.89 (m, 1H), 1.87-1.80 (m, 1H), 1.70 (s, 3H), 1.67-1.44 (m, 2H), 0.92-0.79 (m, 4H). HRMS; calcd. for $C_{36}H_{37}F_3N_5O_3$ (M + H) 644.2848, found 644.2841. |
| 11-2 | (±)-1-(6-(3-((4-(1-(cyclopropanecarbonyl)piperidin-4-yl)-phenyl)amino)-2,3-dihydro-1H-inden-4-yl)pyridin-2-yl)-5-(trifluoromethyl)-1H-pyrazole-4-carboxylic acid | Intermediate 3-5-B and Intermediate 1-2-1 | $^1$H NMR (400 MHz, Methanol-$d_4$) δ 7.96-7.91 (m, 3H), 7.64 (dd, J = 5.5, 3.3 Hz, 1H), 7.52 (dd, J = 5.8, 2.9 Hz, 1H), 7.42-7.38 (m, 2H), 6.89 (d, J = 8.5 Hz, 2H), 6.46 (d, J = 8.5 Hz, 2H), 5.15 (d, J = 6.4 Hz, 1H), 4.63 (d, J = 11.7 Hz, 1H), 4.45 (d, J = 13.5 Hz, 1H), 3.24-3.16 (m, 2H), 2.95-2.86 (m, 1H), 2.78-2.63 (m, 2H), 2.30-2.20 (m, 1H), 2.19-2.10 (m, 1H), 2.05-1.96 (m, 1H), 1.90 (d, J = 13.1 Hz, 1H), 1.83 (d, J = 13.1 Hz, 1H), 1.69-1.44 (m, 2H), 0.93-078 (m, 4H). HRMS; calcd. for $C_{34}H_{33}F_3N_5O_3$ (M + H) 616.2535, found 616.2557. |
| 11-3 | (±)-5-Ethyl-1-(6-(3-((2-methyl-4-(1-(2,2,2-trifluoroethyl)-piperidin-4-yl)phenyl)amino)-2,3-dihydro-1H-inden-4-yl)pyridin-2-yl)-1H-pyrazole-4-carboxylic acid | Intermediate 3-8-1 and Intermediate 2-11 | $^1$H NMR (400 MHz, Methanol-$d_4$) δ 7.92 (s, 1H), 7.87 (t, J = 7.9 Hz, 1H), 7.78-7.74 (m, 1H), 7.58-7.53 (m, 2H), 7.44-7.40 (m, 2H), 6.83 (dd, J = 8.2, 2.2 Hz, 1H), 6.75-6.72 (m, 1H), 6.56 (d, J = 8.2 Hz, 1H), 5.32-5.28 (m, 1H), 3.23-3.15 (m, 3H), 3.10-3.02 (m, 4H), 3.01-2.92 (m, 1H), 2.51-2.40 (m, 3H), 2.37-2.28 (m, 1H), 2.15-2.06 (m, 1H), 1.76-1.71 (m, 3H), 1.69 (s, 3H), 1.09 (t, J = 7.4 Hz, 3H). HRMS; calcd. for $C_{34}H_{37}F_3N_5O_2$ (M + H) 604.2899, found 604.2890. |

| Example | Structure/Chemical Name | Starting material(s) | HRMS and NMR data |
|---|---|---|---|
| 11-4 | (±)-1-(3-(3-((4-(1-(cyclopropanecarbonyl)piperidin-4-yl)-2-methylphenyl)amino)-2,3-dihydro-1H-inden-4-yl)-phenyl)-5-methyl-1H-pyrazole-4- | Intermediate 3-5-A. a) and Intermediate 1-5 | $^1$H NMR (400 MHz, Methanol-$d_4$) δ 7.87 (s, 1H), 7.62-7.58 (m, 2H), 7.49 (t, J = 8.1 Hz, 1H), 7.41-7.36 (m, 1H), 7.36-7.25 (m, 3H), 6.84-6.79 (m, 1H), 6.74-6.71 (m, 1H), 6.51 (d, J = 8.2 Hz, 1H), 5.15-5.11 (m, 1H), 4.61 (d, J = 12.7 Hz, 1H), 4.43 (d, J = 13.4 Hz, 1H), 3.23-3.15 (m, 2H), 3.01-2.92 (m, 1H), 2.76-2.67 (m, 1H), 2.67-2.57 (m, 1H), 2.54-2.43 (m, 1H), 2.18 (s, 3H), 2.09-1.96 (m, 2H), 1.88 (d, J = 13.3 Hz, 1H), 1.79 (d, J = 13.3 Hz, 1H), 1.69 (s, 3H), 1.63-1.41 (m, 2H), 0.92-0.78 (m, 4H). HRMS; calcd. for $C_{36}H_{39}N_4O_3$ (M + H) 575.3022, found 575.3071. |

Example 12

Example 12-A. tert-Butyl 4-(4-((7-(6-(4-(ethoxycarbonyl)-6-(trifluoromethyl)-1H-pyrazol-1-yl)pyridin-2-yl)indolin-1-yl)methyl)phenyl)piperidine-1-carboxylate

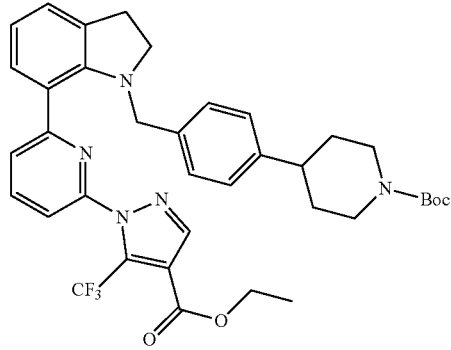 [SMILES: CCOC(=O)c1cnn(-c2cccc(-c3cccc4c3N(Cc3ccc(C5CCN(C(=O)OC(C)(C)C)CC5)cc3)CC4)n2)c1C(F)(F)F]

Triphenylphosphine (117 mg, 0.446 mmol) and CBr$_4$ (CAS #558-13-4, 148 mg, 0.446 mmol) were added to a solution of tert-butyl 4-(4-(hydroxymethyl)phenyl)piperidine-1-carboxylate (CAS #864359-18-2; 130 mg, 0.448 mmol) in dichloromethane (3.0 mL). The mixture was then stirred at room temperature for 16 h, at which point the reaction mixture was concentrated. The resulting residue was dissolved in DMF (1.0 mL). The DMF solution was then added dropwise to a suspension of Intermediate 4-1 (125 mg, 0.311 mmol) and K$_2$CO$_3$ (119 mg, 0.932 mmol) in DMF (1.0 mL). The mixture was stirred at 65° C. for 3 h, and then cooled to room temperature. The reaction mixture was partitioned between EtOAc and H$_2$O. The organic layer was then separated. The organic layer was then washed three times with brine, dried over Na$_2$SO$_4$, filtered, and concentrated. The resulting residue was purified by flash column chromatography on silica gel (heptane/EtOAc=100/0 to 60/40) to afford the title compound. $^1$H NMR (400 MHz, CDCl$_3$) δ 8.09 (s, 1H) 7.79 (d, J=720 Hz, 1H) 7.68 (t, J=7.83 Hz, 1H) 7.39 (d, J=7.07 Hz, 2H) 7.16 (dd, J=7.14, 1.07 Hz, 1H) 7.03-7.12 (m, 4H) 6.87 (t, J=7.45 Hz, 1H) 4.38 (q, J=7.07 Hz, 2H) 4.22 (br. s., 2H) 3.94 (s, 2H) 3.39 (t, J=8.59 Hz, 2H) 3.03 (t, J=8.53 Hz, 2H) 2.79 (t, J=12.44 Hz, 2H) 2.51-2.67 (m, 1H) 1.79 (d, J=13.14 Hz, 2H) 1.55-1.67 (m, 2H) 1.45-1.51 (m, 9H) 1.39 (t, J=7.14 Hz, 3H).

Example 12-8. Ethyl 1-(6-(1-(4-(piperidin-4-yl)benzyl)indolin-7-yl)pyridin-2-yl)-5-(trifluoromethyl)-1H-pyrazole-4-carboxylate

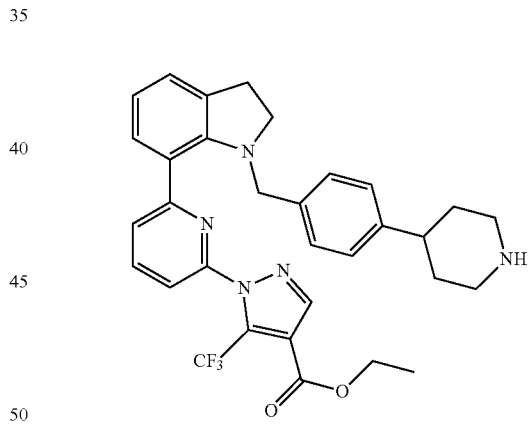

A solution of Example 12-A (230 mg, 0.34 mmol) and TFA (1 mL) in CH$_2$Cl$_2$ (5 mL) was stirred at room temperature for 1 h. The reaction mixture was then concentrated. The resulting residue was partitioned between EtOAc and saturated NaHCO$_3$. The isolated organic layer was washed with brine, dried over Na$_2$SO$_4$, filtered, and then concentrated to furnish the title compound. $^1$H NMR (400 MHz, CDCl$_3$) δ 8.09 (s, 1H) 7.77-7.83 (m, 1H) 7.68 (t, J=7.77 Hz, 1H) 7.39 (dd, J=7.83, 0.76 Hz, 2H) 7.16 (dd, J=7.20, 1.14 Hz, 1H) 7.10 (s, 4H) 6.87 (t, J=7.45 Hz, 2H) 4.38 (q, J=7.20 Hz, 2H) 3.94 (s, 2H) 3.39 (t, J=8.59 Hz, 2H) 3.19 (d, J=12.00 Hz, 2H) 3.03 (t, J=8.59 Hz, 2H) 2.74 (td, J=12.16, 2.34 Hz, 2H) 2.51-2.65 (m, 1H) 1.81 (d, J=12.88 Hz, 2H) 1.71 (br. s, 1H) 1.54-1.68 (m, 2H) 1.39 (t, J=7.14 Hz, 2H).

Example 12-C. Ethyl 1-(6-(1-(4-(1-(cyclopropanecarbonyl)piperidin-4-yl)benzyl)indolin-7-yl)pyridin-2-yl)-5-(trifluoromethyl)-1H-pyrazole-4-carboxylate

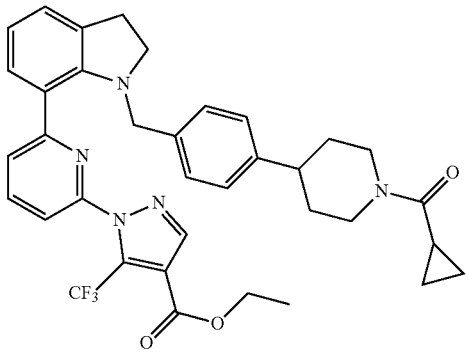 [SMILES: CCOC(=O)c1cnn(-c2cccc(-c3cccc4c3N(Cc3ccc(C5CCN(C(=O)C6CC6)CC5)cc3)CC4)n2)c1C(F)(F)F]

Cyclopropanecarbonyl chloride (0.032 mL, 0.354 mmol) was added to a solution of Example 12-8 (170 mg, 0.295 mmol) in CH$_2$Cl$_2$ (2 mL) and TEA (0.21 mL) at room temperature. The mixture was then stirred at room temperature for 3 h, after which the reaction mixture was concentrated. The resulting residue was partitioned between EtOAc and H$_2$O. The isolated organic layer was washed with brine, dried over Na$_2$SO$_4$, filtered, and then concentrated. The resulting residue was purified by flash column chromatography on silica gel (heptane/EtOAc=100/0 to 20/80) to afford the title compound. $^1$H NMR (400 MHz, CDCl$_3$) δ 8.09 (s, 1H) 7.79 (d, J=7.71 Hz, 1H) 7.65-7.73 (m, 1H) 7.39 (d, J=7.83 Hz, 2H) 7.17 (d, J=7.20 Hz, 1H) 7.09 (q, J=8.29 Hz, 4H) 6.88 (t, J=7.45 Hz, 1H) 4.76 (br. s., 1H) 4.38 (q, J=7.12 Hz, 3H) 3.88-4.00 (m, 2H) 3.39 (t, J=8.59 Hz, 2H) 3.19 (br. s., 1H) 3.03 (t, J=8.53 Hz, 2H) 2.56-2.81 (m, 2H) 1.89 (br. s., 2H) 1.79 (m, 1H) 1.63 (br. s., 2H) 1.39 (t, J=7.14 Hz, 3H) 1.01 (br. s., 2H) 0.77 (dd, J=7.89, 2.72 Hz, 2H).

Example 12. 1-(6-(1-(4-(1-(Cyclopropanecarbonyl)piperidin-4-yl)benzyl)indolin-7-yl)pyridin-2-yl)-5-(trifluoromethyl)-1H-pyrazole-4-carboxylic Acid

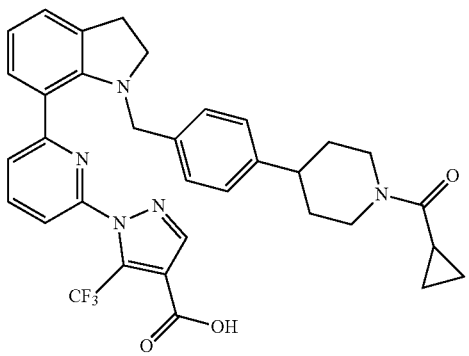 [SMILES: O=C(O)c1cnn(-c2cccc(-c3cccc4c3N(Cc3ccc(C5CCN(C(=O)C6CC6)CC5)cc3)CC4)n2)c1C(F)(F)F]

LiOH (2M in water; 185 μl, 0.37 mmol) was added dropwise to a solution of Example 12-C (80 mg, 0.124 mmol) in MeOH (1 mL) and THF (1 mL) at room temperature and the mixture was stirred for 3 h. 1N HCl was added to adjust pH~2. The mixture was then concentrated. The residue was purified by reverse phase HPLC (HC-B) to provide the title compound. $^1$H NMR (400 MHz, Methanol-d$_4$) δ 7.88 (s, 1H) 7.73-7.85 (m, 2H) 7.48 (dd, J=7.71, 1.01 Hz, 1H) 7.30 (d, J=7.83 Hz, 1H) 7.14 (dd, J=7.20, 1.14 Hz, 1H) 7.09 (s, 4H) 6.79-6.87 (m, 1H) 4.64 (d, J=13.64 Hz, 1H) 4.46 (d, J=11.87 Hz, 1H) 3.92 (s, 2H) 3.58-3.64 (m, 1H) 3.55 (t, J=5.62 Hz, 1H) 3.36-3.42 (m, 1H) 3.00 (t, J=8.65 Hz, 2H) 2.72-2.84 (m, 1H) 2.63-2.69 (m, 1H) 1.98-2.08 (m, 1H) 1.68-1.83 (m, 4H) 0.85-0.92 (m, 2H) 0.81 (d, J=7.96 Hz, 2H). HRMS; calcd. for C$_{34}$H$_{33}$F$_3$N$_5$O$_3$(M+H) 616.2535, found 616.2536.

Example 13

Example 13-A. tert-Butyl 4-(4-((7-(6-(4-(ethoxycarbonyl)-6-(trifluoromethyl)-1H-pyrazol-1-yl)pyridin-2-yl)indolin-1-yl)methyl)-2-ethylphenyl)piperidine-1-carboxylate

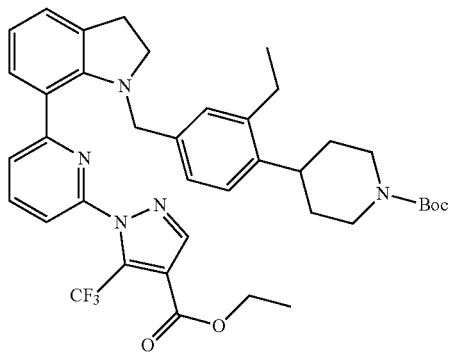 [SMILES: CCOC(=O)c1cnn(-c2cccc(-c3cccc4c3N(Cc3ccc(C5CCN(C(=O)OC(C)(C)C)CC5)c(CC)c3)CC4)n2)c1C(F)(F)F]

Triphenylphosphine (723 mg, 2.76 mmol) and CBr$_4$ (916 mg, 2.76 mmol) were added to a solution of Intermediate 5-1 (840 mg, 2.63 mmol) in dichloromethane (14 mL). The mixture was then stirred at room temperature for 16 h, and then concentrated. The resulting residue was dissolved in DMF (6 mL). The DMF solution was then added dropwise to a suspension of Intermediate 4-1 (325 mg, 0.808 mmol) and K$_2$CO$_3$ (311 mg, 3.423 mmol) in DMF (2.0 mL). The mixture was stirred at 65° C. for 3 h, and then cooled to room temperature. The reaction mixture was partitioned between EtOAc and H$_2$O. The organic layer was then separated. The organic layer was then washed three times with brine, dried over Na$_2$SO$_4$, filtered, and concentrated. The resulting residue was purified by flash column chromatography (0-40% EtOAc/heptane gradient) to afford the title compound. MS (ESI+) m/z 704.6 (M+H)

Example 13-8. Ethyl 1-(6-(1-(3-ethyl-4-(piperidin-4-yl)benzyl)indolin-7-yl)pyridin-2-yl)-5-(trifluoromethyl)-1H-pyrazole-4-carboxylate

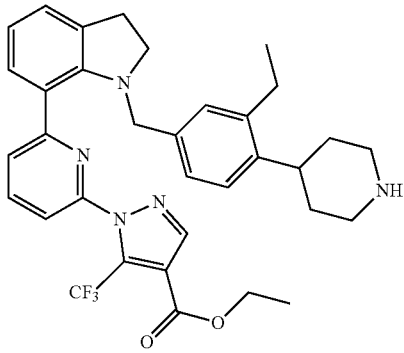 [SMILES: CCOC(=O)c1cnn(-c2cccc(-c3cccc4c3N(Cc3ccc(C5CCNCC5)c(CC)c3)CC4)n2)c1C(F)(F)F]

A solution of Example 13-A (517 mg, 0.735 mmol) and 4 N HCl in dioxane solution (2 mL) in CH$_2$Cl$_2$ (5 mL) was stirred at room temperature for 1 h. The reaction mixture was then concentrated. The resulting residue was partitioned between EtOAc and saturated NaHCO$_3$. The isolated organic layer was washed with brine, dried over Na$_2$SO$_4$, filtered, and then concentrated to furnish the title compound. MS (ESI+) m/z 604.4 (M+H).

Example 13-C. Ethyl 1-(6-(1-(4-(1-(cyclopropanecarbonyl)piperidin-4-yl)-3-ethylbenzyl)indolin-7-yl)pyridin-2-yl)-5-(trifluoromethyl)-1H-pyrazole-4-carboxylate

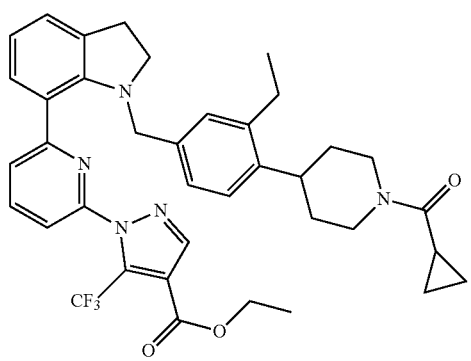 [SMILES: CCOC(=O)c1cnn(-c2cccc(-c3cccc4c3N(Cc3ccc(C5CCN(C(=O)C6CC6)CC5)c(CC)c3)CC4)n2)c1C(F)(F)F]

Cyclopropanecarbonyl chloride (0.028 mL, 0.309 mmol) was added to a solution of Example 13-B (143 mg, 0.237 mmol) in CH$_2$Cl$_2$ (2.0 mL) and TEA (0.165 mL, 1.187 mmol) at room temperature. The mixture was then stirred at room temperature for 3 h. and then concentrated. The resulting residue was partitioned between EtOAc and H$_2$O. The isolated organic layer was washed with brine, dried over Na$_2$SO$_4$, filtered, and then concentrated. The resulting residue was purified by flash column chromatography (0-80% EtOAc/heptane gradient) to afford the title compound. MS (ESI+) m/z 672.5 (M+H).

Example 13. 1-(6-(1-(4-(1-(Cyclopropanecarbonyl)piperidin-4-yl)-3-ethylbenzyl)indolin-7-yl)pyridin-2-yl)-5-trifluoromethyl)-1H-pyrazole-4-carboxylic Acid

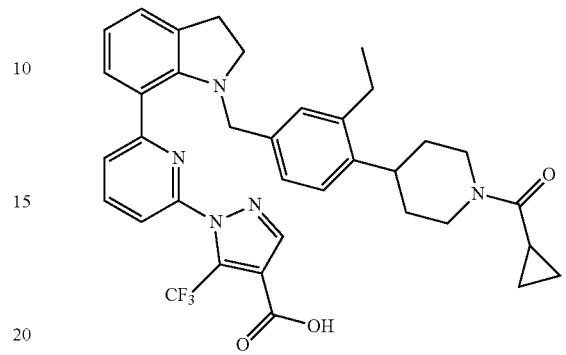

LiOH (2.0M in H$_2$O; 167 μl, 0.335 mmol) was added dropwise to a solution of Example 13-C (75 mg, 0.112 mmol) in EtOH (1 mL) and THF (1 mL). The mixture was then stirred at room temperature for 3 h. The pH of the mixture was adjusted by addition of 1N aqueous HCl to ~2. The mixture was then concentrated. The residue was purified by RP-HPLC (HC-B) to provide the title compound. $^1$H NMR (400 MHz, Methanol-d$_4$) δ 7.94 (s, 1H) 7.73-7.86 (m, 2H) 7.48 (dd, J=7.64, 1.07 Hz, 1H) 7.30 (d, J=6.82 Hz, 1H) 7.14 (dd, J=7.20, 1.14 Hz, 1H) 7.02-7.07 (m, 1H) 6.92-6.98 (m, 1H) 6.88 (d, J=1.52 Hz, 1H) 6.83 (t, J=7.52 Hz, 1H) 4.66 (d, J=12.76 Hz, 1H) 4.47 (d, J=13.64 Hz, 1H) 3.91 (s, 2H) 3.41 (t, J=8.65 Hz, 2H) 3.22-3.28 (m, 1H) 3.03-3.09 (m, 1H) 2.95-3.02 (m, 2H) 2.75 (t, J=12.32 Hz, 1H) 2.63 (q, J=7.45 Hz, 2H) 1.95-2.06 (m, 1H) 1.51-1.86 (m, 4H) 1.13 (t, J=7.52 Hz, 3H) 0.76-0.94 (m, 4H). HRMS; calcd. for C$_{38}$H$_{37}$F$_3$N$_5$O$_3$ (M+H) 644.2849, found 644.2842.

Example 14

Example 14-A. tert-Butyl 4-(4-((7-(6-(4-(ethoxycarbonyl)-5-ethyl)-1H-pyrazol-1-yl)pyridin-2-yl)indolin-1-yl)methyl)-2-ethylphenyl)piperidine-1-carboxylate

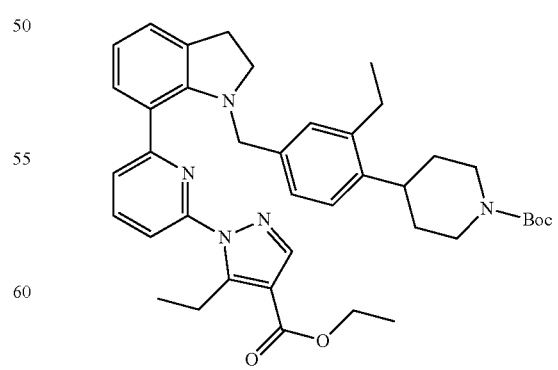

A solution of Intermediate 5-2 (348 mg, 0.911 mmol) was added to a suspension of Intermediate 4-2 (300 mg, 0.828 mmol) and K$_2$CO$_3$ (318 mg, 2.483 mmol) in DMF (6 mL).

The mixture was stirred at 65° C. for 3 h, and then cooled to room temperature. The reaction mixture was partitioned between EtOAc and H₂O. The organic layer was then separated. The organic layer was then washed three times with brine, dried over Na₂SO₄, filtered, and concentrated. The resulting residue was purified by flash column chromatography (0-40% EtOAc/heptane gradient) to afford the title compound. MS (ESI+) m/z 664.6 (M+H).

Example 14-B. Ethyl 5-ethyl-1-(6-(1-(3-ethyl-4-piperidin-4-yl)benzyl)indolin-7-yl)pyridin-2-yl)-1H-pyrazole-4-carboxylate

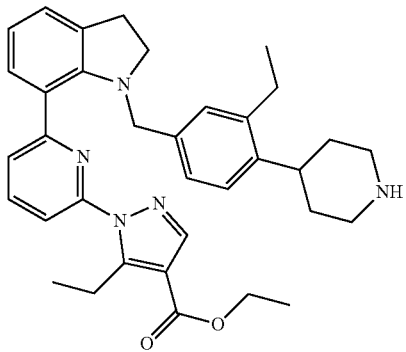 [SMILES: CCOC(=O)c1cnn(-c2cccc(-c3cccc4c3N(Cc3ccc(C5CCNCC5)c(CC)c3)CC4)n2)c1CC]

A solution of Example 14-A (487 mg, 0.734 mmol) and 4 N HCl in dioxane solution (5 mL) in CH₂Cl₂ (2 mL) was stirred at room temperature for 16 h. The reaction mixture was then concentrated to furnish the title compound as the HCl salt. MS (ESI+) m/z 564.3 (M+H).

Example 14-C. Ethyl 1-(6-(1-(4-(1-(cyclopropanecarbonyl)piperidin-4-yl)-3-ethylbenzyl)indolin-7-yl)pyridin-2-yl)-5-ethyl-1H-pyrazole-4-carboxylate

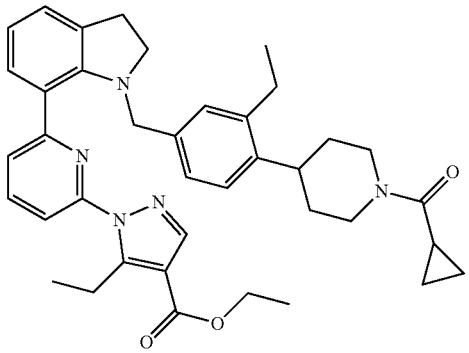 [SMILES: CCOC(=O)c1cnn(-c2cccc(-c3cccc4c3N(Cc3ccc(C5CCN(C(=O)C6CC6)CC5)c(CC)c3)CC4)n2)c1CC]

Cyclopropanecarbonyl chloride (0.031 mL, 0.338 mmol) was added to a solution of Example 14-B (156 mg, 0.245 mmol) in CH₂Cl₂ (2.0 mL) and TEA (0.181 mL, 1.30 mmol) at room temperature. The mixture was then stirred at room temperature for 3 h. The resulting residue was partitioned between EtOAc and H₂O. The isolated organic layer was washed with brine, dried over Na₂SO₄, filtered, and then concentrated. The resulting residue was purified by flash column chromatography (0-80% EtOAc/heptane gradient) to afford the title compound. MS (ESI+) m/z 632.5 (M+H).

Example 14. 1-(6-(1-(4-(1-(Cyclopropanecarbonyl)piperidin-4-yl)-3-ethylbenzyl)indolin-7-yl)pyridin-2-yl)-5-ethyl-1H-pyrazole-4-carboxylic Acid

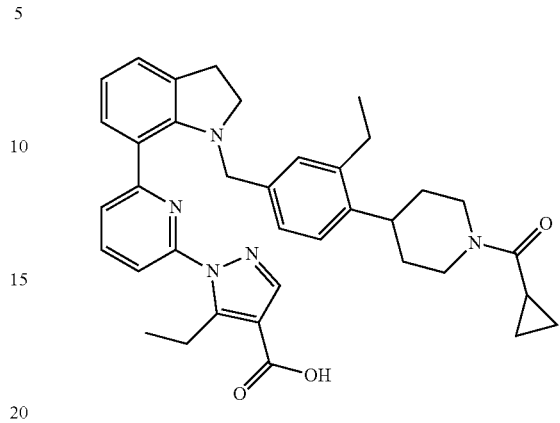

LiOH (2.0M in water; 178 µl, 0.356 mmol) was added dropwise to a solution of Example 14-C (75 mg, 0.119 mmol) in EtOH (1 mL) and THF (1 mL). The mixture was then stirred at 60° C. for 3 h. The pH of the mixture was adjusted by addition of 1N aqueous HCl to ~2. The mixture was then concentrated. The residue was purified by RP-HPLC (HC-B) to provide the title compound. ¹H NMR (400 MHz, Methanol-d₄) δ 7.95 (s, 1H) 7.80-7.87 (m, 1H) 7.64 (dd, J=7.71, 0.76 Hz, 1H) 7.56 (dd, J=8.02, 0.69 Hz, 1H) 7.24 (d, J=7.33 Hz, 1H) 7.14 (dd, J=7.14, 1.07 Hz, 1H) 7.00 (d, J=8.08 Hz, 1H) 6.89 (d, J=8.08 Hz, 1H) 6.79-6.86 (m, 2H) 4.64 (d, J=12.00 Hz, 1H) 4.45 (d, J=12.38 Hz, 1H) 3.91 (s, 2H) 3.37-3.44 (m, 4H) 3.20-3.27 (m, 1H) 2.96-3.04 (m, 3H) 2.69-2.79 (m, 1H) 2.59 (q, J=7.58 Hz, 2H) 1.96-2.06 (m, 1H) 1.49-1.84 (m, 4H) 1.17 (t, J=7.33 Hz, 3H) 1.10 (t, J=7.58 Hz, 3H) 0.79-0.94 (m, 4H). HRMS; calcd. for C₃₇H₄₂N₅O₃ (M+H) 604.3288, found 604.3279.

Example 15

Example 15-A. Ethyl 1-(6-(1-(3-ethyl-4-1-(2,2,2-trifluoroethyl)piperidin-4-yl)benzyl)indolin-7-yl)pyridin-2-yl)-5-(trifluoromethyl)-1H-pyrazole-4-carboxylate

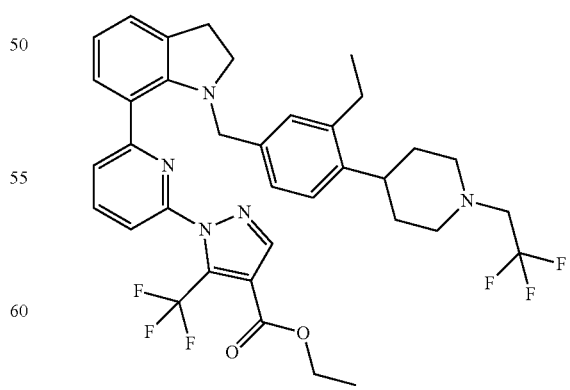

To a solution of Example 13-B (121 mg, 0.200 mmol) in DMF (2 mL) was added potassium carbonate (77 mg, 0.800 mmol), followed by 2,2,2-trifluoroethyl trifluoromethanesulfonate (84 mg, 0.360 mmol). The mixture was then stirred at 70° C. for 3 h. The reaction mixture was diluted with EtOAc. The organic phase was washed successively with H$_2$O and brine, dried over Na$_2$SO$_4$ and concentrated. The resulting residue was purified by flash column chromatography (0-50% EtOAc/heptane gradient) to afford the title compound. MS (ESI+) m/z 686.5 (M+H).

Example 15. 1-(6-(1-(3-Ethyl-4¹-(2,2,2-trifluoroethyl)piperidin-4-yl)benzyl)indolin-7-yl)pyridin-2-yl)-5-(trifluoromethyl)-1H-pyrazole-4-carboxylic Acid

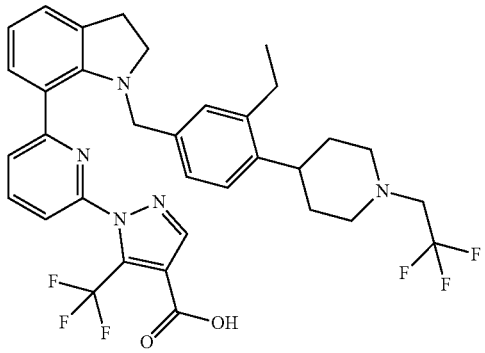 [SMILES: CCc1cc(CN2CCc3cccc(-c4cccc(-n5ncc(C(=O)O)c5C(F)(F)F)n4)c32)ccc1C1CCN(CC(F)(F)F)CC1]

LiOH (2.0M in water; 0.18 mL, 0.36 mmol) was added dropwise to a solution of Example 15-A (83 mg, 0.121 mmol) in EtOH (1 mL) and THF (1 mL). The mixture was then stirred at room temperature for 3 h. The pH of the mixture was adjusted by addition of 1N aqueous HCl to ~2. The mixture was then concentrated. The residue was purified by RP-HPLC (HC-B) to provide the title compound. $^1$H NMR (400 MHz, Methanol-d$_4$) δ 8.09 (s, 1H) 7.83-7.89 (m, 1H) 7.77-7.82 (m, 1H) 7.49 (dd, J=7.71, 1.01 Hz, 1H) 7.27 (d, J=6.69 Hz, 1H) 7.15 (dd, J=7.20, 1.14 Hz, 1H) 7.09 (d, J=7.96 Hz, 1H) 6.94 (dd, J=7.89, 1.71 Hz, 1H) 6.78-6.87 (m, 2H) 3.90 (s, 2H) 3.41 (t, J=8.59 Hz, 2H) 3.09 (q, J=9.81 Hz, 4H) 2.99 (t, J=8.59 Hz, 2H) 2.66-2.77 (m, 1H) 2.57 (q, J=7.58 Hz, 2H) 2.45-2.53 (m, 2H) 1.72-1.87 (m, 2H) 1.60-1.69 (m, 2H) 1.10 (t, J=7.58 Hz, 3H) HRMS; calcd. for C$_{34}$H$_{34}$F$_6$N$_5$O$_2$(M+H) 658.2617, found 658.2590.

Example 16

Example 16-A. Ethyl 5-ethyl-1-(6-(1-(3-ethyl-4-(2,2,22-trifluoroethyl)piperidin-4-yl)benzyl)indolin-7-yl)pyridin-2-yl)-1H-pyrazole-4-carboxylate

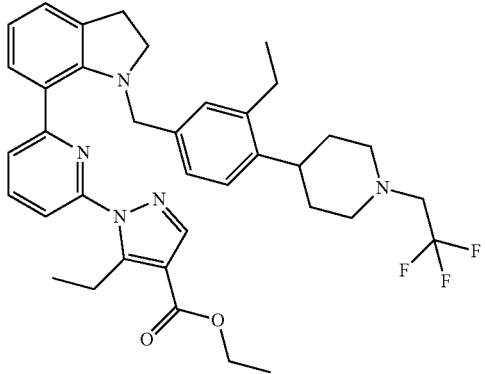 [SMILES: CCOC(=O)c1cnn(-c2cccc(-c3cccc4c3N(Cc3ccc(C5CCN(CC(F)(F)F)CC5)c(CC)c3)CC4)n2)c1CC]

To a solution of Example 14-8 (126 mg, 0.189 mmol) in DMF (2 mL) was added potassium carbonate (81 mg, 0.63 mmol), followed by 2,2,2-trifluoroethyl trifluoromethanesulfonate (88 mg, 0.378 mmol). The mixture was then stirred at 70° C. for 3 h. The reaction mixture was diluted with EtOAc. The organic phase was washed successively with H$_2$O and brine, dried over Na$_2$SO$_4$ and concentrated. The resulting residue was purified by flash column chromatography (0-50% EtOAc/heptane gradient) to afford the title compound. MS (ESI+) m/z 646.5 (M+H).

Example 16. 5-Ethyl-1-(6-(1-(3-ethyl-4-(1-(2,2,2-trifluoroethyl)piperidin-4-yl)benzyl)indolin-7-yl)pyridin-2-yl)-1H-pyrazole-4-carboxylic Acid

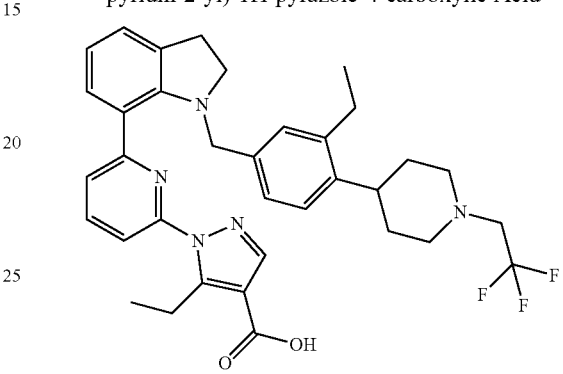

LiOH (2.0M in water; 0.18 mL, 0.356 mmol) was added dropwise to a solution of Example 16-A (75 mg, 0.119 mmol) in EtOH (1 mL) and THF (1 mL). The mixture was then stirred at 60° C. for 3 h. The pH of the mixture was adjusted by addition of 1N aqueous HCl to ~2. The mixture was then concentrated. The residue was purified by RP-HPLC (HC-B) to provide the title compound $^1$H NMR (400 MHz, Methanol-d$_4$) δ 7.97 (s, 1H) 7.82-7.89 (m, 1H) 7.67 (dd, J=7.71, 0.76 Hz, 1H) 7.58 (d, J=7.20 Hz, 1H) 7.24 (d, J=7.71 Hz, 1H) 7.13-7.17 (m, 1H) 7.06 (d, J=7.96 Hz, 1H) 6.89 (d, J=7.71 Hz, 1H) 6.79-6.86 (m, 2H) 4.55 (s, 2H) 3.90 (s, 2H) 3.40-3.43 (m, 2H) 3.38 (d, J=7.20 Hz, 2H) 3.04-3.10 (m, 4H) 2.96-3.03 (m, 2H) 2.54 (q, J=7.75 Hz, 2H) 2.43-2.49 (m, 1H) 1.71-1.85 (m, 2H) 1.58-1.67 (m, 2H) 1.19 (t, J=7.39 Hz, 3H) 1.07 (t, J=7.58 Hz, 3H). HRMS; calcd. for C$_{35}$H$_{30}$F$_3$N$_5$O$_2$ (M+H) 618.3056, found 618.3049.

Example 17

Example 17-A. Ethyl 5-ethyl-1-(6-(3-methyl-1H-indol-7-yl)pyridin-2-yl)-1H-pyrazole-4-carboxylate

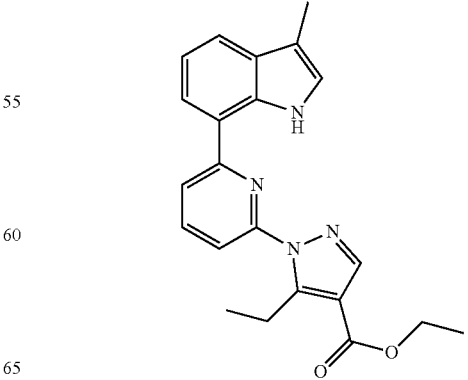

To a suspension of ethyl 1-(6-bromopyridin-2-yl)-5-ethyl-1H-pyrazole-4-carboxylate, Intermediate 1-4-2, (0.8 g, 2.27 mmol), bis(pinacolato)diboron (0.63 g, 2.5 mmol), and potassium acetate (0.31 g, 3.2 mmol) in dioxane (10 mL) was added Pd(dppf)Cl$_2$·CH$_2$Cl$_2$ adduct (0.15 g, 0.13 mmol). The mixture was then stirred for 2 h at 100° C. and then cooled to room temperature. To the reaction mixture were then added 7-bromo-3-methyl-1H-indole (CAS #853355-96-1), Pd(dppf)Cl$_2$·CH$_2$Cl$_2$ adduct (0.15 g, 0.13 mmol), K$_3$PO$_4$ (1.44 g, 6.8 mmol) and dioxane/H$_2$O (3 mL/6 mL). The mixture was then stirred at 100° C. for 2 h, and then diluted with H$_2$O at room temperature. The mixture was then extracted twice with EtOAc. The combined organic layers were washed with brine, dried over Na2SO4, filtered, and then concentrated. The resulting residue was purified by silica gel flash column chromatography (0 to 8% EtOAc in hexane) to afford the title compound. MS (ESI+) m/z 375.2 (M+H).

Example 17-B. (±)-Ethyl 5-ethyl-1-(6-(3-methylindolin-7-yl)pyridin-2-yl)-1H-pyrazole-4-carboxylate

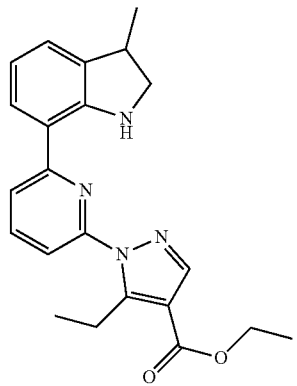 [SMILES: CCOC(=O)c1cnn(-c2cccc(-c3cccc4c3NCC4C)n2)c1CC]

A mixture of ethyl 5-ethyl-1-(6-(3-methyl-1H-indol-7-yl)pyridin-2-yl)-1H-pyrazole-4-carboxylate (0.7 g, 1.87 mmol), triethylsilane (9.0 mL, 56 mmol), and TFA (3.3 mL) was stirred at room temperature for 24 h. The reaction mixture was rendered basic by satd. aq. NaHCO$_3$. The mixture was then extracted twice with EtOAc. The combined organic layers were dried over Na$_2$SO$_4$, filtered, and then concentrated. The resulting residue was purified by silica gel flash column chromatography (0 to 6% EtOAc in hexane) to afford the title compound. MS (ESI+) m/z 377.2 (M+H).

Example 17-C. (±)-Ethyl 5-ethyl-1-6-(3-methylindolin-7-yl)pyridin-2-yl)-1H-pyrazole-4-carboxylate

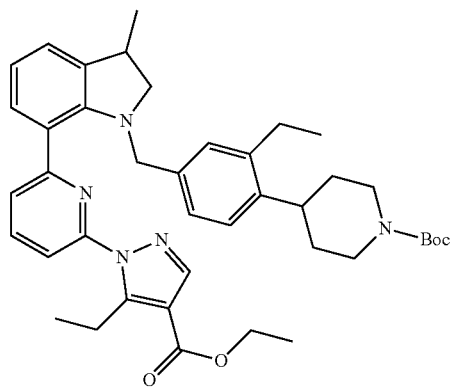 [SMILES: CCOC(=O)c1cnn(-c2cccc(-c3cccc4c3N(Cc3ccc(C5CCN(C(=O)OC(C)(C)C)CC5)c(CC)c3)CC4C)n2)c1CC]

A mixture of (±)-ethyl 5-ethyl-1-(6-(3-methylindolin-7-yl)pyridin-2-yl)-1H-pyrazole-4-carboxylate (0.23 g, 0.6 mmol), tert-butyl 4-(2-ethyl-4-(hydroxymethyl)phenyl)piperidine-1-carboxylate (Intermediate 6-2) (0.27 g, 0.72 mmol), and K$_2$CO$_3$ (0.41 g, 3.0 mmol) in CH$_3$CN (15 mL) was stirred at 65° C. for 24 h. The reaction mixture was then diluted with H$_2$O. The mixture was then extracted twice with EtOAc. The combined organic layers were washed with brine, dried over Na$_2$SO$_4$, filtered, and then concentrated. The resulting residue was purified by silica gel flash column chromatography (0 to 18% EtOAc in hexane) to afford the title compound. MS (ESI+) m/z 678.5 (M+H).

Example 17-D. (±)-Ethyl 5-ethyl-1-(6-1-(3-ethyl-4-(piperidin-4-yl)benzyl)-3-methylindolin-7-yl)pyridin-2-yl)-1H-pyrazole-4-carboxylate

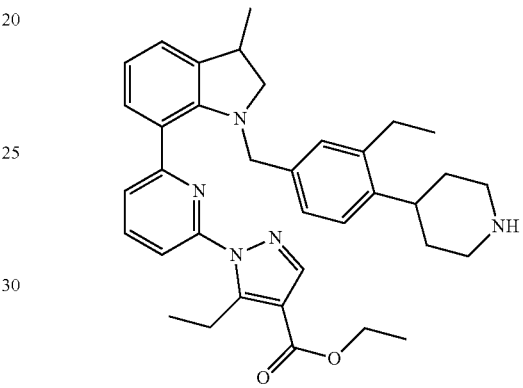

A mixture of (±)-ethyl 5-ethyl-1-(6-(3-methylindolin-7-yl)pyridin-2-yl)-1H-pyrazole-4-carboxylate (0.54 g, 0.80 mmol) and TFA (1.2 mL) in CH$_2$Cl$_2$ (30 mL) was stirred at 0° C. for 3 h. The reaction mixture was rendered basic by satd. aq. NaHCO$_3$. The mixture was then extracted twice with EtOAc. The combined organic layers were dried over Na$_2$SO$_4$, filtered, and then concentrated to furnish the title compound. MS (ESI+) m/z 578.4 (M+H).

Example 17-E. a). Ethyl 5-ethyl-1-(6-(1-(3-ethyl-4-(1-((8S)-2-hydroxypropanoyl)piperidin-4-yl)benzyl)-3-methylindolin-7-yl)pyridin-2-yl)-1H-pyrazole-4-carboxylate

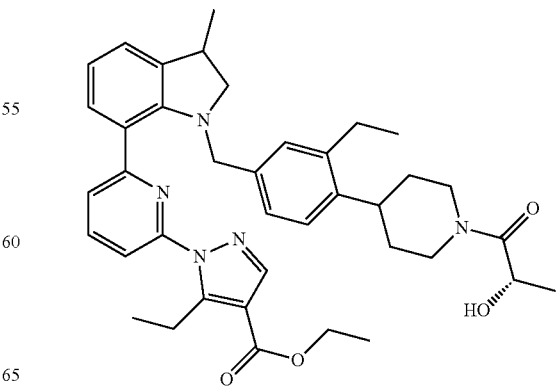

To a solution of (+)-ethyl 5-ethyl-1-(6-(1-(3-ethyl-4-(piperidin-4-yl)benzyl)-3-methylindolin-7-yl)pyridin-2-yl)-1H-pyrazole-4-carboxylate (as TFA salt, 0.2 g, 0.29 mmol), L-lactic acid (0.03 g, 0.35 mmol) and HATU (0.16 g, 0.43 mmol) in DMF (4 mL) at room temperature was added DIPEA (0.3 mL, 1.73 mmol). The mixture was stirred at room temperature for 5 h. The reaction mixture was then diluted with $H_2O$. The mixture was then extracted twice with EtOAc. The combined organic layers were washed with brine, dried over $Na_2SO_4$, filtered, and then concentrated. The resulting residue was purified by silica gel flash column chromatography (0 to 50% EtOAc in hexane) to afford the title compound. MS (ESI+) m/z 650.4 (M+H).

Example 17-E. b). Ethyl 5-ethyl-1-(6-1-(3-ethyl-4-((S)-2-hydroxypropanoyl)piperidin-4-yl)benzyl)-3-methylindolin-2-yl)-1H-pyrazole-4-carboxylate (Diastereomer-1) (Peak-1) and ethyl 5-ethyl-1-(6-(1-(3-ethyl-4-(1-((S)-2-hydroxypropanoyl)piperidin-4-yl)benzyl)-3-methylindolin-7-yl)pyridin-2-yl)-1H-pyrazole-4-carboxylate (Diastereomer-2) (Peak-2)

Resolution of the diastereomers of ethyl 5-ethyl-1-(6-(1-(3-ethyl-4-(1-((S)-2-hydroxypropanoyl)piperidin-4-yl)benzyl)-3-methylindolin-7-yl)pyridin-2-yl)-1H-pyrazole-4-carboxylate was achieved by chiral SFC using CHIRALPAK® AS-H column with 25% 2-propanol in $CO_2$ to afford ethyl 5-ethyl-1-(6-(1-(3-ethyl-4-(1-((S)-2-hydroxypropanoyl)piperidin-4-yl)benzyl)-3-methylindolin-7-yl)pyridin-2-yl)-1H-pyrazole-4-carboxylate (diastereomer-1) (Peak-1, $t_r$=9.8 min) and ethyl 5-ethyl-1-(6-(1-(3-ethyl-4-(1-((S)-2-hydroxypropanoyl)piperidin-4-yl)benzyl)-3-methylindolin-7-yl)pyridin-2-yl)-1H-pyrazole-4-carboxylate (diastereomer-2) (Peak-2, $t_r$=11.8 min).

Example 17a. 5-Ethyl-1-(6-(1-(3-ethyl-4-(1-(S)-2-hydroxypropanoyl)piperidin-4-yl)benzyl)-3-methylindolin-7-yl)pyridin-2-yl)-1H-pyrazole-4-carboxylic Acid (Diastereomer-1)

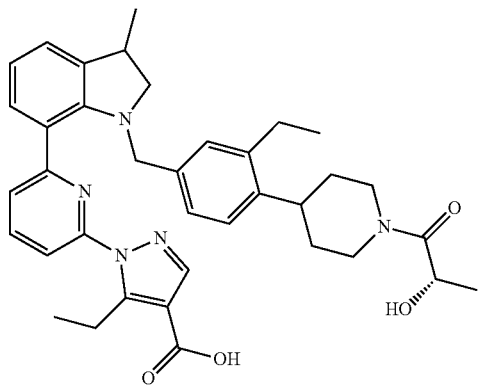 [SMILES: CCc1cc(CN2CC(C)c3cccc(-c4cccc(-n5ncc(C(=O)O)c5CC)n4)c32)ccc1C1CCN(C(=O)[C@H](C)O)CC1]

To a solution of ethyl 5-ethyl-1-(6-(1-(3-ethyl-4-(1-((S)-2-hydroxypropanoyl)piperidin-4-yl)benzyl)-3-methylindolin-7-yl)pyridin-2-yl)-1H-pyrazole-4-carboxylate (diastereomer-1) (Peak-1, $t_r$=9.8 min) (51 mg, 0.078 mmol) in MeOH (0.79 mL) and THF (0.79 mL) was added LiOH (1M aq) (0.79 mL, 0.79 mmol). The mixture was then stirred at 40° C. for 3 h, and then cooled to room temperature. The reaction mixture at 0° C. was rendered acidic by HCl (aq, 1M) (0.86 mL, 0.86 mmol), and then extracted with EtOAc.

The aqueous layer was extracted with EtOAc. The combined organic layers were concentrated. The resulting residue was triturated with a mixture of MeOH and DMSO. The resulting solid was collected by filtration to afford the title compound. $^1$H NMR (400 MHz, Methanol-$d_4$) δ 7.97 (s, 1H), 7.86 (t, J=7.9 Hz, 1H), 7.65-7.62 (m, 1H), 7.60-7.56 (m, 1H), 7.24 (d, J=7.7 Hz, 1H), 7.15-7.11 (m, 1H), 6.98 (d, J=8.0 Hz, 1H), 6.89-6.81 (m, 3H), 4.69-4.54 (m, 2H), 4.16-4.06 (m, 1H), 3.96 (d, J=15.2 Hz, 1H), 3.84 (d, J=15.2 Hz, 1H), 3.59 (t, J=9.5 Hz, 1H), 3.39-3.34 (m, 2H), 3.23-3.14 (m, 2H), 3.06-2.93 (m, 2H), 2.75 (t, J=13.2 Hz, 1H), 2.57 (q, J=7.6 Hz, 2H), 1.79-1.68 (m, 2H), 1.68-1.52 (m, 2H), 1.39-1.30 (m, 3H), 1.27 (d, J=6.8 Hz, 3H), 1.19 (t, J=7.3 Hz, 3H), 1.09 (t, J=7.5 Hz, 3H). HRMS; calcd. for $C_{37}H_{44}N_5O_4$ (M+H) 622.3393, found 622.3401.

Example 17b. 5-Ethyl-1-(6-(1-(3-ethyl-4-(1-((S)-2-hydroxypropanoyl)piperidin-4-yl)benzyl)-3-methylindolin-7-yl)pyridin-2-yl)-1H-pyrazole-4-carboxylic Acid (Diastereomer-2)

Saponification of ethyl 5-ethyl-1-(6-(1-(3-ethyl-4-(1-((S)-2-hydroxypropanoyl)piperidin-4-yl)benzyl)-3-methylindolin-7-yl)pyridin-2-yl)-1H-pyrazole-4-carboxylate (diastereomer-2) (Peak-2, $t_r$=11.8 min) by the similar method as described for the synthesis of Example 17a afforded the title compound after purification by RP-HPLC (HC-B). $^1$H NMR (400 MHz, Methanol-$d_4$) δ 8.05-7.97 (m, 1H), 7.90 (s, 1H), 7.70-7.65 (m, 1H), 7.63 (s, 1H), 7.29-7.25 (m, 1H), 7.19-7.14 (m, 1H), 7.00 (s, 1H), 6.87 (d, J=7.6 Hz, 3H), 4.73-4.56 (m, 2H), 4.20-4.09 (m, 1H), 4.03-3.96 (m, 1H), 3.92-3.84 (m, 1H), 3.67-3.59 (m, 1H), 3.38 (d, J=7.3 Hz, 2H), 3.31-3.13 (m, 2H), 3.02 (s, 2H), 2.85-2.73 (m, 1H), 2.61 (d, J=7.6 Hz, 2H), 1.81-1.54 (m, 4H), 1.41-1.30 (m, 6H), 1.22 (t, J=7.3 Hz, 3H), 1.12 (t, J=7.5 Hz, 3H). HRMS; calcd. for $C_{37}H_{44}N_5O_4$ (M+H) 622.3380, found 622.3383.

Example 18. (S)-5-Ethyl-1-(6-(1-(4-(1-(2-hydroxypropanoyl)piperidin-4-yl)-2-methylbenzyl)indolin-7-yl)pyridin-2-yl)-1H-pyrazole-4-carboxylic Acid

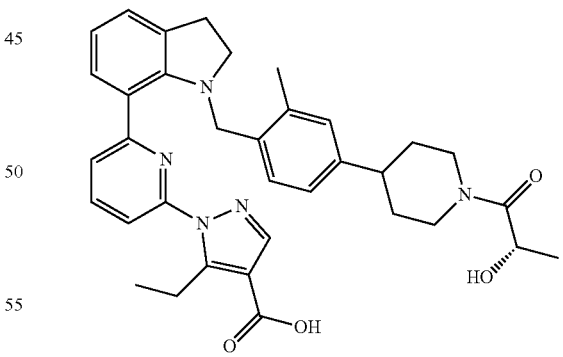

The title compound was synthesized by the method as outlined in the synthesis of Example 17 (i.e. 17-A→17-B→17-C→$_{17}$-D→17-E. a)→17a) but using 7-bromoindole in the place of 7-bromo-3-methyl-1H-indole in the step of Example 17-A. $^1$H NMR (400 MHz, DMSO-$d_4$) δ 7.81 (s, 1H), 7.66 (dd, J=7.8, 8.0 Hz, 1H), 7.57 (dd, J=0.8, 8.0 Hz, 1H), 7.38 (d, J=7.6 Hz, 1H), 7.22 (d, J=7.8 Hz, 1H), 7.17 (d, J=7.2 Hz, 2H), 6.93-7.00 (m, 1H), 6.85-6.91 (m, 1H), 6.80 (dd, J=7.3, 7.6 Hz, 1H), 4.39-4.56 (m, 2H), 4.01-4.14 (m, 1H), 3.84 (s, 2H), 3.32-3.41 (m, 5H), 2.99-3.10 (m, 2H), 2.58-2.73 (m, 2H), 1.86 (s, 3H), 1.68-1.81 (m, 2H), 1.32-1.59 (m, 2H), 1.15-1.23 (m, 3H), 1.08 (t, J=7.3 Hz, 3H). HRMS; calcd. for $C_{35}H_{40}N_5O_4$ (M+H) 594.3080, found 594.3068.

Example 19

Example 19-A. (±)-Ethyl 1-(6-(3-methyl-1H-indol-7-yl)pyridin-2-yl)-5-(trifluoromethyl)-1H-pyrazole-4-carboxylate

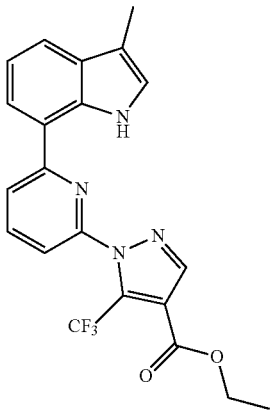 [SMILES: CCOC(=O)c1cnn(-c2cccc(-c3cccc4c(C)c[nH]c34)n2)c1C(F)(F)F]

The title compound was synthesized in fashion analogous to the synthesis of Example 17-A but using ethyl 1-(6-bromopyridin-2-yl)-5-(trifluoromethyl)-1H-pyrazole-4-carboxylate (Intermediate 1-1) instead of Intermediate 1-4-2. MS (ESI+) m/z 415.2 (M+H).

Example 19-B. (±)-Ethyl 1-(6-(3-methylindolin-7-yl)pyridin-2-yl)-5-(trifluoromethyl)-1H-pyrazole-4-carboxylate

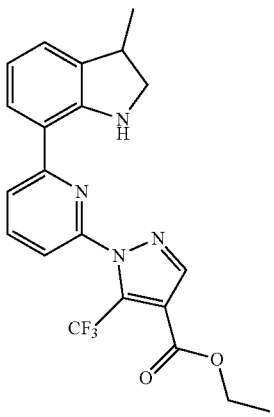 [SMILES: CCOC(=O)c1cnn(-c2cccc(-c3cccc4c3NCC4C)n2)c1C(F)(F)F]

The title compound was synthesized starting from ethyl 1-(6-(3-methyl-1H-indol-7-yl)pyridin-2-yl)-5-(trifluoromethyl)-1H-pyrazole-4-carboxylate in fashion analogous to the synthesis of Example 17-B. MS (ESI+) m/z 417.0 (M+H).

Example 19-C. a). (±)-Ethyl 1-(6-(1-(4-(1-(cyclopropanecarbonyl)piperidin-4-yl)-3-ethylbenzyl)-3-methylindolin-7-yl)pyridin-2-yl)-5-(trifluoromethyl)-1H-pyrazole-4-carboxylate

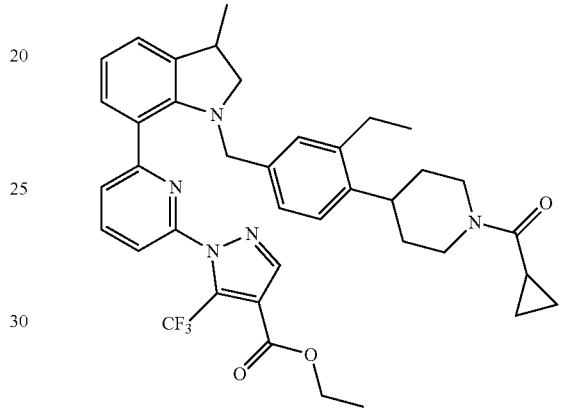

The title compound was synthesized by alkylation of (±)-ethyl 1-(6-(3-methylindolin-7-yl)pyridin-2-yl)-5-(trifluoromethyl)-1H-pyrazole-4-carboxylate with (4-(4-(bromomethyl)-2-ethylphenyl)piperidin-1-yl)(cyclopropyl)methanone, Intermediate 5-3, by an analogous method as described in the synthesis of Example 17-C. MS (ESI+) m/z 686.4 (M+H).

Example 19-C. b). Ethyl 1-(6-(1-(4-(1-(cyclopropanecarbonyl)piperidin-4-yl)-3-ethylbenzyl)-3-methylindolin-7-yl)pyridin-2-yl)-6-(trifluoromethyl)-1H-pyrazole-4-carboxylate (Enantiomer-1) and ethyl 1-(6-(1-(4-(1-(cyclopropanecarbonyl)piperidin-4-yl)-3-ethylbenzyl)-3-methylindolin-7-yl)pyridin-2-yl)-8-(trifluoromethyl)-1H-pyrazole-4-carboxylate (Enantiomer-2)

Resolution of the enantiomers of (±)-ethyl 1-(6-(1-(4-(1-(cyclopropanecarbonyl)piperidin-4-yl)-3-ethylbenzyl)-3-methylindolin-7-yl)pyridin-2-yl)-5-(trifluoromethyl)-1H-pyrazole-4-carboxylate was achieved by chiral HPLC using CHIRALPAK® IA column with 70% (0.1% DEA in hexane) in EtOH to afford ethyl 1-(6-(1-(4-(1-(cyclopropanecarbonyl)piperidin-4-yl)-3-ethylbenzyl)-3-methylindolin-7-yl)pyridin-2-yl)-5-(trifluoromethyl)-1H-pyrazole-4-carboxylate (enantiomer-1, $t_r$=11.6 min) and ethyl 1-(6-(1-(4-(1-(cyclopropanecarbonyl)piperidin-4-yl)-3-ethylbenzyl)-3-methylindolin-7-yl)pyridin-2-yl)-5-(trifluoromethyl)-1H-pyrazole-4-carboxylate (enantiomer-2, $t_r$=13.3 min).

Example 19a. (+)-1-(6-(1-(4-(1-(Cyclopropanecarbonyl)piperidin-4-yl)-3-ethylbenzyl)-3-methylindolin-7-yl)pyridin-2-yl)-1-trifluoromethyl)-1H-pyrazole-4-carboxylic Acid

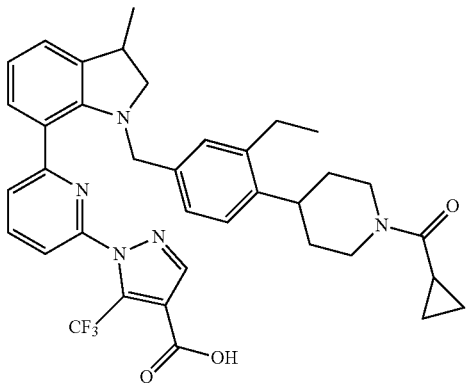 [SMILES: CCc1cc(CN2CC(C)c3cccc(-c4cccc(-n5ncc(C(=O)O)c5C(F)(F)F)n4)c32)ccc1C1CCN(C(=O)C2CC2)CC1]

The title compound was saponified starting from ethyl 1-(6-(1-(4-(1-(cyclopropanecarbonyl)piperidin-4-yl)-3-ethylbenzyl)-3-methylindolin-7-yl)pyridin-2-yl)-5-(trifluoromethyl)-1H-pyrazole-4-carboxylate (enantiomer-1, $t_r$=11.6 min) by the similar method as described for the synthesis of Example 1. a). $^1$H NMR (400 MHz, Methanol-$d_4$) δ 8.12 (s, 1H) 7.85-7.91 (m, 1H) 7.78 (dd, J=7.8, 0.7 Hz, 1H) 7.49 (dd, J=7.8, 0.7 Hz, 1H) 7.27 (d, J=7.6 Hz, 1H) 7.14 (d, J=7.3 Hz, 1H) 6.98-7.03 (m, 1H) 6.90-8.95 (m, 1H) 6.82-6.88 (m, 2H) 4.61-4.71 (m, 1H) 4.42-4.52 (m, 1H) 3.94-4.02 (m, 1H) 3.81-3.89 (m, 1H) 3.60 (t, J=9.5 Hz, 1H) 3.20-3.28 (m, 2H) 2.99-3.09 (m, 1H) 2.92-2.99 (m, 1H) 2.70-2.80 (m, 1H) 2.62 (q, J=7.5 Hz, 2H) 1.96-2.05 (m, 1H) 1.49-1.85 (m, 4H) 1.27 (d, J=6.8 Hz, 3H) 1.12 (t, J=7.6 Hz, 3H) 0.76-0.96 (m, 4H). HRMS; calcd. for $C_{37}H_{39}F_3N_5O_3$ (M+H) 658.3005. found 658.2997.

Example 19b. (−)-1-(6-(1-(4-(1-(Cyclopropanecarbonyl)piperidin-4-yl)-3-ethylbenzyl)-3-methylindolin-7-yl)pyridin-2-yl)-5-(trifluoromethyl)-1H-pyrazole-4-carboxylic Acid Saponification of ethyl 1-(6-(1-(4-(1-(cyclopropanecarbonyl)piperidin-4-yl)-3-ethylbenzyl)-3-methylindolin-7-yl)pyridin-2-yl)-5-(trifluoromethyl)-1H-pyrazole-4-carboxylate (enantiomer-2, $t_r$=13.3 min) as described for the synthesis of Example 1. a) afforded the title compound. $^1$H NMR and HRMS were substantially identical to Example 19a.

Example 20

The following compounds can be synthesized as outlined for the preparation of Example 19 using the appropriate intermediates delineated in the table in place of Intermediate 1-1 and Intermediate 5-4 respectively. The racemic sample was resolved by the conditions described in the table.

| Example | Chemical structure / NMR and HRMS / Resolution conditions of enantiomers. | Chemical name / Intermediate 1 / Intermediate 5 |
|---|---|---|
| 20-1 | (structure shown) | 1-(6-(1-(4-(1-(cyclopropanecarbonyl)piperdin-4-yl)-3-ethylbenzyl)-3-methylindolin-7-yl)pyridin-2-yl)-5-ethyl-1H-pyrazole-4-carboxylic acid<br>Intermediate 1-4-2<br>Intermediate 5-3 |

$^1$H NMR (400 MHz, DMSO-$d_6$ δ 7.92-7.85 (m, 1H), 7.83 (s, 1H), 7.67-7.62 (m, 1H), 7.60 (d, J = 7.7 Hz, 1H), 7.23 (d, J =7.7 Hz, 1H), 7.14 (d, J = 7.1 Hz, 1H), 7.04 (d, J = 7.9 Hz, 1H), 6.92-6.79 (m, 3H), 4.59-4.28 (m, 2H), 4.00-3.90 (m, 1H), 3.81-3.77 (m, 1H), 3.56-3.52 (m, 1H), 3.46-3.36 (m, 3H), 3.17 (s, 2H), 2.98-2.83 (m, 2H), 2.69-2.52 (m, 3H), 2.03-1.94 (m, 1H), 1.73-1.32 (m, 4H), 1.23 (d, J = 6.8 Hz, 3H), 1.13 (t, J = 7.3 Hz, 3H), 1.05 (t, J = 7.5 Hz, 3H), 0.84-0.62 (m, 4H). HRMS; calcd. for $C_{38}H_{44}N_5O_3$ (M + H) 618.3445, found 618.3298.
Resolution conditions of enantiomers of corresponding esters:
Ethyl 1-(6-(1-(4-(1-(cyclopropanecarbonyl)piperidin-4-yl)-3-ethylbenzyl)-3-methylindolin-7-yl)pyridin-2-yl)-5-ethyl-1H-pyrazole-4-carboxylate was subjected to chiral SFC using CHIRALCEL ® OJ-H column with 5% MeOH with 0.1% TFA in $CO_2$ to give (+)-ethyl 1-(6-(1-(4-(1-(cyclopropanecarbonyl)piperidin-4-yl)-3-ethylbenzyl)-3-methylindolin-7-yl)pyridin-2-yl)-5-ethyl-1H-pyrazole-4-carboxylate ($t_r$ = 2.95 min) and (−)-ethyl 1-(6-(1-(4-(1-(cyclopropanecarbonyl)piperidin-4-yl)-3-ethylbenzyl)-3-methylindolin-7-yl)pyridin-2-yl)-5-ethyl-1H-pyrazole-4-carboxylate ($t_r$ = 3.36 min).
(+)-20-1: (+)-1-(6-(1-(4-(1-(Cyclopropanecarbonyl)piperidin-4-yl)-3-ethylbenzyl)-3-methylindolin-7-yl)pyridin-2-yl)-5-ethyl-1H-pyrazole-4-carboxylic acid was derived from saponification of (+)-ethyl 1-(6-(1-(4-(1-(cyclopropanecarbonyl)piperidin-4-yl)-3-ethylbenzyl)-3-methylindolin-7-yl)pyridin-2-yl)-5-ethyl-1H-pyrazole-4-carboxylate ($t_r$ = 2.95 min).

| | Chemical name |
|---|---|
| | Intermediate 1 |
| Chemical structure | Intermediate 5 |
| NMR and HRMS | |
| Resolution conditions of enantiomers. | |
| Example (+)-and (−)-Carboxylic acids derived from their corresponding resolved ester enantiomers. | |

(−)-20-1: (−)-1-(6-(1-(4-(1-(Cyclopropanecarbonyl)piperidin-4-yl)-3-ethylbenzyl)-3-methylindolin-7-yl)pyridin-2-yl)-5-ethyl-1H-pyrazole-4-carboxylic acid was derived from saponification of (−)-ethyl 1-(6-(1-(4-(1-(cyclopropanecarbonyl)piperidin-4-yl)-3-ethylbenzyl)-3-methylindolin-7-yl)pyridin-2-yl)-5-ethyl-1H-pyrazole-4-carboxylate ($t_r$ = 3.36 min).

20-2 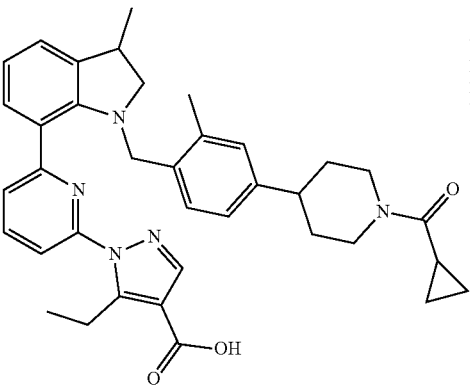 [SMILES: CCc1c(C(=O)O)cnn1-c1cccc(-c2cccc3c2N(Cc2ccc(C4CCN(C(=O)C5CC5)CC4)cc2C)CC3C)n1]

1-(6-(1-(4-(1-(cyclopropanecarbonyl)piperidin-4-yl)-2-methylbenzyl)-3-methylindolin-7-yl)pyridin-2-yl)-5-ethyl-1H-pyrazole-4-carboxylic acid
Intermediate 1-4-2
Intermediate 5-6

$^1$H NMR (400 MHz, DMSO-$d_6$) δ 7.94 (s, 1 H) 7.69-7.78 (m, 1 H) 7.60 (d, J = 7.5 Hz, 1 H) 7.44 (d, J = 7.6 Hz, 1 H) 7.13-7.24 (m, 3 H) 6.96 (d, J = 7.8 Hz, 1 H) 6.90 (s, 1 H) 6.83 (t, J = 7.5 Hz, 1 H 4.45-4.55 (m, 1 H) 4.30-4.40 (m, 1 H) 3.91 (d, J = 15.7 Hz, 1 H) 3.74 (d, J = 15.7 Hz, 1 H) 3.46-3.57 (m, 1 H) 3.25-3.29 (m, 3 H) 3.08-3.20 (m, 1 H) 2.82-2.93 (m, 1 H) 2.58-2.76 (m, 2 H) 1.94-2.04 (m, 1 H) 1.86 (s, 3 H) 1.67-1.83 (m, 2 H) 1.33-1.58 (m, 2 H)1.29 (d, J = 6.7 Hz, 3 H) 1.12 (t, J = 7.3 Hz, 3 H) 0.69 (d, J = 7.8 Hz, 4 H). HRMS; calcd. for $C_{37}H_{42}N_5O_3$ (M + H) 604.3288, found 604.3242.
Resolution conditions of enantiomers of corresponding esters:
(±)-Ethyl 1-(6-(1-(4-(1-(cyclopropanecarbonyl)piperidin-4-yl)-2-methylbenzyl)-3-methylindolin-7-yl)pyridin-2-yl)-5-ethyl-1H-pyrazole-4-carboxylate was subjected to chiral SFC using CHIRALPAK ® IA column with 30% 2-propanol in $CO_2$ to give ethyl 1-(6-(1-(4-(1-(cyclopropanecarbonyl)piperidin-4-yl)-2-methylbenzyl)-3-methylindolin-7-yl)-pyridin-2-yl)-5-ethyl-1H-pyrazole-4-carboxylate (enantiomer-1, $t_r$ = 7.0 min) and ethyl 1-(6-(1-(4-(1-cyclopropanecarbonyl)piperidin-4-yl)-2-methylbenzyl)-3-methylindolin-7-yl)pyridin-2-yl)-5-ethyl-1H-pyrazole-4-carboxylate (enantiomer-2, $t_r$ = 7.8 min)
(+)-20-2: (+)-1-(6-(1-(4-(1-(Cyclopropanecarbonyl)piperidin-4-yl)-2-methylbenzyl)-3-methylindolin-7-yl)pyridin-2-yl)-5-ethyl-1H-pyrazole-4-carboxylic acid was derived from saponification of ethyl 1-(6-(1-(4-(1-cyclopropanecarbonyl)piperidin-4-yl)-2-methylbenzyl)-3-methylindolin-7-yl)pyridin-2-yl)-5-ethyl-1H-pyrazole-4-carboxylate (enantiomer-1, $t_r$ = 7.0 min).
(−)-20-2: (−)-1-(6-(1-(4-(1-(Cyclopropanecarbonyl)piperidin-4-yl)-2-methylbenzyl)-3-methylindolin-7-yl)pyridin-2-yl)-5-ethyl-1H-pyrazole-4-carboxylic acid was derived from saponification of ethyl 1-(6-(1-(4-(1-(cyclopropanecarbonyl)piperidin-4-yl)-2-methylbenzyl)-3-methylindolin-7-yl)pyridin-2-yl)-5-ethyl-1H-pyrazole-4-carboxylate (enantiomer-2, $t_r$ = 7.8 min).

20-3 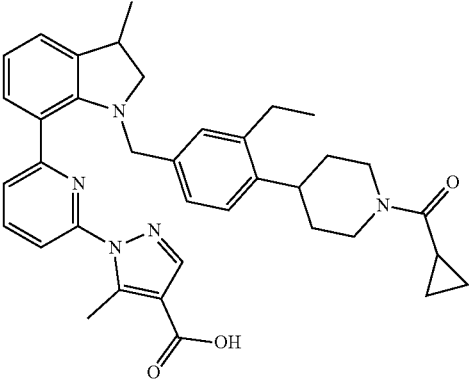 [SMILES: CCc1cc(CN2CC(C)c3cccc(-c4cccc(-n5ncc(C(=O)O)c5C)n4)c32)ccc1C1CCN(C(=O)C2CC2)CC1]

1-(6-(1-(4-(1-(Cyclopropanecarbonyl)piperidin-4-yl)-3-ethylbenzyl)-3-methylindolin-7-yl)pyridin-2-yl)-5-methyl-1H-pyrazole-4-carboxylic acid
Intermediate 1-3
Intermediate 5-3

$^1$H NMR (400 MHz, Methanol-$d_4$) δ 7.96 (s, 1H), 7.85 (t, J = 7.9 Hz, 1H), 7.60 (t, J = 7.3 Hz, 2H), 7.24 (d, J = 7.6 Hz, 1H), 7.13 (d, J = 7.2 Hz, 1H), 6.98 (d, J = 8.0 Hz, 1H), 6.90-6.81 (m, 3H), 4.64 (d, J = 14.2 Hz, 1H), 4.45 (d, J = 14.5 Hz, 1H), 3.97 (d, J = 15.3 Hz, 1H), 3.82 (d, J = 15.3 Hz, 1H), 3.60 (t, J = 9.5 Hz, 1H), 3.22 (q, J = 7.5 Hz, 1H), 3.07-2.91 (m, 3H), 2.79 (s, 3H), 2.73 (t, J = 12.4 Hz, 1H), 2.58 (q, J = 7.5 Hz, 2H), 2.04-1.96 (m, 1H), 1.84-1.48 (m, 4H), 1.28 (d, J = 6.8 Hz, 3H), 1.10 (t, J = 7.5 Hz, 3H), 0.96-0.75 (m, 4H). HRMS; calcd. for $C_{37}H_{42}N_5O_3$ (M + H) 604.3288, found 604.3287.

| | Chemical name |
|---|---|
| | Intermediate 1 |
| Chemical structure | Intermediate 5 |
| NMR and HRMS | |
| Resolution conditions of enantiomers. | |
| Example (+)-and (−)-Carboxylic acids derived from their corresponding resolved ester enantiomers. | |

Resolution conditions of enantiomers of corresponding esters:

(±)-Ethyl 1-(6-(1-(4-(1-(cyclopropanecarbonyl)piperidin-4-yl)-3-ethylbenzyl)-3-methylindolin-7-yl)pyridin-2-yl)-5-methyl-1H-pyrazole-4-carboxylate was subjected to chiral SFC using CHIRALPAK ® column with 30% 2-propanol in $CO_2$ to give ethyl 1-(6-(1-(4-(1-(cyclopropanecarbonyl)piperidin-4-yl)-3-ethylbenzyl)-3-methylindolin-7-yl)-pyridin-2-yl)-5-methyl-1H-pyrazole-4-carboxylate (enantiomer-1, $t_r$ = 7.9 min) and ethyl 1-(6-(1-(4-(1-(cyclopropane-carbonyl)piperidin-4-yl)-3-ethylbenzyl)-3-methylindolin-7-yl)pyridin-2-yl)-5-methyl-1H-pyrazole-4-carboxylate (enantiomer-2, $t_r$ = 9.8 min).

(+)-20-3: (+)-1-(6-(1-(4-(1-(Cyclopropanecarbonyl)piperidin-4-yl)-3-ethylbenzyl)-3-methylindolin-7-yl)pyridin-2-yl)-5-methyl-1H-pyrazole-4-carboxylic acid was derived from saponification of ethyl 1-(6-(1-(4-(1-cyclopropane-carbonyl)piperidin-4-yl)-3-ethylbenzyl)-3-methylindolin-7-yl)pyridin-2-yl)-5-methyl-1H-pyrazole-4-carboxylate (enantiomer-1, $t_r$ = 7.9 min).

(−)-20-3: (−)-1-(6-(1-(4-(1-(Cyclopropanecarbonyl)piperidin-4-yl)-3-ethylbenzyl)-3-methylindolin-7-yl)pyridin-2-yl)-5-methyl-1H-pyrazole-4-carboxylic acid was derived from saponification of ethyl 1-(6-(1-(4-(1-(cyclopropane-carbonyl)piperidin-4-yl)-3-ethylbenzyl)-3-methylindolin-7-yl)pyridin-2-yl)-5-methyl-1H-pyrazole-4-carboxylate (enantiomer-2, $t_r$ = 9.8 min).

Example 21

The following compounds can be synthesized as outlined for the preparation of Example 19, using appropriate materials in the table (Intermediate 1 and Intermediate 5) in place of (Intermediate 1-1 and Intermediate 5-4) respectively.

| | IUPAC name |
|---|---|
| | Intermediate 1 |
| structure | Intermediate 5 |
| Example ¹H NMR and HRMS data | |

| 21-1 | 1-(6-(1-(4-(1-(Cyclopropanecarbonyl)piperidin-4-yl)-2-methylbenzyl)indolin-7-yl)pyridin-2-yl)-5-methyl-1H-pyrazole-4-carboxylic acid |
|---|---|
| | Intermediate 1-3 |
| | Intermediate 5-6 |

$^1$H NMR (400 MHz, Methanol-$d_4$) δ 7.93 (s, 1 H) 7.65-7.72 (m, 1 H) 7.52 (dd, J = 8.0, 0.8 Hz, 1 H) 7.45 (dd, J = 7.7, 0.8 Hz, 1 H) 7.29 (d, J = 8.0 Hz, 1 H) 7.14-7.20 (m, 2 H) 6.92 (d, J = 7.8 Hz, 1 H) 6.84 (s, 1 H) 6.80 (t, J = 7.5 Hz, 1 H) 4.52-4.69 (m, 2 H) 4.44 (d, J = 12.6 Hz, 1 H) 3.87 (s, 2 H) 3.37-3.46 (m, 2 H) 3.18-3.26 (m, 1 H) 3.03-3.12 (m, 2 H) 2.76 (s, 3 H) 2.66-2.78 (m, 1 H), 1.96-2.04 (m, 1 H) 1.86 (s, 3 H) 1.78-1.94 (m, 1 H) 1.45-1.67 (m, 2 H) 1.26-1.34 (m, 1 H) 0.76-0.94 (m, 4 H). HRMS; calcd. for $C_{35}H_{38}N_5O_3$ (M + H) 576.2975, found 576.2975.

| Example | structure ¹H NMR and HRMS data | IUPAC name Intermediate 1 Intermediate 5 |
|---|---|---|
| 21-2 | 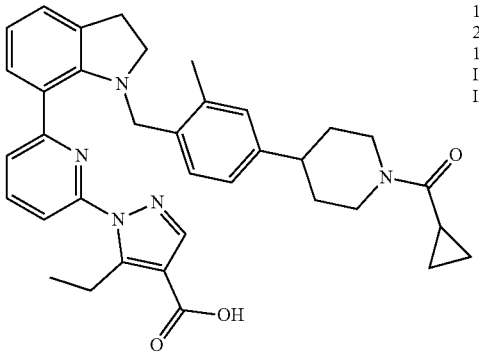 | 1-(6-(1-(4-(1-(Cyclopropanecarbonyl)piperidin-4-yl)-2-methylbenzyl)indolin-7-yl)pyridin-2-yl)-5-ethyl-1H-pyrazole-4-carboxylic acid<br>Intermediate 1-4-2<br>Intermediate 5-6 |
| | ¹H NMR (400 MHz, Methanol-d₄) δ 7.91 (s, 1 H) 7.58-7.65 (m, 1 H) 7.49-7.40 (2 H, m), 7.29 (d, J = 8.1 Hz, 1 H) 7.21 (d, J = 7.8 Hz, 1 H) 7.16 (dd, J = 7.1, 1.2 Hz, 1 H) 6.98 (d, J = 7.8 Hz, 1 H) 6.88 (s, 1 H) 6.81 (t, J = 7.5 Hz, 1 H) 4.41-4.68 (m, 4 H) 3.89 (s, 2 H) 3.37-3.46 (m, 4 H) 3.02-3.11 (m, 2 H) 2.67-2.83 (m, 2 H) 1.97-2.06 (m, 1 H) 1.90 (s, 3 H) 1.83 (d, J = 8.6 Hz, 1 H) 1.47-1.70 (m, 2 H) 1.13 (t, J = 7.4 Hz, 3 H) 0.78-0.95 (m, 4 H). HRMS; calcd. for $C_{36}H_{40}N_5O_3$ (M + H) 590.3131, found 590.3105. | |

Example 22

Example 22-A. a). (±)-Ethyl 5-ethyl-1-(6-(2-methylindolin-7-yl)pyridin-2-yl)-1H-pyrazole-4-carboxylate

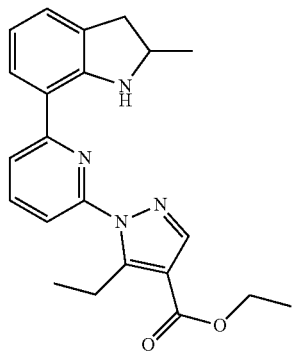 [SMILES: CCOC(=O)c1cnn(-c2cccc(-c3cccc4c3NC(C)C4)n2)c1CC]

The title compound was synthesized in fashion analogous to the synthesis of (±)-ethyl 5-ethyl-1-(6-(3-methylindolin-7-yl)pyridin-2-yl)-1H-pyrazole-4-carboxylate (Example 17-B) but using 7-bromo-2-methyl-1H-indole (CAS #302912-38-5) instead of 7-bromo-3-methyl-1H-indole. MS (ESI+) m/z 377.2 (M+H).

Example 22-A. b). Ethyl 5-ethyl-1-(6-(2-methylindolin-7-yl)pyridin-2-yl)-1H-pyrazole-4-carboxylate (Enantiomer-1) and ethyl 5-ethyl-1-(6-(2-methylindolin-7-yl)pyridin-2-yl)-1H-pyrazole-4-carboxylate (Enantiomer-2)

Resolution of the enantiomers of (±)-ethyl 5-ethyl-1-(6-(2-methylindolin-7-yl)pyridin-2-yl)-1H-pyrazole-4-carboxylate was achieved by HPLC using CHIRALPAK® IA column with 90% (0.1% DEA in hexane) in 2-propanol to afford ethyl 5-ethyl-1-(6-(2-methylindolin-7-yl)pyridin-2-yl)-1H-pyrazole-4-carboxylate (enantiomer-1, $t_r$=6.3 min) and ethyl 5-ethyl-1-(6-(2-methylindolin-7-yl)pyridin-2-yl)-1H-pyrazole-4-carboxylate (enantiomer-2, $t_r$=9.5 min).

Example 22a. (+)-1-(6-(1-(4-(1-(Cyclopropanecarbonyl)piperidin-4-yl)-3-ethylbenzyl)-2-methylindolin-7-yl)pyridin-2-yl)-6-ethyl-1H-pyrazole-4-carboxylic Acid The title compound was synthesized starting from ethyl 5-ethyl-1-(6-(2-methylindolin-7-yl)pyridin-2-yl)-1H-pyrazole-4-carboxylate (enantiomer-1, $t_r$=6.3 min) by a similar method described for the preparation of Example 19-8. a) and saponified as in the Example 7a. ¹H NMR (400 MHz, Methanol-d₄) δ 8.00 (s, 1H), 7.84 (dd, J=7.8, 8.0 Hz, 1H), 7.55-7.62 (m, 2H), 7.18 (d, J=8.0 Hz, 1H), 7.11 (dd, J=1.2, 7.2 Hz, 1H), 6.88-6.94 (m, 1H), 6.69-6.82 (m, 3H), 4.58-4.67 (m, 1H), 4.36-4.48 (m, 1H), 3.97-4.08 (m, 2H), 3.67-3.78 (m, 1H), 3.33-3.44 (m, 2H), 3.17-3.28 (m, 2H), 2.92-3.03 (m, 1H), 2.66-2.77 (m, 1H), 2.47-2.63 (m, 3H), 1.94-

2.03 (m, 1H), 1.44-1.79 (m, 4H), 1.24-1.31 (m, 3H), 1.20 (t, J=7.27 Hz, 3H), 1.00-1.08 (m, 3H), 0.76-0.94 (m, 4H) HRMS: calcd. for: $C_3H_{44}N_5O_3$ (M+H) 618.3444, found 618.3450.

Example 22b. (−)-1-(6-(1-(4-(1-(Cyclopropanecarbonyl)piperidin-4-yl)-3-ethylbenzyl)-2-methylindolin-7-yl)pyridin-2-yl)-8-ethyl-1H-pyrazole-4-carboxylic Acid The title compound was synthesized starting from ethyl 5-ethyl-1-(6-(2-methylindolin-7-yl)pyridin-2-yl)-1H-pyrazole-4-carboxylate (enantiomer-2, $t_r$=9.5 min) by an analogous method as described for the synthesis of Example 22a. $^1$H NMR and HRMS data were substantially identical to Example 22a.

Example 23

Example 23-A. (4-(4-((7-Bromo-3,3-dimethylindolin-1-yl)methyl)-2-ethylphenyl)piperidin-1-yl)(cyclopropyl)methanone

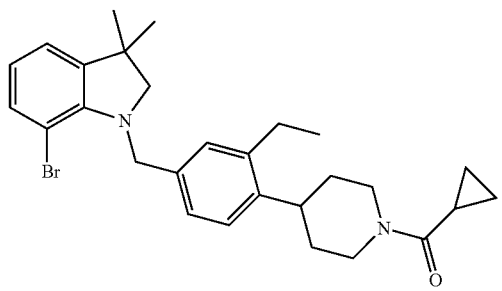 [SMILES: CCc1cc(CN2CC(C)(C)c3cccc(Br)c32)ccc1C1CCN(C(=O)C2CC2)CC1]

The title compound was synthesized by reaction of 7-bromo-3,3-dimethylindoline (CAS #1260675-93-1) with (4-(4-(bromomethyl)-2-ethylphenyl)piperidin-1-yl)(cyclopropyl)methanone (Intermediate 5-3) by analogous method as described in the synthesis of Example 17-C. MS (ESI+) m/z 495.4 (M+H).

Example 23. 1-(6-(1-(4-(1-(Cyclopropanecarbonyl)piperidin-4-ylethyl)-3-ethylbenzyl)-3,3-dimethylindolin-7-yl)pyridin-2-yl)-5-ethyl-1H-pyrazole-4-carboxylic Acid

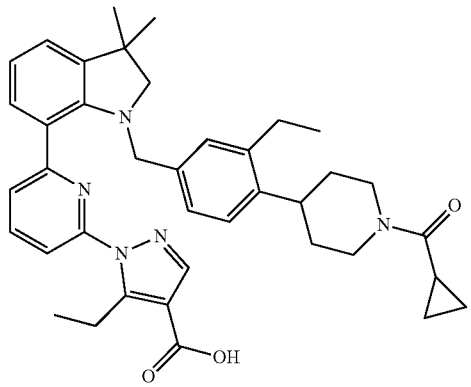 [SMILES: CCc1cc(CN2CC(C)(C)c3cccc(-c4cccc(-n5ncc(C(=O)O)c5CC)n4)c32)ccc1C1CCN(C(=O)C2CC2)CC1]

The title compound was synthesized by reaction of ethyl 1-(6-bromopyridin-2-yl)-5-ethyl-1H-pyrazole-4-carboxylate (Intermediate 1-4-2) with (4-(4-((7-Bromo-3,3-dimethylindolin-1-yl)methyl)-2-ethylphenyl)piperidin-1-yl)(cyclopropyl)methanone by the similar method as described for the synthesis of Example 17-A, which was then saponified similarly to Example 7a. $^1$H NMR (400 MHz, Methanol-$d_4$) δ 7.97 (s, 1H), 7.85 (dd, J=7.7, 8.0 Hz, 1H), 7.58 (d, J=7.8 Hz, 2H), 7.21 (dd, J=1.3, 7.7 Hz, 1H), 7.10 (dd, J=1.2, 7.3 Hz, 1H), 6.98 (d, J=8.0 Hz, 1H), 6.80-6.88 (m, 3H), 4.64 (d, J=12.1 Hz, 1H), 4.45 (br. d, J=12.9 Hz, 1H), 3.92 (s, 2H), 3.32-3.38 (m, 2H), 3.20-3.28 (m, 1H), 3.18 (s, 2H), 2.96-3.06 (m, 1H), 2.67-2.79 (m, 1H), 2.57 (q, J=7.5 Hz, 2H), 1.95-2.04 (m, 1H), 1.47-1.82 (m, 4H), 1.29 (s, 6H), 1.20 (t, J=7.3 Hz, 3H), 1.09 (t, J=7.5 Hz, 3H), 0.76-0.95 (m, 4H) HRMS; calcd. for $C_3H_{46}N_5O_3$ (M+H) 632.3601, found 632.3595.

Example 24

Example 24-A. Ethyl 5-methyl-1-(6-(1-(2-methyl-4-(piperidin-4-yl)benzyl)indolin-7-yl)pyridin-2-yl)-1H-pyrazole-4-carboxylate

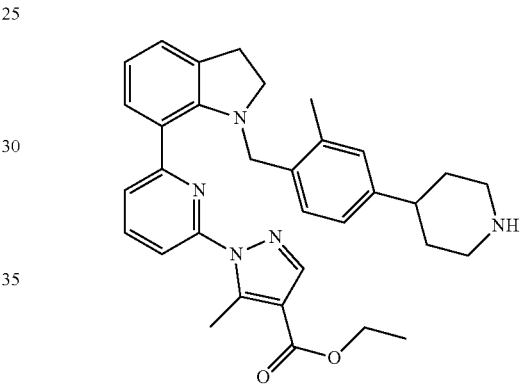

The title compound was synthesized by the methods as described as outlined in the preparation of Example 17 (i.e. Example 17-A→17-B→17-C→17-D) starting from Intermediate 1-3, 7-bromoindole and Intermediate 5-5. MS (ESI+) m/z 536.5 (M+H).

Example 24-B. Ethyl 1-(6-(1-(4-(1-cyclopropylpiperidin-4-yl)-2-methylbenzyl)indolin-7-yl)pyridin-2-yl)-5-methyl-1H-pyrazole-4-carboxylate

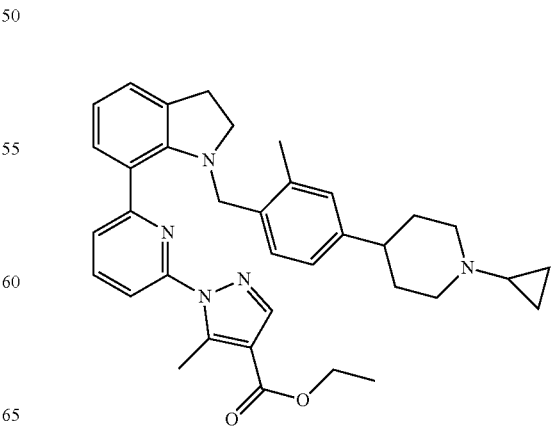

To a solution of ethyl 5-methyl-1-(6-(1-(2-methyl-4-(piperidin-4-yl)benzyl)indolin-7-yl)pyridin-2-yl)-1H-pyrazole-4-carboxylate (130 mg, 0.24 mmol) in EtOH (2 mL) was added 1-ethoxycyclopropyl)oxy-trimethylsilane (CAS #27374-25-0) (0.078 mL, 0.39 mmol), followed by AcOH (0.015 mL, 0.27 mmol) and NaCNBH$_3$ (31 mg, 0.49 mmol). The mixture was then stirred at 70° C. for 16 h, and then diluted with H$_2$O. The mixture was then extracted with CH$_2$Cl$_2$. The organic layer was then washed with brine, dried over MgSO$_4$, filtered and then concentrated. The resulting residue was purified by silica gel flash column chromatography (isocratic, 40% EtOAc in heptane) to afford the title compound. MS (ESI+) m/z 576.5 (M+H).

Example 24. 1-(6-(1-(4-(1-Cyclopropylpiperidin-4-yl)-2-methylbenzyl)indolin-7-yl)pyridin-2-yl)-5-methyl-1H-pyrazole-4-carboxylic Acid

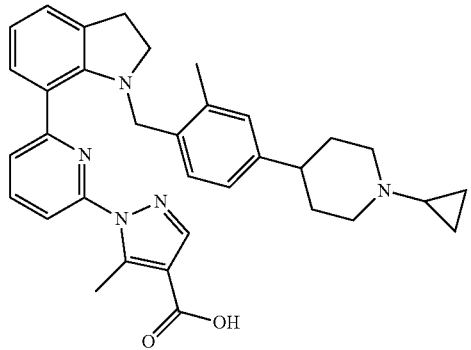 [SMILES: Cc1cc(C2CCN(C3CC3)CC2)ccc1CN1CCc2cccc(-c3cccc(-n4ncc(C(=O)O)c4C)n3)c21]

The title compound was synthesized by saponification of ethyl 1-(6-(1-(4-(1-cyclopropylpiperidin-4-yl)-2-methylbenzyl)indolin-7-yl)pyridin-2-yl)-5-methyl-1H-pyrazole-4-carboxylate by an analogous method as described for the synthesis of Example 7a. $^1$H NMR (400 MHz, DMSO-d$_6$) δ 7.89 (s, 1H), 7.71 (dd, J=7.8, 8.0 Hz, 1H), 7.61 (dd, J=0.8, 8.2 Hz, 1H), 7.39 (dd, J=0.8, 7.5 Hz, 1H), 7.14-7.20 (m, 3H), 6.90-6.95 (m, 1H), 6.85 (br. s, 1H), 6.79 (dd, J=7.2, 7.7 Hz, 1H), 3.82 (s, 2H), 3.33 (t, J=8.7 Hz, 2H), 2.97-3.07 (m, 4H), 2.78 (s, 3H), 2.31-2.41 (m, 1H), 2.17-2.26 (m, 2H), 1.83 (s, 3H), 1.56-1.70 (m, 3H), 1.43-1.55 (m, 2H), 0.38-0.44 (m, 2H), 0.26-0.32 (m, 2H). HRMS; calcd. for C$_{34}$H$_{38}$N$_5$O$_2$ (M+H) 548.3026, found 548.3000.

Example 25

Example 25-A. Ethyl 1-(6-(1-((1,2,3,4-tetrahydroisoquinolin-6-yl)methyl)indolin-7-yl)pyridin-2-yl)-5-(trifluoromethyl)-1H-pyrazole-4-carboxylate

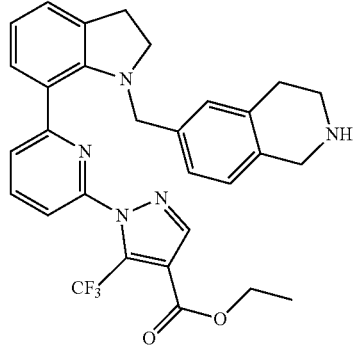 [SMILES: CCOC(=O)c1cnn(-c2cccc(-c3cccc4c3N(Cc3ccc5c(c3)CCNC5)CC4)n2)c1C(F)(F)F]

The title compound was synthesized by reaction of ethyl 1-(6-(indolin-7-yl)pyridin-2-yl)-5-(trifluoromethyl)-1H-pyrazole-4-carboxylate (Intermediate 4-1) with tert-butyl 6-(bromomethyl)-3,4-dihydroisoquinoline-2(1H)-carboxylate (CAS #622867-53-2) as outlined in the synthesis of Example 14 (i.e. Example 14-A→14-B). MS (ESI+) m/z 548.4 (M+H).

Example 25-B. Ethyl 1-(6-(1-((2-(pyridin-2-ylmethyl)-1,2,3,4-tetrahydroisoquinolin-6-yl)methyl)indolin-7-yl)pyridin-2-yl)-5-(trifluoromethyl)-1H-pyrazole-4-carboxylate

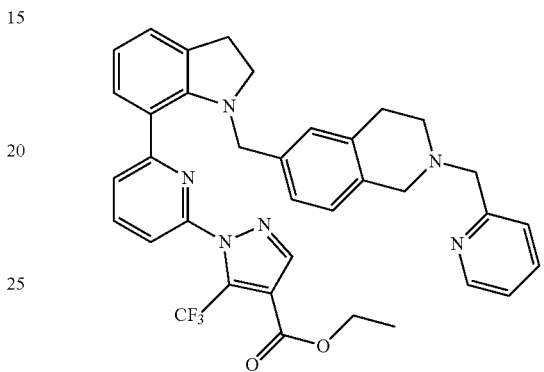

To a solution of ethyl 1-(6-(1-((1,2,3,4-tetrahydroisoquinolin-6-yl)methyl)indolin-7-yl)pyridin-2-yl)-5-(trifluoromethyl)-1H-pyrazole-4-carboxylate (90 mg, 0.16 mmol), picolinaldehyde (0.039 mL, 0.41 mmol), and AcOH (0.033 mL, 0.58 mmol) in DCE (2 mL) was added Na(OAc)$_3$BH (174 mg, 0.82 mmol). The mixture was then stirred at room temperature for 16 h. The reaction was then quenched with sat. aq. NaHCO$_3$. The mixture was then extracted with CH$_2$Cl$_2$. The organic layer was then washed successively with H$_2$O, and brine, dried over Na$_2$SO$_4$, filtered, and then concentrated to furnish the title compound. MS (ESI+) m/z 639.5 (M+H).

Example 25. 1-(6-(1-((2-(Pyridin-2-ylmethyl)-1,2,3,4-tetrahydroisoquinolin-6-yl)methyl)indolin-7-yl)pyridin-2-yl)-5-(trifluromethyl)-1H-pyrazole-4-carboxylic Acid

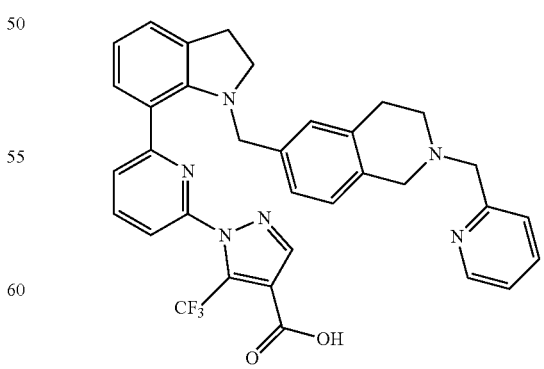

The title compound was synthesized by saponification of ethyl 1-(6-(1-((2-(pyridin-2-ylmethyl)-1,2,3,4-tetrahydroisoquinolin-6-yl)methyl)indolin-7-yl)pyridin-2-yl)-5-

(trifluoromethyl)-1H-pyrazole-4-carboxylate by an analogous method as described for the synthesis of Example 1. a). $^1$H NMR (400 MHz, DMSO-d$_6$) δ 8.48-8.54 (m, 1H), 8.12 (s, 1H), 7.96-8.02 (m, 1H), 7.74-7.83 (m, 2H), 7.57-7.62 (m, 1H), 7.48 (d, J=7.8 Hz, 1H), 7.25-7.30 (m, 1H), 7.14-7.23 (m, 2H), 6.79-6.91 (m, 4H), 3.82 (s, 2H), 3.76 (s, 2H), 3.55 (s, 2H), 3.30 (t, J=8.6 Hz, 2H), 2.98 (t, J=8.6 Hz, 2H), 2.66-2.77 (m, 4H). HRMS; calcd. for C$_{34}$H$_{30}$F$_3$N$_6$O$_2$(M+H) 609.2177, found 609.2196.

Example 26. 1-(6-(1-(4-(1-(Cyclopropanecarbonyl) piperidin-4-yl)benzyl)-1H-indol-7-yl)pyridin-2-yl)-5-(trifluoromethyl)-1H-pyrazole-4-carboxylic Acid

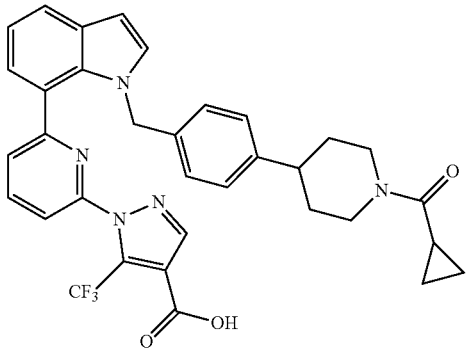 [SMILES: O=C(O)c1cnn(-c2cccc(-c3cccc4ccn(Cc5ccc(C6CCN(C(=O)C7CC7)CC6)cc5)c34)n2)c1C(F)(F)F]

To a mixture of 1-(6-(1-(4-(1-(cyclopropanecarbonyl)piperidin-4-yl)benzyl)indolin-7-yl)pyridin-2-yl)-5-(trifluoromethyl)-1H-pyrazole-4-carboxylic acid, Example 12, (21 mg, 0.034 mmol) in cyclopentylmethyl ether (1.0 mL) was added o-chloranil (20 mg, 0.081 mmol) and the resulting orange mixture was permitted to stir for ca. 20 minutes. The mixture was then diluted with saturated aqueous Na$_2$S$_2$O$_3$ and MeOH and stirred for ca. 5 minutes. The mixture was then further diluted with dichloromethane. The resulting layers were separated, and the aqueous layer was extracted two additional times with CH$_2$Cl$_2$. The organic layers were combined, dried over Na$_2$SO$_4$, filtered, and concentrated. The resulting residue was purified by RP-HPLC (HC-A) to afford the title compound. $^1$H NMR (400 MHz, Methanol-d$_4$) δ8.11 (s, 1H) 7.75-7.86 (m, 1H) 7.66-7.74 (m, 1H) 7.48-7.61 (m, 1H) 7.31 (d, J=3.16 Hz, 1H) 7.20 (d, J=6.95 Hz, 1H) 7.09-7.16 (m, 1H) 7.04 (dd, J=7.33, 1.14 Hz, 1H) 6.83 (d, J=8.21 Hz, 2H) 6.63 (d, J=3.28 Hz, 1H) 6.29 (d, J=8.08 Hz, 2H) 5.21 (s, 2H) 4.55-4.64 (m, 1H) 4.36-4.48 (m, 1H) 2.61-2.74 (m, 2H) 2.27 (t, J=7.45 Hz, 1H) 1.93-2.02 (m, 1H) 1.37-1.86 (m, 4H) 0.77-0.94 (m, 4H). HRMS; calcd. for C$_{34}$H$_{31}$F$_3$N$_5$O$_3$(M+H) 614.2379, found 614.2372.

Example 27. 1-(6-(1-(4-(1-(Cyclopropanecarbonyl) piperidin-4-yl)-3-ethylbenzyl)-1H-indol-7-yl)pyridin-2-yl)-4-ethyl-1H-pyrazole-4-carboxylic Acid

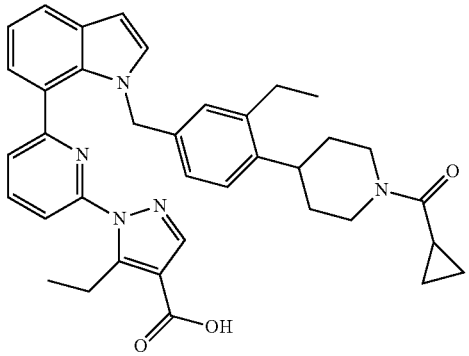 [SMILES: CCc1cc(Cn2ccc3cccc(-c4cccc(-n5ncc(C(=O)O)c5CC)n4)c32)ccc1C1CCN(C(=O)C2CC2)CC1]

To a mixture of 1-(6-(1-(4-(1-(cyclopropanecarbonyl)piperidin-4-yl)-3-ethylbenzyl)indolin-7-yl)pyridin-2-yl)-5-ethyl-1H-pyrazole-4-carboxylic acid (Example 14) (30 mg, 0.05 mmol) in cyclopropylmethyl ether (1.1 mL) was added o-chloranil (28 mg, 0.114 mmol) and the resulting orange mixture was permitted to stir for ca. 20 minutes. The mixture was then diluted with dichloromethane, saturated aqueous Na$_2$S$_2$O$_3$, and MeOH and stirred for ca. 5 minutes. The mixture was then further diluted with dichloromethane. The resulting layers were separated, and the aqueous layer was extracted two additional times with dichloromethane. The organic layers were dried via passing through a phase separator and then concentrated. The resulting residue was purified by RP-HPLC (HC-A) to afford the title compound. $^1$H NMR (400 MHz, Methanol-d$_4$) δ8.04 (s, 1H) 7.79-7.88 (m, 1H) 7.72 (td, J=7.15, 0.98 Hz, 2H) 7.34 (d, J=3.18 Hz, 1H) 7.19 (dd, J=7.58, 0.61 Hz, 1H) 7.10-7.15 (m, 1H) 7.03-7.07 (m, 1H) 6.75 (d, J=7.82 Hz, 1H) 6.65 (d, J=3.18 Hz, 1H) 6.02-6.10 (m, 2H) 5.17 (s, 2H) 4.55-4.66 (m, 1H) 4.33-4.44 (m, 1H) 3.10-3.21 (m, 3H) 2.88 (tt, J=11.92, 3.48 Hz, 1H) 2.67 (t, J=12.35 Hz, 1H) 2.41 (q, J=7.58 Hz, 2H) 1.92-2.02 (m, 1H) 1.39-1.69 (m, 4H) 1.02 (t, J=7.34 Hz, 3H) 0.95 (t, J=7.52 Hz, 3H) 0.77-0.90 (m, 4H). HRMS; calcd. for C$_{37}$H$_{40}$N$_5$O$_3$ (M+H) 602.3131, found 602.3103.

Example 28

Example 28-A. Ethyl 1-(6-(1-(4-(1-(cyclopropanecarbonyl)piperidin-4-yl)-3-ethylbenzyl)-3-methyl-1H-indol-7-yl)pyridin-2-yl)-6-(trifluoromethyl)-1H-pyrazole-4-carboxylate

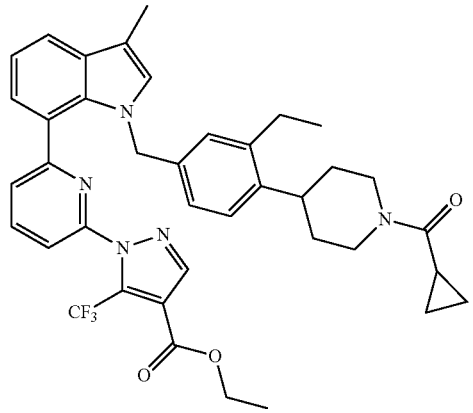 [SMILES: CCOC(=O)c1cnn(-c2cccc(-c3cccc4c(C)cn(Cc5ccc(C6CCN(C(=O)C7CC7)CC6)c(CC)c5)c34)n2)c1C(F)(F)F]

To a solution of ethyl 1-(6-(3-methyl-1H-indol-7-yl)pyridin-2-yl)-5-(trifluoromethyl)-1H-pyrazole-4-carboxylate (Example 19-A). (130 mg, 0.314 mmol) in THF (2 mL) at 0° C. was added 60% NaH in oil (12 mg, 0.3 mmol). The mixture was permitted to stir for 10 minutes, at which time a solution of (4-(4-(bromomethyl)-2-ethylphenyl)piperidin-1-yl)(cyclopropyl)methanone, Intermediate 5-3, (90 mg, 0.26 mmol) in THF (1 mL) was added. After ca. 10 minutes the mixture was brought to room temperature and DMF (1 mL) was added. The mixture was then placed at 45° C. for 1.5 h, and then an additional aliquot of NaH was added (3 mg, 0.075 mmol) and heating at 45° C. was continued for another 1.5 h. The mixture was then cooled to room temperature and quenched with a 3:1 mixture of MeOH:AcOH. The resulting mixture was diluted with sat aq. NaHCO$_3$, and further diluted with ethyl acetate. The resulting layers were separated, and the aqueous layer was extracted an additional two times with ethyl acetate. The organic layers were combined, dried over Na₂SO₄, filtered and concentrated. The resulting residue was purified by silica gel flash column chromatograph (heptane/EtOAc=90/10 to 10/90) to afford the title compound. MS (ESI+) m/z 684.5 (M+H).

Example 28. 1-(6-(1-(4-(1-(Cyclopropanecarbonyl) piperidin-4-yl)-3-ethylbenzyl)-3-methyl-1H-indol-7-yl)pyridin-2-yl)-5-(trifluoromethyl)-1H-pyrazole-4-carboxylic Acid

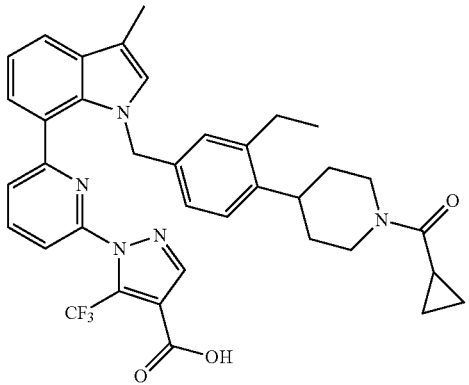 [SMILES: CCc1cc(Cn2cc(C)c3cccc(-c4cccc(-n5ncc(C(=O)O)c5C(F)(F)F)n4)c32)ccc1C1CCN(C(=O)C2CC2)CC1]

The title compound was synthesized by saponification of ethyl 1-(6-(1-(4-(1-(cyclopropanecarbonyl)piperidin-4-yl)-3-ethylbenzyl)-3-methyl-1H-indol-7-yl)pyridin-2-yl)-5-(trifluoromethyl)-1H-pyrazole-4-carboxylate by the similar method as described for the synthesis of Example 1. a). ¹H NMR (400 MHz, Methanol-d₄) δ 8.15 (s, 1H) 7.77 (t, J=7.83 Hz, 1H) 7.66 (dd, J=7.83, 1.14 Hz, 1H) 7.48-7.57 (m, 1H) 7.09-7.22 (m, 2H) 6.99-7.09 (m, 2H) 6.78 (d, J=8.08 Hz, 1H) 6.08-6.22 (m, 2H) 5.12 (s, 2H) 4.57-4.68 (m, 1H) 4.35-4.48 (m, 1H) 2.87-3.00 (m, 1H) 2.64-2.79 (m, 1H) 2.45 (q, J=7.58 Hz, 2H) 2.38 (s, 3H) 1.92-2.03 (m, 1H) 1.36-1.79 (m, 5H) 0.99 (t, J=7.58 Hz, 3H) 0.77-0.89 (m, 4H). HRMS; calcd. for C₃₇H₃₇F₃N₅O₃ (M+H) 656.2849, found 656.2863.

Example 29

Example 29-A. (S)-tert-Butyl 4-(4-((7-(4-(4-(ethoxycarbonyl)-5-ethyl-1H-pyrazol-1-yl)pyridin-2-yl)-2,3-dihydro-1H-inden-1-yl)oxy)-2-ethylphenyl) piperidine-1-carboxylate

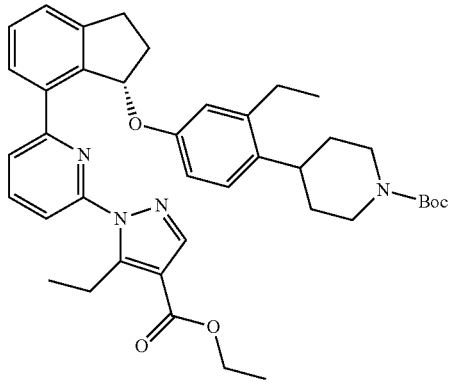 [SMILES: CCOC(=O)c1cnn(-c2cccc(-c3cccc4c3[C@@H](Oc3ccc(C5CCN(C(=O)OC(C)(C)C)CC5)c(CC)c3)CC4)n2)c1CC]

To a suspension of ethyl 1-(6-bromopyridin-2-yl)-5-ethyl-1H-pyrazole-4-carboxylate, Intermediate 1-4-2, (0.85 g, 2.62 mmol), KOAc (0.4 g, 4.08 mmol), and bis(pinacolato) diboron (0.8 g, 3.15 mmol) in dioxane (10 mL) was added Pd(dppf)Cl₂·CH₂Cl₂ adduct (0.1 g, 0.122 mmol). The mixture was then stirred at 100° C. for 1 h, and then cooled to room temperature.

To a suspension of (S)-tert-butyl 4-(4-((7-bromo-2,3-dihydro-1H-inden-1-yl)oxy)-2-ethylphenyl)piperidine-1-carboxylate, Intermediate 3-44, (0.8 g, 1.6 mmol) and K₃PO₄ (1 g, 4.71 mmol) in dioxane/H₂O (5 mL/10 mL) was added the reaction mixture prepared above, followed by Pd(dppf)Cl₂CH₂Cl₂ adduct (0.1 g, 0.122 mmol). The mixture was then stirred at 100° C. for 15 h, and then cooled to room temperature. The reaction mixture was then diluted with EtOAc. The organic phase was washed with H₂O and brine, and then dried over Na₂SO₄. The organic extracts were then filtered through a plug of silica gel, which was rinsed with EtOAc. The filtrate was then concentrated. The resulting residue was purified by silica gel flash column chromatography (heptane/EtOAc=88/12) to afford the title compound. MS (ESI+) m/z 665.5 (M+H).

Example 29-B. (S)-Ethyl 5-ethyl-1-(6-(3-(3-ethyl-4-(piperidin-4-yl)phenoxy)-2,3-dihydro-1H-inden-4-yl)pyridin-2-yl)-1H-pyrazole-4-carboxylate

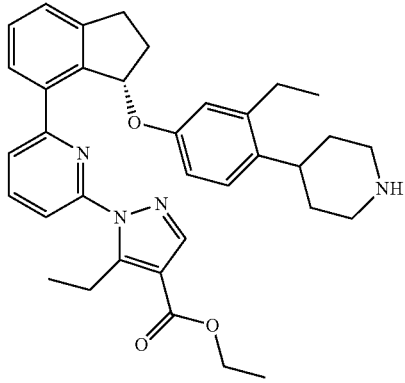 [SMILES: CCOC(=O)c1cnn(-c2cccc(-c3cccc4c3[C@@H](Oc3ccc(C5CCNCC5)c(CC)c3)CC4)n2)c1CC]

To a solution of (S)-tert-butyl 4-(4-((7-(6-(4-(ethoxycarbonyl)-5-ethyl-1H-pyrazol-1-yl)pyridin-2-yl)-2,3-dihydro-1H-inden-1-yl)oxy)-2-ethylphenyl)piperidine-1-carboxylate (720 mg, 1.08 mmol) in CH₂Cl₂ (15 mL) at 0° C. was added diisopropylethylamine (840 mg, 6.50 mmol), followed by TMSOTf (481 mg, 2.17 mmol). The mixture was stirred at 0° C. for 10 minutes. The reaction was quenched with addition of satd. aq. NaHCO₃ (15 mL). The bi-phasic mixture was separated. The organic phase was washed with brine, dried over Na₂SO₄, filtered, and then concentrated. The resulting residue was purified by silica gel flash column chromatography (CH₂Cl₂/MeOH=100:0 to 90:10) to afford the title compound. MS (ESI+) m/z 565.4 (M+H).

Example 29-C. (S)-Ethyl 4-(4-((7-(6-(4-(ethoxycarbonyl)-6-ethyl-1H-pyrazol-1-yl)pyridin-2-yl)-2,3-dihydro-1H-inden-1-yl)oxy)-2-ethylphenyl)piperidine-1-carboxylate

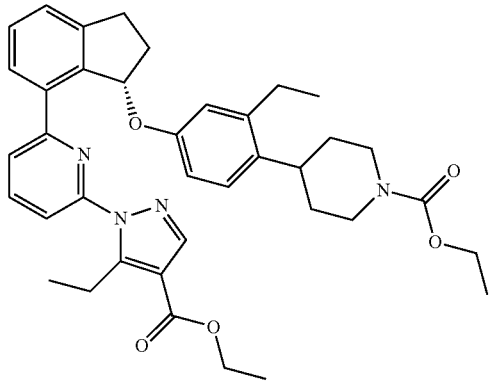 [SMILES: CCOC(=O)c1cnn(-c2cccc(-c3cccc4c3[C@@H](Oc3ccc(C5CCN(C(=O)OCC)CC5)c(CC)c3)CC4)n2)c1CC]

To a solution of (S)-ethyl 5-ethyl-1-(6-(3-(3-ethyl-4-(piperidin-4-yl)phenoxy)-2,3-dihydro-1H-inden-4-yl)pyridin-2-yl)-1H-pyrazole-4-carboxylate (100 mg, 0.177 mmol) in CH$_2$Cl$_2$ (1.25 mL) at room temperature were added triethylamine (54 mg, 0.531 mmol) and ethyl chloroformate (21 mg, 0.195 mmol). The mixture was stirred at room temperature for 1 h, and then diluted with EtOAc. The mixture was then washed successively with satd. aq. NaHCO$_3$, and brine, dried over Na$_2$SO$_4$, filtered, and then concentrated. The resulting residue was purified by silica gel flash column chromatography (heptane/EtOAc=100:0 to 50:50) to afford the title compound. MS (ESI+) m/z 637.4 (M+H).

Example 29. (S)-1-(6-(3-(4-(1-(Ethoxycarbonyl)piperidin-4-yl)-3-ethylphenoxy)-2,3-dihydro-1H-inden-4-yl)pyridin-2-yl)-5-ethyl-1H-pyrazole-4-carboxylic Acid

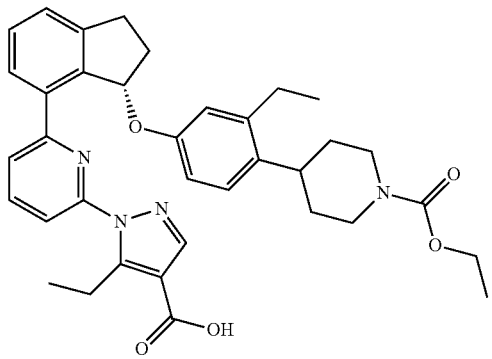 [SMILES: CCOC(=O)N1CCC(c2ccc(O[C@H]3CCc4cccc(-c5cccc(-n6ncc(C(=O)O)c6CC)n5)c43)cc2CC)CC1]

The title compound was synthesized by a saponification of (S)-ethyl 4-(4-((7-(6-(4-(ethoxycarbonyl)-5-ethyl-1H-pyrazol-1-yl)pyridin-2-yl)-2,3-dihydro-1H-inden-1-yl)oxy)-2-ethylphenyl)piperidine-1-carboxylate by a similar manner as described for the synthesis of Example 7a, followed by RP-HPLC purification (HC-B). $^1$H NMR (400 MHz, Methanol-d$_4$) δ 7.93 (s, 1H) 7.84-7.90 (m, 1H) 7.70 (dd, J=7.8, 0.7 Hz, 1H) 7.59 (d, J=8.0 Hz, 2H) 7.42-7.49 (m, 2H) 6.97 (d, J=8.6 Hz, 1H) 6.55 (dd, J=8.5, 2.7 Hz, 1H) 6.50 (d, J=2.7 Hz, 1H) 6.17 (dd, J=6.2, 2.3 Hz, 1H) 4.25 (d, J=11.7 Hz, 2H) 4.14 (q, J=7.1 Hz, 2H) 3.28-3.37 (m, 2H) 3.21 (dt, J=15.9, 7.8 Hz, 1H) 2.80-3.04 (m, 4H) 2.53-2.62 (m, 2H) 2.38-2.50 (m, 1H) 2.17-2.27 (m, 1H) 1.64-1.75 (m, 2H) 1.50-1.63 (m, 2H) 1.28 (t, J=7.1 Hz, 3H) 1.09-1.15 (m, 6H). HRMS; calcd. for C$_{36}$H$_{41}$N$_4$O$_5$ (M+H) 609.3077, found 609.3072.

Example 30

Example 30-A. Ethyl 5-ethyl-6-((S)-3-(3-ethyl-4-(1-((S)-2-hydroxypropanoyl)piperidin-4-yl)phenoxy)-2,3-dihydro-1H-inden-4-yl)pyridin-2-yl)-1H-pyrazole-4-carboxylate

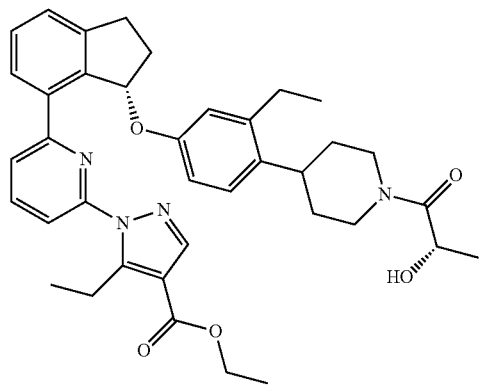 [SMILES: CCOC(=O)c1cnn(-c2cccc(-c3cccc4c3[C@@H](Oc3ccc(C5CCN(C(=O)[C@H](C)O)CC5)c(CC)c3)CC4)n2)c1CC]

To a solution of (S)-ethyl 5-ethyl-1-(6-(3-(3-ethyl-4-(piperidin-4-yl)phenoxy)-2,3-dihydro-1H-inden-4-yl)pyridin-2-yl)-1H-pyrazole-4-carboxylate (Example 29-8) (0.146 g, 0.259 mmol), DIPEA (0.135 mL, 0.776 mmol), and L-(+)-lactic acid (0.047 g, 0.517 mmol) in DMF (1.3 mL) was added HATU (0.123 g, 0.323 mmol). The mixture was then stirred at room temperature for 0.5 h, and then diluted with H$_2$O/brine (ca. 1/1). The mixture was then extracted twice with EtOAc. The combined organic layers were washed with brine, dried over Na$_2$SO$_4$, filtered, and then concentrated. The resulting residue was absorbed onto silica gel, which was purified by silica gel flash column chromatography (0-60% EtOAc in heptane) to afford the title compound. MS (ESI+) m/z 637.4 (M+H).

Example 30. 5-Ethyl-1-(6-(S)-3-(3-ethyl-4-(1-((S)-2-hydroxypropanoyl)piperidin-4-yl)phenoxy)-2,3-dihydro-1H-inden-4-yl)pyridin-2-yl)-H-pyrazole-4-carboxylic Acid

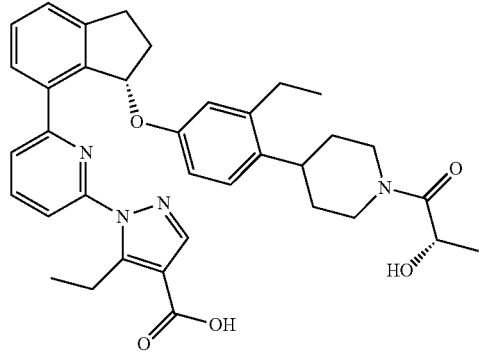 [SMILES: CCc1cc(O[C@H]2CCc3cccc(-c4cccc(-n5ncc(C(=O)O)c5CC)n4)c32)ccc1C1CCN(C(=O)[C@H](C)O)CC1]

The title compound was synthesized by saponification of ethyl 5-ethyl-1-(6-((S)-3-(3-ethyl-4-(1-((S)-2-hydroxypropanoyl)piperidin-4-yl)phenoxy)-2,3-dihydro-1H-inden-4-yl)pyridin-2-yl)-1H-pyrazole-4-carboxylate by the similar method for the synthesis of Example 7a, followed by RP-HPLC purification (HC-C). ¹H NMR (400 MHz, DMSO-d₆) δ 7.92-8.00 (m, 2H) 7.71-7.77 (m, 1H) 7.68 (dd, J=8.1, 0.6 Hz, 1H) 7.56-7.62 (m, 1H) 7.48-7.54 (m, 1H) 7.44-7.48 (m, 1H) 6.97 (d, J=8.3 Hz, 1H) 6.58 (dd, J=8.6, 2.6 Hz, 1H) 6.50 (s, 1H) 6.13 (dd, J=6.0, 2.2 Hz, 1H) 4.80 (br. s., 1H) 4.31-4.59 (m, 2H) 4.06 (d, J=11.0 Hz, 1H) 3.22-3.28 (m, 2H) 3.03-3.20 (m, 2H) 2.80-3.00 (m, 2H) 2.59-2.73 (m, 1H) 2.52-2.58 (m, 2H) 2.38-2.47 (m, 1H) 2.02-2.18 (m, 1H) 1.64 (d, J=12.10 Hz, 2H) 1.33-1.57 (m, 2H) 1.23-1.18 (m, 3H) 1.03-1.14 (m, 6H). HRMS; calcd. for $C_3H_{41}N_4O_5$ (M+H) 609.3077, found 609.3077.

Example 31

The following compound can be synthesized by a similar method as outlined for the synthesis of Example 30 but using the carboxylic acid in the table instead of employing the L-(+)-lactic acid used in Example 30-A.

| Example | Chemical structure ¹H NMR and HRMS data | IUPAC name Carboxylic acid |
|---|---|---|
| 31-1 | 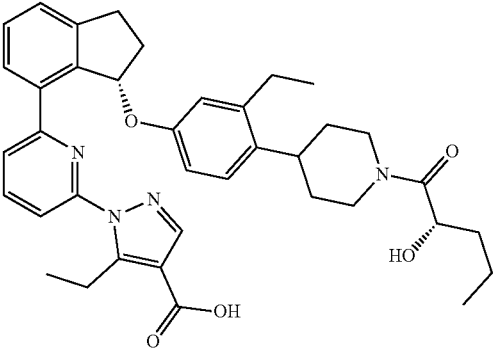 [SMILES: CCC[C@H](O)C(=O)N1CCC(c2ccc(O[C@H]3CCc4cccc(-c5cccc(-n6ncc(C(=O)O)c6CC)n5)c43)cc2CC)CC1] | 5-Ethyl-1-(6-((S)-3-(3-ethyl-4-(1-((S-2-hydroxypentanoyl)piperidin-4-yl)phenoxy)-2,3-dihydro-1H-inden-4-yl)pyridin-2-yl)-1H-pyrazole-4-carboxylic acid (S)-2-hydroxypentanoic acid (CAS# 41014-93-1) |

¹H NMR (400 MHz, CDCl₃) δ 8.05 (d, J = 4.0 Hz, 1 H) 7.66-7.82 (m, 4 H) 7.42-7.53 (m, 2 H) 696-7.02 (m, 1 H) 6.66 (t, J = 8.1 Hz, 2 H) 5.91-5.84 (m, 1 H) 4.78 (br. s., 1 H) 4.43 (br. s., 1 H) 3.85 (d, J = 12.5 Hz, 1 H) 3.37-3.47 (m, 2 H) 3.26-3.14 (m, 1 H), 3.13-3.00 (m, 1 H) 2.80-2.90 (m, 2 H) 2.72-2.80 (m, 1 H) 2.57-2.66 (m, 2 H) 2.35 (d, J = 3.9 Hz, 2 H) 1.83 (br. s., 2 H) 1.44-1.71 (m, 6 H) 1.09-1.29 (m, 6 H) 0.79-1.03 (m, 4 H). HRMS; calcd. for $C_{38}H_{45}N_4O_5$ (M + H) 637.3390, found 637.3379.

| 31-2 | 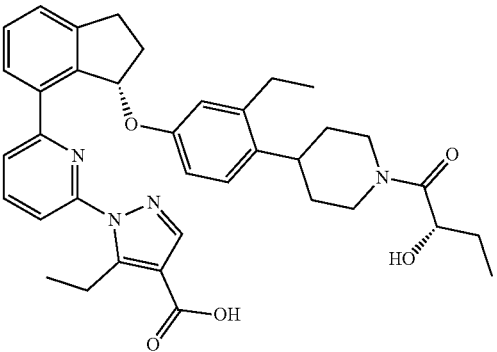 [SMILES: CCc1cc(O[C@H]2CCc3cccc(-c4cccc(-n5ncc(C(=O)O)c5CC)n4)c32)ccc1C1CCN(C(=O)[C@@H](O)CC)CC1] | 5-Ethyl-1-(6-((S)-3-(3-ethyl-4-(1-((S)-2-hydroxybutanoyl)piperidin-4-yl)phenoxy)-2,3-dihydro-1H-inden-4-yl)pyridin-2-yl)-pyridin-2-yl)-1H-pyrazole-4-carboxylic acid (S)-2-hydroxybutanoic acid (CAS# 3347-90-8) |

¹H NMR (400 MHz, DMSO-d₆) δ 7.93-8.01 (m, 2 H) 7.72-7.77 (m, 1 H) 7.69 (d, J = 8.1 Hz, 1 H) 7.56-7.62 (m, 1 H) 7.49-7.54 (m, 1 H) 7.44-7.48 (m, 1 H) 6.97 (d, J = 8.6 Hz, 1 H) 6.59 (dd, J = 8.6, 2.7 Hz, 1 H) 6.50 (br. s., 1 H) 6.13 (dd, J = 6.0, 2.2 Hz, 1 H) 4.67 (br. s., 1 H) 4.53 (d, J = 12.2 Hz, 1 H) 4.20-4.31 (m, 1 H) 4.06 (d, J = 13.3 Hz, 1 H) 3.22-3.30 (m, 2 H) 3.06-3.18 (m, 2 H) 3.06-3.18 (m, 2 H) 2.80-3.01 (m, 2 H) 2.62-2.74 (m, 1 H) 2.53-2.59 (m, 2 H) 2.44 (dd, J = 14.1, 6.4 Hz, 1 H) 2.01-2.16 (m, 1 H) 1.57-1.73 (m, 3 H) 1.32-1.56 (m, 3 H) 1.02-1.17 (m, 6 H) 0.90 (q, J = 7.5 Hz, 3 H). HRMS; calcd. for $C_{37}H_{43}N_4O_5$ (M + H) 623.3233, found 623.3236.

| Example | Chemical structure<br>¹H NMR and HRMS data | IUPAC name<br>Carboxylic acid |
|---|---|---|
| 31-3 | ![structure] | 5-Ethyl-1-(6-((S)-3-(3-ethyl-4-(1-((S)-3-hydroxy-2-methylpropanoyl)piperidin-4-yl)-phenoxy)-2-3-dihydro-1H-inden-4-yl)pyridin-2-yl)-1H-pyrazole-4-carboxylic acid<br>(S)-3-hydroxy-2-methylpropanoic acid<br>(CAS# 26543-05-5) |
| | ¹H NMR (400 MHz, DMSO-d₆) δ 7.93-8.00 (m, 2 H) 7.72-7.77 (m, 1 H) 7.69 (dd, J = 8.1, 0.6 Hz, 1 H) 7.57-7.62 (m, 1 H) 7.49-7.54 (m, 1 H) 7.44-7.49 (m, 1 H) 6.94-7.02 (m, 1 H) 6.59 (dd, J = 8.6, 2.5 Hz, 1 H) 6.51 (d, J = 2.2 Hz, 1 H) 6.11-6.16 (m, 1 H), 4.58 (d, J = 13.0 Hz, 1 H) 4.10 (br. s., 1 H) 3.58 (br. s., 1 H) 3.21-3.29 (m, 4 H) 3.07-3.19 (m, 2 H) 2.83-3.02 (m, 3 H) 2.53-2.65 (m, 2 H) 2.44 (dd, J = 14.0, 6.5 Hz, 1 H) 2.07-2.17 (m, 1 H) 1.31-1.74 (m, 4 H) 1.13-1.06 (m, 6 H) 1.01-0.95 (m, 3H). HRMS; calcd. for C₃₇H₄₃N₄O₅ (M + H) 623.3233, found 623.3222 | |
| 31-4 | ![structure] | (S)-5-Ethyl-1-(6-(3-(3-ethyl-4-(1-(1-hydroxy-cyclobutanecarbonyl)piperidin-4-yl)phenoxy)-2,3-dihydro-1H-inden-4-yl)pyridin-2-yl)-1H-pyrazole-4-carboxylic acid<br>1-hydroxycyclobutanecarboxylic acid<br>(CAS# 41248-13-9) |
| | ¹H NMR (400 MHz, DMSO-d₆) δ 7.94-8.00 (m, 2 H) 7.75 (dd, J = 7.7, 0.6 Hz, 1 H) 7.69 (dd, J = 8.1, 0.6 Hz, 1 H) 7.56-7.62 (m, 1 H) 7.49-7.54 (m, 1 H) 7.45-7.49 (m, 1 H) 6.99 (d, J = 8.6 Hz, 1 H) 6.59 (dd, J = 8.6, 2.7 Hz, 1 H) 6.50 (br. s., 1 H) 6.13 (d, J = 4.0 Hz, 1 H) 5.89 (br. s., 1 H) 4.51 (d, J = 12.5 Hz, 1 H) 4.18 (d, J = 13.1 Hz, 1 H) 3.27 (d, J = 7.6 Hz, 2 H) 3.14 (dt, J = 15.9, 7.8 Hz, 1 H) 2.82-3.06 (m, 3 H) 2.53-2.70 (m, 5 H) 2.44 (dd, J = 14.5, 6.9 Hz, 1 H) 1.97-2.15 (m, 3 H) 1.69-1.80 (m, 1 H) 1.55-1.67 (m, 3 H) 1.51-1.39 (m, 2 H) 1.05-1.24 (m, 6 H). HRMS; calcd. for C₃₈H₄₃N₄O₅ (M + H) 635.3233, found 635.3248. | |

Example 32

Example 32-A. (±)-Potassium 4-hydroxy-2-methylbutanoate

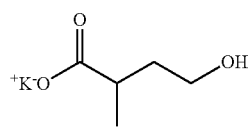

To a solution of (+)-3-methyldihydrofuran-2(3H)-one (CAS #1679-47-6) (0.95 mL, 10 mmol) in THF (25 mL) and MeOH (25 mL) was added 1M aq. KOH (10.5 mL, 10.5 mmol). The mixture was then stirred at room temperature for 3 h, and then concentrated. The resulting residue was triturated with acetone, and then the resulting white solid was collected by filtration to furnish the title compound. ¹H NMR (400 MHz, D₂O) δ 3.58 (t, J=7.0 Hz, 2H) 2.24-2.53 (m, 1H) 1.79 (dq, J=14.8, 6.9 Hz, 1H) 1.58 (dq, J=13.6, 6.9 Hz, 1H) 1.08 (d, J=7.0 Hz, 3H).

Example 32-B. a). Ethyl 5-ethyl-1-(6-(3S)-3-(3-ethyl-4-(1-(4-hydroxy-2-methylbutanoyl)piperidin-4-yl)phenoxy)-2,3-dihydro-1H-inden-4-yl)pyridin-2-yl)-1H-pyrazole-4-carboxylate

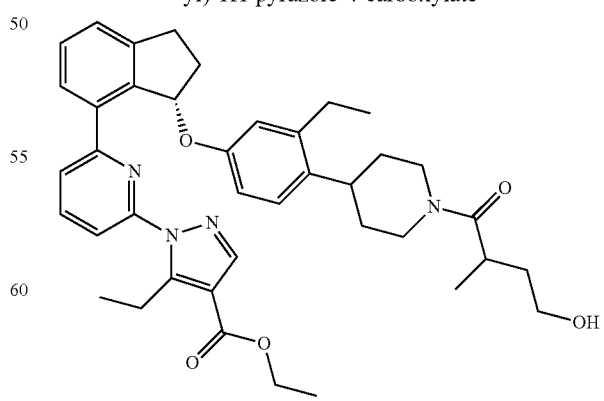

The title compound was synthesized by reaction of (S)-ethyl 5-ethyl-1-(6-(3-(3-ethyl-4-(piperidin-4-yl)phenoxy)-2, 3-dihydro-1H-inden-4-yl)pyridin-2-yl)-1H-pyrazole-4-carboxylate (Example 29-B) with (+)-potassium 4-hydroxy-2-methylbutanoate as described for the synthesis of Example 30-A. MS (ESI+) m/z 665.5 (M+H).

Example 32-B. b). Ethyl 5-ethyl-1-(6-((3S)-3-(3-ethyl-4-(1-(4-hydroxy-2-methylbutanoyl)piperidin-4-yl)phenoxy)-2,3-dihydro-1H-inden-4-yl)pyridin-2-yl)-1H-pyrazole-4-carboxylate (Diastereomer-1) and ethyl 5-ethyl-1-6-((3S)-3-(3-ethyl-4-(1-(4-hydroxy-2-methylbutanoyl)piperidin-4-yl)phenoxy)-2,3-dihydro-1H-inden-4-yl)pyridin-2-yl)-1H-pyrazole-4-carboxylate (Diastereomer-2)

Resolution of the diastereomers of ethyl 5-ethyl-1-(6-((3S)-3-(3-ethyl-41-(4-hydroxy-2-methylbutanoyl)piperidin-4-yl)phenoxy)-2,3-dihydro-1H-inden-4-yl)pyridin-2-yl)-1H-pyrazole-4-carboxylate was achieved by chiral SFC using CHIRALPAK® AS-H column with 20% MeOH in $CO_2$ to give ethyl 5-ethyl-1-(6-((3S)-3-(3-ethyl-4-(1-(4-hydroxy-2-methylbutanoyl)piperidin-4-yl)phenoxy)-2,3-dihydro-1H-inden-4-yl)pyridin-2-yl)-1H-pyrazole-4-carboxylate (diastereomer-1) ($t_r$=3.0 min) and ethyl 5-ethyl-1-(6-((3S)-3-(3-ethyl-4-(1-(4-hydroxy-2-methylbutanoyl)piperidin-4-yl)phenoxy)-2,3-dihydro-1H-inden-4-yl)pyridin-2-yl)-1H-pyrazole-4-carboxylate (diastereomer-2) ($t_r$=4.7 min).

Example 32a. 5-Ethyl-1-(6-((3S)-3-(3-ethyl-4-(1-(4-hydroxy-2-methylbutanoyl)piperidin-4-yl)phenoxy)-2,3-dihydro-H-inden-4-yl)pyridin-2-yl)-H-pyrazole-4-carboxylic Acid (Diastereomer-1)

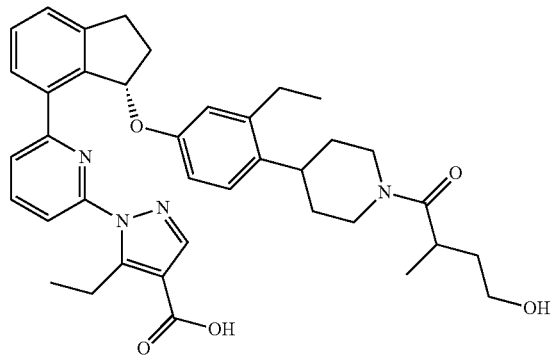 [SMILES: CCc1cc(O[C@H]2CCc3cccc(-c4cccc(-n5ncc(C(=O)O)c5CC)n4)c32)ccc1C1CCN(C(=O)C(C)CCO)CC1]

The title compound was synthesized by saponification of ethyl 5-ethyl-1-(6-((3S)-3-(3-ethyl-4-(1-(4-hydroxy-2-methylbutanoyl)piperidin-4-yl)phenoxy)-2,3-dihydro-1H-inden-4-yl)pyridin-2-yl)-1H-pyrazole-4-carboxylate (diastereomer-1) ($t_r$=3.0 min) in fashion analogous to Example 7a. $^1$H NMR (400 MHz, DMSO-de) δ 7.89-8.01 (m, 2H) 7.74 (d, J=7.6 Hz, 1H) 7.68 (d, J=8.0 Hz, 1H) 7.56-7.61 (m, 1H) 7.48-7.54 (m, 1H) 7.43-7.48 (m, 1H) 6.97 (d, J=8.2 Hz, 1H) 6.58 (d, J=8.6 Hz, 1H) 6.50 (d, J=2.6 Hz, 1H) 6.13 (d, J=4.8 Hz, 1H) 4.57 (d, J=11.6 Hz, 1H) 4.09 (d, J=13.0 Hz, 1H) 3.36-3.46 (m, 2H) 3.21-3.28 (m, 2H) 3.06-3.19 (m, 2H) 2.82-3.01 (m, 3H) 2.52-2.64 (m, 3H) 2.37-2.47 (m, 2H) 2.02-2.17 (m, 1H) 1.58-1.82 (m, 3H) 1.30-1.54 (m, 3H) 1.05-1.14 (m, 6H) 1.01 (m, 3H). HRMS; calcd. for $C_{38}H_{45}N_4O_5$ (M+H) 637.3392, found 637.3390.

Example 32b. 5-Ethyl-1-(6-((3S)-3-(3-ethyl-4-(1-(4-hydroxy-2-methylbutanoyl)piperidin-4-yl)phenoxy)-2,3-dihydro-1H-inden-4-yl)pyridin-2-yl)-H-pyrazole-4-carboxylic Acid (Diastereomer-2)

The title compound was synthesized from ethyl 5-ethyl-1-(6-((3S)-3-(3-ethyl-4-(1-(4-hydroxy-2-methylbutanoyl)piperidin-4-yl)phenoxy)-2,3-dihydro-1H-inden-4-yl)pyridin-2-yl)-1H-pyrazole-4-carboxylate (diastereomer-2) ($t_r$=4.7 min) by a similar manner to Example 32a. $^1$H NMR (400 MHz, DMSO-de) δ 7.91-8.01 (m, 2H) 7.74 (d, J=7.3 Hz, 1H) 7.69 (d, J=8.0 Hz, 1H) 7.56-7.61 (m, 1H) 7.41-7.55 (m, 2H) 6.97 (d, J=8.4 Hz, 1H) 6.58 (d, J=8.4 Hz, 1H) 6.50 (d, J=7.1 Hz, 1H) 6.12 (d, J=4.3 Hz, 1H) 4.57 (d, J=12.1 Hz, 1H) 4.43 (br. s., 1H) 4.08 (d, J=11.9 Hz, 1H) 3.35-3.47 (m, 2H) 3.26 (d, J=7.5 Hz, 2H) 3.05-3.18 (m, 2H) 2.81-3.01 (m, 3H) 2.53-2.63 (m, 3H) 2.38-2.47 (m, 1H) 2.06-2.15 (m, 1H) 1.57-1.85 (m, 3H) 1.30-1.55 (m, 3H) 1.13-1.06 (m 6H) 1.04-0.98 (m, 3H). HRMS; calcd. for $C_{38}H_{45}N_4O_5$ (M+H) 637.3401, found 637.3430.

Example 33

Example 33-A. (S)-1-(6-(3-(4-(1-(tert-Butoxycarbonyl)piperidin-4-yl)-3-ethylphenoxy)-2,3-dihydro-1H-inden-4-yl)pyridin-2-yl)-5-ethyl-1H-pyrazole-4-carboxylic Acid

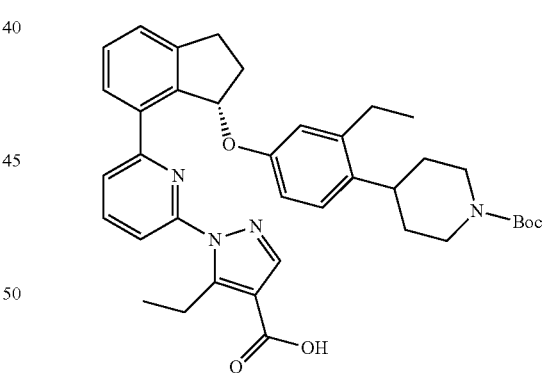

A mixture of (S)-tert-butyl 4-(4-((7-(6-(4-(ethoxycarbonyl)-5-ethyl-1H-pyrazol-1-yl)pyridin-2-yl)-2,3-dihydro-1H-inden-1-yl)oxy)-2-ethylphenyl)piperidine-1-carboxylate (Example 29-A) (0.204 g, 0.307 mmol) and potassium trimethylsilanolate (0.525 g, 3.68 mmol) in MTBE (1.5 mL) was stirred at 50° C. for 2 h. The reaction mixture was diluted with $H_2O$ and EtOAc. The pH of the aqueous phase was adjusted around pH 3. The organic layer was then separated from the aqueous layer, dried over $Na_2SO_4$, filtered and then concentrated to furnish the title compound. MS (ESI+) m/z 637.4 (M+H).

Example 33. (S)-5-ethyl-1-(6-(3-(3-ethyl-4-(1-(1-hydroxycyclopropanecarbonyl)piperidin-4-yl)phenoxy)-2,3-dihydro-1H-inden-4-yl)pyridin-2-yl)-1H-pyrazole-4-carboxylic Acid

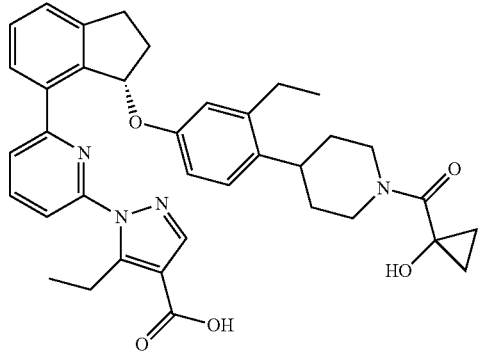 [SMILES: CCc1cc(O[C@H]2CCc3cccc(-c4cccc(-n5ncc(C(=O)O)c5CC)n4)c32)ccc1C1CCN(C(=O)C2(O)CC2)CC1]

To a solution of (S)-1-(6-(3-(4-(1-(tert-butoxycarbonyl)piperidin-4-yl)-3-ethylphenoxy)-2,3-dihydro-1H-inden-4-yl)pyridin-2-yl)-5-ethyl-1H-pyrazole-4-carboxylic acid (0.097 g, 0.15 mmol) and DIPEA (0.080 mL, 0.457 mmol) in $CH_2Cl_2$ (0.6 mL) at 0° C. was added TMSOTf (0.030 mL, 0.168 mmol). The mixture was then stirred at 0° C. for 0.25 h. To the mixture was then added additional DIPEA (0.24 mL, 1.38 mmol), followed by TMSOTf (0.060 mL, 0.336 mmol). The mixture was then stirred at 0° C. while in a separate flask, a solution of 1-hydroxycyclopropanecarboxylic acid (0.062 g, 0.610 mmol) in DMF (0.6 ml) was charged with DIPEA (0.080 mL, 0.457 mmol) and HATU (0.131 g, 0.345 mmol). The mixture was then stirred for 1 h at room temperature, and was then added to the reaction mixture above at 0° C. The whole mixture was then stirred at room temperature for 025 h. To this mixture was then added an additional aliquot of a solution of 1-hydroxycyclopropanecarboxylic acid (0.062 g, 0.610 mmol) and DIPEA (0.080 mL, 0.457 mmol) and HATU (0.131 g, 0.345 mmol) in DMF (0.6 L). The combined mixture was then stirred at room temperature for 2 h. The reaction mixture was then diluted with $H_2O$, and then the aqueous layer was brought to ca. pH 3 with 1 N aq. HCl. The organic layer was then dried over $Na_2SO_4$, filtered, and then concentrated. The resulting residue was purified by RP-HPLC (HC-C) to afford the title compound. $^1$H NMR (400 MHz, $CDCl_3$) δ 8.05 (s, 1H) 7.79-7.84 (m, 1H) 7.70-7.75 (m, 1H) 7.61-7.69 (m, 2H) 7.45-7.50 (m, 1H) 7.40-7.44 (m, 1H) 6.94 (d, J=8.6 Hz, 1H) 6.62 (dd, J=8.5, 2.6 Hz, 1H) 6.57 (d, J=2.6 Hz, 1H) 6.10 (d, J=2.7 Hz, 1H) 4.71 (d, J=12.5 Hz, 2H) 3.22-3.40 (m, 2H) 2.86-3.12 (m, 3H) 2.60 (q, J=7.5 Hz, 2H) 2.27 (d, J=7.3 Hz, 2H) 1.71-1.84 (m, 3H) 1.53-1.70 (m, 2H) 1.46 (d, J=6.7 Hz, 2H) 1.09-1.27 (m, 8H) 1.03 (br. s., 2H). HRMS; calcd. for $C_{37}H_{41}N_4O_5$ (M+H) 621.3077, found 621.3063.

Example 34

Example 34-A. a). (±)-Ethyl 1-(6-3-((4-(1-(cyclopropanecarbonyl)piperidin-4-yl)-2-methylphenyl)amino)-2,3-dihydrobenzofuran-4-yl)pyridin-2-yl)-5-methyl-1H-pyrazole-4-carboxylate

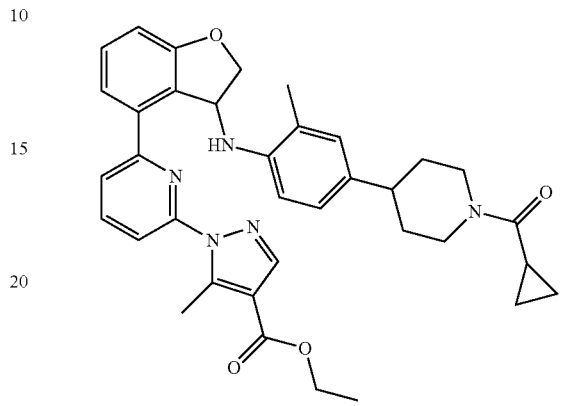

To a solution of ethyl 1-(6-bromopyridin-2-yl)-5-methyl-1H-pyrazole-4-carboxylate (Intermediate 1-3) (155 mg, 0.50 mmol), bis(pinacolato)diboron (127 mg, 0.50 mmol), KOAc (82 mg, 0.83 mmol) in dioxane (1.1 ml) at room temperature was added Pd(dppf)$Cl_2$—$CH_2Cl_2$ adduct (24 mg, 0.029 mmol). The mixture was then stirred at 90° C. for 2.5 h, and then cooled to room temperature.

Separately, palladium diacetate (4.7 mg, 0.021 mmol) and 1,1-bis(di-tert-butylphosphino)ferrocene (CAS #84680-95-5) (9.9 mg, 0.021 mmol) were stirred in EtOH (0.56 mL) at 50° C. for 1 h, which was then added to the reaction mixture above. To this mixture was then added a solution of (±)-(4-(4-((4-bromo-2,3-dihydrobenzofuran-3-yl)amino)-3-methylphenyl)piperidin-1-yl)(cyclopropyl)methanone (Intermediate 3-9) (190 mg, 0.42 mmol) in dioxane (1.1 ml), followed by potassium phosphate (2M in water) (0.63 mL, 1.25 mmol). The mixture was then stirred at 90° C. for 0.25 h, and then cooled to room temperature. The aqueous phase was removed and the organic phase was concentrated. The resulting residue was purified by silica gel flash chromatography to afford the title compound. MS (ESI+) m/z 606.5 (M+H).

Example 34-A. b). (+)-Ethyl 1-(6-(3-((4-(1-(cyclopropanecarbonyl)piperidin-4-yl)-2-methylphenyl)amino)-2,3-dihydrobenzofuran-4-yl)pyridin-2-yl)-5-methyl-1H-pyrazole-4-carboxylate and (−)-ethyl 1-(6-(3-((4-(1-(cyclopropanecarbonyl)piperidin-4-yl)-2-methylphenyl)amino)-2,3-dihydrobenzofuran-4-yl)pyridin-2-yl)-6-methyl-1H-pyrazole-4-carboxylate Resolution of the enantiomers of (±)-ethyl 1-(6-(3-((4-(1-(cyclopropanecarbonyl)piperidin-4-yl)-2-methylphenyl)amino)-2,3-dihydrobenzofuran-4-yl)pyridin-2-yl)-5-methyl-1H-pyrazole-4-carboxylate was achieved by chiral SFC using CHIRALPAK® AD-H column with 35% MeOH in $CO_2$ to give (+)-ethyl 1-(6-(3-((4-(1-(cyclopropanecarbonyl)piperidin-4-yl)-2-methylphenyl)amino)-2,3-dihydrobenzofuran-4-yl)pyridin-2-yl)-5-methyl-1H-pyrazole-4- carboxylate ($t_r$=4.15 min) and (−)-ethyl 1-(6-(3-((4-(1-(cyclopropanecarbonyl)piperidin-4-yl)-2-methylphenyl)amino)-2,3-dihydrobenzofuran-4-yl)pyridin-2-yl)-5-methyl-1H-pyrazole-4-carboxylate ($t_r$=5.40 min).

Example 34a. (+)-1-(6-(3-((4-(1-(Cyclopropanecarbonyl)piperidin-4-yl)-2-methylphenyl)amino)-2,3-dihydrobenzofuran-4-yl)pyridin-2-yl)-5-methyl-1H-pyrazole-4-carboxylic Acid

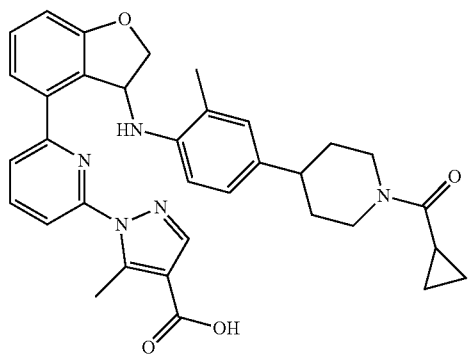 [SMILES: Cc1cc(C2CCN(C(=O)C3CC3)CC2)ccc1NC1COc2cccc(-c3cccc(-n4ncc(C(=O)O)c4C)n3)c21]

The title compound was synthesized starting from (+)-ethyl 1-(6-(3-((4-(1-(cyclopropanecarbonyl)piperidin-4-yl)-2-methylphenyl)amino)-2,3-dihydrobenzofuran-4-yl)pyridin-2-yl)-5-methyl-1H-pyrazole-4-carboxylate ($t_r$=4.15 min) by the similar method as described for the synthesis of Example 7a. $^1$H NMR (400 MHz, Methanol-$d_4$) δ 7.99 (dd, J=7.8, 8.0 Hz, 1H), 7.83-7.91 (m, 2H), 7.55 (dd, J=0.9, 8.0 Hz, 1H), 7.36-7.45 (m, 2H), 6.93-7.02 (m, 1H), 6.79 (dd, J=2.1, 8.1 Hz, 1H), 6.71 (d, J=1.7 Hz, 1H), 6.41 (d, J=8.3 Hz, 1H), 5.55 (dd, J=3.2, 7.1 Hz, 1H), 4.74-4.80 (m, 1H), 4.62 (br. d, J=12.7 Hz, 1H), 4.38-4.48 (m, 2H), 3.18-3.26 (m, 2H), 2.58-2.77 (m, 2H), 2.51 (s, 3H), 1.96-2.04 (m, 1H), 1.76-1.95 (m, 2H), 1.63 (s, 3H), 1.41-1.61 (m, 2H), 0.76-0.94 (m, 4H). HRMS; calcd. for $C_{34}H_{36}N_5O_4$ (M+H) 578.2767, found 578.2762.

Example 34b. (−)-1-(6-(3-((4-1-(Cyclopropanecarbonyl)piperidin-4-yl)-2-methylphenyl)amino)-2,3-dihydrobenzofuran-4-yl)pyridin-2-yl)-5-methyl-1H-pyrazole-4-carboxylic Acid The title compound was synthesized starting from (−)-ethyl 1-(6-(3-((4-(1-(cyclopropanecarbonyl)piperidin-4-yl)-2-methylphenyl)amino)-2,3-dihydrobenzofuran-4-yl)pyridin-2-yl)-5-methyl-1H-pyrazole-4-carboxylate ($t_r$=5.40 min) by saponification using a similar method as described for the synthesis of Example 7a. $^1$H NMR and HRMS data were substantially identical to Example 34a.

Example 35

Example 35-A. (±)-tert-Butyl 4-(4-((4-(6-(4-(ethoxycarbonyl)-6-methyl-1H-pyrazol-1-yl)pyridin-2-yl)-2,3-dihydrobenzofuran-3-yl)amino)-3-methylphenyl)piperidine-1-carboxylate

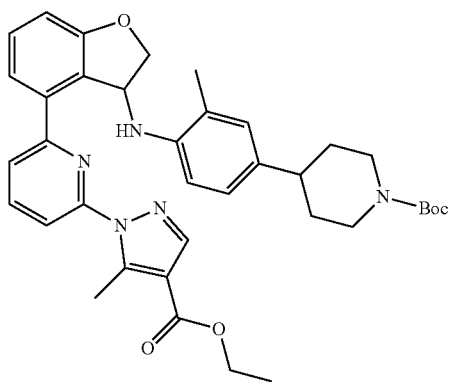 [SMILES: CCOC(=O)c1cnn(-c2cccc(-c3cccc4c3C(Nc3ccc(C5CCN(C(=O)OC(C)(C)C)CC5)cc3C)CO4)n2)c1C]

To a solution of ethyl 1-(6-bromopyridin-2-yl)-5-methyl-1H-pyrazole-4-carboxylate (Intermediate 1-3) (0.82 g, 2.65 mmol), bis(pinacolato)diboron (0.74 g, 2.92 mmol), KOAc (0.39 g, 3.98 mmol) in dioxane (20 ml) at room temperature was added P Pd(dppf)Cl$_2$.CH$_2$Cl$_2$ adduct (0.13 g, 0.16 mmol). The mixture was then stirred at 100° C. for 3 h, and then cooled to room temperature. To the reaction mixture were then added a solution of (±)-tert-butyl 4-(4-((4-bromo-2,3-dihydrobenzofuran-3-yl)amino)-3-methylphenyl)piperidine-1-carboxylate (Intermediate 3-11) (0.9 g, 1.86 mmol) in dioxane/H2O (15 mL/15 mL), K3PO4 (1.69 g, 7.96 mmol), and Pd(dppf)Cl$_2$.CH$_2$Cl$_2$ adduct (0.22 g, 0.27 mmol). The mixture was then stirred at 100° C. for 2 h, and then cooled to room temperature. The reaction mixture was then diluted with EtOAc, and then washed successively with H2O and brine, dried over Na2SO4, filtered, and then concentrated. The resulting residue was purified by flash chromatography (0% to 25% EtOAc in hexanes) to afford the title compound. MS (ESI+) m/z 638.4 (M+H).

Example 35-B. (±)-Ethyl 5-methyl-1-(6-(3-((2-methyl-4-(piperidin-4-yl)phenyl)amino)-2,3-dihydrobenzofuran-4-yl)pyridin-2-yl)-1H-pyrazole-4-carboxylate

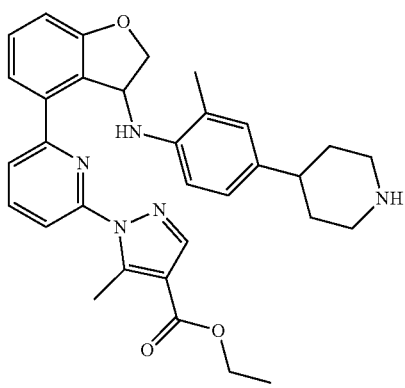 [SMILES: CCOC(=O)c1cnn(-c2cccc(-c3cccc4c3C(Nc3ccc(C5CCNCC5)cc3C)CO4)n2)c1C]

The title compound was synthesized by treatment of (±)-tert-butyl 4-(4-((4-(6-(4-(ethoxycarbonyl)-5-methyl-1H-pyrazol-1-yl)pyridin-2-yl)-2,3-dihydrobenzofuran-3-yl)amino)-3-methylphenyl)piperidine-1-carboxylate with TFA similar to the method described for the synthesis of Example 17-D. MS (ESI+) m/z 538.3 (M+H).

Example 35-C. a). Ethyl 1-(6-(3-((4-(1-((S)-2-hydroxypropanoyl)piperidin-4-yl)-2-methylphenyl)amino)-2,3-dihydrobenzofuran-4-yl)pyridin-2-yl)-5-methyl-1H-pyrazole-4-carboxylate

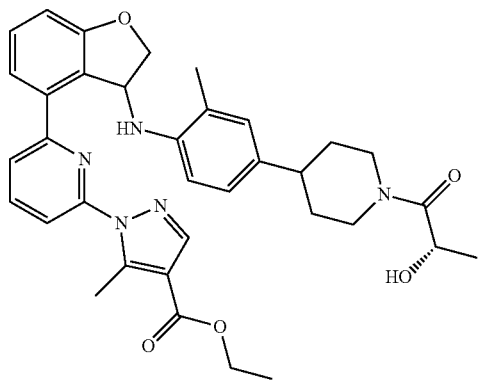 [SMILES: CCOC(=O)c1cnn(-c2cccc(-c3cccc4c3C(Nc3ccc(C5CCN(C(=O)[C@H](C)O)CC5)cc3C)CO4)n2)c1C]

To a solution of (±)-ethyl 5-methyl-1-(6-(3-((2-methyl-4-(piperidin-4-yl)phenyl)amino)-2,3-dihydrobenzofuran-4-yl)pyridin-2-yl)-1H-pyrazole-4-carboxylate (as TFA salt, 0.9 g, 1.38 mmol), L-lactic acid (0.15 g, 1.66 mmol) and HATU (0.78 g, 2.1 mmol) in DMF (20 mL) at room temperature was added DIPEA (1.2 mL, 6.9 mmol). The mixture was stirred at room temperature for 18 h. The reaction mixture was then diluted with H$_2$O. The mixture was then extracted twice with EtOAc. The combined organic layers were washed with brine, dried over Na$_2$SO$_4$, filtered, and then concentrated. The resulting residue was purified by silica gel flash column chromatography (0% to 4% MeOH in CH$_2$Cl$_2$) to afford the title compound. MS (ESI+) m/z 610.3 (M+H).

Example 35-C. b). Ethyl 1-(6-(3-((4-(1-((S)-2-hydroxypropanoyl)piperidin-4-yl)-2-methylphenyl)amino)-2,3-dihydrobenzofuran-4-yl)pyridin-2-yl)-5-methyl-1H-pyrazole-4-carboxylate (Diastereomer-1) and ethyl 1-(6-(3-((4-(1-((S)-2-hydroxypropanoyl)piperidin-4-yl)-2-methylphenyl)amino)-2,3-dihydrobenzofuran-4-yl)pyridin-2-yl)-5-methyl-1H-pyrazole-4-carboxylate (Diastereomer-2)

Resolution of the diastereomers of ethyl 1-(6-(3-((4-(1-((S)-2-hydroxypropanoyl)piperidin-4-yl)-2-methylphenyl)amino)-2,3-dihydrobenzofuran-4-yl)pyridin-2-yl)-5-methyl-1H-pyrazole-4-carboxylate was achieved by chiral HPLC using CHIRALPAK® IA column with 30% (0.2% Et$_3$N in EtOH) in hexane to afford ethyl 1-(6-(3-((4-(1-((S)-2-hydroxypropanoyl)piperidin-4-yl)-2-methylphenyl)amino)-2,3-dihydrobenzofuran-4-yl)pyridin-2-yl)-5-methyl-1H-pyrazole-4-carboxylate (diastereomer-1) (t$_r$=9.6 min) and ethyl 1-(6-(3-((4-(1-((S)-2-hydroxypropanoyl)piperidin-4-yl)-2-methylphenyl)amino)-2,3-dihydrobenzofuran-4-yl)pyridin-2-yl)-5-methyl-1H-pyrazole-4-carboxylate (diastereomer-2) (t$_r$=10.9 min).

Example 35a. (+)-1-(6-(3-((4-(1-((S)-2-Hydroxypropanoyl)piperidin-4-yl)-2-methylphenyl)amino)-2,3-dihydrobenzofuran-4-yl)pyridin-2-yl)-1-methyl-1H-pyrazole-4-carboxylic Acid

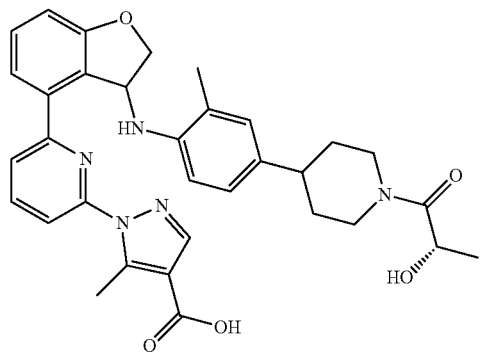 [SMILES: Cc1cc(C2CCN(C(=O)[C@H](C)O)CC2)ccc1NC1COc2cccc(-c3cccc(-n4ncc(C(=O)O)c4C)n3)c21]

A mixture of ethyl 1-(6-(3-((4-(1-((S)-2-hydroxypropanoyl)piperidin-4-yl)-2-methylphenyl)amino)-2,3-dihydrobenzofuran-4-yl)pyridin-2-yl)-5-methyl-1H-pyrazole-4-carboxylate (diastereomer-1) (t$_r$=9.6 min) (65 mg, 0.11 mmol) and LiOH—H$_2$O (45 mg, 1.1 mmol) in THF/MeOH/H$_2$O (3 mL/3 mL/3 mL) was stirred at 60° C. for 3 h, and the cooled to room temperature. The reaction mixture was neutralized with 1N HCl, and then extracted twice with CH$_2$Cl$_2$. The combined organic layers were washed with brine, dried over Na$_2$SO$_4$, filtered, and then concentrated. The resulting residue was purified by silica gel flash column chromatography (0% to 10% MeOH in CH$_2$Cl$_2$) to afford the title compound. $^1$H NMR (400 MHz, Methanol-d$_4$) δ 7.97-8.03 (m, 1H), 7.89 (d, J=7.6 Hz, 1H), 7.85 (s, 1H), 7.55 (dd, J=0.8, 7.9 Hz, 1H), 7.38-7.45 (m, 2H), 6.97 (dd, J=2.1, 6.9 Hz, 1H), 6.78 (d, J=8.3 Hz, 1H), 6.70 (s, 1H), 6.40 (d, J=8.3 Hz, 1H), 5.52-5.58 (m, 1H), 4.77 (dd, J=7.2, 9.3 Hz, 1H), 4.58-4.66 (m, 2H), 4.44 (dd, J=3.2, 9.3 Hz, 1H), 4.04-4.14 (m, 1H), 3.14-3.22 (m, 1H), 2.69-2.79 (m, 1H), 2.57-2.68 (m, 1H), 2.50 (d, J=4.4 Hz, 3H), 1.80-1.93 (m, 2H), 1.62 (s, 3H), 1.43-1.60 (m, 2H), 1.30-1.39 (m, 3H). HRMS; calcd. for C$_{33}$H$_{36}$N$_5$O$_5$ (M+H) 582.2716, found 582.2709.

Example 35b. (−)-1-(6-(3-((4-1-((S)-2-Hydroxypropanoyl)piperidin-4-yl)-2-methylphenyl)amino)-2,3-dihydrobenzofuran-4-yl)pyridin-2-yl)-5-methyl-1H-pyrazole-4-carboxylic Acid Saponification of ethyl 1-(6-(3-((4-(1-((S)-2-hydroxypropanoyl)piperidin-4-yl)-2-methylphenyl)amino)-2,3-dihydrobenzofuran-4-yl)pyridin-2-yl)-5-methyl-1H-pyrazole-4-carboxylate (diastereomer-2) (t$_r$=10.9 min) by the similar method as described for the synthesis of Example 35a afforded the title compound. $^1$H NMR (400 MHz, Methanol-d) δ 7.95-8.02 (m, 1H), 7.82-7.89 (m, 2H), 7.55 (d, J=8.0 Hz, 1H), 7.37-7.45 (m, 2H), 6.97 (dd, J=2.0, 6.9 Hz, 1H), 6.76-6.81 (m, 1H), 6.70 (br. s, 1H), 6.41 (d, J=8.0 Hz, 1H), 5.56 (dd, J=2.9, 7.1 Hz, 1H), 4.73-4.78 (m, 1H), 4.54-4.66 (m, 2H), 4.44 (dd, J=3.2, 9.3 Hz, 1H), 4.04-4.14 (m, 1H), 3.15-3.22 (m, 1H), 2.69-2.79 (m, 1H), 2.58-2.68 (m, 1H), 2.52 (s, 3H), 1.81-1.92 (m, 2H), 1.63 (s, 3H), 1.44-1.61 (m, 2H), 1.27-1.39 (m, 3H) HRMS; calcd. for C$_{33}$H$_{36}$N$_6$O$_5$ (M+H) 582.2716, found 582.2707.

Example 36

The following compounds can be synthesized as outlined for preparations of Example 35 using appropriate materials in the table (Intermediate 1 and Intermediate 3, and carboxylic acid). The racemic sample was resolved by the conditions described in the table, for those cases $^1$H NMR and HRMS data for (+)- and (−)-enantiomers were substantially identical to the racemic sample.

| Example | Chemical structure<br>¹H NMR and HRMS<br>Resolution conditions of enantiomers.<br>(+)- and (−)-Carboxylic acids derived from their correspoding resolved ester enantiomers. | Chemical name<br>Intermediate 1<br>Intermediate 3<br>Carboxylic acid |
|---|---|---|
| 36-1 | [Chemical structure] | 1-(6-(3((4-(1-(Cyclopropanecarbonyl)-piperidin-4-yl)-3-ethylphenyl)amino)-2,3-dihydrobenzofuran-4-yl)pyridin-2-yl)-5-(trifluoromethyl)-1H-pyrazole-4-carboxylic acid<br>Intermediate 1-1<br>Intermediate 3-10<br>Cyclopropanecarboxylic acid (CAS# 1759-53-1)) |

¹H NMR (400 MHz, Methanol-$d_4$) δ 8.00-8.07 (m, 2H), 7.95 (s, 1H), 7.53 (dd, J = 2.2, 6.5 Hz, 1H), 7.44-7.49 (m, 1H), 7.36-7.42 (m, 1H), 6.97 (dd, J = 0.7, 8.0 Hz, 1H), 6.81 (d, J = 8.9 Hz, 1H) 6.20-6.27 (m, 2H), 5.42-5.50 (m, 1H), 4.62-4.70 (m, 1H), 4.59 (dd, J = 6.7, 9.3 Hz, 1H), 4.41-4.51 (m, 2H), 3.19-3.29 (m, 1H), 2.88-2.99 (m, 1H), 2.68-2.78 (m, 1H), 2.55 (q, J = 7.5 Hz, 2H), 1.97-2.06 (m, 1H), 1.78-1.87 (m, 1H), 1.70-1.77 (m, 1H), 1.47-1.69 (m, 2H), 1.13 (t, J = 7.5 Hz, 3H), 0.77-0.96 (m, 4H). HRMS; calcd. for $C_{35}H_{35}F_3N_5O_4$ (M + H) 646.2641, found 646.2651
Resolution conditions of enantiomers of corresponding esters:
Ethyl 1-(6-(3-((4-(1-(cyclopropanecarbonyl)piperidin-4-yl)-3-ethylphenyl)amino)-2,3-dihydrobenzofuran-4-yl)pyridin-2-yl)-5-(trifluoromethyl)-1H-pyrazole-4-carboxylate was subjected to chiral HPLC using CHIRALPAK ® IA column with 60% (0.2% Et3N in hexane) in EtOH to give ethyl 1-(6-(3-((4-(1-(cyclo-propanecarbonyl)piperidin-4-yl)-3-ethylphenyl)amino)-2,3-dihydrobenzofuran-4-yl)pyridin-2-yl)-5-(trifluoro-methyl)-1H-pyrazole-4-carboxylate (enantiomer-1, $t_r$ = 5.8 min) and ethyl 1-(6-(3-((4-(1-(cyclopropane-carbonyl)piperidin-4-yl)-3-ethylphenyl)amino)-2,3-dihydrobenzofuran-4-yl)pyridin-2-yl)-5-(trifluoromethyl)-1H-pyrazole-4-carboxylate (enantiomer-2, $t_r$ = 6.8 min)
(+)-36-1: (+)-1-(6-(3-((4-(1-(Cyclopropanecarbonyl)piperidin-4-yl)-3-ethylphenyl)amino)-2,3-dihydrobenzo-furan-4-yl)pyridin-2-yl)-5-(trifluoromethyl)-1H-pyrazole-4-carboxylic acid was derived from saponification of ethyl 1-(6-(3-((4-(1-(cyclopropanecarbonyl)piperidin-4-yl)-3-ethylphenyl)amino)-2,3-dihydrobenzofuran-4-yl)pyridin-2-yl)-5-(trifluoromethyl)-1H-pyrazole-4-carboxylate (enantiomer-2, $t_r$ = 6.8 min).
(−)-36-1: (−)-1-(6-(3-((4-(1-(Cyclopropanecarbonyl)piperidin-4-yl)-3-ethylphenyl)amino)-2,3-dihydrobenzo-furan-4-yl)pyridin-2-yl)-5-(trifluoromethyl)-1H-pyrazole-4-carboxylic acid was derived from saponification of ethyl 1-(6-(3-((4-(1-(cyclopropanecarbonyl)piperidin-4-yl)-3-ethylphenyl)amino)-2,3-dihydrobenzofuran-4-yl)pyridin-2-yl)-5-(trifluoromethyl)-1H-pyrazole-4-carboxylate (enantiomer-1, $t_r$ = 5.8 min)

| 36-2 | [Chemical structure] | 1-(6-(3-((4-(1-(cyclopropanecarbonyl)-piperidin-4-yl)-3-ethylphenyl)amino-2,3-dihydrobenzofuran-4-yl)pyridin-2-yl)-5-ethyl-1H-pyrazole-4-carboxylic acid<br>Intermediate 1-4-2<br>Intermediate 3-10<br>Cyclopropanecarboxylic acid (CAS# 1759-53-1)) |

¹H NMR (400 MHz, Methanol-$d_4$) δ 7.91-8.01 (m, 3 H) 7.58 (dd, J = 7.7, 1.1 Hz, 1 H) 7.36-7.41 (m, 2 H) 6.93-6.99 (m, 1 H) 6.80-6.85 (m, 1 H) 6.23-6.29 (m, 2 H) 5.50 (br. s., 1 H) 4.59-4.68 (m, 1 H) 4.40-4.50 (m, 2 H) 3.14-3.27 (m, 3 H) 2.87-2.98 (m, 1 H) 2.67-2.78 (m, 1 H) 2.54 (q, J = 7.5 Hz, 2 H) 1.95-2.05 (m, 1 H) 1.44-1.84 (m, 4 H) 1.12 (t, J = 7.5 Hz, 3 H) 1.05 (t, J = 7.4 Hz, 3 H) 0.76-0.95 (m, 4 H). HRMS; calcd. for $C_{36}H_{40}N_5O_4$ (M + H) 606.3080, found 606.3066
Resolution conditions of enantiomers of correpsonding esters:
Ethyl 1-(6-(3-((4-(1-(cyclopropanecarbonyl)piperidin-4-yl)-3-ethylphenyl)amino-2,3-dihydrobenzofuran-4-yl)-pyridin-2-yl)-5-ethyl-1H-pyrazole-4-carboxylate was subjected to chiral HPLC using CHIRALPAK ® IA column with 70% (0.2% Et3N in hexane) in EtOH to give ethyl 1-(6-(3-((4-(1-(cyclopropanecarbonyl)-piperidin-4-yl)-3-ethylphenyl)amino)-2,3-dihydrobenzofuran-4-yl)pyridin-2-yl)-5-ethyl-1H-pyrazole-4-carboxylate (enantiomer-1, $t_r$ = 9.6 min) and ethyl 1-(6-(3-((4-(1-(cyclopropanecarbonyl)piperidin-4-yl)-3-ethylphenyl)amino)-2,3-dihydrobenzofuran-4-yl)pyridin-2-yl)-5-ethyl-1H-pyrazole-4-carboxylate (enantiomer-2, $t_r$ = 13.4 min)

-continued

| Chemical structure<br>¹H NMR and HRMS<br>Resolution conditions of enantiomers. | Chemical name<br>Intermediate 1<br>Intermediate 3<br>Carboxylic acid |
|---|---|
| Example | (+)- and (−)-Carboxylic acids derived from their correspoding resolved ester enantiomers. |

(+)-36-2: (+)-1-(6-(3-((4-(1-(Cyclopropanecarbonyl)piperidin-4-yl)-3-ethylphenyl)amino)-2,3-dihydrobenzo-
furan-4-yl)pyridin-2-yl)-5-ethyl-1H-pyrazole-4-carboxylic acid was derived from saponification of ethyl 1-
(6-(3-((4-(1-(cyclopropanecarbonyl)piperidin-4-yl)-3-ethylphenyl)amino)-2,3-dihydrobenzofuran-4-yl)-
pyridin-2-yl)-5-ethyl-1H-pyrazole-4-carboxylate (enantiomer-1, $t_r$ = 9.6 min)..
(−)-36-2: (−)-1-(6-(3-((4-(1-(Cyclopropanecarbonyl)piperidin-4-yl)-3-ethylphenyl)amino)-2,3-dihydrobenzo-
furan-4-yl)pyridin-2-yl)-5-ethyl-1H-pyrazole-4-carboxylic acid was derived from saponification of ethyl 1-
(6-(3-((4-(1-(cyclopropanecarbonyl)piperidin-4-yl)-3-ethylphenyl)amino)-2,3-dihydrobenzofuran-4-yl)-
pyridin-2-yl)-5-ethyl-1H-pyrazole-4-carboxylate (enantiomer-2, $t_r$ = 13.4 min)

Example 37

Example 37-A. a.) (±)-Ethyl 1-(6-3-(4-(1-(cyclopropanecarbonyl)piperidin-4-yl)-2-methylbenzyl)-2,3-dihydro-1H-inden-4-yl)pyridin-2-yl)-6-methyl-1H-pyrazole-4-carboxylate

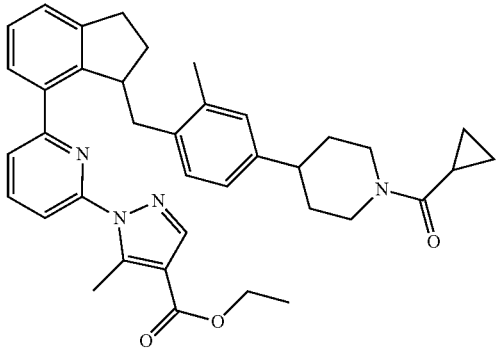 [SMILES: CCOC(=O)c1cnn(-c2cccc(-c3cccc4c3C(Cc3ccc(C5CCN(C(=O)C6CC6)CC5)cc3C)CC4)n2)c1C]

To a solution of Intermediate 1-3 (137 mg, 0.44 mmol), bis(pinacolato)diboron (112 mg, 0.44 mmol), and KOAc (80 mg, 0.80 mmol) in dioxane (2.0 mL) was added chloro(2-dicyclohexylphosphino-2',6'-dimethoxy-1,1'-biphenyl)[2-(2-aminoethylphenyl)]palladium(I)-methyl-t-butyl ether adduct (CAS #1028206-58-7; 13.5 mg, 0.020 mmol). The mixture was stirred at 110° C. for 3 h, and then cooled to room temperature.
To a solution of (+)-3-(4-(1-(cyclopropanecarbonyl)piperidin-4-yl)-2-methylbenzyl)-2,3-dihydro-1H-inden-4-yl trifluoromethanesulfonate (Intermediate 6-1) (209 mg, 0.40 mmol) in dioxane (2.0 mL) was added the reaction mixture above, followed by 2M aq. $K_3PO_4$ (0.4 mL, 0.80 mmol) and chloro(2-dicyclohexylphosphino-2',6'-dimethoxy-1,1'-biphenyl)[2-(2-aminoethylphenyl)]palladium(II)-methyl-t-butyl ether adduct (CAS #1028206-58-7; 13.5 mg, 0.020 mmol). The mixture was then stirred at 100° C. for 15 h, and then cooled to room temperature, and then concentrated with Celite®. The resulting residue was purified by silica gel flash chromatography to afford the title compound. MS (ESI+) m/z 603.5 (M+H).

Example 37. a). (+)-1-(6-(3-(4-1-(Cyclopropanecarbonyl)piperidin-4-yl)-2-methylbenzyl)-2,3-dihydro-1H-inden-4-yl)pyridin-2-yl)-5-methyl-1H-pyrazole-4-carboxylic Acid

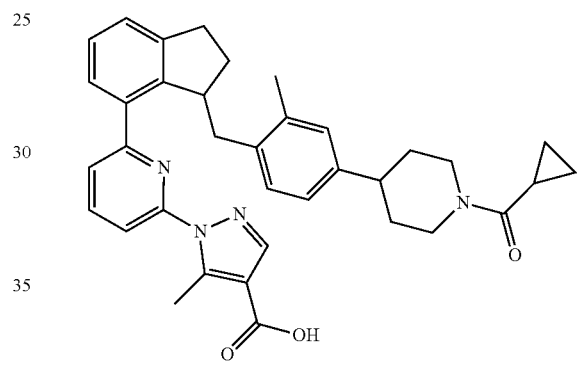

Saponification of (±)-ethyl 1-(6-(3-(4-(1-(cyclopropanecarbonyl)piperidin-4-yl)-2-methylbenzyl)-2,3-dihydro-1H-inden-4-yl)pyridin-2-yl)-5-methyl-1H-pyrazole-4-carboxylate using the similar procedure as described for the synthesis of Example 7a afforded the title compound. ¹H NMR (400 MHz, Methanol-$d_4$) δ 8.02 (s, 1H), 7.92 (t, J=7.9 Hz, 1H), 7.66 (dd, J=8.1, 0.8 Hz, 1H), 7.44 (dd, J=7.7, 0.8 Hz, 1H), 7.36-7.31 (m, 2H), 7.31-7.25 (m, 1H), 6.73-6.67 (m, 2H), 6.56 (d, J=7.7 Hz, 1H), 4.60 (d, J=13.5 Hz, 1H), 4.41 (d, J=13.4 Hz, 1H), 4.28 (q, J=7.7 Hz, 1H), 3.26-3.07 (m, 2H), 2.94-2.85 (m, 1H), 2.84 (s, 3H), 2.71 (d, J=12.9 Hz, 1H), 2.60 (d, J=12.1 Hz, 1H), 2.49 (dd, J=13.5, 6.7 Hz, 1H), 2.41 (dd, J=13.6, 9.1 Hz, 1H), 2.17-2.05 (m, 1H), 2.03-1.89 (m, 2H), 1.87-1.71 (m, 5H), 1.62-1.38 (m, 2H), 0.90-0.85 (m, 2H), 0.84-0.77 (m, 2H). HRMS; calcd. for $C_{36}H_{39}N_4O_3$ (M+H) 575.3022, found 575.3056.

Example 37. b). (+)-1-(6-(3-(4-(1-(Cyclopropanecarbonyl)piperidin-4-yl)-2-methylbenzyl)-2,3-dihydro-1H-inden-4-yl)pyridin-2-yl)-5-methyl-1H-pyrazole-4-carboxylic acid and (−)-1-(6-(3-(4-(1-(cyclopropanecarbonyl)piperidin-4-yl)-2-methylbenzyl)-2,3-dihydro-1H-inden-4-yl)pyridin-2-yl)-5-methyl-1H-pyrazole-4-carboxylic Acid Resolution of the enantiomers of (+)-1-(6-(3-(4-(1-(cyclopropanecarbonyl)piperidin-4-yl)-2-methylbenzyl)-2,3-dihydro-1H-inden-4-yl)pyridin-2-yl)-5-methyl-1H-pyrazole-4-carboxylic acid was achieved by chiral SFC using CHIRALCEL® OJ-H column with 25% MeOH in $CO_2$ to afford (−)-1-(6-(3-(4-(1-(cyclopropanecarbonyl)piperidin-4-yl)-2-methylbenzyl)-2,3-dihydro-1H-inden-4-yl)pyridin-2-yl)-5-methyl-1H-pyrazole-4-carboxylic acid ($t_r$=4.7 min) and (+)-1-(6-(3-(4-(1-(cyclopropanecarbonyl)piperidin-4-yl)-2-methylbenzyl)-2,3-dihydro-1H-inden-4-yl)pyridin-2-yl)-5-methyl-1H-pyrazole-4-carboxylic acid ($t_r$=7.2 min). $^1$H NMR and HRMS data for (+)- and (−)-enantiomers were substantially identical to (±)-1-(6-(3-(4-(1-(cyclopropanecarbonyl)piperidin-4-yl)-2-methylbenzyl)-2,3-dihydro-1H-inden-4-yl)pyridin-2-yl)-5-methyl-1H-pyrazole-4-carboxylic acid.

Example 38

The following compounds can be synthesized as outlined for preparations of Example 37 using appropriate materials in the table (Intermediate 1 and Intermediate 6). The racemic sample was resolved by the conditions described in the table. $^1$H NMR and HRMS data for (+)- and (−)-enantiomers were substantially identical to the racemic form.

| Example | Chemical structure<br>$^1$H NMR and HRMS<br>Resolution conditions of enantiomers. | Chemical name<br>Intermediate 1<br>Intermediate 6 |
|---|---|---|
| 38-1 | <chemical structure> | 1-(6-(3-(4-(1-(Cyclopropanecarbonyl)-piperidin-4-yl)-3-ethylbenzyl)-2,3-dihydro-1H-inden-4-yl)pyridin-2-yl)-5-ethyl-1H-pyrazole-4-carboxylic acid<br>Intermediate 1-4-2<br>Intermediate 6-2 |
| | $^1$H NMR (400 MHz, Methanol-d4) δ 8.09-8.03 (m, 2H), 7.71 (d, J = 8.1 Hz, 1H), 7.68 (d, J = 7.6 Hz, 1H), 7.45-7.40 (m, 1H), 7.31-7.27 (m, 2H), 6.88 (d, J = 8.0 Hz, 1H), 6.58 (d, J = 7.9 Hz, 1H), 6.52 (s, 1H), 4.64 (d, J = 11.3 Hz, 1H), 4.49-4.40 (m, 1H), 4.24-4.16 (m, 1H), 3.45-3.34 (m, 2H), 3.26-3.20 (m, 1H), 3.30-2.93 (m, 1H), 2.93-2.78 (m, 2H), 2.77-2.68 (m, 1H), 2.55-2.44 (m, 3H), 2.30-2.21 (m, 1H), 2.13-2.03 (m, 1H), 2.03-1.95 (m, 1H), 1.95-1.86 (m, 1H), 1.83-1.45 (m, 4H), 1.17 (t, J = 7.3 Hz, 3H), 1.06 (t, J = 7.5 Hz, 3H), 0.94-0.86 (m, 2H), 0.86-0.77 (m, 2H). HRMS; calcd. for $C_{38}H_{43}N_4O_3$ (M + H) 603.3335, found 603.3345.<br>Resolution of the enantiomers of (±)-1-(6-(3-(4-(1-(cyclopropanecarbonyl)piperidin-4-yl)-3-ethylbenzyl)-2,3-dihydro-1H-inden-4-yl)pyridin-2-yl)-5-ethyl-1H-pyrazole-4-carboxylic acid was achieved by chiral SFC using CHIRALCEL ® OJ-H column with 15% MeOH in $CO_2$ to give (−)-1-(6-(3-(4-(1-(cyclopropanecarbonyl)-piperidin-4-yl)-3-ethylbenzyl)-2,3-dihydro-1H-inden-4-yl)pyridin-2-yl)-5-ethyl-1H-pyrazole-4-carboxylic acid ($t_r$ = 4.50 min) and (+)-1-(6-(3-(4-(1-(cyclopropanecarbonyl)piperidin-4-yl)-3-ethylbenzyl)-2,3-dihydro-1H-inden-4-yl)pyridin-2-yl)-5-ethyl-1H-pyrazole-4-carboxylic acid ($t_r$ = 5.25 min). | |
| 38-2 | <chemical structure> | 1-(6-(3-(4-(1-(Cyclopropanecarbonyl)-piperidin-4-yl)-3-ethylbenzyl)-2,3-dihydro-1H-inden-4-yl)pyridin-2-yl)-5-methyl-1H-pyrazole-4-carboxylic acid<br>Intermediate 1-3<br>Intermediate 6-2 |
| | $^1$H NMR (400 MHz, Methanol-d4) δ 8.09-8.03 (m, 2H), 7.76-7.73 (m, 1H), 7.68 (d, J = 7.7 Hz, 1H), 7.47-7.42 (m, 1H), 7.30 (s, 1H), 7.29 (s, 1H), 6.86 (d, J = 7.9 Hz, 1H), 6.57 (d, J = 8.0 Hz, 1H), 6.53 (s, 1H), 4.64 (d, J = 12.9 Hz, 1H) 4.49-4.40 (m, 1H), 4.26-4.18 (m, 1H), 3.27-3.19 (m, 1H), 3.02-2.89 (m, 2H), 2.88-2.79 (m, 4H), 2.72 (t, J = 12.3 Hz, 1H), 2.54-2.46 (m, 3H), 2.28-2.20 (m, 1H), 2.12-1.95 (m, 2H), 1.95-1.87 (m, 1H), 1.82-1.46 (m, 4H), 1.05 (t, J = 7.5 Hz, 3H), 0.94-0.86 (m, 2H), 0.86-0.78 (m, 2H). HRMS; calcd. for $C_{37}H_{41}N_4O_3$ (M + H) 589.3179, found 589.3174. | |

| Example | Chemical structure<br>¹H NMR and HRMS<br>Resolution conditions of enantiomers. | Chemical name<br>Intermediate 1<br>Intermediate 6 |
|---|---|---|
| | Resolution of the enantiomers of (±)-1-(6-(3-(4-(1-(cyclopropanecarbonyl)piperidin-4-yl)-3-ethylbenzyl)-2,3-dihydro-1H-inden-4-yl)pyridin-2-yl)-5-methyl-1H-pyrazole-4-carboxylic acid was achieved by chiral SFC using CHIRALPAK ® AD-H column with 30% MeOH with 5mM NH₄OH in CO2 to give (−)-1-(6-(3-(4-(1-(cyclopropanecarbonyl)piperidin-4-yl)-3-ethylbenzyl)-2,3-dihydro-1H-inden-4-yl)pyridin-2-yl)-5-methyl-1H-pyrazole-4-carboxylic acid (t$_r$ = 3.25 min) and (+)-1-(6-(3-(4-(1-(cyclopropanecarbonyl)piperidin-4-yl)-3-ethylbenzyl)-2,3-dihydro-1H-inden-4-yl)pyridin-2-yl)-5-methyl-1H-pyrazole-4-carboxylic acid (t$_r$ = 4.65 min). | |
| 38-3 | | 1-(6-(3-(4-(1-cyclopropanecarbonyl)-piperidin-4-yl)-2-methylbenzyl)-2,3-dihydro-1H-inden-4-yl)pyridin-2-yl)-5-ethyl-1H-pyrazole-4-carboxylic acid<br>Intermediate 1-4-2<br>Intermediate 6-1 |
| | ¹H NMR (400 MHz, Methanol-d₄) δ 8.05 (s, 1H), 7.94 (t, J = 7.9 Hz, 1H), 7.66-7.62 (m, 1H), 7.47 (d, J = 7.1 Hz, 1H), 7.33-7.26 (m, 3H), 6.75-6.67 (m, 2H), 6.57 (d, J = 7.8 Hz, 1H), 4.60 (d, J = J = 13.0 Hz, 1H), 4.42 (br s, 1H), 4.23 (q, J = 7.7 Hz, 1H), 3.42-3.34 (m, 2H), 3.27-3.07 (m, 2H), 2.90 (dd, J = 16.2, 8.0 Hz, 1H), 2.74-2.56 (m, 2H), 2.52-2.42 (m, 2H), 2.20--2.04 (m, 1H), 2.04--1.88 (m, 2H), 1.84-1.74 (m, 5H), 1.61--1.38 (m, 2H), 1.18 (t, J = 7.3 Hz, 3H), 0.90-0.80 (m, 4H). HRMS; calcd. for C₃₇H₄₁N₄O₃ (M + H) 589.3179, found 589.3193. Resolution of the enantiomers of (±)-1-(6-(3-(4-(1-(cyclopropanecarbonyl)piperidin-4-yl)-2-methylbenzyl)-2,3-dihydro-1H-inden-4-yl)pyridin-2-yl)-5-ethyl-1H-pyrazole-4-carboxylic acid was achieved by chiral SFC using CHIRALCEL ® OJ-H column with 30% MeOH in CO₂ to give (+)-1-(6-(3-(4-(1-(cyclopropanecarbonyl)-piperidin-4-yl)-2-methylbenzyl)-2,3-dihydro-1H-inden-4-yl)pyridin-2-yl)-5-ethyl-1H-pyrazole-4-carboxylic acid (t$_r$ = 2.3 min) and (−)-1-(6-(3-(4-(1-(cyclopropanecarbonyl)piperidin-4-yl)-2-methylbenzyl)-2,3-dihydro-1H-inden-4-yl)pyridin-2-yl)-5-ethyl-1H-pyrazole-4-carboxylic acid (t$_r$ = 3.5 min). | |

Example 39

Example 39-A. (±)-tert-Butyl 4-(4-((7-(6-(4-(ethoxycarbonyl)-5-ethyl)-1H-pyrazol-1-yl)pyridin-2-yl)-2,3-dihydro-1H-inden-1-yl)methyl)-2-ethyl-phenyl)piperidine-1-carboxylate

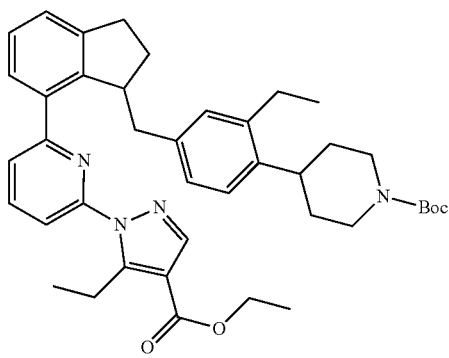 [SMILES: CCOC(=O)c1cnn(-c2cccc(-c3cccc4c3C(Cc3ccc(C5CCN(C(=O)OC(C)(C)C)CC5)c(CC)c3)CC4)n2)c1CC]

To a suspension of ethyl 1-(6-bromopyridin-2-yl)-5-ethyl-1H-pyrazole-4-carboxylate (Intermediate 1-4-2) (448 mg, 1.382 mmol), bis(pinacolato)diboron (383 mg, 1.51 mmol), and KOAc (185 mg, 1.88 mmol) in dioxane (6.3 mL) was added Pd(dppf)Cl₂.CH₂Cl₂ adduct (48 mg, 0.063 mmol). The mixture was then stirred at 90° C. for 2 h, and then cooled to room temperature. To the reaction mixture was added a solution of (±)-tert-butyl 4-(2-ethyl-4-((7-(((trifluoromethylsulfonyl)oxy)-2,3-dihydro-1H-inden-1-ylmethyl-phenyl)piperidine-1-carboxylate (Intermediate 6-3) (713 mg, 1.256 mmol) in dioxane (6.3 mL), followed by K₃PO₄ (2M in water) (1.25 mL, 2.5 mmol) and chloro(2-dicyclohexylphosphino-2',6'-dimethoxy-1,1'-biphenyl)[2-(2-aminoethylphenyl)]palladium(II)-methyl-t-butyl ether adduct (CAS #1028206-58-7; 48 mg, 0.063 mmol). The mixture was then stirred at 90° C. for 0.5 h, and then cooled to room temperature. The mixture was filtered through a plug of Celite®, and then the filtrate was diluted with EtOAc. The mixture was then washed with H₂O. The organic layer was then passed through an ISOLUTE® Phase Separator and then concentrated. The resulting residue was purified by silica gel flash column chromatography to afford the title compound. MS (ESI+) n/z 663.1 (M+H).

185

Example 39-B. (±)-Ethyl 5-ethyl-1-(6-(3-(3-ethyl-4-(piperidin-4-yl)benzyl)-2,3-dihydro-1H-inden-4-yl)pyridin-2-yl)-1H-pyrazole-4-carboxylate

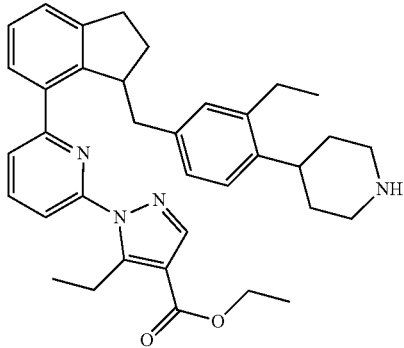 [SMILES: CCOC(=O)c1cnn(-c2cccc(-c3cccc4c3C(Cc3ccc(C5CCNCC5)c(CC)c3)CC4)n2)c1CC]

A mixture of (±)-tert-butyl 4-(4-(6-(4-(ethoxycarbonyl)-5-ethyl-1H-pyrazol-1-yl)pyridin-2-yl)-2,3-dihydro-1H-inden-1-yl)methyl)-2-ethylphenyl)piperidine-1-carboxylate (204 mg, 0.308 mmol) and TFA (240 μL, 3.1 mmol) in CH$_2$Cl$_2$ (3.1 mL) was stirred at room temperature for 5 h, and then concentrated to afford the title compound. MS (ESI+) m/z 563.4 (M+H).

Example 39-C. Ethyl 5-ethyl-1-(6-(3-(3-ethyl-4-(1(S)-2-hydroxypropanoyl)piperidin-4-yl)benzyl)-2,3-dihydro-1H-inden-4-yl)pyridin-2-yl)-1H-pyrazole-4-carboxylate

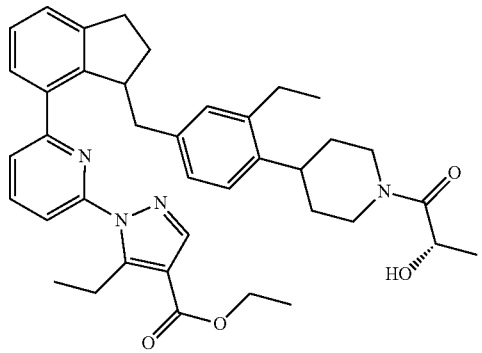 [SMILES: CCOC(=O)c1cnn(-c2cccc(-c3cccc4c3C(Cc3ccc(C5CCN(C(=O)[C@H](C)O)CC5)c(CC)c3)CC4)n2)c1CC]

To a solution of ethyl 5-ethyl-1-(6-(3-(3-ethyl-4-(piperidin-4-yl)benzyl)-2,3-dihydro-1H-inden-4-yl)pyridin-2-yl)-1H-pyrazole-4-carboxylate (as TFA salt, 173 mg, 0.31 mmol), DIPEA (160 μL, 0.92 mmol), and L-(+)-lactic acid (28 mg, 0.31 mmol) in DMF (3.1 mL) was added HATU (130 mg, 0.338 mmol). The mixture was stirred at room temperature for 2 h, and then diluted with EtOAc. The mixture was then washed with half saturated brine. The aqueous layer was extracted with EtOAc. The combined organic layers were washed twice with brine, passed through a phase separator, and concentrated. The resulting residue was purified by silica gel flash column chromatography to afford the title compound. MS (ESI+) m/z 635.4 (M+H).

186

Example 39. a). 5-Ethyl-1-(6-3-3-ethyl-4-(1-((S)-2-hydroxypropanoyl)piperidin-4-yl)benzyl)-2,3-dihydro-1H-inden-4-yl)pyridin-2-yl)-1H-pyrazole-4-carboxylic Acid

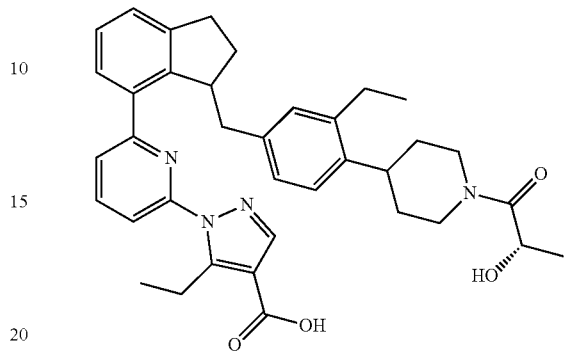

To a solution of a diastereomeric mixture of ethyl 5-ethyl-1-(6-(3-(3-ethyl-4-(1-((S)-2-hydroxypropanoyl)piperidin-4-yl)benzyl)-2,3-dihydro-1H-inden-4-yl)pyridin-2-yl)-1H-pyrazole-4-carboxylate (104 mg, 0.164 mmol) in MeOH (1.6 mL) and THF (1.6 mL) was added LiOH (1M in water) (1.64 mL, 1.64 mmol). The mixture was stirred for 1 h at 50° C., and then cooled to room temperature. The reaction was then quenched with 1N HCl (1.8 mL, 1.8 mmol). The resulting suspension was extracted with EtOAc. The aqueous layer was extracted with EtOAc. The combined organic layers were concentrated to afford the title compound.

Example 39. b). (−)-5-Ethyl-1-(6-(3-(3-ethyl-4-(1-((S)-2-hydroxypropanoyl)piperidin-4-yl)benzyl)-2,3-dihydro-1H-inden-4-yl)pyridin-2-yl)-1H-pyrazole-4-carboxylic Acid (Diastereomer-1) and (+)-5-ethyl-1-(6-(3-(3-ethyl-4-(1-((S)-2-hydroxypropanoyl)piperidin-4-yl)benzyl)-2,3-dihydro-1H-inden-4-yl)pyridin-2-yl)-1H-pyrazole-4-carboxylic Acid (Diastereomer-2)

Resolution of the diastereomers of 5-ethyl-1-(6-(3-(3-ethyl-4-(1-((S)-2-hydroxypropanoyl)piperidin-4-yl)benzyl)-2,3-dihydro-1H-inden-4-yl)pyridin-2-yl)-1H-pyrazole-4-carboxylic acid was achieved by chiral SFC using CHIRALPAK® AD-H column with 25% IPA in CO2 to give (−)-5-ethyl-1-(6-(3-(3-ethyl-4-(1-((S)-2-hydroxypropanoyl)piperidin-4-yl)benzyl)-2,3-dihydro-1H-inden-4-yl)pyridin-2-yl)-1H-pyrazole-4-carboxylic acid (diastereomer-1) (t$_r$=6.95 min) and (+)-5-ethyl-1-(6-(3-(3-ethyl-4-(1-((S)-2-hydroxypropanoyl)piperidin-4-yl)benzyl)-2,3-dihydro-1H-inden-4-yl)pyridin-2-yl)-1H-pyrazole-4-carboxylic acid (diastereomer-2) (t$_r$=9.75 min).

Analytical data for (−)-5-ethyl-1-(6-(3-(3-ethyl-4-(1-((S)-2-hydroxypropanoyl)piperidin-4-yl)benzyl)-2,3-dihydro-1H-inden-4-yl)pyridin-2-yl)-1H-pyrazole-4-carboxylic acid (diastereomer-1) (t$_r$=6.95 min): $^1$H NMR (400 MHz, Methanol-d$_4$) δ 8.10-8.02 (m, 2H), 7.74-7.66 (m, 2H), 7.45-7.38 (m, 1H), 7.32-7.26 (m, 2H), 6.87 (d, J=7.7 Hz, 1H), 6.58 (dd, J=1.7, 8.0 Hz, 1H), 6.52 (s, 1H), 4.68-4.55 (m, 2H), 4.24-4.16 (m, 1H), 4.10 (br. d, J=12.7 Hz, 1H), 3.47-3.33 (m, 1H), 3.23-3.13 (m, 1H), 3.03-2.69 (m, 4H), 2.55-2.43 (m, 3H), 2.31-2.21 (m, 1H), 2.13-2.00 (m, 1H), 1.95-1.84 (m, 1H), 1.77-1.65 (m, 2H), 1.64-1.49 (m, 2H), 1.40-1.26 (m, 4H), 1.17 (t, J=7.3 Hz, 3H), 1.08-1.02 (m, 3H). HRMS: calcd. for C₃₇H₄₃N₄O₄(M+H) 607.3284, found 607.3276. Analytical data for (+)-5-ethyl-1-(6-(3-(3-ethyl-4-(1-((S)-2-hydroxypropanoyl)piperidin-4-yl)benzyl)-2,3-dihydro-1H-inden-4-yl)pyridin-2-yl)-1H-pyrazole-4-carboxylic acid (diastereomer-2); ¹H NMR (400 MHz, Methanol-d₄) δ 8.09-8.04 (m, 2H), 7.73-7.67 (m, 2H), 7.45-7.39 (m, 1H), 7.32-7.27 (m, 2H), 6.87 (d, J=7.7 Hz, 1H), 6.58 (dd, J=7.9, 1.7 Hz, 1H), 6.52 (s, 1H), 4.68-4.55 (m, 2H), 4.24-4.16 (m, 1H), 4.14-4.07 (m, 1H), 3.46-3.34 (m, 2H), 3.22-3.14 (m, 1H), 3.03-2.69 (m, 4H), 2.55-2.44 (m, 3H), 2.30-2.21 (m, 1H), 2.13-2.00 (m, 1H), 1.95-1.86 (m, 1H), 1.77-1.50 (m, 4H), 1.34 (dd, J=16.9, 6.6 Hz, 3H), 1.17 (t, J=7.4 Hz, 3H), 1.06 (t, J=7.5 Hz, 3H). HRMS; calcd. for C₃₇H₄₃N₄O₄ (M+H) 607.3284, found 607.3276.

Example 40

The following compounds were synthesized as outlined for the preparation of Example 39 using appropriate starting materials in the table (Intermediate 1, Intermediate 6, and carboxylic acid). The racemic sample was resolved by the conditions described in the table.

| Example | Compound structure<br>diastereomer separation condition<br>Analytical data for the diastereomer-1 (peak-1 in the diastereomer separation)<br>Analytical data for the diastereomer-2 (peak-2-in the diasterermer separation) | IUPAC name<br>Intermediate 1<br>Intermediate 6<br>Carboxylic Acid |
|---|---|---|
| 40-1 | [structure] | 5-Ethyl-1-(6-(3-(3-ethyl-4-(1-((S)-2-hydroxypentanoyl)piperidin-4-yl)benzyl)-2,3-dihydro-1H-inden-4-yl)pyridin-2-yl)-1H-pyrazole-4-carboxylic acid<br>Intermediate 1-4-2<br>Intermediate 6-3<br>(S)-2-hydroxypentanoic acid<br>(CAS# 41014-93-1) |

Resolution of the diastereomers of 5-ethyl-1-(6-(3-(3-ethyl-4-(1-((S)-2-hydroxypentanoyl)piperidin-4-yl)benzyl)-2,3-dihydro-1H-inden-4-yl)pyridin-2-yl)-1H-pyrazole-4-carboxylic acid was achieved by chiral SFC using CHIRALPAK ® AD-H column with 25% IPA with 10 mM NH4OH in CO2 to give (−)-5-ethyl-1-(6-(3-(3-ethyl)-4-(1-((S)-2-hydroxypentanoyl)piperidin-4-yl)benzyl)-2,3-dihydro-1H-inden-4-yl)pyridin-2-yl)-1H-pyrazole-4-carboxylic acid (diastereomer-1) (t_r = 3.90 min) and (+)-5-ethyl-1-(6-(3-(3-ethyl-4-(1-((S)-2-hydroxypentanoyl)-piperidin-4-yl)benzyl)-2,3-dihydro-1H-inden-4-yl)pyridin-2-yl)-1H-pyrazole-4-carboxylic acid (diastereomer-2) (t_r = 5.10 min).
(−)-5-ethyl-1-(6-(3-(3-ethyl-4-(1-((S)-2-hydroxypentanoyl)piperidin-4-yl)benzyl)-2,3-dihydro-1H-inden-4-yl)-pyridin-2-yl)-1H-pyrazole-4-carboxylic acid (diastereomer-1) (t_r = 3.90 min): ¹ H NMR (400 MHz, Methanol-d₄) δ 8.09-8.03 (m, 2H), 7.73-7.66 (m, 2H), 7.44-7.39 (m, 1H), 7.32-7.26 (m, 2H), 6.90-6.83 (m, 1H), 6.58 (br. d, J = 7.6 Hz, 1H), 6.52 (br. s, 1H), 4.64 (br. d, J = 13.1 Hz, 1H), 4.52-4.43 (m, 1H), 4.24-4.16 (m, 1H), 4.13-4.01 (m, 1H), 3.46-3.32 (m, 2H), 3.22-3.14 (m, 1H), 3.03-2.80 (m, 3H), 2.80-2.68 (m, 1H), 2.55-2.43 (m, 3H), 2.30-2.20 (m, 1H), 2.13-1.99 (m, 1H), 1.95-1.86 (m, 1H), 1.77-1.40 (m, 7H), 1.17 (t, J = 7.3 Hz, 3H), 1.05 (t, J = 7.6 Hz, 3H), 1.02-0.93 (m, 3H), 0.93-0.81 (m, 1H). HRMS: calcd. for C₃₉H₄₇N₄O₄ (M + H) 635.3597, found 635.3611.
(+)-5-ethyl-1-(6-(3-(3-ethyl-4-(1-((S)-2-hydroxypentanoyl)piperidin-4-yl)benzyl)-2,3-dihydro-1H-inden-4-yl)-pyridin-2-yl)-1H-pyrazole-4-carboxylic acid (diastereomer-2) (t_r = 5.10 min): ¹H NMR (400 MHz, Methanol-d₄) δ 8.09-8.03 (m, 2H), 7.71 (d, J = 7.9 Hz, 1H), 7.68 (d, J = 7.7 Hz, 1H), 7.45-7.39 (m, 1H), 7.32-7.26 (m, 2H), 6.89-6.84 (m, 1H), 6.58 (d, J = 7.6 Hz, 1H), 6.52 (s, 1H), 4.64 (d, J = 13.0 Hz, 1H), 4.52-4.43 (m, 1H), 4.24-4.16 (m, 1H), 4.13-4.03 (m, 1H), 3.46-3.33 (m, 2H), 3.22-3.14 (m, 1H), 2.97 (t, J = 12.2 Hz, 1H), 2.93-2.80 (m, 2H), 2.75 (t, J = 14.1 Hz, 1H), 2.55-2.44 (m, 3H), 2.30-2.21 (m, 1H), 2.13-2.00 (m, 1H), 1.95-1.86 (m, 1H), 1.77-1.42 (m, 9H), 1.17 (t, J = 7.3 Hz, 3H), 1.06 (t, J = 7.5 Hz, 3H), 1.02-0.94 (m, 3H). HRMS; calcd. for C₃₉H₄₇N₄O₄ (M + H) 635.3597, found 635.3618.

| 40-2 | [structure] | 5-Ethyl-1-(6-(3-(4-(1-((S)-2-hydroxypropanoyl)piperidin-4-yl)-2-methylbenzyl)-2,3-dihydro-1H-inden-4-yl)-pyridin-2-yl)-1H-pyrazole-4-carboxylic acid<br>Intermediate 1-4-2<br>Intermediate 6-4<br>L-(+)-lactic acid |

| | IUPAC name<br>Intermediate 1<br>Intermediate 6<br>Carboxylic Acid |
|---|---|
| Compound structure<br>diastereomer separation condition<br>Analytical data for the diastereomer-1 (peak-1 in the diastereomer separation)<br>Example Analytical data for the diastereomer-2 (peak-2-in the diasterermer separation) | |

Resolution of the diastereomers of 5-ethyl-1-(6-(3-(4-(1-((S)-2-hydroxypropanoyl)piperidin-4-yl)-2-methylbenzyl)-2,3-dihydro-1H-inden-4-yl)pyridin-2-yl)-1H-pyrazole-4-carboxylic acid was achieved by chiral SFC using CHIRALCEL ® OJ-H column with 25% MeOH in CO$_2$ to give (−)-5-ethyl-1-(6-(3-(4-(1-((S)-2-hydroxypropanoyl)-piperidin-4-yl)-2-methylbenzyl)-2,3-dihydro-1H-inden-4-yl)pyridin-2-yl)-1H-pyrazole-4-carboxylic acid (diastereomer-1) (t$_r$ = 2.6 min) and (+)-5-ethyl-1-(6-(3-(4-(1-((S)-2-hydroxypropanoyl)piperidin-4-yl)-2-methyl-benzyl)-2,3-dihydro-1H-inden-4-yl)pyridin-2-yl)-1H-pyrazole-4-carboxylic acid (diastereomer-2) (t$_r$ = 4.3 min).
(−)-5-ethyl-1-(6-(3-(4-(1-((S)-2-hydroxypropanoyl)piperidin-4-yl)-2-methylbenzyl)-2,3-dihydro-1H-inden-4-yl)-pyridin-2-yl)-1H-pyrazole-4-carboxylic acid (diastereomer-1) (t$_r$ = 2.6 min); $^1$H NMR (400 MHz, Methanol-d$_4$) δ 8.04 (s, 1H), 7.94 (dd, J = 7.8, 8.0 Hz, 1H), 7.64 (d, J = 8.0 Hz, 1H), 7.47 (d, J = 7.7 Hz, 1H), 7.25-7.37 (m, 3H), 6.67-6.74 (m, 2H), 6.54-6.60 (m, 1H), 4.55-4.65 (m, 2H), 4.23 (q, J = 7.4 Hz, 1H), 4.07 (br. d, J = 13.0 Hz, 1H), 3.25-3.44 (m, 2H), 3.08-3.19 (m, 2H), 2.86-2.95 (m, 1H), 2.65-2.76 (m, 1H), 2.55-2.65 (m, 1H), 2.37-2.52 (m, 2H), 2.05-2.18 (m, 1H), 1.87-1.97 (m, 1H), 1.71-1.84 (m, 5H), 1.41-1.62 (m, 2H), 1.29-1.38 (m, 3H), 1.17 (t, J = 7.3 Hz, 3H). HRMS; calcd. for for C$_{36}$H$_{41}$N$_4$O$_4$ (M + H) 593.3128, found 593.3115.
(+)-5-ethyl-1-(6-(3-(4-(1-((S)-2-hydroxypropanoyl)piperidin-4-yl)-2-methylbenzyl)-2,3-dihydro-1H-inden-4-yl)-pyridin-2-yl)-1H-pyrazole-4-carboxylic acid (diastereomer-2) (t$_r$ = 4.3 min); $^1$H NMR (400 MHz, Methanol-d$_4$) δ 8.04 (s, 1H), 7.94 (t, J = 7.9 Hz, 1H), 7.64 (d, J = 8.1 Hz, 1H), 7.47 (d, J = 7.7 Hz, 1H), 7.35-7.26 (m, 3H), 6.74-6.66 (m, 2H), 6.57 (d, J = 7.6 Hz, 1H), 4.60 (d, J = 10.3 Hz, 2H), 4.23 (q, J = 7.4 Hz, 1H), 4.07 (d, J = 13.0 Hz, 1H), 3.42-3.30 (m, 2H), 3.19-3.07 (m, 2H), 2.90 (dd, J = 15.9, 8.4 Hz, 1H), 2.70 (t, J = 13.0 Hz, 1H), 2.60 (t, J = 12.1 Hz, 1H), 2.50-2.40 (m, 2H), 2.17-2.05 (m, 1H), 1.92 (dd, J = 12.4, 7.3 Hz, 1H), 1.85-1.75 (m, 5H), 1.55-1.45 (m, 2H), 1.33 (dd, J = 11.6, 6.6 Hz, 3H), 1.18 (t, J = 7.3 Hz, 3H). HRMS; calcd. for C$_{36}$H$_{41}$N$_4$O$_4$ (M + H) 593.3128, found 593.3139.

40-3 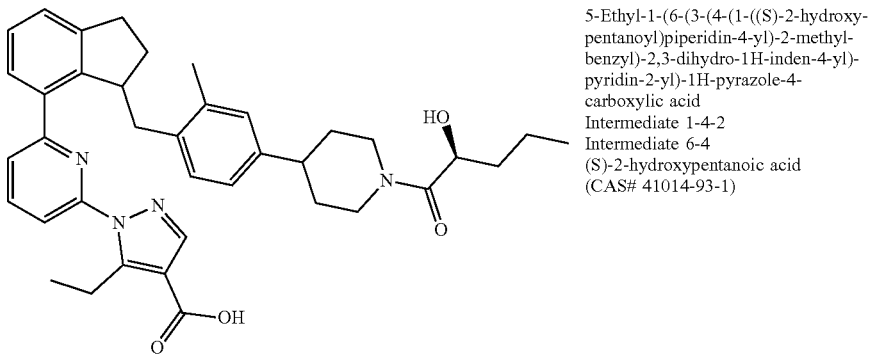 5-Ethyl-1-(6-(3-(4-(1-((S)-2-hydroxy-pentanoyl)piperidin-4-yl)-2-methyl-benzyl)-2,3-dihydro-1H-inden-4-yl)-pyridin-2-yl)-1H-pyrazole-4-carboxylic acid
Intermediate 1-4-2
Intermediate 6-4
(S)-2-hydroxypentanoic acid
(CAS# 41014-93-1)

Resolution of the diastereomers of (±)-5-ethyl-1-(6-(3-(4-(1-((S)-2-hydroxypentanoyl)piperidin-4-yl)-2-methylbenzyl)-2,3-dihydro-1H-inden-4-yl)pyridin-2-yl)-1H-pyrazole-4-carboxylic acid was achieved by chiral SFC using CHIRALCEL ® OJ-H column with 25% in CO$_2$ to give (−)-5-ethyl-1-(6-(3-(4-(1-((S)-2-hydroxypentanoyl)piperidin-4-yl)-2-methylbenzyl)-2,3-dihydro-1H-inden-4-yl)pyridin-2-yl)-1H-pyrazole-4-carboxylic acid (diastereomer-1) (t$_r$ = 2.4 min) and (+)-5-ethyl-1-(6-(3-(4-(1-((S)-2-hydroxypentanoyl)piperidin-4-yl)-2-methylbenzyl)-2,3-dihydro-1H-inden-4-yl)pyridin-2-yl)-1H-pyrazole-4-carboxylic acid (diastereomer-2) (t$_r$ = 4.6 min).
(−)-5-Ethyl-1-(6-(3-(4-(1-((S)-2-hydroxypentanoyl)piperidin-4-yl)-2-methylbenzyl)-2,3-dihydro-1H-inden-4-yl)-pyridin-2-yl)-1H-pyrazole-4-carboxylic acid (diastereomer-1) (t$_r$ = 2.4 min): $^1$H NMR (400 MHz, Methanol-d$_4$) δ 8.04 (s, 1H), 7.93 (dd, J = 7.8, 8.0 Hz, 1H), 7.64 (dd, J = 0.6, 8.1 Hz, 1H), 7.47 (d, J = 7.7 Hz, 1H), 7.36-7.25 (m, 3H), 6.74-6.66 (m, 2H), 6.60-6.54 (m, 1H), 4.65-4.57 (m, 1H), 4.50-4.42 (m, 1H), 4.27-4.19 (m, 1H), 4.10-4.00 (m, 1H), 3.44-3.24 (m, 2H), 3.18-3.07 (m, 2H), 2.94-2.85 (m, 1H), 2.76-2.66 (m, 1H), 2.65-2.54 (m, 1H), 2.53-2.36 (m, 2H), 2.17-2.04 (m, 1H), 1.96-1.88 (m, 1H), 1.84-1.71 (m, 5H), 1.70-1.38 (m, 6H), 1.17 (t, J = 7.3 Hz, 3H), 1.01-0.93 (m, 3H). HRMS; calcd. for C$_{38}$H$_{45}$N$_4$O$_4$ (M + H) 621.3441, found 621.3445.
(+)-5-Ethyl-1-(6-(3-(4-(1-((S)-2-hydroxypentanoyl)piperidin-4-yl)-2-methylbenzyl)-2,3-dihydro-1H-inden-4-yl)-pyridin-2-yl)-1H-pyrazole-4-carboxylic acid (diastereomer-2) (t$_r$ = 4.6 min): $^1$H NMR (400 MHz, Methanol-d$_4$) δ 8.04 (s, 1H), 7.93 (t, J = 7.9 Hz, 1H), 7.64 (d, J = 7.5 Hz, 1H), 7.47 (d, J = 7.8 Hz, 1H), 7.33-7.26 (m, 3H), 6.74-6.67 (m, 2H), 6.57 (dd, J = 7.7, 3.9 Hz, 1H), 4.60 (d, J = 11.6 Hz, 1H), 4.50-4.40 (m, 1H), 4.23 (q, J = 7.8 Hz, 1H), 4.05 (br s, 1H), 3.40-3.30 (m, 2H), 3.20-3.06 (m, 2H), 2.90 (dd, J = 15.8, 8.3 Hz, 1H), 2.70 (t, J = 11.3 Hz, 1H), 2.61 (t, J = 12.1 Hz, 1H), 2.52-2.39 (m, 2H), 2.18-2.04 (m, 1H), 1.92 (dd, J = 12.2, 7.6 Hz, 1H), 1.85-1.76 (m, 5H), 1.70-1.38 (m, 6H), 1.17 (t, J = 7.3 Hz, 3H), 1.03-0.93 (m, 3H). HRMS; calcd. for C$_{38}$H$_{45}$N$_4$O$_4$ (M + H) 621.3441, found 621.3446.

Example 41

Example 41. a). (±)-5-Ethyl-1-(6-(3-(3-ethyl-4-(1-(methoxycarbonyl)piperidin-4-yl)benzyl)-2,3-dihydro-1H-inden-4-yl)pyridin-2-yl)-1H-pyrazole-4-carboxylic Acid

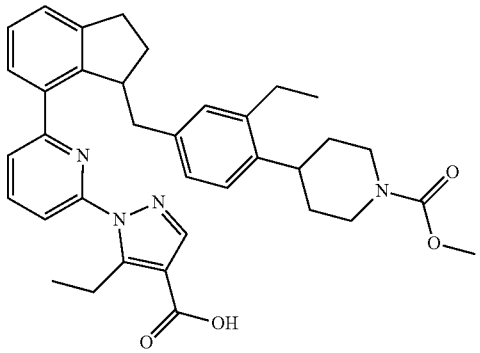 [SMILES: CCc1cc(CC2CCc3cccc(-c4cccc(-n5ncc(C(=O)O)c5CC)n4)c32)ccc1C1CCN(C(=O)OC)CC1]

The title compound was synthesized by reaction of (±)-ethyl 5-ethyl-1-(6-(3-(3-ethyl-4-(piperidin-4-yl)benzyl)-2,3-dihydro-1H-inden-4-yl)pyridin-2-yl)-1H-pyrazole-4-carboxylate (Example 39-B) with methyl chloroformate employing a similar manner as described for the synthesis of Example 29-C, followed by saponification as described in Example 7a. $^1$H NMR (400 MHz, Methanol-$d_4$) δ 8.09-8.03 (m, 2H), 7.71 (dd, J=8.0, 0.7 Hz, 1H), 7.68 (dd, J=7.7, 0.7 Hz, 1H), 7.45-7.39 (m, 1H), 7.32-7.26 (m, 2H), 6.87 (d, J=7.9 Hz, 1H), 6.58 (dd, J=7.9, 1.8 Hz, 1H), 6.53-6.50 (m, 1H), 4.26-4.15 (m, 3H), 3.70 (s, 3H), 3.45-3.33 (m, 2H), 2.96-2.78 (m, 5H), 2.53-2.44 (m, 3H), 2.30-2.20 (m, 1H), 2.12-2.00 (m, 1H), 1.95-1.86 (m, 1H), 1.69-1.48 (m, 4H), 1.17 (t, J=7.4 Hz, 3H), 1.04 (t, J=7.6 Hz, 3H). HRMS; calcd. for $C_3H_{41}N_4O_4$ (M+H) 593.3128, found 593.3149.

Example 41. b) (+)-Ethyl-1-(6-(3-(3-ethyl-4-(1-(methoxycarbonyl)piperidin-4-yl)benzyl)-2,3-dihydro-1H-inden-4-yl)pyridin-2-yl)-1H-pyrazole-4-carboxylic acid and (−)-ethyl-1-(6-(3-(3-ethyl-4-(1-(methoxycarbonyl)piperidin-4-yl)benzyl)-2,3-dihydro-1H-inden-4-yl)pyridin-2-yl)-1H-pyrazole-4-carboxylic Acid Resolution of the enantiomers of (±)-5-ethyl-1-(6-(3-(3-ethyl-4-(1-(methoxycarbonyl)piperidin-4-yl)benzyl)-2,3-dihydro-1H-inden-4-yl)pyridin-2-yl)-1H-pyrazole-4-carboxylic acid was achieved by chiral SFC using CHIRALPAK® AD-H column with 25% IPA in $CO_2$ to give (−)-5-ethyl-1-(6-(3-(3-ethyl-4-(1-(methoxycarbonyl)piperidin-4-yl)benzyl)-2,3-dihydro-1H-inden-4-yl)pyridin-2-yl)-1H-pyrazole-4-carboxylic acid ($t_r$=3.5 min) and (+)-5-ethyl-1-(6-(3-(3-ethyl-4-(1-(methoxycarbonyl)piperidin-4-yl)benzyl)-2,3-dihydro-1H-inden-4-yl)pyridin-2-yl)-1H-pyrazole-4-carboxylic acid ($t_r$=5.1 min). $^1$H NMR and HRMS data for (+)- and (−)-enantiomers were substantially identical to (±)-5-ethyl-1-(6-(3-(3-ethyl-4-(1-(methoxycarbonyl)piperidin-4-yl)benzyl)-2,3-dihydro-1H-inden-4-yl)pyridin-2-yl)-1H-pyrazole-4-carboxylic acid.

Example 42

Example 42. a). (±)-6-Ethyl-1-(6-(3-(4-(1-(methoxycarbonyl)piperidin-4-yl)-2-methylbenzyl)-2,3-dihydro-1H-inden-4-yl)pyridin-2-yl)-1H-pyrazole-4-carboxylic Acid

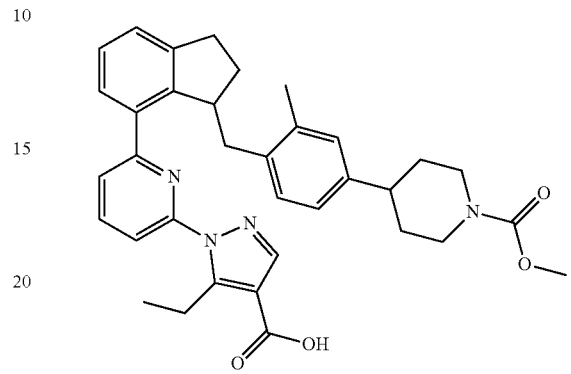

The title compound was synthesized as outlined in the synthesis of Example 41 but starting from ethyl 1-(6-bromopyridin-2-yl)-5-ethyl-1H-pyrazole-4-carboxylate (Intermediate 14-2) and (±)-tert-butyl 4-(3-methyl-4-((7-(((trifluoromethyl)sulfonyl)oxy)-2,3-dihydro-1H-inden-1-yl)methyl)phenyl)piperidine-1-carboxylate (Intermediate 6-4) as the starting materials. $^1$H NMR (400 MHz, Methanol-$d_4$) δ 8.04 (s, 1H), 7.93 (t, J=7.9 Hz, 1H), 7.64 (dd, J=8.1, 0.7 Hz, 1H), 7.47 (dd, J=7.7, 0.7 Hz, 1H), 7.35-725 (m, 3H), 6.73-6.66 (m, 2H), 6.56 (d, J=7.7 Hz, 1H), 4.28-4.14 (m, 3H), 3.69 (s, 3H), 3.42-3.32 (m, 2H), 3.18-3.07 (m, 1H), 2.95-2.90 (m, 3H), 2.50-2.40 (m, 3H), 2.13-2.08 (m, 1H), 1.92 (dd, J=12.5, 7.5 Hz, 1H), 1.79 (s, 3H), 1.72 (t, J=12.2 Hz, 2H), 1.55-1.39 (m, 2H), 1.18 (t, J=7.3 Hz, 3H). HRMS; calcd. for $C_{35}H_{39}N_4O_4$(M+H) 579.2971. found 579.2971.

Example 42. b). (+)-6-Ethyl-1-(6-(3-4-(1-(methoxycarbonyl)piperidin-4-yl)-2-methylbenzyl)-2,3-dihydro-1H-inden-4-yl)pyridin-2-yl)-1H-pyrazole-4-carboxylic acid and (−)-5-ethyl-1-(6-(3-(4-(1 methoxycarbonyl)piperidin-4-yl)-2-methylbenzyl)-2,3-dihydro-1H-inden-4-yl)pyridin-2-yl)-1H-pyrazole-4-carboxylic Acid Resolution of the enantiomers of (+)-5-ethyl-1-(6-(3-(4-(1-(methoxycarbonyl)piperidin-4-yl)-2-methylbenzyl)-2,3-dihydro-1H-inden-4-yl)pyridin-2-yl)-1H-pyrazole-4-carboxylic acid was achieved by chiral SFC using CHIRALCEL® OJ-H column with 30% MeOH in $CO_2$ to give (−)-5-ethyl-1-(8-(3-(4-(1-(methoxycarbonyl)piperidin-4-yl)-2-methylbenzyl)-2,3-dihydro-1H-inden-4-yl)pyridin-2-yl)-1H-pyrazole-4-carboxylic acid ($t_r$=2.3 min) and (+)-5-ethyl-1-(6-(3-(4-(1-(methoxycarbonyl)piperidin-4-yl)-2-methylbenzyl)-2,3-dihydro-1H-inden-4-yl)pyridin-2-yl)-1H-pyrazole-4-carboxylic acid ($t_r$=3.9 min). $^1$H NMR and HRMS data for (+)- and (−)-enantiomers were substantially identical to (+)-5-ethyl-1-(6-(3-(4-(1-(methoxycarbonyl)piperidin-4-yl)-2-methylbenzyl)-2,3-dihydro-1H-inden-4-yl)pyridin-2-yl)-1H-pyrazole-4-carboxylic acid.

Example 43. (+)- and (−)-16-(3-((4-(1-(Cyclopropanecarbonyl)piperidin-4-yl)-2-methylphenyl)amino)-6-methyl-2,3-dihydro-1H-inden-4-yl)pyridin-2-yl)-5-(trifluoromethyl)-1H-pyrazole-4-carboxylic Acid

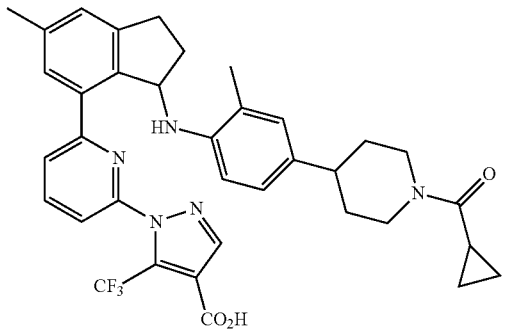 [SMILES: Cc1cc2c(c(-c3cccc(-n4ncc(C(=O)O)c4C(F)(F)F)n3)c1)C(Nc1ccc(C3CCN(C(=O)C4CC4)CC3)cc1C)CC2]

The title compounds were isolated via resolution of the enantiomers of (±)-1-(6-(3-((4-(1-cyclopropanecarbonyl)piperidin-4-yl)-2-methylphenyl)amino)-6-methyl-2,3-dihydro-1H-inden-4-yl)pyridin-2-yl)-5-(trifluoromethyl)-1H-pyrazole-4-carboxylic acid (Example 11-1) by chiral SFC using CHIRALCEL® OJ-H column with 5% to 55% MeOH in $CO_2$ to give (+)-1-(6-(3-((4-(1-(Cyclopropanecarbonyl)piperidin-4-yl)-2-methylphenyl)amino)-6-methyl-2,3-dihydro-1H-inden-4-yl)pyridin-2-yl)-5-(trifluoromethyl)-1H-pyrazole-4-carboxylic acid ($t_r$=3.23 min) and (−)-1-(6-(3-((4-(1-(Cyclopropanecarbonyl)piperidin-4-yl)-2-methylphenyl)amino)-6-methyl-2,3-dihydro-1H-inden-4-yl)pyridin-2-yl)-5-(trifluoromethyl)-1H-pyrazole-4-carboxylic acid ($t_r$=4.73 min). $^1$H NMR and HRMS data for (+)- and (−)-enantiomer were substantially identical to Example 11-1.

Example 44. (+)- and (−)-1-(3-(3-((4-(1-(Cyclopropanecarbonyl)piperidin-4-yl)-2-methylphenyl)amino)-2,3-dihydro-1H-inden-4-yl)phenyl)-5-methyl-1H-pyrazole-4-carboxylic Acid

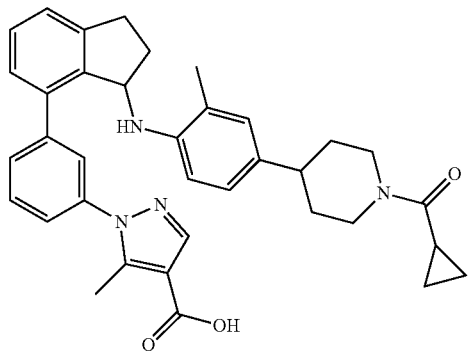 [SMILES: Cc1cc(C2CCN(C(=O)C3CC3)CC2)ccc1NC1CCc2cccc(-c3cccc(-n4ncc(C(=O)O)c4C)c3)c21]

The title compounds were isolated via resolution of the enantiomers of (±)-1-(3-(3-((4-(1-(cyclopropanecarbonyl)piperidin-4-yl)-2-methylphenyl)amino)-2,3-dihydro-1H-inden-4-yl)phenyl)-5-methyl-1H-pyrazole-4-carboxylic acid (Example 11-4) by chiral SFC using CHIRALPAK® AS-H column with 5-55% MeOH in $CO_2$ to give (+)-1-(3-(3-((4-(1-(cyclopropanecarbonyl)piperidin-4-yl)-2-methylphenyl)amino)-2,3-dihydro-1H-inden-4-yl)phenyl)-5-methyl-1H-pyrazole-4-carboxylic acid ($t_r$=2.59 min) and (−)-1-(3-(3-((4-(1-(cyclopropanecarbonyl)piperidin-4-yl)-2-methylphenyl)amino)-2,3-dihydro-1H-inden-4-yl)phenyl)-5-methyl-1H-pyrazole-4-carboxylic acid ($t_r$=2.81 min). $^1$H NMR and HRMS data for (+)- and (−)-enantiomer were substantially identical to Example 11-4.

Example 45

Example 45-A. tert-Butyl 4-(4-((7-(6-(4-(ethoxycarbonyl)-5-methyl-1H-pyrazol-1-yl)pyridin-2-yl)-2,3-dihydro-1H-inden-1-yl)amino)-3-methylphenyl)piperidine-1-carboxylate

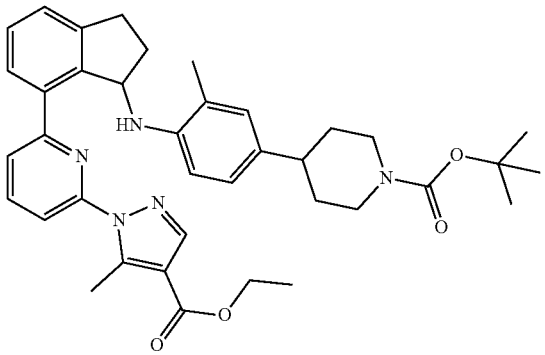 [SMILES: CCOC(=O)c1cnn(-c2cccc(-c3cccc4c3C(Nc3ccc(C5CCN(C(=O)OC(C)(C)C)CC5)cc3C)CC4)n2)c1C]

TsOH (0.016 g, 0.083 mmol) was added to a solution of Intermediate 3-7 (0.3 g, 0.830 mmol) and Intermediate 2-13 (0.24 g, 0.83 mmol) in toluene (8.3 mL), flask was fitted with a Dean-Stark trap and the mixture was stirred at 130° C. for 17 hours. The mixture was cooled to room temperature and then concentrated. The residue was dissolved in anhydrous MeOH (8.3 mL) and cooled to 0° C. Sodium borohydride (0.031 g, 0.83 mmol) was added and then the mixture was stirred at room temperature for 2 hours. Sodium borohydride (0.031 g, 0.83 mmol) was added again and the mixture was stirred for another 16 hours before one more portion of sodium borohydride (0.031 g, 0.83 mmol) was added. After a total of 24 hours of stirring, the reaction was quenched with water, followed by saturated aq. ammonium chloride. The aqueous layer was extracted with $CH_2Cl_2$. The organic layers were passed through an ISOLUTE® Phase Separator, and then concentrated. The resulting residue was purified by silica gel flash chromatography to give the title compound. MS (ESI+) m/z 636.5 (M+H).

Example 45-B. Ethyl 5-methyl-1-(6-(3-(2-methyl-4-piperidin-4-yl)phenyl)amino)-2,3-dihydro-1H-inden-4-yl)pyridin-2-yl)-1H-pyrazole-4-carboxylate

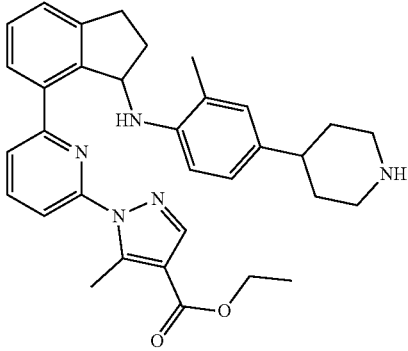 [SMILES: CCOC(=O)c1cnn(-c2cccc(-c3cccc4c3C(Nc3ccc(C5CCNCC5)cc3C)CC4)n2)c1C]

A 4M HCl in dioxane (700 µl, 2.8 mmol) was added to a solution of Example 45-A (356 mg, 0.560 mmol) in anhydrous MeOH (5.6 mL) at 0° C. The mixture was then stirred at room temperature for 19 hours. The reaction was quenched with 1M Na₂CO₃ (3 mL), and then extracted twice with CH₂Cl₂. Combined organic extracts were passed through an ISOLUTE® Phase Separator. The organic layer was concentrated to furnish the title compound. MS (ESI+) m/z 536.4 (M+H).

Example 45-C. a) (±)-Ethyl 1-(6-(3-((4-(1-(cyclobutanecarbonyl)piperidin-4-yl)-2-methylphenyl) amino)-2,3-dihydro-1H-inden-4-yl)pyridin-2-yl)-6-methyl-1H-pyrazole-4-carboxylate

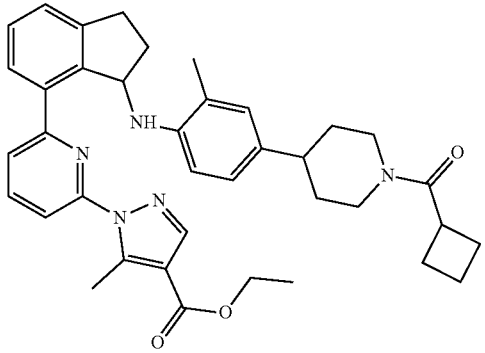 [SMILES: CCOC(=O)c1cnn(-c2cccc(-c3cccc4c3C(Nc3ccc(C5CCN(C(=O)C6CCC6)CC5)cc3C)CC4)n2)c1C]

HATU (94 mg, 0.246 mmol) was added to a solution of (+)-ethyl 5-methyl-1-(6-(3-((2-methyl-4-(piperidin-4-yl) phenyl)amino)-2,3-dihydro-1H-inden-4-yl)pyridin-2-yl)-1H-pyrazole-4-carboxylate (120 mg, 0.224 mmol), DIPEA (117 µL, 0.672 mmol), and cyclobutanecarboxylic acid (18.32 µL, 0.220 mmol) in DMF (22 mL). The mixture was then stirred for 2 h, and then diluted with H₂O/brine (ca. 1/1) and EtOAc. The bi-layer was then separated. The aqueous layer was then extracted with EtOAc. The combined organic layers were washed with brine, dried, and concentrated to furnish the title compound. MS (ESI+) m/z 618.5 (M+H).

Example 45-C. b). (+)-Ethyl 1-(6-(3-((4-(1-(cyclobutanecarbonyl)piperidin-4-yl)-2-methylphenyl) amino)-2,3-dihydro-1H-inden-4-yl)pyridin-2-yl)-5-methyl-H-pyrazole-4-carboxylate and (−)-ethyl 1-(6-(3-((4-(1-(cyclobutanecarbonyl)piperidin-4-yl)-2-methylphenyl)amino)-2,3-dihydro-1H-inden-4-yl) pyridin-2-yl)-5-methyl-1H-pyrazole-4-carboxylate Resolution of the enantiomers of (±)-ethyl 1-(6-(3-((4-(1-(cyclobutanecarbonyl)piperidin-4-yl)-2-methylphenyl) amino)-2,3-dihydro-1H-inden-4-yl)pyridin-2-yl)-5-methyl-1H-pyrazole-4-carboxylate was achieved by chiral SFC using CHIRALPAK® AD-H column with 35% IPA in CO₂ to give (+)-ethyl 1-(6-(3-((4-(1-(cyclobutanecarbonyl)piperidin-4-yl)-2-methylphenyl)amino)-2,3-dihydro-1H-inden-4-yl)pyridin-2-yl)-5-methyl-1H-pyrazole-4-carboxylate (t$_r$=4.77 min) and (−)-ethyl 1-(6-(3-((4-(1-(cyclobutanecarbonyl)piperidin-4-yl)-2-methylphenyl)amino)-2,3-dihydro-1H-inden-4-yl)pyridin-2-yl)-5-methyl-1H-pyrazole-4-carboxylate (t$_r$=6.13 min).

Example 45a. (+)-(6-(3-((4-(1-(cyclobutanecarbonyl)piperidin-4-yl)-2-methylphenyl)amino)-2,3-dihydro-1H-inden-4-yl)pyridin-2-yl)-6-methyl-1H-pyrazole-4-carboxylic Acid

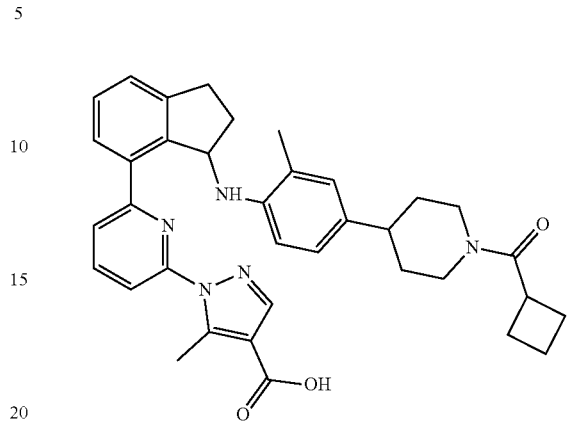

The title compound was derived from saponification of (+)-ethyl 1-(6-(3-((4-(1-(cyclobutanecarbonyl)piperidin-4-yl)-2-methylphenyl)amino)-2,3-dihydro-1H-inden-4-yl) pyridin-2-yl)-5-methyl-1H-pyrazole-4-carboxylate as described for the synthesis of Example 7a. ¹H NMR (400 MHz, Methanol-d₄) δ 7.90-7.85 (m, 2H), 7.72 (dd, J=7.8, 0.9 Hz, 1H), 7.56 (dd, J=6.4, 2.5 Hz, 1H), 7.53 (dd, J=8.1, 0.8 Hz, 1H), 7.45-7.39 (m, 2H), 6.80-6.75 (m, 1H), 6.69-6.66 (m, 1H), 6.54 (d, J=8.2 Hz, 1H), 5.35-5.30 (m, 1H), 4.64-4.57 (m, 1H), 3.89 (d, J=13.4 Hz, 1H), 3.45-3.42 (m, 1H), 3.24-3.15 (m, 1H), 3.12-3.03 (m, 1H), 2.97 (ddd, J=16.0, 8.7, 4.4 Hz, 1H), 2.72-2.63 (m, 1H), 2.62-2.53 (m, 4H), 2.47 (ddt, J=12.9, 8.6, 7.1 Hz, 1H), 2.37-2.25 (m, 2H), 2.24-2.16 (m, 2H), 2.13-2.06 (m, 1H), 2.06-1.97 (m, 1H), 1.90-1.77 (m, 3H), 1.64 (s, 3H), 1.52-1.39 (m, 2H). HRMS; calcd. for C₃₆H₄₀N₅O₃ (M+H) 590.3131, found 590.3106.

Example 45b. (−)-(6-(3-((4-(1-(cyclobutanecarbonyl)piperidinyl)piperidin-4-yl)-2-methylphenyl) amino)-2,3-dihydro-1H-inden-4-yl)pyridin-2-yl)-5-methyl-1H-pyrazole-4-carboxylic Acid The title compound was synthesized by saponification of (−)-ethyl 1-(6-(3-((4-(1-(cyclobutanecarbonyl)piperidin-4-yl)-2-methylphenyl)amino)-2,3-dihydro-1H-inden-4-yl) pyridin-2-yl)-5-methyl-1H-pyrazole-4-carboxylate as described for the synthesis of Example 7a. ¹H NMR and HRMS data were substantially identical to Example 45a.

Example 46

The following compounds were synthesized using appropriate materials denoted in the table below (Intermediate 3, Intermediate 2 and Carboxylic acid). Ketones as such as those described by Intermediate 3 were condensed with anilines described in Intermediate 2 and reduced by analogous method as described in Example 45-A. The resulting racemic esters were then deprotected (Boc removal) as described in Example 45-8. The resulting piperidine amines were coupled with the appropriate Carboxylic acid denoted in the table below as outlined in Example 45-C. a). The resulting racemic esters were then resolved by the conditions described in the table. Each enantiomer was independently saponified as described in Example 45a to provide the title compound. ¹H NMR and HRMS data for (+)- and (−)-enantiomers were substantially identical to the racemic form.

| Example | Chemical structure<br>¹H NMR and HRMS<br>Resolution conditions of enantiomers.<br>(+)- and (−)-Carboxylic acids derived from their corresponding resolved ester enantiomers. | Chemical name<br>Intermediate 3<br>Intermediate 2<br>Carboxylic acid |
|---|---|---|
| 46-1 | 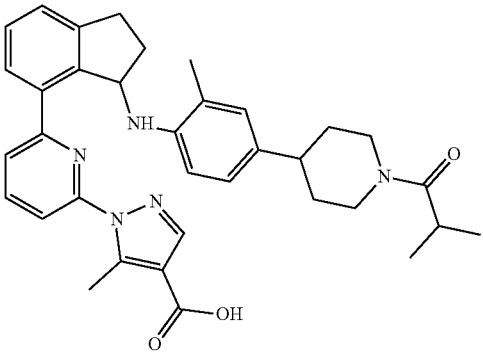 [SMILES: Cc1cc(C2CCN(C(=O)C(C)C)CC2)ccc1NC1CCc2cccc(-c3cccc(-n4ncc(C(=O)O)c4C)n3)c21] | 1(6-(3-((4-(1-Isobutyrylpiperidin-4-yl)-2-methylphenyl)amino)-2,3-dihydro-1H-inden-4-yl)pyridin-2-yl)-5-methyl-1H-pyrazole-4-carboxylic acid<br>Intermediate 3-7<br>Intermediate 2-13<br>Isobutyric acid (CAS# 79-31-2) |

¹H NMR (400 MHz, Methanol-d₄) δ 7.92-7.85 (m, 2H), 7.73 (dd, J = 7.8, 0.9 Hz, 1H), 7.58-7.51 (m, 2H), 7.45-7.39 (m, 2H), 6.78 (dd, J = 8.7, 2.1 Hz, 1H), 6.69 (d, J = 2.1 Hz, 1H), 6.55 (d, J = 8.2 Hz, 1H), 5.35-5.30 (m, 1H), 4.66 (d, J = 13.0 Hz, 1H), 4.14 (d, J = 13.6 Hz, 1H), 3.25-3.15 (m, 2H), 3.03-2.91 (m, 2H), 2.72-2.58 (m, 2H), 2.57 (d, J = 1.1 Hz, 3H), 2.53-2.42 (m, 1H), 2.13-2.04 (m, 1H), 1.92-1.79 (m, 2H), 1.64 (s, 3H), 1.59-1.40 (m, 2H), 1.12 (dd, J = 14.7, 6.7 Hz, 6H). HRMS; calcd. for $C_{35}H_{40}N_5O_3$ (M + H) 578.3131, found 578.2963.
Resolution of the enantiomers of (±)-ethyl 1-(6-(3-((4-(1-isobutyrylpiperidin-4-yl)-2-methylphenyl)-amino)-2,3-dihydro-1H-iden-4-yl)pyridin-2-yl)-5-methyl-1H-pyrazole-4-carboxylate was achieved by chiral SFC using CHIRALPAK ® AS-H column with 5-55% IPA in $CO_2$ to give (+)-ethyl 1-(6-(3-((4-(1-isobutyrylpiperidin-4-yl)-2-methylphenyl)amino)-2,3-dihydro-1H-inden-4-yl)pyridin-2-yl)-5-methyl-1H-pyrazole-4-carboxylate ($t_r$ = 2.70 min) and (−)-ethyl 1-(6-(3-((4-(1-isobutyrylpiperidin-4-yl)-2-methylphenyl)amino)-2,3-dihydro-1H-inden-4-yl)pyridin-2-yl)-5-methyl-1H-pyrazole-4-carboxylate ($t_r$ = 2.95 min).
(+)-46.1: (+)-1-(6-(3-((4-(1-isobutyrylpiperidin-4-yl)-2-methylphenyl)amino-2,3-dihydro-1H-inden-4-yl)pyridin-2-yl)-5-methyl-1H-pyrazole-4-carboxylic acid was derived from saponification of (+)-ethyl 1-(6-(3-((4-(1-isobutyrylpiperidin-4-yl)-2-methylphenyl)amino)-2,3-dihydro-1H-inden-2-yl)-5-methyl-1H-pyrazole-4-carboxylate.
(−)-46-1: (−)-1-(6-(3-((4-(1-isobutyrylpiperidin-4-yl)-2-methylphenyl)amino)-2,3-dihydro-1H-inden-4-yl)pyridin-2-yl)-5-methyl-1H-pyrazole-4-carboxylic acid was derived from saponification of (−)-ethyl 1-(6-(3-((4-(1-isobutyrylpiperidin-4-yl)-2-methylphenyl)amino)-2,3-dihydro-1H-inden-4-yl)pyridin-2-yl)-5-methyl-1H-pyrazole-4-carboxylate.

| 46-2 | 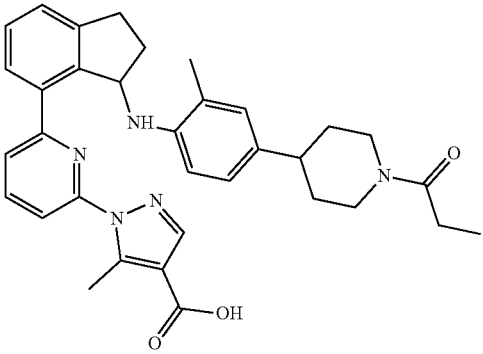 [SMILES: CCC(=O)N1CCC(c2ccc(NC3CCc4cccc(-c5cccc(-n6ncc(C(=O)O)c6C)n5)c43)c(C)c2)CC1] | 5-Methyl-1-(6-(3-((2-methyl-4-(1-propionylpiperidin-4-yl)phenyl)-amino-2-3-dihydro-1H-inden-4-yl)-pyridin-2-yl)-1H-pyrazole-4-carboxylic acid<br>Intermediate 3-7<br>Intermediate 2-13<br>Propionic acid (CAS# 79-09-4) |
|---|---|---|

¹H NMR (400 MHz, Methanol-d₄) δ 7.92-7.85 (m, 2H), 7.72 (dd, J = 7.8, 0.9 Hz, 1H), 7.58-7.51 (m, 2H), 7.45-7.38 (m, 2H), 6.78 (d, J = 8.1 Hz, 1H), 6.59 (d, J = 2.1 Hz, 1H), 6.55 (d, J = 8.3 Hz, 1H), 5.36-5.30 (m, 1H), 4.69-4.60 (m, 1H), 4.04 (d, J = 13.8 Hz, 1H), 3.25-3.14 (m, 2H), 2.97 (ddd, J = 16.1, 8.8, 4.4 Hz, 1H), 2.72-2.63 (m, 1H), 2.63-2.54 (m, 4H), 2.53-2.40 (m, 3H), 2.13-2.03 (m, 1H), 1.90-1.77 (m, 2H), 1.64 (s, 3H), 1.60-1.41 (m, 2H), 1.14 (t, J = 7.5 Hz, 3H). HRMS; calcd. for $C_{34}H_{38}N_5O_3$ (M + H) 564.2974, found 564.2747.
Resolution of the enantiomers of (±)-ethyl 5-methyl-1-(6-(3-((2-methyl-4-(1-propionylpiperidin-4-yl)-phenyl)amino)-2,3-dihydro-1H-inden-4-yl)pyridin-2-yl)-1H-pyrazole-4-carboxylate was achieved by chiral SFC using CHIRALPAK ® AS-H column with 5-55% IPA in $CO_2$ to give (+)-ethyl 5-methyl-1-(6-(3-((2-methyl-4-(1-propionyipiperidin-4-yl)phenyl)amino)-2,3-dihydro-1H-inden-4-yl)pyridin-2-yl)-1H-pyrazole-4-carboxylate ($t_r$ = 3.02 min) and (−)-ethyl 5-methyl-1-(6-(3-((2-methyl-4-(1-propionylpiperidin-4-yl)phenyl)amino)-2,3-dihydro-1H-inden-4-yl)pyridin-2-yl)-1H-pyrazole-4-carboxylate ($t_r$ = 3.20 min).

| | Chemical structure<br>¹H NMR and HRMS<br>Resolution conditions of enantiomers. | Chemical name<br>Intermediate 3<br>Intermediate 2<br>Carboxylic acid |
|---|---|---|
| Example | (+)- and (−)-Carboxylic acids derived from their corresponding resolved ester enantiomers. | |

(+)-46-2: (−)-5-Methyl-1-(6-(3-((2-methyl-4-(1-propionylpiperidin-4-yl)phenyl)amino)-2,3-dihydro-1H-inden-4-yl)pyridin-2-yl)-1H-pyrazole-4-carboxylic acid was derived from saponifcation of (+)-ethyl 5-methyl-1-(6-(3-((2-methyl-4-(1-propionylpiperidin-4-yl)phenyl)amino)-2,3-dihydro-1H-inden-4-yl)-pyridin-2-yl)-1H-pyrazole-4-carboxylate.
(−)-46-2: (−)-5-Methyl-1-(6-(3-((2-methyl-4-(1-propionylpiperidin-4-yl)phenyl)amino)-2,3-dihydro-1H-inden-4-yl)pyridin-2-yl)-1H-pyrazole-4-carboxylic acid was derived from saponifcation of (+)-ethyl 5-methyl-1-(6-(3-((2-methyl-4-(1-propionylpiperidin-4-yl)phenyl)amino)-2,3-dihydro-1H-inden-4-yl)-pyridin-2-yl)-1H-pyrazole-4-carboxylate.

| 46-3 | [Chemical structure] | 1-(6-(3-((4-(1-(2-Cyclopropyl-acetyl)piperidin-4-yl)-2-methyl-phenyl)amino)-2,3-dihydro-1H-inden-4-yl)pyridin-2-yl)-5-methyl-1H-pyrazole-4-carboxylic acid<br>Intermediate 3-7<br>Intermediate 2-23<br>Cyclopropylacetic acid (CAS# 5239-82-7) |

¹H NMR (400 MHz, Methanol-d₄) δ 7.91-7.86 (m, 2H), 7.72 (dd, J = 7.8, 0.9 Hz, 1H), 7.56 (dd, J = 6.4, 2.6 Hz, 1H), 7.53 (dd, J = 8.1, 0.8 Hz, 1H), 7.45-7.39 (m, 2H), 6.78 (d, J = 8.2 Hz, 1H), 6.70-6.68 (m, 1H), 6.55 (d, J = 8.3 Hz, 1H), 5.35-5.30 (m, 1H), 4.66 (d, J = 12.7 Hz, 1H), 4.05 (d, J = 13.6 Hz, 1H), 3.22-3.15 (m, 2H), 2.97 (ddd, J = 16.0, 8.7, 4.4 Hz, 1H), 2.68 (t, J = 12.9 Hz, 1H), 2.64-2.55 (m, 4H), 2.53-2.42 (m, 1H), 2.37 (d, J = 6.9 Hz, 2H), 2.13-2.04 (m, 1H), 1.84 (t, J = 14.4 Hz, 2H), 1.64 (s, 3H), 1.60-1.42 (m, 2H), 1.07-0.99 (m, 1H), 0.59-0.52 (m, 2H), 0.24-0.19 (m, 2H). HRMS; calcd. for C₃₆H₄₀N₅O₃ (M + H) 590.3131, found 590.2906.
Resolution of the enantiomers of (±)-ethyl 1-(6-(3-((4-(1-(2-cyclopropylacetyl)piperidin-4-yl)-2-methyl-phenyl)amino)-2,3-dihydro-1H-inden-4-yl)pyridin-2-yl)-5-methyl-1H-pyrazole-4-carboxylate was achieved by chiral SFC using CHIRALPAK ® AS-H column with 5-55% IPA in CO₂ to give (+)-ethyl 1-(6-(3-((4-(1-(2-cyclopropylacetyl)piperidin-4-yl)-2-methylphenyl)amino)-2,3-dihydro-1H-inden-4-yl)pyridin-2-yl)-5-methyl-1H-pyrazole-4-carboxylate (t_r = 3.28 min) and (−)-ethyl 1-(6-(3-((4-(1-(2-cyclopropylacetyl)piperidin-4-yl)-2-methylphenyl)amino)-2,3-dihydro-1H-inden-4-yl)pyridin-2-yl)-5-methyl-1H-pyrazole-4-carboxylate (t_r = 3.53 min).
(+)-46-3: (+)-1-(6-(3-((4-(1-(2-Cyclopropylacetyl)piperidin-4-yl)-2-methylphenyl)amino)-2,3-dihydro-1H-inden-4-yl)pyridin-2-yl)-5-methyl-1H-pyrazole-4-carboxylic acid was derived from saponification of (+)-ethyl 1-(6-(3-((4-(1-(2-cyclopropylacetyl)piperidin-4-yl)-2-methylphenyl)-amino)-2,3-dihydro-1H-inden-4-yl)pyridin-2-yl)-5-methyl-1H-pyrazole-4-carboxylate.
(−)-46-3: (−)-1-(6-(3-((4-(1-(2-cyclopropylacetyl)piperidin-4-yl)-2-methylphenyl)amino)-2,3-dihydro-1H-inden-4-yl)pyridin-2-yl)-5-methyl-1H-pyrazole-4-carboylic acid was derived from saponification of (−)-ethyl 1-(6-(3-((4-(1-(2-cyclopropylacetyl)piperidin-4-yl)-2-methylphenyl)amino)-2,3-dihydro-1H-inden-4-yl)pyridin-2-yl)-5-methyl-1H-pyrazole-4-carboxylate.

| 46-4 | [Chemical structure] | 1-(6-(3-((4-(1-(2-Cyclopropylacetyl)-piperidin-4-yl)-3-fluoro-2-methyl-phenyl)amino)-2,3-dihydro-1H-inden-4-yl)pyridin-2-yl)-5-methyl-1H-pyrazole-4-carboxylic acid<br>Intermediate 3-7<br>Intermediate 2-12-1<br>Cyclopropylacetic acid (CAS# 5239-82-7) |

¹H NMR (400 MHz, Methanol-d₄) δ 8.13 (t, J = 8.0 Hz, 1H), 7.91 (d, J = 7.7 Hz, 1H), 7.76-7.65 (m, 3H), 7.57 (t, J = 7.6 Hz, 1H), 7.50 (d, J = 7.6 Hz, 1H), 6.93 (s, 1H), 6.62 (d, J = 8.3 Hz. 1H), 5.48 (d, J = 7.6 Hz, 1H), 4.75-4.64 (m, 1H), 4.13-4.02 (m, 1H), 3.27-3.14 (m, 2H), 3.09-2.97 (m, 2H), 2.78-2.66 (m, 4H), 2.51-2.42 (m, 1H), 2.38 (t, J = 6.2 Hz, 2H), 2.21-2.12 (m, 1H), 1.94-1.78 (m, 5H), 1.69-1.49 (m,

|  | Chemical structure<br>¹H NMR and HRMS<br>Resolution conditions of enantiomers. | Chemical name<br>Intermediate 3<br>Intermediate 2<br>Carboxylic acid |
|---|---|---|
| Example | (+)- and (−)-Carboxylic acids derived from their corresponding resolved ester enantiomers. | |

2H), 1.10-0.97 (m, 1H), 0.61-0.50 (m, 2H), 0.22 (t, J = 4.9 Hz, 2H). HRMS; calcd. for $C_{36}H_{39}FN_5O_3$ (M + H) 608.3037, found 608.2809.

Resolution of the enantiomers of (±)-ethyl 1-(6-(3-((4-(1-(2-cyclopropylacetyl)piperidin-4-yl)-3-fluoro-2-methylphenyl)amino)-2,3-dihydro-1H-inden-4-yl)pyridin-2-yl)-5-methyl-1H-pyrazole-4-carboxylate was achieved by chiral SFC using CHIRALPAK ® AD-H column with 40% IPA in $CO_2$ to give a.) ethyl 1-(6-(3-((4-(1-(2-cyclopropylacetyl)piperidin-4-yl)-3-fluoro-2-methylphenyl)amino)-2,3-dihydro-1H-inden-4-yl)pyridin-2-yl)-5-methyl-1H-pyrazole-4-carboxylate (Peak-1) ($t_r$ = 3.01 min) and b.) ethyl 1-(6-(3-((4-(1-(2-cyclopropylacetyl)piperidin-4-yl)-3-fluoro-2-methylphenyl)amino)-2,3-dihydro-1H-inden-4-yl)pyridin-2-yl)-5-methyl-1H-pyrazole-4-carboxylate (Peak-2) ($t_r$ = 4.89 min).

(+)- or (−)-46-4: 1-(6-(3-((4-(1-(2-cyclopropylacetyl)piperidin-4-yl)-3-fluoro-2-methylphenyl)amino)-2,3-dihydro-1H-inden-4-yl)pyridin-2-yl)-5-methyl-1H-pyrazole-4-carboxylic acid was derived from saponification of ethyl 1-(6-(3-((4-(1-(2-cyclopropylacetyl)piperidin-4-yl)-3-fluoro-2-methylphenyl)-amino)-2,3-dihydro-1H-inden-4-yl)pyridin-2-yl)-5-methyl-1H-pyrazole-4-carboxylate (Peak-1) ($t_r$ = 3.01 min).

(−)- or (+)-46-4: 1-(6-(3-((4-(1-(2-cyclopropylacetyl)piperidin-4-yl)-3-fluoro-2-methylphenyl)amino)-2,3-dihydro-1H-inden-4-yl)pyridin-2-yl)-5-methyl-1H-pyrazole-4-carboxylic acid was derived from saponification of ethyl 1-(6-(3-((4-(1-(2-cyclopropylacetyl)piperidin-4-yl)-3-fluoro-2-methylphenyl)-amino)-2,3-dihydro-1H-inden-4-yl)pyridin-2-yl)-5-methyl-1H-pyrazole-4-carboxylate (Peak-2) ($t_r$ = 4.89 min).

46-5 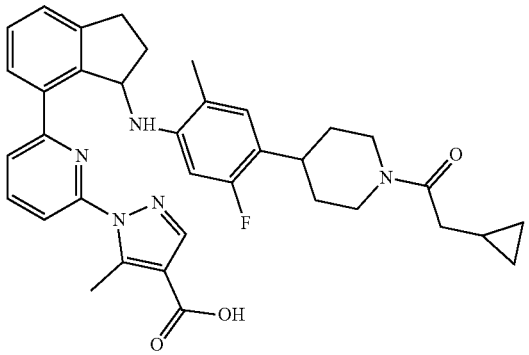 [SMILES: Cc1cc(C2CCN(C(=O)CC3CC3)CC2)c(F)cc1NC1CCc2cccc(-c3cccc(-n4ncc(C(=O)O)c4C)n3)c21]

1-(6-(3-((4-(1-(2-Cyclopropylacetyl)-piperidin-4-yl)-5-fluoro-2-methyl-phenyl)amino)-2,3-dihydro-1H-inden-4-yl)pyridin-2-yl)-5-methyl-1H-pyrazole-4-carboxylic acid
Intermediate 3-7
Intermediate 2-12-2
Cyclopropylacetic acid (CAS# 5239-82-7)

¹H NMR (400 MHz, Methanol-$d_4$) δ 7.93-7.87 (m, 2H), 7.70 (dd, J = 7.7, 0.8 Hz, 1H), 7.58-7.52 (m, 2H), 7.46-7.38 (m, 2H), 6.63 (d, J = 8.5 Hz, 1H), 6.24 (dd, J = 13.5, 3.3 Hz, 1H), 5.37-5.31 (m, 1H), 4.73-4.62 (m, 1H), 4.05 (t, J = 13 8 Hz, 1H), 3.23-3.14 (m, 2H), 3.03-2.93 (m, 1H), 2.93-2.85 (m, 1H), 2.74-2.63 (m, 1H), 2.61 (d, J = 1.8 Hz, 3H), 2.57-2.46 (m, 1H), 2.36 (t, J = 6.6 Hz, 2H), 2.08-1.99 (m, 1H), 1.90-1.73 (m, 2H), 1.69-1.46 (m, 5H), 1.08-0.98 (m, 1H), 0.59-0.52 (m, 2H), 0.25-0.17 (m, 2H). HRMS; calcd. for $C_{36}H_{39}FN_5O_3$ (M + H) 608.3037, found 608.2852.

Resolution of the enantiomers of (±)-ethyl 1-(6-(3-((4-(1-(2-cyclopropylacetyl)piperidin-4-yl)-5-fluoro-2-methylphenyl)amino)-2,3-dihydro-1H-inden-4-yl)pyridin-2-yl)-5-methyl-1H-pyrazole-4-carboxylate was achieved by chiral SFC using CHIRALPAK ® AS-H column with 42% IPA in $CO_2$ to give (+)-ethyl 1-(6-(3-((4-(1-(2-cyclopropylacetyl)piperidin-4-yl)-5-fluoro-2-methylphenyl)amino)-2,3-dihydro-1H-inden-4-yl)pyridin-2-yl)-5-methyl-1H-pyrazole-4-carboxylate ($t_r$ = 4.18 min) and (−)-ethyl 1-(6-(3-((4-(1-(2-cyclopropylacetyl)piperidin-4-yl)-5-fluoro-2-methylphenyl)amino)-2,3-dihydro-1H-inden-4-yl)pyridin-2-yl)-5-methyl-1H-pyrazole-4-carboxylate ($t_r$ = 6.45 min).

(+)-46-5: (+)-1-(6-(3-((4-(1-(2-Cyclopropylacetyl)piperidin-4-yl)-5-fluoro-2-methylphenyl)amino)-2,3-dihydro-1H-inden-4-yl)pyridin-2-yl)-5-methyl-1H-pyrazole-4-carboxylic acid was derived from saponification of (+)-ethyl 1-(6-(3-((4-(1-(2-cyclopropylacetyl)piperidin-4-yl)-5-fluoro-2-methylphenyl)-amino)-2,3-dihydro-1H-inden-4-yl)pyridin-2-yl)-5-methyl-1H-pyrazole-4-carboxylate.

(−)-46-5: (−)-1-(6-(3-((4-(1-(2-cyclopropylacetyl)piperidin-4-yl)-5-fluoro-2-methylphenyl)amino)-2,3-dihydro-1H-inden-4-yl)pyridin-2-yl)-5-methyl-1H-pyrazole-4-carboxylic acid was derived from saponification of (−)-ethyl 1-(6-(3-((4-(1-(2-cyclopropylacetyl)piperidin-4-yl)-5-fluoro-2-methylphenyl)-amino)-2,3-dihydro-1H-inden-4-yl)pyridin-2-yl)-5-methyl-1H-pyrazole-4-carboxylate.

| Example | Chemical structure<br>¹H NMR and HRMS<br>Resolution conditions of enantiomers.<br>(+)- and (−)-Carboxylic acids derived from their corresponding resolved ester enantiomers. | Chemical name<br>Intermediate 3<br>Intermediate 2<br>Carboxylic acid |
|---|---|---|
| 46-6 | 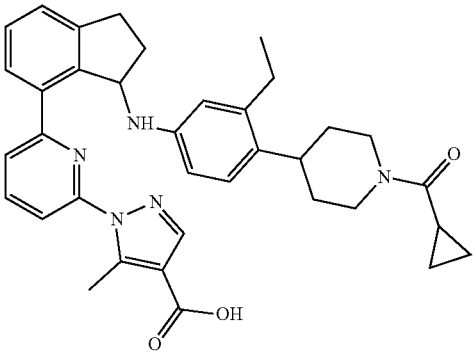 [SMILES: CCc1cc(NC2CCc3cccc(-c4cccc(-n5ncc(C(=O)O)c5C)n4)c32)ccc1C1CCN(C(=O)C2CC2)CC1] | 1(6-(3-((4-(1-(cyclopropanecarbonyl)-piperidin-4-yl)-3-ethylphenyl)amino)-2,3-dihydro-1H-inden-4-yl)pyridin-2-yl)-5-methyl-1H-pyrazole-4-carboxylic acid<br>Intermediate 3-7<br>Intermediate 2-10<br>Cyclopropanecarboxylic acid |

¹H NMR (400 MHz, Methanol-d₄) δ 7.95-7.90 (m, 2H), 7.82 (dd, J = 7 8, 0.9 Hz, 1H), 7.60-7.56 (m, 2H), 7.44-7.37 (m, 2H), 6.80 (d, J = 8.3 Hz, 1H), 6.32-6.27 (m, 2H), 5.26 (dd, J = 6.7, 2.6 Hz, 1H), 4.64 (d, J = 13.2 Hz, 1H), 4.45 (d, J = 13.5 Hz, 1H), 3.26-3.14 (m, 2H), 2.97-2.86 (m, 2H), 2.77-2.67 (m, 4H), 2.52 (q, J = 7.5 Hz, 2H), 2.39-2.28 (m, 1H), 2.17-2.09 (m, 1H), 2.04-1.96 (m, 1H), 1.79 (d, J = 13.3 Hz, 1H), 1.71 (d, J = 13.1 Hz, 1H), 1.66-1.44 (m, 2H), 1.11 (t, J = 7.5 Hz, 3H), 0.93-0.86 (m, 2H), 0.85-0.78 (m, 2H). HRMS; calcd. for C₃₆H₄₀N₅O₃ (M + H) 590.3131, found 590.3104.
Resolution of the enantiomers of (±)-ethyl-(6-(3-((4-(1-(cyclopropanecarbonyl)piperidin-4-yl)-3-ethyl-phenyl)amino)-2,3-dihydro-1H-inden-4-yl)pyridin-2-yl)-5-methyl-1H-pyrazole-4-carboxylate-was achieved by chiral SFC using CHIRALPAK ® AS-H column with 30% IPA in CO₂ to give (+)-ethyl 1-(6-(3-((4-(1-(cyclopropanecarbonyl)piperidin-4-yl)-3-ethylphenyl)amino)-2,3-dihydro-1H-inden-4-yl)pyridin-2-yl)-5-methyl-1H-pyrazole-4-carboxylate (t,. = 3.25 min) and (−)-ethyl 1-(6-(3-((4-(1-(cyclopropanecarbonyl)piperidin-4-yl)-3-ethylphenyl)amino)-2,3-dihydro-1H-inden-4-yl)pyridin-2-yl)-5-methyl-1H-pyrazole-4-carboxylate (t,. = 6.25 min).
(+)-46-6: (+)-1-(6-(3-((4-(1-(Cyclopropanocarbonyl)piperidin-4-yl)-3-ethylphenyl)amino-2,3-dihydro-1H-inden-4-yl)pyridin-2-yl)-5-methyl-1H-pyrzaole-4-carboxylic acid was derived from saponification of (+)-ethyl 1-(6-(3-((4-(1-(cyclopropanecarbonyl)piperidin-4-yl)-3-ethylphenyl)amino)-2,3-dihydro-1H-inden-4-yl)pyridin-2-yl)-5-methyl-1H-pyrazole-4-carboxylate (t,. = 3.25 min).

Example 47

Example 47-A. a). Ethyl 1-(6-(3-((4-(1-((S)-2-hydroxypropanoyl)piperidin-2-yl)-2-methylphenyl)amino)-2,3-dihydro-1H-inden-4-yl)pyridin-2-yl)-5-methyl-1H-pyrazole-4-carboxylate

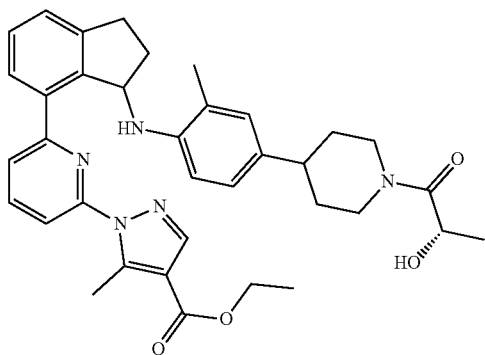 [SMILES: CCOC(=O)c1cnn(-c2cccc(-c3cccc4c3C(Nc3ccc(C5CCN(C(=O)[C@H](C)O)CC5)cc3C)CC4)n2)c1C]

The title compound was synthesized by reaction of ethyl 5-methyl-1-(8-(3-((2-methyl-4-(piperidin-4-yl)phenyl)amino)-2,3-dihydro-1H-inden-4-yl)pyridin-2-yl)-1H-pyrazole-4-carboxylate (Example 45-B) with (+)-lactic acid in fashion analogous to the preparation of Example 45-C. a) MS (ESI+) m/z 608.5 (M+H).

Example 47-A. b). (+)-Ethyl 1-(6-(3-((4-(1-((S)-2-hydroxypropanoyl)piperidin-4-yl)-2-methylphenyl)amino)-2,3-dihydro-1H-inden-4-yl)pyridin-2-yl)-5-methyl-1H-pyrazole-4-carboxylate (Diastereomer-1) and (−)-ethyl 1-(6-(3-((4-(1-((S)-2-hydroxypropanoyl)piperidin-4-yl)-2-methylphenyl)amino)-2,3-dihydro-1H-inden-4-yl)pyridin-2-yl)-5-methyl-1H-pyrazole-4-carboxylate (Diastereomer-2)

Resolution of the diastereomers of ethyl 1-(8-(3-((4-(1-((S)-2-hydroxypropanoyl)piperidin-4-yl)-2-methylphenyl)amino)-2,3-dihydro-1H-inden-4-yl)pyridin-2-yl)-5-methyl-1H-pyrazole-4-carboxylate was achieved by chiral SFC using CHIRALCEL® OJ-H column with 5% to 55% EtOH gradient in CO₂ to give (+)-ethyl 1-(6-(3-((4-(1-((S)-2-hydroxypropanoyl)piperidin-4-yl)-2-methylphenyl)amino)-2,3-dihydro-1H-inden-4-yl)pyridin-2-yl)-5-methyl-1H-pyrazole-4-carboxylate (diastereomer-1) (t,.=2.58 min) and (−)-ethyl 1-(6-(3-((4-(1-((S)-2-hydroxypropanoyl)piperidin-4-yl)-2-methylphenyl)amino)-2,3-dihydro-1H-inden-4-yl)pyridin-2-yl)-5-methyl-1H-pyrazole-4-carboxylate (diastereomer-2) (t,.=2.99 min).

Example 47a. (+)-1-(6-(3-((4-(1-(S)-2-Hydroxypropanoyl)piperidin-4-yl)-2-methylphenyl)amino)-2,3-dihydro-1H-inden-4-yl)pyridin-2-yl)-5-methyl-1H-pyrazole-4-carboxylic Acid (Diastereomer-1)

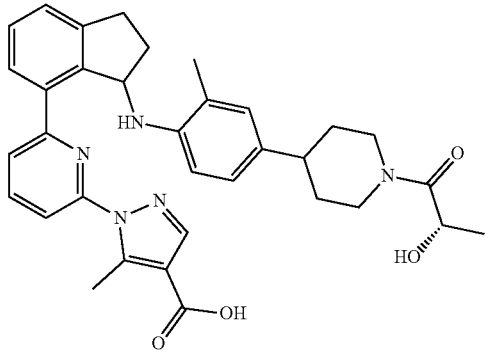 [SMILES: Cc1cc(C2CCN(C(=O)[C@H](C)O)CC2)ccc1NC1CCc2cccc(-c3cccc(-n4ncc(C(=O)O)c4C)n3)c21]

Saponification of (+)-ethyl 1-(6-(3-((4-(1-((S)-2-hydroxypropanoyl)piperidin-4-yl)-2-methylphenyl)amino)-2,3-dihydro-1H-inden-4-yl)pyridin-2-yl)-5-methyl-1H-pyrazole-4-carboxylate (diastereomer-1) ($t_r$=2.58 min) by the similar method to the preparation of Example 7a, followed by RP-HPLC (HC-B) purification afforded the title compound. $^1$H NMR (400 MHz, Methanol-$d_4$) δ 7.91-7.86 (m, 2H), 7.72 (dd, J=7.8, 0.9 Hz, 1H), 7.57-7.54 (m, 1H), 7.54-7.51 (m, 1H), 7.45-7.38 (m, 2H), 6.78 (d, J=8.0 Hz, 1H), 6.69 (d, J=2.1 Hz, 1H), 6.55 (d, J=8.2 Hz, 1H), 5.38-5.30 (m, 1H), 4.65-4.58 (m, 2H), 4.13-4.04 (m, 1H), 3.25-3.15 (m, 2H), 3.00-2.93 (m, 1H), 2.78-2.69 (m, 1H), 2.67-2.59 (m, 1H), 2.59-2.56 (m, 3H), 2.52-2.42 (m, 1H), 2.13-2.04 (m, 1H), 1.91-1.79 (m, 2H), 1.64 (s, 3H), 1.61-1.45 (m, 2H), 1.34 (dd, J=16.0, 6.6 Hz, 3H). HRMS; calcd. for $C_{34}H_{38}N_5O_4$ (M+H) 580.2924, found 580.2697.

Example 47b. (−)-1-(6-(3-((4-(1-((S)-2-Hydroxypropanoyl)piperidin-4-yl)-2-methylphenyl)amino)-2,3-dihydro-1H-inden-4-yl)pyridin-2-yl)-5-methyl-1H-pyrazole-4-carboxylic Acid (Diastereomer-2)

(−)-Ethyl 1-(6-(3-((4-(1-((S)-2-hydroxypropanoyl)piperidin-4-yl)-2-methylphenyl)amino)-2,3-dihydro-1H-inden-4-yl)pyridin-2-yl)-5-methyl-1H-pyrazole-4-carboxylate (diastereomer-2) ($t_r$=2.99 min) was saponified as described in Example 7a and purified by reverse phase HPLC (HC-B) to afford the title compound. $^1$H NMR (400 MHz, Methanol-$d_4$) δ 7.91-7.84 (m, 2H), 7.71 (dd, J=0.7, 7.8 Hz, 1H), 7.58-7.50 (m, 2H), 7.45-7.38 (m, 2H), 6.82-6.76 (m, 1H), 6.70 (d, J=1.7 Hz, 1H), 6.55 (d, J=8.2 Hz, 1H), 5.37-5.31 (m, 1H), 4.66-4.53 (m, 2H), 4.15-4.05 (m, 1H), 3.24-3.14 (m, 2H), 3.02-2.92 (m, 1H), 2.79-2.68 (m, 1H), 2.67-2.55 (m, 4H), 2.54-2.41 (m, 1H), 2.13-2.03 (m, 1H), 1.91-1.79 (m, 2H), 1.64 (s, 3H), 1.61-1.42 (m, 2H), 1.39-1.29 (m, 3H). HRMS: calcd. for $C_{34}H_{38}N_5O_4$ (M+H) 580.2924, found 580.2697.

Example 48

Example 48-A. (±)-Ethyl 5-ethyl-1-(6-(3-((3-ethyl-4-(piperidin-4-yl)phenyl)amino)-2,3-dihydro-1H-inden-4-yl)pyridin-2-yl)-1H-pyrazole-4-carboxylate

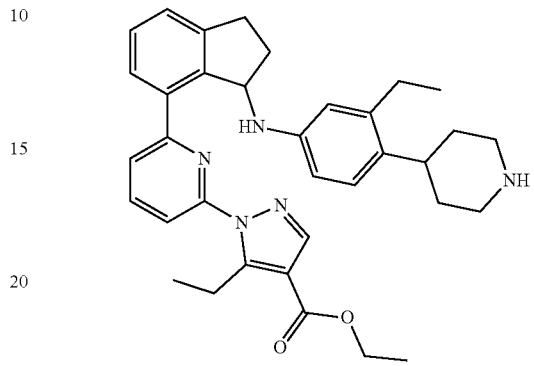

The title compound was synthesized by the similar method to the synthesis of Example 45-A and then Example 45-B but starting from ethyl 1-(6-bromopyridin-2-yl)-5-ethyl-1H-pyrazole-4-carboxylate (Intermediate 1-4-2) in the place of Intermediate 1-3 and (±)-tert-butyl 4-(4-((7-bromo-2,3-dihydro-1H-inden-1-yl)amino)-2-ethylphenyl)piperidine-1-carboxylate instead of Intermediate 3-6-C. MS (ESI+) m/z 564.4 (M+H).

Example 48-B. a). Ethyl 5-ethyl-1-(6-(3-((3-ethyl-4-(1-((S)-2-hydroxypropanoyl)piperidin-4-yl)phenyl)amino)-2,3-dihydro-1H-inden-4-yl)pyridin-2-yl)-1H-pyrazole-4-carboxylate

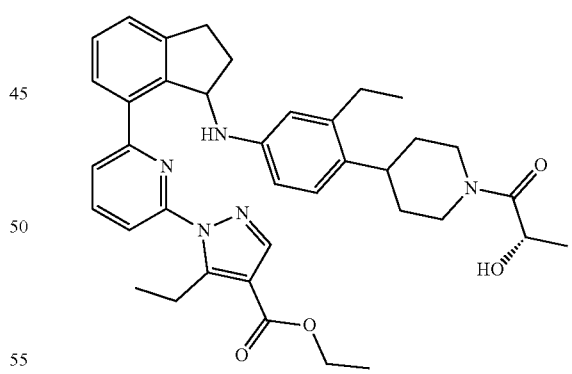

The title compound was synthesized analogously to the preparation of ethyl 1-(6-(3-((4-(1-((S)-2-hydroxypropanoyl)piperidin-4-yl-2-methylphenyl)amino)-2,3-dihydro-1H-inden-4-yl)pyridin-2-yl)-5-methyl-1H-pyrazole-4-carboxylate (Example 47-A) but starting with (+)-ethyl 5-ethyl-1-(6-(3-((3-ethyl-4-(piperidin-4-yl)phenyl)amino)-2,3-dihydro-1H-inden-4-yl)pyridin-2-yl)-1H-pyrazole-4-carboxylate (Example 48-A). MS (ESI+) nm/z 636.4 (M+H).

Example 48-B. b). Ethyl 5-ethyl-1-(6-(3-((3-ethyl-4-1-((S)-2-hydroxypropanoyl)piperidin-4-yl)phenyl)amino)-2,3-dihydro-1H-inden-4-yl)pyridin-2-yl)-1H-pyrazole-4-carboxylate (Diastereomer-1) and ethyl 5-ethyl-1-(6-(3-((3-ethyl-4-(1-((S)-2-hydroxypropanoyl)piperidin-4-yl)phenyl)amino)-2,3-dihydro-1H-inden-4-yl)pyridin-2-yl)-1H-pyrazole-4-carboxylate (Diastereomer-2)

Resolution of the diastereomers of ethyl 5-ethyl-1-(6-(3-((3-ethyl-4-(1-((S)-2-hydroxypropanoyl)piperidin-4-yl)phenyl)amino)-2,3-dihydro-1H-inden-4-yl)pyridin-2-yl)-1H-pyrazole-4-carboxylate was achieved by chiral HPLC using CHIRALPAK® IA column with 60% hexane with 0.1% DEA in EtOH to give ethyl 5-ethyl-1-(6-(3-((3-ethyl-4-(1-((S)-2-hydroxypropanoyl)piperidin-4-yl)phenyl)amino)-2,3-dihydro-1H-inden-4-yl)pyridin-2-yl)-1H-pyrazole-4-carboxylate (diastereomer-1) ($t_r$=7.6 min) and ethyl 5-ethyl-1-(6-(3-((3-ethyl-4-(1-((S)-2-hydroxypropanoyl)piperidin-4-yl)phenyl)amino)-2,3-dihydro-1H-inden-4-yl)pyridin-2-yl)-1H-pyrazole-4-carboxylate (diastereomer-2) ($t_r$=11.3 min).

Example 48a. (+)-6-Ethyl-1-(6-(3-((3-ethyl-4-(1-((S)-2-hydroxypropanoyl)piperidin-4-yl)phenyl)amino)-2,3-dihydro-1H-inden-4-yl)pyridin-2-yl)-1H-pyrazole-4-carboxylic Acid

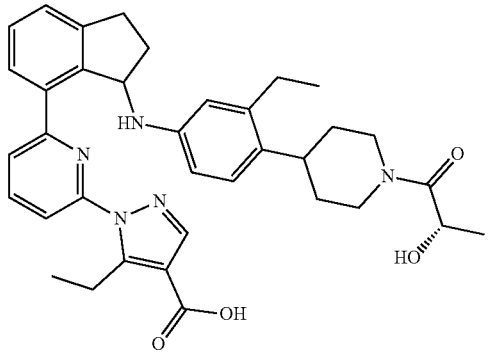 [SMILES: CCc1cc(NC2CCc3cccc(-c4cccc(-n5ncc(C(=O)O)c5CC)n4)c32)ccc1C1CCN(C(=O)[C@H](C)O)CC1]

Saponification of ethyl 5-ethyl-1-(6-(3-((3-ethyl-4-(1-((S)-2-hydroxypropanoyl)piperidin-4-yl)phenyl)amino)-2,3-dihydro-1H-inden-4-yl)pyridin-2-yl)-1H-pyrazole-4-carboxylate (diastereomer-2, $t_r$=11.3 min) as described for the synthesis of Example 7a afforded the title compound. $^1$H NMR (600 MHz, Methanol-$d_4$) δ 7.94 (s, 1H), 7.91 (dd, J=7.8, 7.9 Hz, 1H), 7.87 (d, J=7.6 Hz, 1H), 7.55-7.59 (m, 2H), 7.37-7.42 (m, 2H), 6.82 (dd, J=4.1, 8.3 Hz, 1H), 6.29-6.34 (m, 2H), 5.23 (d, J=6.1 Hz, 1H), 4.58-4.67 (m, 2H), 4.10 (t, J=11.7 Hz, 1H), 3.14-3.25 (m, 3H), 2.88-2.96 (m, 2H), 2.71-2.78 (m, 1H), 2.54 (q, J=7.6 Hz, 2H), 2.26-2.34 (m, 1H), 2.12-2.18 (m, 1H), 1.70-1.80 (m, 2H), 1.49-1.68 (m, 2H), 1.30-1.39 (m, 4H), 1.08-1.14 (m, 6H). HRMS: calcd. for $C_{36}H_{42}N_5O_4$ (M+H) 608.3237, found 608.3256.

Example 48b. (−)-8-Ethyl-1-(6-(3-((3-ethyl-4-(1-((S)-2-hydroxypropanoyl)piperidin-4-yl)phenyl)amino)-2,3-dihydro-1H-inden-4-yl)pyridin-2-yl)-1H-pyrazole-4-carboxylic Acid Ethyl 5-ethyl-1-(6-(3-((3-ethyl-4-(1-((S)-2-hydroxypropanoyl)piperidin-4-yl)phenyl)amino)-2,3-dihydro-1H-inden-4-yl)pyridin-2-yl)-1H-pyrazole-4-carboxylate (diastereomer-1, $t_r$=7.6 min) was saponified as described for the synthesis of Example 7a to afford the title compound. $^1$H NMR (600 MHz, Methanol-d) δ 7.94 (s, 1H), 7.91 (dd, J=7.8, 7.9 Hz, 1H), 7.87 (d, J=7.7 Hz, 1H), 7.57 (d, J=7.9 Hz, 2H), 7.38-7.42 (m, 2H), 6.79-6.84 (m, 1H), 6.29-6.34 (m, 2H), 5.23 (br. d, J=6.1 Hz, 1H), 4.58-4.67 (m, 2H), 4.07-4.14 (m, 1H), 3.13-3.24 (m, 3H), 2.88-2.95 (m, 2H), 2.71-2.78 (m, 1H), 2.54 (q, J=7.5 Hz, 2H), 2.26-2.35 (m, 1H), 2.12-2.18 (m, 1H), 1.70-1.80 (m, 2H), 1.48-1.67 (m, 2H), 1.31-1.38 (m, 4H), 1.08-1.14 (m, 6H). HRMS: calcd. for $C_{36}H_{42}N_5O_4$ (M+H) 608.3237, found 608.3240.

Example 49

Example 49-A. a). Ethyl 5-ethyl-1-6-3-(3-ethyl-4-(1-((S)-2-hydroxypentanoyl)piperidin-4-yl)phenyl)amino)-2,3-dihydro-1H-inden-4-yl)pyridin-2-yl)-1H-pyrazole-4-carboxylate

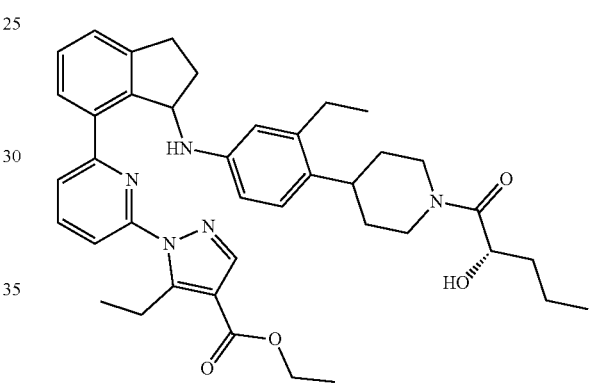

The title compound was synthesized analogously to the preparation of ethyl 5-ethyl-1-(6-(3-((3-ethyl-4-(1-((S)-2-hydroxypropanoyl)piperidin-4-yl)phenylamino)-2,3-dihydro-1H-inden-4-yl)pyridin-2-yl)-1H-pyrazole-4-carboxylate (Example 48-B. a)) but using (S)-2-hydroxypentanoic acid in the place of L-(+)-lactic acid. MS (ESI+) m/z 664.4 (M+H).

Example 49-A. b). Ethyl 5-ethyl-1-(6-(3-((3-ethyl-4-(1-((S)-2-hydroxypentanoyl)piperidin-4-yl)phenyl)amino)-2,3-dihydro-1H-inden-4-yl)pyridin-2-yl)-1H-pyrazole-4-carboxylate (Diastereomer-1) and ethyl 5-ethyl-1-(6-(3-((3-ethyl-4-(1 (S)-2-hydroxypentanoyl)piperidin-4-yl)phenyl)amino)-2,3-dihydro-1H-inden-4-yl)pyridin-2-yl)-1H-pyrazole-4-carboxylate (Diastereomer-2)

Resolution of the diastereomers of ethyl 5-ethyl-1-(6-(3-((3-ethyl-4-(1-((S)-2-hydroxypentanoyl)piperidin-4-yl)phenyl)amino)-2,3-dihydro-1H-inden-4-yl)pyridin-2-yl)-1H-pyrazole-4-carboxylate was achieved by chiral HPLC using CHIRALPAK® IA column with 65% hexane with 0.1% DEA in EtOH to give ethyl 5-ethyl-1-(6-(3-((3-ethyl-4-(1-((S)-2-hydroxypentanoyl)piperidin-4-yl)phenyl)amino)-2,3-dihydro-1H-inden-4-yl)pyridin-2-yl)-1H-pyrazole-4-carboxylate (diastereomer-1) ($t_r$=7.5 min) and ethyl 5-ethyl-1-

(6-(3-((3-ethyl-4-(1-((S)-2-hydroxypentanoyl)piperidin-4-yl)phenyl)amino)-2,3-dihydro-1H-inden-4-yl)pyridin-2-yl)-1H-pyrazole-4-carboxylate (diastereomer-2) ($t_r$=10.2 min).

Example 49a. (+)-8-Ethyl-1-(6-(3-((3-ethyl-4l-((S)-2-hydroxypentanoyl)piperidin-4-yl)phenyl)amino)-2,3-dihydro-1H-inden-4-yl)pyridin-2-yl)-1H-pyrazole-4-carboxylic Acid

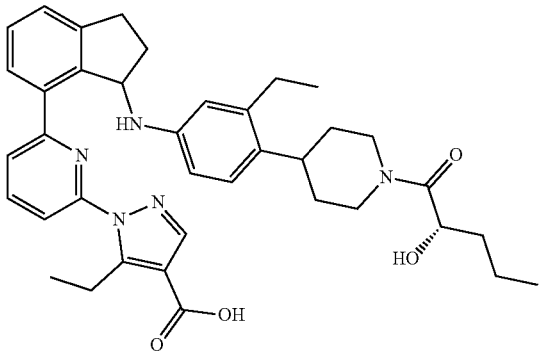 [SMILES: CCC[C@H](O)C(=O)N1CCC(c2ccc(NC3CCc4cccc(-c5cccc(-n6ncc(C(=O)O)c6CC)n5)c43)cc2CC)CC1]

Saponification of ethyl 5-ethyl-1-(6-(3-((3-ethyl-4-(1-((S)-2-hydroxypentanoyl)piperidin-4-yl)phenyl)amino)-2,3-dihydro-1H-inden-4-yl)pyridin-2-yl)-1H-pyrazole-4-carboxylate (diastereomer-2, $t_r$=10.2 min) as described for the synthesis of Example 7a afforded the title compound. $^1$H NMR (600 MHz, Methanol-$d_4$) δ 7.94 (s, 1H), 7.89-7.93 (m, 1H), 7.85-7.88 (m, 1H), 7.55-7.60 (m, 2H), 7.38-7.43 (m, 2H), 6.78-6.84 (m, 1H), 6.29-6.34 (m, 2H), 5.23 (br. d, J=6.4 Hz, 1H), 4.64 (br. d, J=12.4 Hz, 1H), 4.44-4.52 (m, 1H), 4.04-4.13 (m, 1H), 3.14-3.27 (m, 4H), 2.88-2.96 (m, 2H), 2.71-2.78 (m, 1H), 2.54 (q, J=7.5 Hz, 2H), 2.26-2.35 (m, 1H), 2.12-2.18 (m, 1H), 1.70-1.81 (m, 2H), 1.41-1.69 (m, 6H), 1.08-1.16 (m, 6H), 0.94-1.02 (m, 3H). HRMS: calcd. for $C_{38}H_{46}N_5O_4$(M+H) 636.3550, found 636.3555.

Example 49b. (−)-5-Ethyl-1-(6-3-((3-ethyl-4-(1-((S)-2-hydroxypentanoyl)piperidin-4-yl)phenyl)amino)-2,3-dihydro-1H-inden-4-yl)pyridin-2-yl)-1H-pyrazole-4-carboxylic Acid Ethyl 5-ethyl-1-(6-(3-((3-ethyl-4-(1-((S)-2-hydroxypentanoyl)piperidin-4-yl)phenyl)amino)-2,3-dihydro-1H-inden-4-yl)pyridin-2-yl)-1H-pyrazole-4-carboxylate (diastereomer-1, $t_r$=7.5 min) was saponified as described for the synthesis of Example 7a to afford the title compound. $^1$H NMR (600 MHz, Methanol-$d_4$) δ 7.94 (s, 1H), 7.88-7.93 (m, 1H), 7.85-7.88 (m, 1H), 7.55-7.59 (m, 2H), 7.37-7.42 (m, 2H), 6.81 (dd, J=8.3, 9.2 Hz, 1H), 629-6.33 (m, 2H), 5.21-5.26 (m, 1H), 4.82-4.67 (m, 1H), 4.45-4.51 (m, 1H), 4.04-4.13 (m, 1H), 3.14-3.28 (m, 4H), 2.88-2.95 (m, 2H), 2.71-2.78 (m, 1H), 2.54 (q, J=7.5 Hz, 2H), 2.26-2.35 (m, 1H), 2.11-2.18 (m, 1H), 1.71-1.81 (m, 2H), 1.41-1.70 (m, 6H), 1.08-116 (m, 6H), 0.94-1.02 (m, 3H). HRMS: calcd. for $C_{38}H_{48}N_5O_4$ (M+H) 636.3550, found 636.3558.

Example 50

Example 50-A. a). Ethyl 5-ethyl-1-(6-3-(3-ethyl-4-(1-((S)-2-hydroxybutanoyl)piperidin-4-yl)phenyl)amino)-2,3-dihydro-1H-inden-4-yl)pyridin-2-yl)-1H-pyrazole-4-carboxylate

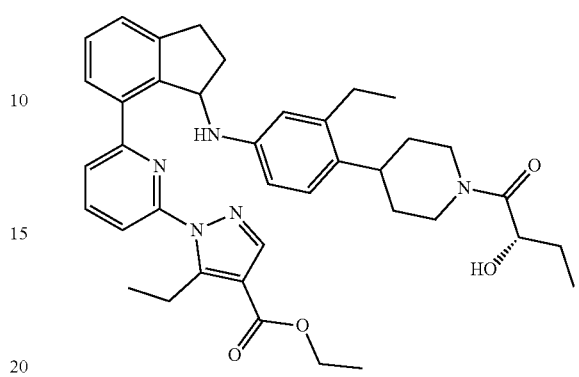

The title compound was synthesized analogously to the preparation of ethyl 5-ethyl-1-(6-(3-((3-ethyl-4-(1-((S)-2-hydroxypropanoyl)piperidin-4-yl)phenyl)amino)-2,3-dihydro-1H-inden-4-yl)pyridin-2-yl)-1H-pyrazole-4-carboxylate (Example 48-B. a)) but using (S)-2-hydroxybutanoic acid in the place of L-(+)-lactic acid. MS (ESI+) m/z 650.4 (M+H).

Example 50-A. b) Ethyl 5-ethyl-1-(6-(3-((3-ethyl-4-(1-(S)-2-hydroxybutanoyl)piperidin-4-yl)phenyl)amino)-2,3-dihydro-1H-inden-4-yl)pyridin-2-yl)-1H-pyrazole-4-carboxylate (Diastereomer-1) and ethyl 5-ethyl-1-(6-(3-((3-ethyl-4-(1-((S)-2-hydroxybutanoyl)piperidin-4-yl)phenyl)amino)-2,3-dihydro-1H-inden-4-yl)pyridin-2-yl)-1H-pyrazole-4-carboxylate (Diastereomer-2)

Resolution of the diastereomers of ethyl 5-ethyl-1-(6-(3-((3-ethyl-4-(1-((S)-2-hydroxybutanoyl)piperidin-4-yl)phenyl)amino)-2,3-dihydro-1H-inden-4-yl)pyridin-2-yl)-1H-pyrazole-4-carboxylate was achieved by chiral HPLC using CHIRALPAK® IA column with 60% hexane with 0.1% DEA in EtOH to give ethyl 5-ethyl-1-(6-(3-((3-ethyl-4-(1-((S)-2-hydroxybutanoyl)piperidin-4-yl)phenyl)amino)-2,3-dihydro-1H-inden-4-yl)pyridin-2-yl)-1H-pyrazole-4-carboxylate (diastereomer-1) ($t_r$=7.5 min) and ethyl 5-ethyl-1-(6-(3-((3-ethyl-4-(1-((S)-2-hydroxybutanoyl)piperidin-4-yl)phenyl)amino)-2,3-dihydro-1H-inden-4-yl)pyridin-2-yl)-1H-pyrazole-4-carboxylate (diastereomer-2) ($t_r$=10.8 min).

Example 50a. (+)-6-Ethyl-1-(6-3-((3-ethyl-4-(1-((S)-2-hydroxybutanoyl)piperidin-4-yl)phenyl)amino)-2,3-dihydro-1H-inden-4-yl)pyridin-2-yl)-1H-pyrazole-4-carboxylic Acid

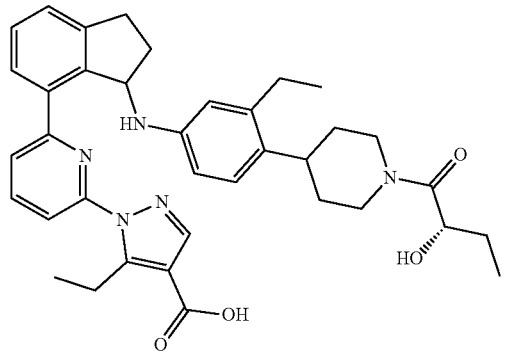 [SMILES: CCc1cc(NC2CCc3cccc(-c4cccc(-n5ncc(C(=O)O)c5CC)n4)c32)ccc1C1CCN(C(=O)[C@@H](O)CC)CC1]

Saponification of ethyl 5-ethyl-1-(6-(3-((3-ethyl-4-(1-((S)-2-hydroxybutanoyl)piperidin-4-yl)phenyl)amino)-2,3-dihydro-1H-inden-4-yl)pyridin-2-yl)-1H-pyrazole-4-carboxylate (diastereomer-2, $t_r$=10.8 min) as described for the synthesis of Example 7a afforded the title compound. $^1$H NMR (400 MHz, Methanol-$d_4$) δ 7.85-7.96 (m, 3H), 7.55-7.60 (m, 2H), 7.37-7.43 (m, 2H), 6.78-6.84 (m, 1H), 6.29-6.34 (m, 2H), 5.20-5.25 (m, 1H), 4.61-4.69 (m, 1H), 4.39-4.46 (m, 1H), 4.04-4.13 (m, 1H), 3.14-3.28 (m, 3H), 2.87-2.97 (m, 2H), 2.70-2.80 (m, 1H), 2.54 (q, J=7.6 Hz, 2H), 2.25-2.36 (m, 1H), 2.10-2.19 (m, 1H), 1.48-1.82 (m, 7H), 1.08-1.15 (m, 6H), 0.96-1.05 (m, 3H). HRMS: calcd. for $C_{37}H_{44}N_5O_4$ (M+H) 622.3393, found 622.3402.

Example 50b. (−)-6-Ethyl-1-(6-(3-((3-ethyl-4-(1-(S)-2-hydroxybutanoyl)piperidin-4-yl)phenyl)amino)-2,3-dihydro-1H-inden-4-yl)pyridin-2-yl)-1H-pyrazole-4-carboxylic Acid Ethyl 5-ethyl-1-(6-(3-((3-ethyl-4-(1-((S)-2-hydroxybutanoyl)piperidin-4-yl)phenyl)amino)-2,3-dihydro-1H-inden-4-yl)pyridin-2-yl)-1H-pyrazole-4-carboxylate (diastereomer-1, $t_r$=7.5 min) was saponified as described for the synthesis of Example 7a to afford the title compound. $^1$H NMR (400 MHz, Methanol-$d_4$) δ 7.84-7.97 (m, 3H), 7.55-7.60 (m, 2H), 7.37-7.43 (m, 2H), 8.78-6.84 (m, 1H), 6.29-6.35 (m, 2H), 5.20-5.27 (m, 1H), 4.61-4.69 (m, 1H), 4.38-4.46 (m, 1H), 4.04-4.14 (m, 1H), 3.14-3.29 (m, 3H), 2.87-2.97 (m, 2H), 2.70-2.80 (m, 1H), 2.54 (q, =7.5 Hz, 2H), 2.24-2.37 (m, 1H), 2.10-2.19 (m, 1H), 1.45-1.83 (m, 7H), 1.08-1.16 (m, 8H), 0.95-1.05 (m, 3H). HRMS: calcd. for $C_{37}H_{44}N_5O_4$ (M+H) 622.3393, found 622.3413.

Example 51

Example 51-A. a). (±)-Isopropyl 4-(4-((7-6-4-ethoxycarbonyl)-5-ethyl-1H-pyrazol-1-yl)pyridin-2-yl)-2,3-dihydro-1H-inden-1-yl)amino)-2-ethylphenyl)piperidine-1-carboxylate

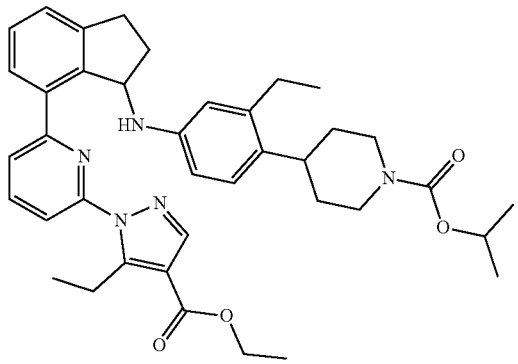 [SMILES: CCOC(=O)c1cnn(-c2cccc(-c3cccc4c3C(Nc3ccc(C5CCN(C(=O)OC(C)C)CC5)c(CC)c3)CC4)n2)c1CC]

To a solution of (±)-ethyl 5-ethyl-1-(6-(3-((3-ethyl-4-(piperidin-4-yl)phenyl)amino)-2,3-dihydro-1H-inden-4-yl)pyridin-2-yl)-1H-pyrazole-4-carboxylate (Example 48-A) (253 mg, 0.449 mmol) in MeOH (2 mL) was added Et$_3$N (0.188 mL, 1.35 mmol), followed by a solution of isopropylchloroformate (0.494 mL, 0.494 mmol) in MeOH (0.25 mL) dropwise. The mixture was stirred at the same temperature for ca. 0.5 h. The reaction mixture was then concentrated. The resulting residue was purified by silica gel flash column chromatography (heptane/EtOAc=8/2, isocratic) to afford the title compound. MS (ESI+) m/z 650.0 (M+H).

Example 51-A. b). Isopropyl 4-(4-((7-(6-(4-(ethoxycarbonyl)-6-ethyl-ethyl-1H-pyrazol-1-yl)pyridin-2-yl)-2,3-dihydro-1H-inden-1-yl)amino)-2-ethylphenyl)piperidine-1-carboxylate (Enantiomer-1) and isopropyl 4-(4-((7-(6-(4-(ethoxycarbonyl)-6-ethyl-1H-pyrazol-1-yl)pyridin-2-yl)-2,3-dihydro-1H-inden-1-yl)amino)-2-ethylphenyl)piperidine-1-carboxylate (Enantiomer-2)

Resolution of the enantiomers of (±)-isopropyl 4-(4-((7-(6-(4-(ethoxycarbonyl)-5-ethyl-1H-pyrazol-1-yl)pyridin-2-yl)-2,3-dihydro-1H-inden-1-yl)amino)-2-ethylphenyl)piperidine-1-carboxylate was achieved by chiral SFC using CHIRALPAK® AD-H column with 30% IPA in CO$_2$ to give isopropyl 4-(4-((7-(6-(4-(ethoxycarbonyl)-5-ethyl-1H-pyrazol-1-yl)pyridin-2-yl)-2,3-dihydro-1H-inden-1-yl)amino)-2-ethylphenyl)piperidine-1-carboxylate (enantiomer-1, $t_r$=3.4 min) and Isopropyl 4-(4-((7-(6-(4-(ethoxycarbonyl)-5-ethyl-1H-pyrazol-1-yl)pyridin-2-yl)-2,3-dihydro-1H-inden-1-yl)amino)-2-ethylphenyl)piperidine-1-carboxylate (enantiomer-2, $t_r$=5.3 min).

Example 51a. (+)-Ethyl-1-(6-3-((3-ethyl-4-(1-(isopropoxycarbonyl)piperidin-4-yl)phenyl)amino)-2,3-dihydro-1H-inden-4-yl)pyridin-2-yl)-1H-pyrazole-4-carboxylic Acid

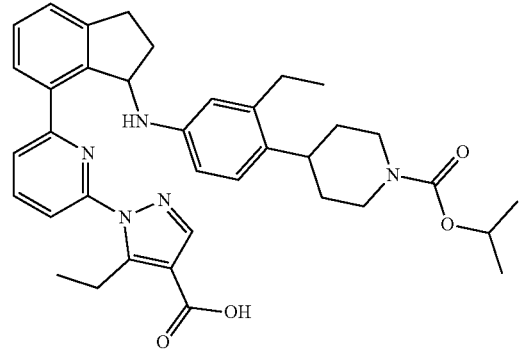 [SMILES: CCc1cc(NC2CCc3cccc(-c4cccc(-n5ncc(C(=O)O)c5CC)n4)c32)ccc1C1CCN(C(=O)OC(C)C)CC1]

Saponification of isopropyl 4-(4-((7-(6-(4-(ethoxycarbonyl)-5-ethyl-1H-pyrazol-1-yl)pyridin-2-yl)-2,3-dihydro-1H-inden-1-yl)amino)-2-ethylphenyl)piperidine-1-carboxylate (enantiomer-1, $t_r$=3.4 min) as described for the synthesis of Example 7a afforded the title compound. $^1$H NMR (400 MHz, Methanol-$d_4$) δ 7.96 (s, 1H) 7.85-7.94 (m, 2H) 7.55-7.62 (m, 2H) 7.37-7.44 (m, 2H) 6.84 (d, J=8.1 Hz, 1H) 6.29-6.37 (m, 2H) 5.24 (dd, J=6.4, 2.2 Hz, 1H) 4.86-4.95 (m, 2H) 4.20-4.26 (m, 1H) 3.16-3.29 (m, 3H) 2.75-2.99 (m, 4H) 2.54 (q, J=7.5 Hz, 2H) 2.25-2.38 (m, 1H) 2.10-2.22 (m, 1H) 1.68 (br, d, J=15.0 Hz, 2H) 1.45-1.63 (m, 2H) 1.28 (d, J=6.2 Hz, 6H) 1.13 (m, 6H). HRMS: calcd. for $C_{37}H_{44}N_5O_4$ (M+H) 622.3280, found 622.3270.

Example 51b. (−)-Ethyl-1-(6-(3-((3-ethyl-4-(1-(isopropoxycarbonyl)piperidin-4-yl)phenyl)amino)-2,3-dihydro-1H-inden-4-yl)pyridin-2-yl)-1H-pyrazole-4-carboxylic Acid Isopropyl 4-(4-((7-(6-(4-(ethoxycarbonyl)-5-ethyl-1H-pyrazol-1-yl)pyridin-2-yl)-2,3-dihydro-1H-inden-1-yl)

amino)-2-ethylphenyl)piperidine-1-carboxylate (enantiomer-2, t$_r$=5.3 min) was saponified as described for the synthesis of Example 7a to afford the title compound. ¹HNMR and HRMS data were substantially identical to Example 51a.

Example 52

The following compounds in the table below were synthesized in a similar manner as described for Example 51, employing the appropriate starting materials, Example 45-B or Example 48-A, and the appropriate chloroformate as outlined. Saponification of the resulting racemic esters was accomplished via the method described for Example 7a. In some instances, the racemic esters were first resolved by the conditions described in the table, and then each resulting enantiomer was independently saponified via the method described for Example 7a. ¹H NMR and HRMS data for (−)-enantiomer were substantially identical to (+)-enantiomer.

| Example | Chemical structure<br>¹H NMR and HRMS<br>Resolution conditions of enantiomers when performed (+)- and (−)-Carboxylic acids derived from their corresponding resolved ester enantiomers. | Chemical name<br>Example 45-B or Example 48-A<br>chloroformate |
|---|---|---|
| 52-1 | 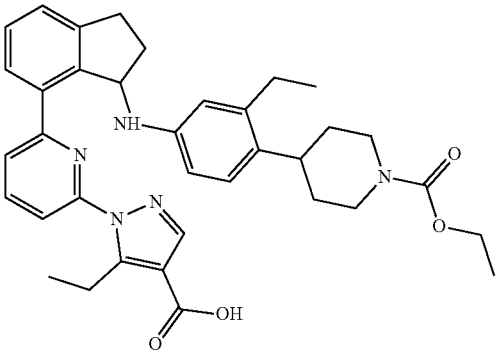 [SMILES: CCOC(=O)N1CCC(c2ccc(NC3CCc4cccc(-c5cccc(-n6ncc(C(=O)O)c6CC)n5)c43)cc2CC)CC1] | 1-6-(3-((4-(1-(Ethoxycarbonyl)-piperidin-4-yl)-3-ethylphenyl)-amino-2,3-dihydro-1H-inden-4-yl)pyridin-2-yl)-5-ethyl-1H-pyrazole-4-carboxylic acid<br>Example 48-A<br>Ethyl chloroformate |

¹H NMR (400 MHz, Methanol-d₄) δ 7.94 (s, 1H), 7.88-7.67 (m, 2H), 7.60-7.55 (m, 2H), 7.30-7.27 (m, 2H), 6.82 (d, J = 8.3 Hz, 1H), 6.33-6.31 (m, 2H), 5.23-5.19 (m, 1H), 4.23 (d, J = 13.3 Hz, 2H), 4.14-4.12 (m, 2H), 3.29-3.06 (m, 3H), 3.00-2.69 (m, 4H), 2.53-2.51 (m, 2H), 2.32-2.25 (m, 1H), 2.18-2.03 (m, 1H), 1.67-1.65 (m, 2H), 1.60-1.48 (m, 2H), 1.27 (m, 3H), 1.15-1.04 (m, 6H). HRMS; calcd. for C₃₆H₄₂N₅O₄ (M + H), 608.3192, found 608.2935
Resolution of the enantiomers of (±)-ethyl 4-(4-((7-(6-(4-(ethoxycarbonyl)-5-ethyl-1H-pyrazol-1-yl)pyridin-2-yl)-2,3-dihydro-1H-inden-1-yl)amino)-2-ethylphenyl)piperidine-1-carboxylate was achieved by chiral SFC using CHIRALPAK ® AD-H column with 30% IPA in CO₂ to give ethyl 4-(4-((7-(6-(4-(ethoxycarbonyl)-5-ethyl-1H-pyrazol-1-yl)pyridin-2-yl)-2,3-dihydro-1H-inden-1-yl)amino)-2-ethylphenyl)piperidine-1-carboxylate (enantiomer-1, t$_r$ = 3.3 min) and ethyl 4-(4-((7-(6-(4-(ethoxycarbonyl)-5-ethyl-1H-pyrazol-1-yl)pyridin-2-yl)-2,3-dihydro-1H-inden-1-yl)amino)-2-ethylphenyl)piperidine-1-carboxylate (enantiomer-2, t$_r$ = 4.9 min).
(−)-52-1: (−)-1-(6-(3-((4-(1-(Ethoxycarbonyl)piperidin-4-yl)-3-ethylphenyl)amino)-2,3-dihydro-1H-inden-4-yl)pyridin-2-yl)-5-ethyl-1H-pyrazole-4-carboxylic acid was derived from saponification of ethyl 4-(4-((7-(6-(4-(ethoxycarbonyl)-5-ethyl-1H-pyrazol-1-yl)pyridin-2-yl)-2,3-dihydro-1H-inden-1-yl)amino)-2-ethylphenyl)piperidine-1-carboxylate (enantiomer-1, t$_r$ = 3.3 min).
(+)-52-1: (+)-1-(6-(3-((4-(1-(Ethoxycarbonyl)piperidin-4-yl)-3-ethylphenyl)amino-2,3-dihydro-1H-inden-4-yl)pyridin-2-yl)-5-ethyl-1H-pyrazole-4-carboxylic acid was derived from saponification of ethyl 4-(4-((7-(6-(4-(ethoxycarbonyl)-5-ethyl-1H-pyrazol-1-yl)pyridin-2-yl)-2,3-dihydro-1H-inden-1-yl)amino)-2-ethylphenyl)piperidine-1-carboxylate (enantiomer-2, t$_r$ = 4.9 min).

| 52-2 | 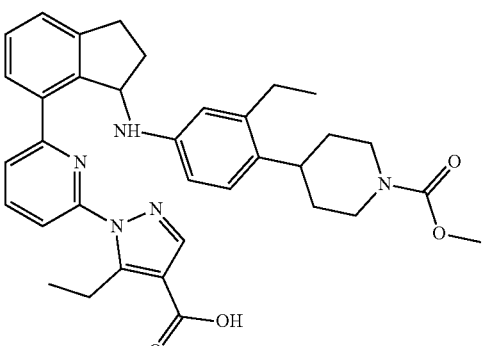 | 5-Ethyl-1-(6-(3-((3-ethyl-4-(1-(methoxycarbonyl)piperidin-4-yl)phenyl)amino)-2,3-dihydro-1H-inden-4-yl)pyridin-2-yl)-1H-pyrazole-4-carboxylic acid<br>Example 48-A<br>Methyl chloroformate |

¹H NMR (400 MHz, DMSO-d₆) δ 12.47 (s, 1H), 8.01-7.90 (m, 3H), 7.72-7.64 (m, 1H), 7.63-7.55 (m, 1H), 7.48-7.37 (m, 2H), 6.83 (d, J = 8.2 Hz, 1H), 6.41-6.33 (m, 2H), 5.44 (d, J = 9.1 Hz, 1H), 5.30-5.12 (m, 1H), 4.07 (s, 2H), 3.60 (s, 3H), 3.28 (s, 3H), 3.20-3.06 (m, 1H), 2.96-2.78 (m, 3H), 2.77-2.69 (m, 1H), 2.25-2.13 (m, 1H), 2.04-1.94 (m, 1H), 1.58 (d, J = 12.1 Hz, 2H), 1.50-1.36 (m, 2H), 1.17 (t, J = 7.3 Hz, 3H), 1.07 (t, J =7.5 Hz, 3H). HRMS; calcd. for C₃₅H₄₀N₅O₄ (M + H)

| Example | Chemical structure<br>¹H NMR and HRMS<br>Resolution conditions of enantiomers when performed (+)- and (−)-Carboxylic acids derived from their corresponding resolved ester enantiomers. | Chemical name<br>Example 45-B or Example 48-A chloroformate |
|---|---|---|

594.3075, found 594.2903
Resolution of the enantiomers of (±)-methyl 4-(4-((7-(6-(4-(ethoxycarbonyl)-5-ethyl-1H-pyrazol-1-yl)pyridin-2-yl)-2,3-dihydro-1H-inden-1-yl)amino)-2-ethylphenyl)piperidine-1-carboxylate was achieved by chiral SFC using CHIRALPAK ® AD-H column with 30% IPA in $CO_2$ to give methyl 4-(4-((7-(6-(4-(ethoxycarbonyl)-5-ethyl-1H-pyrazol-1-yl)pyridin-2-yl)-2,3-dihydro-1H-inden-1-yl)amino)-2-ethylphenyl)piperidine-1-carboxylate (enantiomer-1, $t_r$ = 4.3 min) and methyl 4-(4-((7-(6-(4-(ethoxycarbonyl)-5-ethyl-1H-pyrazol-1-yl)pyridin-2-yl)-2,3-dihydro-1H-inden-1-yl)amino)-2-ethylphenyl)piperidine-1-carboxylate (enantiomer-2, $t_r$ = 7.4 min).

(−)-52-2: (−)-5-Ethyl-1-(6-(3-((3-ethyl-4-(1-(methoxycarbonyl)piperidin-4-yl)phenyl)amino)-2,3-dihydro-1H-inden-4-yl)pyridin-2-yl)-1H-pyrazole-4-carboxylic acid was derived from saponification of methyl 4-(4-((7-(6-(4-(ethoxycarbonyl)-5-ethyl-1H-pyrazol-1-yl)pyridin-2-yl)-2,3-dihydro-1H-inden-1-yl)amino)-2-ethylphenyl)piperidine-1-carboxylate (enantiomer-1, $t_r$ = 4.3 min).

(+)-52-2: (+)-5-Ethyl-1-(6-(3-((3-ethyl-4-(1-(methoxycarbonyl)piperidin-4-yl)phenyl)amino)-2,3-dihydro-1H-inden-4-yl)pyridin-2-yl)-1H-pyrazole-4-carboxylic acid was derived from saponification of methyl 4-(4-((7-(6-(4-(ethoxycarbonyl)-5-ethyl-1H-pyrazol-1-yl)pyridin-2-yl)-2,3-dihydro-1H-inden-1-yl)amino)-2-ethylphenyl)piperidine-1-carboxylate (enantiomer-2, $t_r$ = 7.4 min).

| 52-3 | 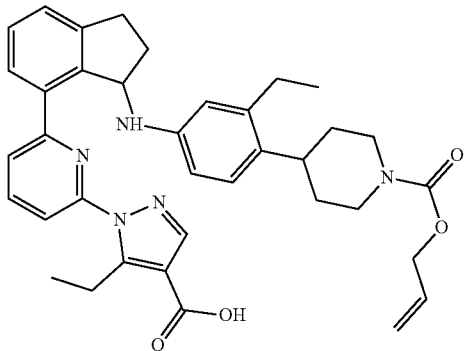 [SMILES: C=CCOC(=O)N1CCC(c2ccc(NC3CCc4cccc(-c5cccc(-n6ncc(C(=O)O)c6CC)n5)c43)cc2CC)CC1] | 1-(6-(3-((4-(1-((Allyloxy)-carbonyl)piperidin-4-yl)-3-ethylphenyl)amino)-2,3-dihydro-1H-inden-4-yl)pyridin-2-yl)-5-ethyl-1H-pyrazole-4-carboxylic acid<br>Example 48-A<br>Allyl chloroformate |
|---|---|---|

¹H NMR (400 MHz, DMSO-$d_6$) δ 12.52 (s, 1H), 8.03-7.89 (m, 3H), 7.70-7.64 (m, 1H), 7.63-7.56 (m, 1H), 7.47-7.38 (m, 2H), 6.83 (d, J = 8.2 Hz, 1H), 6.45-6.33 (m, 2H), 6.03-5.89 (m, 1H), 5.44 (d, J = 9.0 Hz, 1H), 5.35-5.14 (m, 3H), 4.54 (dt, J = 5.2, 1.5 Hz, 2H), 4.11 (d, J = 13.0 Hz, 2H), 3.28 (s, 4H), 3.20-3.08 (m, 1H), 3.00-2.79 (m, 3H), 2.79-2.69 (m, 1H), 2.27-2.13 (m, 1H), 2.05-1.92 (m, 1H), 1.67-1.53 (m, 2H), 1.53-1.36 (m, 2H), 1.17 (t, J = 7.3 Hz, 3H), 1.07 (t, J = 7.5 Hz, 3H). HRMS; calcd. for $C_{37}H_{42}N_5O_4$ (M + H) 620.323, found 620.3034.

Resolution of the enantiomers of (±)-allyl 4-(4-((7-(6-(4-(ethoxycarbonyl)-5-ethyl-1H-pyrazol-1-yl)pyridin-2-yl)-2,3-dihydro-1H-inden-1-yl)amino)-2-ethylphenyl)piperidine-1-carboxylate was achieved by chiral SFC using CHIRALPAK ® AD-H column with 35% IPA in $CO_2$ to give allyl 4-(4-((7-(6-(4-(ethoxycarbonyl)-5-ethyl-1H-pyrazol-1-yl)pyridin-2-yl)-2,3-dihydro-1H-inden-1-yl)amino)-2-ethylphenyl)piperidine-1-carboxylate (enantiomer-1, $t_r$ = 3.2 min) and allyl 4-(4-((7-(6-(4-(ethoxycarbonyl)-5-ethyl-1H-pyrazol-1-yl)pyridin-2-yl)-2,3-dihydro-1H-inden-1-yl)amino)-2-ethylphenyl)piperidine-1-carboxylate (enantiomer-2, $t_r$ = 5.7 min).

(−)-52-3: (−)-1-(6-(3-((4-(1-((Allyloxy)carbonyl)piperidin-4-yl)-3-ethylphenyl)amino)-2,3-dihydro-1H-inden-4-yl)pyridin-2-yl)-5-ethyl-1H-pyrazole-4-carboxylic acid was derived from saponification of allyl 4-(4-((7-(6-(4-(ethoxycarbonyl)-5-ethyl-1H-pyrazol-1-yl)pyridin-2-yl)-2,3-dihydro-1H-inden-1-yl)amino)-2-ethylphenyl)piperidine-1-carboxylate (enantiomer-1, $t_r$ = 3.2 min).

(+)-52-3: (+)-1-(6-(3-((4-(1-((Allyloxy)carbonyl))piperidin-4-yl)-3-ethylphenyl)amino)-2,3-dihydro-1H-inden-4-yl)pyridin-2-yl)-5-ethyl-1H-pyrazole-4-carboxylic acid was derived from saponification of allyl 4-(4-((7-(6-(4-(ethoxycarbonyl)-5-ethyl-1H-pyrazol-1-yl)pyridin-2-yl)-2,3-dihydro-1H-inden-1-yl)amino)-2-ethylphenyl)piperidine-1-carboxylate (enantiomer-2, $t_r$ = 5.7 min).

-continued

| Example | Chemical structure<br>$^1$H NMR and HRMS<br>Resolution conditions of enantiomers when performed (+)- and (−)-Carboxylic acids derived from their corresponding resolved ester enantiomers. | Chemical name<br>Example 45-B or Example 48-A<br>chloroformate |
|---|---|---|
| 52-4 | 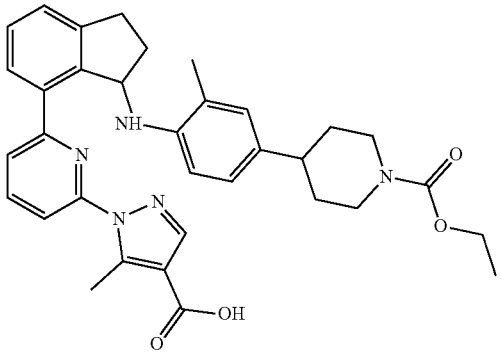 [SMILES: CCOC(=O)N1CCC(c2ccc(NC3CCc4cccc(-c5cccc(-n6ncc(C(=O)O)c6C)n5)c43)c(C)c2)CC1] | 1-(6-(3-((4-(1-(Ethoxycarbonyl)-piperidin-4-yl)-2-methylphenyl)-amino-2,3-dihydro-1H-inden-4-yl)pyridin-2-yl)-5-methyl-1H-pyrazole-4-carboxylic acid<br>Example 45-B<br>Ethyl chloroformate |

$^1$H NMR (400 MHz, Methanol-d$_4$) δ 7.89 (s, 1H), 7.80 (t, J = 7.9 Hz, 1H), 7.66-7.55 (m, 1H), 7.54-7.51 (m, 2H), 7.47-7.37 (m, 2H), 6.81-679 (m, 1H), 6.71 (s, 1H), 6.56-6.55 (d, J = 8.3 Hz, 1H), 5.39-5.37 (m, 1H), 4.30-4.15 (m, 2H), 4.11 (t, J = 7.1 Hz, 2H), 3.24-3.08 (m, 1H), 3.05-2.79 (m, 3H), 2.69(s, 3H), 2.57-2.41 (m, 2H), 2.08-2.06 (m, 1H), 1.76 (d, J = 12.2 Hz, 2H), 1.67 (s, 3H), 1.50-1.48 (m, 2H), 1.27 (t, J = 7.1 Hz, 3H). HRMS calcd. for C$_{34}$H$_{38}$N$_5$O$_4$ (M + H), 580.2879, found 580.2920.

| 52-5 | 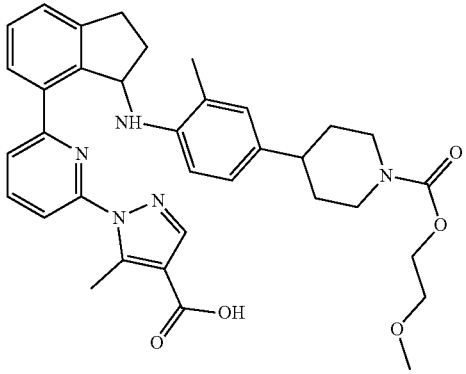 [SMILES: COCCOC(=O)N1CCC(c2ccc(NC3CCc4cccc(-c5cccc(-n6ncc(C(=O)O)c6C)n5)c43)c(C)c2)CC1] | 1-(6-(3-((4-(1-((2-methoxy-ethoxy)carbonyl)-piperidin-4-yl)-2-methylphenyl)amino-2,3-dihydro-1H-inden-4-yl)pyridin-2-yl)-5-methyl-1H-pyrazole-4-carboxylic acid<br>Example 45-B<br>2-Methoxyethyl carbono-chloridate (CAS# 628-12-6) |

$^1$H NMR (400 MHz, Methanol-d$_4$) δ 7.90 (s, 1H), 7.88-7.86 (m, 1H), 7.73 (d, J = 7.5 Hz, 1H), 7.58-7.52 (m, 2H), 7.46-7.36 (m, 2H), 6.79-6.76 (m, 1H), 6.68 (d, J = 1.7 Hz, 1H), 6.54 (d, J = 8.3 Hz,1H), 5.32-5.29 (m, 1H), 4.27-4.16 (m, 4H), 3.65-3.59 (m, 2H), 3.39 (s, 3H), 3.23-3.15 (m, 1H), 3.03-2.79 (m, 3H), 2.56 (s, 3H), 2.48-2.42 (m, 2H), 2.15-2.03 (m, 1H), 1.77 (d, J = 12.0 Hz, 2H), 1.64 (s, 3H), 1.58-1.45 (m, 2H). HRMS calcd. for C$_{35}$H$_{40}$N$_5$O$_6$ (M + H), 610.2985, found 610.303.

| 52-6 | 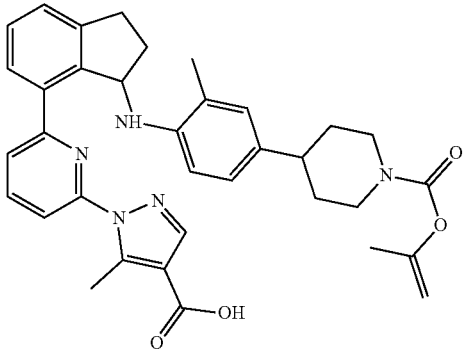 [SMILES: C=C(C)OC(=O)N1CCC(c2ccc(NC3CCc4cccc(-c5cccc(-n6ncc(C(=O)O)c6C)n5)c43)c(C)c2)CC1] | 5-Methyl-1-(6-(3-((2-methyl-4-(1-((prop-1-en-2-yloxy)-carbonyl)piperidin-4-yl)phenyl)-amino)-2,3-dihydro-1H-inden-4-yl)pyridin-2-yl)-1H-pyrazole-4-carboxylic acid<br>Example 45B<br>Prop-1-en-2-yl carbonochloridate (CAS# 57933-83-2) |

| | Chemical structure<br>¹H NMR and HRMS<br>Resolution conditions of enantiomers when performed (+)- and (−)-Carboxylic acids derived from their corresponding resolved ester enantiomers. | Chemical name<br>Example 45-B or Example 48-A chloroformate |
|---|---|---|
| Example | | |

¹H NMR (400 MHz, Methanol-d₄) δ 7.96-7.83 (m, 2H) 7.74-7.72 (m, 1H), 7.54-7.52 (m, 2H), 7.49-7.33 (m, 2H), 6.80-6.78 (m, 1H), 6.70-6.68 (m, 1H), 6.55 (d, J = 8.3 Hz, 1H), 5.33-5.30 (m, 1H), 4.71-4.56 (m, 2H), 4.22 (d, J = 12.3 Hz, 2H), 3.24-3.14 (m, 1H), 3.07-2.81 (m, 3H), 2.64-2.39 (m, 5H), 2.12-2.05 (m, 1H), 1.98-1.92 (m, 3H), 1.82-179 (m, 2H), 1.71-1.44 (m, 5H). HRMS; calcd. for $C_{35}H_{38}N_5O_4$ (M + H), 592.2871, found 592.2821

Example 53

The following compounds were synthesized using the appropriate materials denoted in the table below (Intermediate 3, Intermediate 2, and Carboxylic acid). Ketones of the type represented in Intermediate 3 underwent reductive amination with anilines of the type represented in Intermediate 2 by analogous methods described by Example 7-A. a). The resulting racemic esters can be saponified as described in Example 7a, and the resulting racemic carboxylic acids can be separated by the conditions denoted in the table below to afford each enantiomer.

When the anilines represented by Intermediate 2 contain a Boc protected piperidine, the Boc group can be removed after reductive amination as described in Example 35-8, and the resulting amine can be coupled with the Carboxylic acid denoted in table below as outlined by the procedure used to access Example 35-C. a). The esters of the resulting amides can then be saponified as in Example 7a to provide the title compound in racemic form. The racemic acids were then resolved by the conditions described in the table below to afford enantiomerically pure form of the title compound. ¹H NMR and HRMS data for (+)- and (−)-enantiomers were substantially identical to the racemic form.

| Example | Chemical structure<br>¹H NMR and HRMS<br>Resolution condition for enantiomers | Chemical name<br>Intermediate 3<br>Intermediate 2<br>Carboxylic acid |
|---|---|---|
| 53-1 | 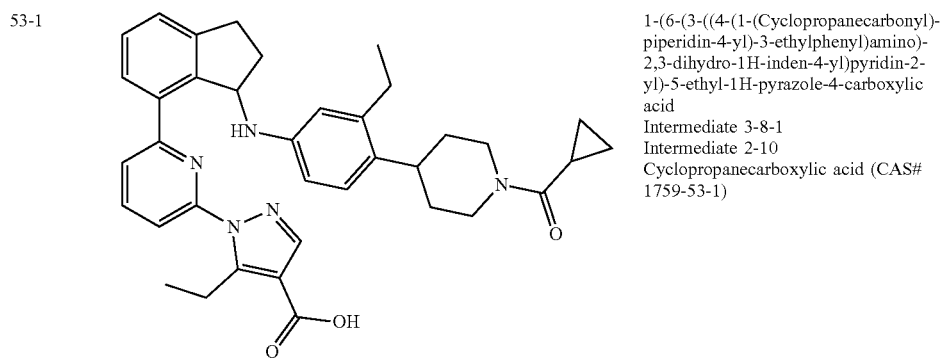 | 1-(6-(3-((4-(1-(Cyclopropanecarbonyl)-piperidin-4-yl)-3-ethylphenyl)amino)-2,3-dihydro-1H-inden-4-yl)pyridin-2-yl)-5-ethyl-1H-pyrazole-4-carboxylic acid<br>Intermediate 3-8-1<br>Intermediate 2-10<br>Cyclopropanecarboxylic acid (CAS# 1759-53-1) |

¹H NMR (400 MHz, Methanol-d₄) δ 7.94 (s, 1H), 7.92-7.87 (m, 1H), 7.87-7.84 (m, 1H), 7.60-7.54 (m, 2H), 7.41-7.38 (m, 2H), 6.83 (d, J = 8.5 Hz, 1H), 6.35-6.29 (m, 2H), 5.26-5.20 (m, 1H), 4.64 (d, J = 12.8 Hz, 1H), 4.45 (d, J = 13.4 Hz, 1H), 3.26-3.15 (m, 4H), 2.97-2.88 (m, 2H), 2.73 (t, J = 12.9 Hz, 1H), 2.54 (q, J = 7.5 Hz, 2H), 2.36-2.25 (m, 1H), 2.19-2.11 (m, 1H), 2.05-1.96 (m, 1H), 1.79 (d, J = 13.2 Hz, 1H), 1.71 (d, J = 13.0 Hz, 1H), 1.65-1.45 (m, 2H), 1.16-1.08 (m, 6H), 0.94-0.77 (m, 4H). HRMS; calcd. for $C_{37}H_{42}N_5O_3$ (M + H) 604.3288, found 604.3284.

Resolution of the enantiomers of (±)-1-(6-(3-((4-(1-(cyclopropanecarbonyl)piperidin-4-yl)-3-ethylphenyl)amino)-2,3-dihydro-1H-inden-4-yl)pyridin-2-yl)-5-ethyl-1H-pyrazole-4-carboxylic acid was achieved by chiral SFC using CHIRALPAK® AD-H column with 45% IPA in CO₂ to give (−)-1-(6-(3-((4-(1-(cyclopropanecarbonyl)piperidin-4-yl)-3-ethylphenyl)amino)-2,3-dihydro-1H-inden-4-yl)pyridin-2-yl)-5-ethyl-1H-pyrazole-4-carboxylic acid ($t_r$ = 2.02 min) and (+)-1-(6-(3-((4-(1-(cyclopropanecarbonyl)piperidin-4-yl)-3-ethylphenyl)amino)-2,3-dihydro-1H-inden-4-yl)pyridin-2-yl)-5-ethyl-1H-pyrazole-4-carboxylic acid ($t_r$ = 4.12 min).

| Example | Chemical structure<br>¹H NMR and HRMS<br>Resolution condition for enantiomers | Chemical name<br>Intermediate 3<br>Intermediate 2<br>Carboxylic acid |
|---|---|---|
| 53-2 | 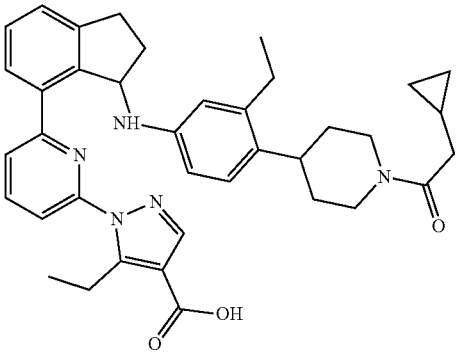 [SMILES: CCc1cc(NC2CCc3cccc(-c4cccc(-n5ncc(C(=O)O)c5CC)n4)c32)ccc1C1CCN(C(=O)CC2CC2)CC1] | 1-(6-(3-((4-(1-(2-Cyclopropylacetyl)-piperidin-4-yl)-3-ethylphenyl)amino)-2,3-dihydro-1H-inden-4-yl)pyridin-2-yl)-5-ethyl-1H-pyrazole-4-carboxylic acid<br>Intermediate 3-8-1<br>Intermediate 2-10<br>Cyclopropylacetic acid (CAS# 5239-82-7) |

¹H NMR (400 MHz, Methanol-d₄) δ 7.93 (s, 1H), 7.90-7.83 (m, 2H), 7.60-7.53 (m, 2H), 7.41-7.37 (m, 2H), 6.33 (d, J = 8.6 Hz, 1H), 6.36-6.30 (m, 2H), 5.26-5.21 (m, 1H), 4.69 (d, J = 13.5 Hz, 1H), 4.06 (d, J = 13.6 Hz, 1H), 3.24-3.15 (m, 4H), 2.97-2.85 (m, 2H), 2.74-2.65 (m, 1H), 2.58-2.50 (m, 2H), 2.37 (d, J = 6.9 Hz, 2H), 2.34-2.24 (m, 1H), 2.19-2.11 (m, 1H), 1.74 (t, J = 13.9 Hz, 2H), 1.67-1.49 (m, 2H), 1.15-1.08 (m, 6H), 1.08-1.00 (m, 1H), 0.59-0.53 (m, 2H), 0.23 (dd, J = 5.7, 4.3 Hz, 2H). HRMS; calcd. for $C_{38}H_{44}N_5O_3$ (M + H) 618.3444, found 618.3422.
Resolution of the enantiomers of (±)-1-(6-(3-((4-(1-(2-cyclopropylacetyl)piperidin-4-yl)-3-ethylphenyl)amino)-2,3-dihydro-1H-inden-4-yl)pyridin-2-yl)-5-ethyl-1H-pyrazole-4-carboxylic acid was achieved by chiral SFC using CHIRALCEL ® OJ-H column with 40% IPA in $CO_2$ to give (−)-1-(6-(3-((4-(1-(2-cyclopropylacetyl)piperidin-4-yl)-3-ethylphenyl)amino)-2,3-dihydro-1H-inden-4-yl)-pyridin-2-yl)-5-ethyl-1H-pyrazole-4-carboxylic acid ($t_r$ = 2.80 min) and (+)-1-(6-(3-((4-(1-(2-cyclo-propylacetyl)piperidin-4-yl)-3-ethylphenyl)amino)-2,3-dihydro-1H-inden-4-yl)pyridin-2-yl)-5-ethyl-1H-pyrazole-4-carboxylic acid ($t_r$ = 6.60 min).

| 53-3 | 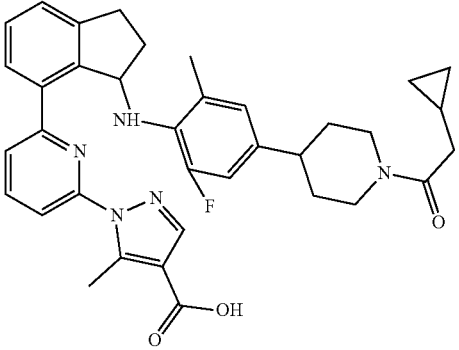 [SMILES: Cc1cc(C2CCN(C(=O)CC3CC3)CC2)cc(F)c1NC1CCc2cccc(-c3cccc(-n4ncc(C(=O)O)c4C)n3)c21] | 1-(6-(3-((4-(1-(2-Cyclopropylacetyl)-pipendin-4-yl)-2-fluoro-6-methyl-phenyl)amino)-2,3-dihydro-1H-inden-4-yl)pyridin-2-yl)-5-methyl-1H-pyrazole-4-carboxylic acid<br>Intermediate 3-7<br>Intermediate 2-12-3<br>Cyclopropanecarboxylic acid (CAS# 1759-53-1) |

¹H NMR (400 MHz, Methanol-d₄) δ 8.04-7.98 (m, 1H), 7.84 (t, J = 7.9 Hz, 1H), 7.64 (d, J = 4.0 Hz, 1H), 7.62 (d, J = 3.7 Hz, 1H), 7.48-7.42 (m, 1H), 7.42-7.35 (m, 2H), 6.50 (s, 1H), 6.47-6.40 (m, 1H), 5.59 (d, J = 6.6 Hz, 1H), 4.64 (d, J = 13.0 Hz, 1H), 4.02 (d, J = 13.9 Hz, 1H), 3.19-3.08 (m, 2H), 2.99-2.90 (m, 1H), 2.87 (s, 3H), 2.65 (t, J = 12.8 Hz, 1H), 2.58-2.48 (m, 1H), 2.42-2.30 (m, 3H), 2.16 (dd, J = 13.3, 7.4 Hz, 1H), 1.78 (s, 5H), 1.52-1.34 (m, 2H), 1.06-0.99 (m, 1H), 0.59-0.52 (m, 2H), 0.24-0.18 (m, 2H). HRMS; calcd. for $C_{36}H_{39}FN_5O_3$ (M + H) 608.3037, found 608.2897.
Resolution of the enantiomers of (±)-1-(6-(3-((4-(1-(2-cyclopropylacetyl)piperidin-4-yl)-2-fluoro-6-methylphenyl)amino)-2,3-dihydro-1H-inden-4-yl)pyridin-2-yl)-5-methyl-1H-pyrazole-4-carboxylic acid was achieved by chiral SFC using CHIRALCEL ® OJ-H column with 5-55% MeOH in $CO_2$ to give (+)-1-(6-(3-((4-(1-(2-cyclopropyacetyl)piperidin-4-yl)-2-fluoro-6-methylphenyl)amino)-2,3-dihydro-1H-inden-4-yl)pyridin-2-yl)-5-methyl-1H-pyrazole-4-carboxylic acid ($t_r$ = 2.30 min) and (−)-1-(6(3-((4-(1-(2-cyclopropylacetyl)piperidin-4-yl)-2-fluoro-6-methylphenyl)amino)-2,3-dihydro-1H-inden-4-yl)pyridin-2-yl)-5-methyl-1H-pyrazole-4-carboxylic acid ($t_r$ = 2.48 min).

| Example | Chemical structure<br>¹H NMR and HRMS<br>Resolution condition for enantiomers | Chemical name<br>Intermediate 3<br>Intermediate 2<br>Carboxylic acid |
|---|---|---|
| 53-4 | 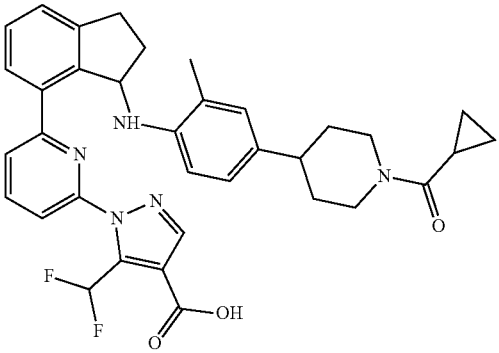 [SMILES: Cc1cc(C2CCN(C(=O)C3CC3)CC2)ccc1NC1CCc2cccc(-c3cccc(-n4ncc(C(=O)O)c4C(F)F)n3)c21] | 1-(6-(3-((4-(1-(Cyclopropanecarbonyl)-piperindin-4-yl)-2-methylphenyl)-amino)-2,3-dihydro-1H-inden-4-yl)-pyridin-2-yl)-5-(difluoromethyl)-1H-pyrazole-4-carboxylic acid<br>Intermediate 3-8-4<br>Intermediate 2-8<br>not applicable |
| | ¹H NMR (400 MHz, Methanol-d₄) δ 7.97-7.91 (m, 2H), 7.82 (d, J = 7.8 Hz, 1H), 7.65-7.60 (m, 1H), 7.55 (d, J = 7 9 Hz, 1H), 7.47-7 40 (m, 2H), 7.38 (t, J = 53.2 Hz, 1H), 6.82-6.77 (m, 1H), 6.74-6.71 (m. 1H), 6.56 (d, J = 8.2 Hz, 1H), 5.26 (dd, J = 6.7, 2.7 Hz, 1H), 4.63 (d, J = 12.9 Hz, 1H), 4.44 (d, J = 13.2 Hz, 1H), 3.26-3.16 (m, 2H), 2.99-2.90 (m, 1H), 2.78-2.69 (m, 1H), 2.69-2.61 (m, 1H), 2.43-2.33 (m, 1H), 2.16-2.08 (m, 1H), 2.04-1.96 (m, 1H), 1.92 (d, J = 13.0 Hz, 1H), 1.84 (d, J = 13.0 Hz, 1H), 1.70 (s, 3H), 1.66-1.42 (m, 2H) 0.94-0.86 (m, 2H), 0.86-0.78 (m, 2H). HRMS: calcd. for C₃₅H₃₅F₂N₅O₃ C₃₅H₃₆F₂N₅O₃ (M + H) 612.2786, found 612.2514.<br>Resolution of the enantiomers of (±)-1-(6-(3-((4-(1-(cyclopropanecarbonyl)piperidin-4-yl)-2-methyl-phenyl)amino-2,3-dihydro-1H-inden-4-yl)pyridin-2-yl)-5-(difluoromethyl)-1H-pyrazole-4-carboxylic acid was achieved by chiral SFC using CHIRALCEL ® OJ-H column with 5% to 55% MeOH in CO₂ to give (+)-1-(6-(3-((4-(1-(cyclopropanecarbonyl)piperidin-4-yl)-2-methylphenyl)amino)-2,3-dihydro-1H-inden-4-yl)pyridin-2-yl)-5-(difluoromethyl)-1H-pyrazole-4-carboxylic acid (t,. = 2.53 min) and (−)-1-(6-(3-((4-(1-(cyclopropanecarbonyl)piperidin-4-yl)-2-methylphenyl)amino)-2,3-dihydro-1H-inden-4-yl)pyridin-2-yl)-5-(difluoromethyl)-1H-pyrazole-4-carboxylic acid (t,= 3.25 min). | |

Example 54

Example 54-A. (±)-Ethyl 1-(3-(3-(4-(1-(cyclopropanecarbonyl)piperidin-4-yl)-2-methylbenzyl)-2,3-dihydro-1H-inden-4-yl)phenyl)-5-methyl-1H-pyrazole-4-carboxylate

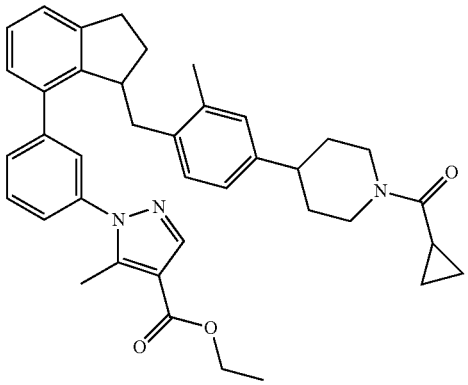 [SMILES: CCOC(=O)c1cnn(-c2cccc(-c3cccc4c3C(Cc3ccc(C5CCN(C(=O)C6CC6)CC5)cc3C)CC4)c2)c1C]

To a suspension of (±)-3-(4-(1-(cyclopropanecarbonyl)piperidin-4-yl)-2-methylbenzyl)-2,3-dihydro-1H-inden-4-yl trifluoromethanesulfonate (Intermediate 6-1) (250 mg, 0.479 mmol), ethyl 5-methyl-1-(3-(4,4,5,5-tetramethyl-1,3,2-dioxaborolan-2-yl)phenyl)-1H-pyrazole-4-carboxylate (Intermediate 1-5) (205 mg, 0.575 mmol) and K₃PO₄ (2M in H₂O) (0.479 mL, 0.959 mmol) in dioxane (4 mL) was added chloro(2-dicyclohexylphosphino-2',6'-dimethoxy-1,1'-biphenyl)[2-(2-aminoethylphenyl)]palladium(II)-methyl-t-butyl ether adduct (CAS #1028206-58-7; 19.6 mg, 0.024 mmol). The mixture was then stirred at 100° C. for 2 h, and then cooled to room temperature. The reaction mixture was diluted with EtOAc, and then washed successively with H₂O and brine, dried over Na₂SO₄, filtered, and then concentrated. The resulting residue was purified by silica gel flash column chromatography (0-50% EtOAc in heptane) to afford the title compound. MS (ESI+) m/z 602.4 (M+H).

Example 54. a). (±)-1-(3-(3-(4-1-(Cyclopropanecarbonyl)piperidin-4-yl)-2-methylbenzyl)-2,3-dihydro-1H-inden-4-yl)phenyl)-6-methyl-1H-pyrazole-4-carboxylic Acid

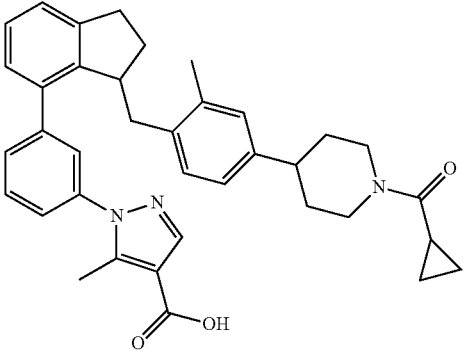 [SMILES: Cc1cc(C2CCN(C(=O)C3CC3)CC2)ccc1CC1CCc2cccc(-c3cccc(-n4ncc(C(=O)O)c4C)c3)c21]

The title compound was synthesized by saponification of (±)-ethyl 1-(3-(3-(4-(1-(cyclopropanecarbonyl)piperidin-4-yl)-2-methylbenzyl)-2,3-dihydro-1H-inden-4-yl)phenyl)-5-methyl-1H-pyrazole-4-carboxylate by the similar method as described for the synthesis of Example 7a. ¹H NMR (400

MHz, Methanol-d$_4$) δ 8.02 (s, 1H), 7.59 (t, J=7.8 Hz, 1H), 7.52-7.48 (m, 1H), 7.45 (dt, J=7.9, 1.6 Hz, 1H), 7.39 (s, 1H), 7.30-7.22 (m, 2H), 7.08 (d, J=6.8 Hz, 1H), 6.82 (d, J=5.9 Hz, 2H), 6.72 (d, J=8.3 Hz, 1H), 4.60 (d, J=12.0 Hz, 1H), 4.41 (d, J=13.6 Hz, 1H), 3.79-3.75 (m, 1H), 3.26-3.05 (m, 2H), 2.90 (dd, J=16.1, 7.2 Hz, 1H), 2.66-2.61 (m, 2H), 2.58 (s, 3H), 2.48 (dd, J=13.7, 5.2 Hz, 1H), 2.30 (dd, J=13.7, 10.3 Hz, 1H), 2.14-1.88 (m, 3H), 1.86-1.78 (m, 5H), 1.65-1.43 (m, 2H), 0.94-0.76 (m, 4H). HRMS; calcd. for C$_{37}$H$_{40}$N$_3$O$_3$ (M+H) 574.3070, found 574.3081.

Example 54. b). (+)-1-(3-(3-4-(1-(Cyclopropanecarbonyl)piperidin-4-yl)-2-methylbenzyl)-2,3-dihydro-1H-inden-4-yl)phenyl)-5-methyl-1H-pyrazole-4-carboxylic acid and (−)-1-(3-(3-(4-(1-(Cyclopropanecarbonyl)piperidin-4-yl)-2-methylbenzyl)-2,3-dihydro-1H-inden-4-yl)phenyl)-5-methyl-1H-pyrazole-4-carboxylic Acid Resolution of the enantiomers of (±)-1-(3-(3-(4-(1-(cyclopropanecarbonyl)piperidin-4-yl)-2-methylbenzyl)-2,3-dihydro-1H-inden-4-yl)phenyl)-5-methyl-1H-pyrazole-4-carboxylic acid was achieved by chiral SFC using CHIRALCEL® OJ-H column with 35% IPA in CO$_2$ to give (−)-1-(3-(3-(4-(1-(cyclopropanecarbonyl)piperidin-4-yl)-2-methylbenzyl)-2,3-dihydro-1H-inden-4-yl)phenyl)-5-methyl-1H-pyrazole-4-carboxylic acid (t$_r$=3.1 min) and (+)-1-(3-(3-(4-(1-(cyclopropanecarbonyl)piperidin-4-yl)-2-methylbenzyl)-2,3-dihydro-1H-inden-4-yl)phenyl)-5-methyl-1H-pyrazole-4-carboxylic acid (t$_r$=4.5 min). $^1$H NMR and HRMS data for (+)- and (−)-enantiomers were substantially identical to the racemic form.

Example 55

The following compounds were synthesized using appropriate materials in the table below (Intermediate 1 and Intermediate 6) by the methods described above, specifically Example 56-1, was prepared in a fashion similar to the procedure described for Example 54, and Example 55-2 was prepared in a fashion similar to the procedure described for Example 6. In the case of Example 55-1, the racemic form of the title compound was then resolved by the conditions described in the table to afford enantiomerically pure form of the title compound. $^1$H NMR and HRMS data for (+)- and (−)-enantiomers were substantially identical to the racemic form

| Example | structure<br>$^1$H NMR and HRMS data<br>enantiomer separation conditions | IUPAC name<br>Intermediate 1<br>Intermediate 6 |
|---|---|---|
| 55-1 | 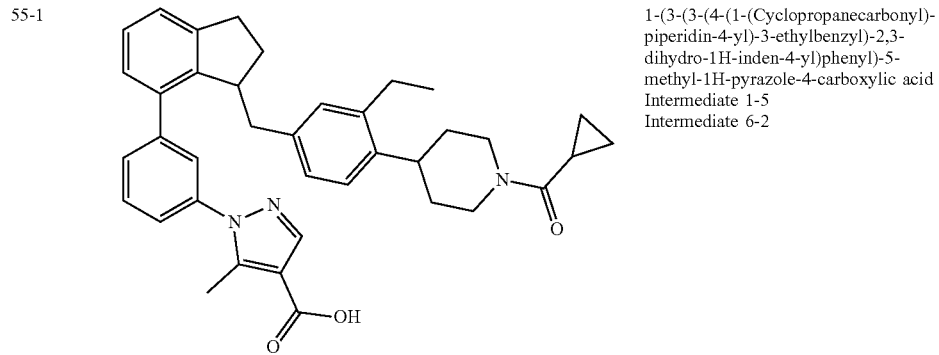 | 1-(3-(3-(4-(1-(Cyclopropanecarbonyl)-piperidin-4-yl)-3-ethylbenzyl)-2,3-dihydro-1H-inden-4-yl)phenyl)-5-methyl-1H-pyrazole-4-carboxylic acid<br>Intermediate 1-5<br>Intermediate 6-2 |

$^1$H NMR (400 MHz, Methanol-d$_4$) δ 8.02 (s, 1H), 7.68 (t, J = 7.7 Hz, 1H), 7.65-7.61 (m, 1H), 7.59 (s, 1H), 7.52-7.48 (m, 1H), 7.28-7.23 (m, 1H), 7.21 (d, J = 6.4 Hz, 1H), 7.18-7.14 (m, 1H), 6.96 (d, J = 7.9 Hz, 1H), 6.67 (dd, J = 7.9, 1.6 Hz, 1H), 6.60 (s, 1H), 4.64 (d, J = 12.3 Hz, 1H), 4.45 (d, J = 13.2 Hz, 1H), 3.85-3.78 (m, 1H), 3.27-3.20 (m, 1H), 3.06-2.96 (m, 1H), 2.87-2.81 (m, 2H), 2.73 (t, J = 12.2 Hz, 1H), 2.62-2.57 (m, 2H), 2.56 (s, 3H), 2.44 (dd, J = 13.5, 3.7 Hz, 1H), 2.21 (dd, J = 13.5, 9.8 Hz, 1H), 2.13-2.04 (m, 1H), 2.03-1.96 (m, 1H), 1.95-1.87 (m, 1H), 1.78 (d, J = 13.5 Hz, 1H), 1.74-1.48 (m, 3H), 1.11 (t, J = 7.5 Hz, 3H), 0.93-0.85 (m, 2H), 0.85-0.76 (m, 2H). HRMS; calcd. for C$_{38}$H$_{42}$N$_3$O$_3$ (M + H) 588.3226, found 588.3224.

Resolution of the enantiomers of (±)-1-(3-(3-(4-(1-(cyclopropanecarbonyl)piperidin-4-yl)-3-ethylbenzyl)-2,3-dihydro-1H-inden-4-yl)phenyl)-5-methyl-1H-pyrazole-4-carboxylic acid was achieved by chiral SFC using CHIRALCEL ® OJ-H column with 15% MeOH in CO2 to give (−)-1-(3-(3-(4-(1-(cyclopropanecarbonyl)piperidin-4-yl)-3-ethylbenzyl)-2,3-dihydro-1H-inden-4-yl)phenyl)-5-methyl-1H-pyrazole-4-carboxylic acid (t$_r$ = 5.40 min) and (+)-1-(3-(3-(4-(1-(cyclopropanecarbonyl)piperidin-4-yl)-3-ethylbenzyl)-2,3-dihydro-1H-inden-4-yl)phenyl)-5-methyl-1H-pyrazole-4-carboxylic acid (t$_r$ = 7.50 min).

| Example | structure<br>¹H NMR and HRMS data<br>enantiomer separation conditions | IUPAC name<br>Intermediate 1<br>Intermediate 6 |
|---|---|---|
| 55-2 | 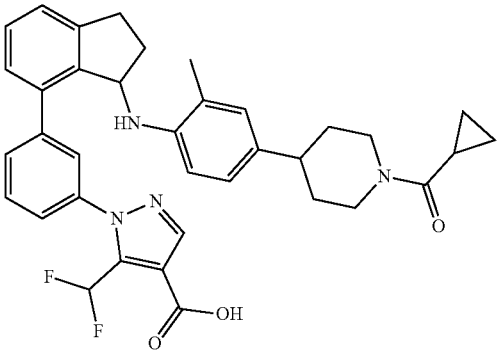 [SMILES: Cc1cc(C2CCN(C(=O)C3CC3)CC2)ccc1NC1CCc2cccc(-c3cccc(-n4ncc(C(=O)O)c4C(F)F)c3)c21]<br>¹H NMR (400 MHz, Methanol-d₄) δ 7.93 (d, J = 1.0 Hz, 1H), 7.76 (s, 1H), 7.66-7.62 (m, 1H), 7.48 (t, J = 52.7 Hz, 1H), 7.44-7.40 (m, 2H), 7.38 (d, J = 7.3 Hz, 1H), 7.36-7.34 (m, 1H), 7.31-7 27 (m, 1H), 6.84-6.78 (m, 1H), 6.74 (d, J = 2.1 Hz, 1H), 6.51 (d, J = 8.3 Hz, 1H), 5.11-5.04 (m, 1H), 4.62 (d, J = 12.6 Hz, 1H), 4.43 (d, J = 13.3 Hz, 1H), 3.26-3.17 (m, 2H), 3.00-2.88 (m, 1H), 2.77-2.56 (m, 2H), 2.45-2.31 (m, 1H), 2.14-2.05 (m, 1H), 2.04-1.96 (m, 1H), 1.88 (d, J = 13.3 Hz, 1H), 1.80 (d, J = 13.3 Hz, 1H), 1.74 (s, 3H), 1.64-1.41 (m, 2H), 0.93-0.85 (m, 2H), 0.81 (d, J = 7.9 Hz, 2H). HRMS; calcd. for $C_{38}H_{37}F_2N_4O_3$ (M + H) 611.2834, found 611.2808. | (+)-1-(3-(3-((4-(1-(Cyclopropane-carbonyl)piperidin-4-yl)-2-methyl-phenyl)amino)-2,3-dihydro-1H-inden-4-yl)phenyl)-5-(difluoro-methyl)-1H-pyrazole-4-carboxylic acid<br>Intermediate 1-4-5<br>Intermediate 3-5-A. b) (+) |

Example 56

Example 56-A. a). (±)-tert-Butyl 4-(4-((7-(3-(4-(ethoxycarbonyl)-5-(trifluoromethyl)-1H-pyrazol-1-yl)phenyl)-2,3-dihydro-1H-inden-1-yl)amino)-3-methylphenyl)piperidine-1-carboxylate

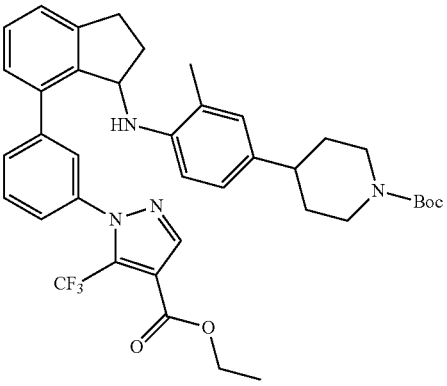 [SMILES: CCOC(=O)c1cnn(-c2cccc(-c3cccc4c3C(Nc3ccc(C5CCN(C(=O)OC(C)(C)C)CC5)cc3C)CC4)c2)c1C(F)(F)F]

The title compound was synthesized by the similar method as described for the synthesis of Example 7-A. a) starting from ethyl 1-(3-(3-oxo-2,3-dihydro-1H-inden-4-yl)phenyl)-5-(trifluoromethyl)-1H-pyrazole-4-carboxylate (Intermediate 3-6) and tert-butyl 4-(4-amino-3-methylphenyl)piperidine-1-carboxylate (Intermediate 2-13). MS (ESI+) m/z 689.5 (M+H).

Example 56-A. b). (+)-tert-Butyl 4-(4-((7-(3-(4-(ethoxycarbonyl)-5-(trifluoromethyl)-1H-pyrazol-1-yl)phenyl)-2,3-dihydro-1H-inden-1-yl)amino)-3-methylphenyl)piperidine-1-carboxylate and (−)-tert-butyl 4-(4-((7-(3-(4-(ethoxycarbonyl)-5-(trifluoromethyl)-1H-pyrazol-1-yl)phenyl)-2,3-dihydro-1H-inden-1-yl)amino)-3-methylphenyl)piperidine-1-carboxylate Resolution of the enantiomers of (±)-tert-butyl 4-(4-((7-(3-(4-(ethoxycarbonyl)-5-(trifluoromethyl)-1H-pyrazol-1-yl)phenyl)-2,3-dihydro-1H-inden-1-yl)amino)-3-methylphenyl)piperidine-1-carboxylate was achieved by chiral SFC using CHIRALPAK® IA column with 25% IPA with 10% $CH_3CN$ in $CO_2$ for the first peak elution, and then 45% IPA with 10% $CH_3CN$ in $CO_2$ to give (−)-tert-butyl 4-(4-((7-(3-(4-(ethoxycarbonyl)-5-(trifluoromethyl)-1H-pyrazol-1-yl)phenyl)-2,3-dihydro-1H-inden-1-yl)amino)-3-methylphenyl)piperidine-1-carboxylate ($t_r$=2.9 min) and (+)-tert-butyl 4-(4-((7-(3-(4-(ethoxycarbonyl)-5-(trifluoromethyl)-1H-pyrazol-1-yl)phenyl)-2,3-dihydro-1H-inden-1-yl)amino)-3-methylphenyl)piperidine-1-carboxylate ($t_r$=5.2 min).

Example 56. (+)-13-(3-((4-(1-(2-Hydroxyacetyl) piperidin-4-yl)-2-methylphenyl)amino)-2,3-dihydro-1H-inden-4-yl)phenyl)-5-(trifluoromethyl)-1H-pyrazole-4-carboxylic Acid

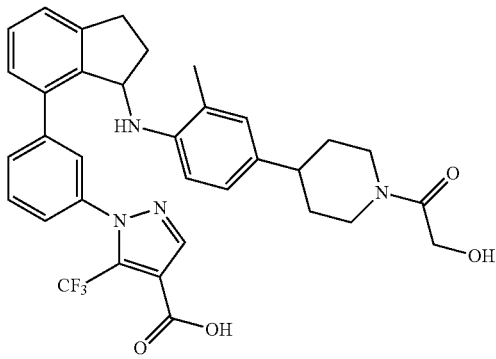 [SMILES: Cc1cc(C2CCN(C(=O)CO)CC2)ccc1NC1CCc2cccc(-c3cccc(-n4ncc(C(=O)O)c4C(F)(F)F)c3)c21]

The title compound was synthesized starting from (+)-tert-butyl 4-(4-((7-(3-(4-(ethoxycarbonyl)-5-(trifluoromethyl)-1H-pyrazol-1-yl)phenyl)-2,3-dihydro-1H-inden-1-yl)amino)-3-methylphenyl)piperidine-1-carboxylate ($t_r$=5.2 min) by the similar method as outlined for the preparation of Example 51 using 2-chloro-2-oxoethyl acetate (CAS #13831-31-7) instead of using isopropyl chloroformate. $^1$H NMR (400 MHz, Chloroform-d) δ7.93 (s, 1H), 7.63 (d, J=1.6 Hz, 1H), 7.58 (d, J=8.0 Hz, 1H), 7.20-7.38 (m, 5H), 6.77 (d, J=8.2 Hz, 1H), 6.68 (br. s., 1H), 6.46 (d, J=8.2 Hz, 1H), 4.85-4.94 (m, 1H), 4.62 (br. d, J=12.7 Hz, 1H), 4.16-4.24 (m, 1H), 4.08-4.16 (m, 1H), 3.48-3.60 (m, 1H), 3.06-3.17 (m, 1H), 2.96-3.05 (m, 1H), 2.81-2.90 (m, 1H), 2.65-2.74 (m, 1H), 2.50-2.58 (m, 1H), 2.18-2.29 (m, 2H), 2.04-2.13 (m, 1H), 1.81 (br. d, J=12.0 Hz, 2H), 1.74 (s, 3H), 1.31-1.56 (m, 2H). HRMS; calcd. for $C_{34}H_{34}F_3N_4O_4$ (M+H) 619.2532, found 619.2503.

Example 57. (+)-1-(6-(3-((4-(1-(Cyclopropanecarbonyl)piperidin-4-yl)-2-methylphenyl)amino)-2,3-dihydro-1H-inden-4-yl)pyridin-2-yl)-6-(2,2,2-trifluoroethyl)-1H-pyrazole-4-carboxylic Acid

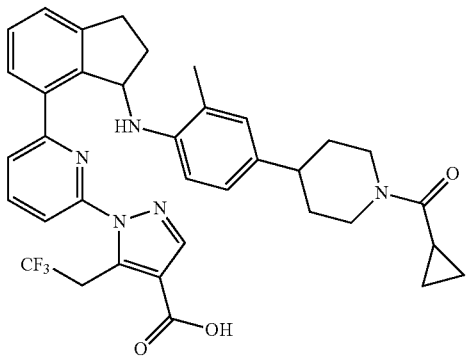 [SMILES: Cc1cc(C2CCN(C(=O)C3CC3)CC2)ccc1NC1CCc2cccc(-c3cccc(-n4ncc(C(=O)O)c4CC(F)(F)F)n3)c21]

The title compound was synthesized by the similar method as described for the synthesis of Example 35-A followed by saponification similarly to the preparation of Example 7a starting with ethyl 1-(6-bromopyridin-2-yl)-5-(2,2,2-trifluoroethyl)-1H-pyrazole-4-carboxylate (Intermediate 1-8) and (+)-(4-(4-((7-bromo-2,3-dihydro-1H-inden-1-yl)amino)-3-methylphenyl)piperidin-1-yl)(cyclopropyl)methanone (Intermediate 3-5-A. b) (+), $t_r$=2.93 min). $^1$H NMR (400 MHz, Methanol-$d_4$) δ 7.99 (s, 1H), 7.86 (t, J=7.9 Hz, 1H), 7.73 (dd, J=7.7, 0.9 Hz, 1H), 7.66 (dd, J=8.0, 0.8 Hz, 1H), 7.59-7.53 (m, 1H), 7.46-7.40 (m, 2H), 6.78 (dd, J=8.3, 2.2 Hz, 1H), 6.71 (d, J=2.1 Hz, 1H), 6.54 (d, J=8.3 Hz, 1H), 5.32 (dd, J=6.8, 3.6 Hz, 1H), 4.74-4.64 (m, 2H), 4.64-4.57 (m, 1H), 4.43 (d, J=13.5 Hz, 1H), 3.27-3.15 (m, 2H), 2.97 (ddd, J=16.1, 8.7, 4.6 Hz, 1H), 2.72 (t, J=12.7 Hz, 1H), 2.67-2.58 (m, 1H), 2.52-2.41 (m, 1H), 2.12-2.03 (m, 1H), 2.03-1.95 (m, 1H), 1.90 (d, J=13.1 Hz, 1H), 1.85-1.77 (m, 1H), 1.65 (s, 3H), 1.62-1.41 (m, 2H), 0.92-0.85 (m, 2H), 0.85-0.78 (m, 2H). HRMS; calcd. for $C_{36}H_{37}F_3N_5O_3$ (M+H) 644.2848, found 644.2682.

Example 58

Example 58-A. (±)-Ethyl 5-methyl-1-(6-(3-((2-methyl-4-(1-(5-methyl-1,3,4-oxadiazol-2-yl)piperidin-4-yl)phenyl)amino)-2,3-dihydro-1H-inden-4-yl)pyridin-2-yl)-1H-pyrazole-4-carboxylate

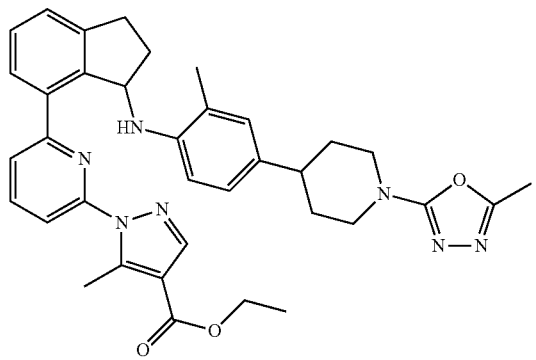 [SMILES: CCOC(=O)c1cnn(-c2cccc(-c3cccc4c3C(Nc3ccc(C5CCN(c6nnc(C)o6)CC5)cc3C)CC4)n2)c1C]

DIPEA (62 µl, 0.355 mmol) was added to a solution of (±)-ethyl 5-methyl-1-(6-(3-((2-methyl-4-(piperidin-4-yl)phenyl)amino)-2,3-dihydro-1H-inden-4-yl)pyridin-2-yl)-1H-pyrazole-4-carboxylate (Example 45-8) (95 mg, 0.177 mmol) and 2-bromo-5-methyl-1,3,4-oxadiazole (CAS #864750-58-3, 29 mg, 0.177 mmol) in EtOH (1.8 ml) and the resulting mixture was stirred at 68° C. 1.5 hour. The reaction mixture was cooled to room temperature and then concentrated. The resulting residue was purified by silica gel flash chromatography (0-75% EtOAc in heptane then 10% MeOH in CH$_2$Cl$_2$) to afford the title compound. MS (ESI+) m/z 618.5 (M+H).

Example 58. a). (±)-8-Methyl-1-(6-(3-((2-methyl-4-(1-(5-methyl-1,3,4-oxadiazol-2-yl)piperidin-4-yl)phenyl)amino)-2,3-dihydro-1H-inden-4-yl)pyridin-2-yl)-1H-pyrazole-4-carboxylic Acid

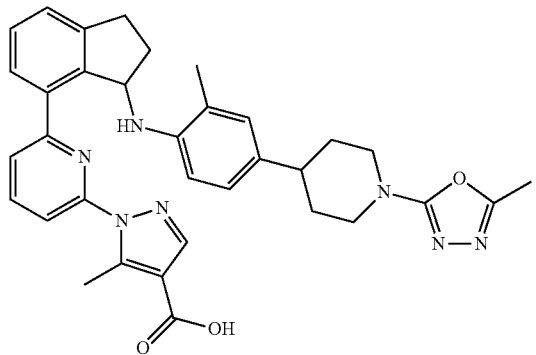 [SMILES: Cc1nnc(N2CCC(c3ccc(NC4CCc5cccc(-c6cccc(-n7ncc(C(=O)O)c7C)n6)c54)c(C)c3)CC2)o1]

The title compound was synthesized by saponification of (±)-ethyl 5-methyl-1-(6-(3-((2-methyl-4-(1-(5-methyl-1,3,4-oxadiazol-2-yl)piperidin-4-yl)phenyl)amino)-2,3-dihydro-1H-inden-4-yl)pyridin-2-yl)-1H-pyrazole-4-carboxylate by the method as described for the preparation of Example 7a, followed by RP-HPLC purification (HC-A). $^1$H NMR (400 MHz, Methanol-$d_4$) δ 7.92-7.85 (m, 2H), 7.73 (d, J=7.7 Hz, 1H), 7.58-7.50 (m, 2H), 7.48-7.38 (m, 2H), 6.80 (d, J=8.0 Hz, 1H), 6.71 (s, 1H), 6.55 (d, J=8.2 Hz, 1H), 5.33 (dd, J=6.8, 3.4 Hz, 1H), 4.01 (d, J=12.9 Hz, 2H), 3.25-3.16 (m, 3H), 3.01-2.92 (m, 1H), 2.62-2.51 (m, 4H), 2.51-2.42 (m, 1H), 2.39 (s, 3H), 2.13-2.04 (m, 1H), 1.86 (d, J=13.6 Hz, 2H), 1.74-1.62 (m, 5H). HRMS; calcd. for $C_3H_{36}N_7O_3$ (M+H) 590.2880, found 590.2786.

Example 58. b). (+)-5-Methyl-1-(6-(3-((2-methyl-4-(1-(5-methyl-1,3,4-oxadiazol-2-yl)piperidin-4-yl)phenyl)amino)-2,3-dihydro-1H-inden-4-yl)pyridin-2-yl)-1H-pyrazole-4-carboxylic acid and (−)-5-Methyl-1-(6-(3-((2-methyl-4-(1-(5-methyl-1,3,4-oxadiazol-2-yl)piperidin-4-yl)phenyl)amino)-2,3-dihydro-1H-inden-4-yl)pyridin-2-yl)-1H-pyrazole-4-carboxylic Acid Resolution of the enantiomers of (±)-5-methyl-1-(6-(3-((2-methyl-4-(1-(5-methyl-1,3,4-oxadiazol-2-yl)piperidin-4-yl)phenyl)amino)-2,3-dihydro-1H-inden-4-yl)pyridin-2-yl)-1H-pyrazole-4-carboxylic acid was achieved by chiral SFC using CHIRALPAK® AD-H column with 5-55% IPA gradient in $CO_2$ to give (−)-5-methyl-1-(6-(3-((2-methyl-4-(1-(5-methyl-1,3,4-oxadiazol-2-yl)piperidin-4-yl)phenyl)amino)-2,3-dihydro-1H-inden-4-yl)pyridin-2-yl)-1H-pyrazole-4-carboxylic acid ($t_r$=3.64 min) and (+)-5-methyl-1-(6-(3-((2-methyl-4-(1-(5-methyl-1,3,4-oxadiazol-2-yl)piperidin-4-yl)phenyl)amino)-2,3-dihydro-1H-inden-4-yl)pyridin-2-yl)-1H-pyrazole-4-carboxylic acid ($t_r$=3.88 min). $^1$H NMR and HRMS data for (+)- and (−)-enantiomers were substantially identical to (±)-5-methyl-1-(6-(3-((2-methyl-4-(1-(5-methyl-1,3,4-oxadiazol-2-yl)piperidin-4-yl)phenyl)amino)-2,3-dihydro-1H-inden-4-yl)pyridin-2-yl)-1H-pyrazole-4-carboxylic acid.

Example 59

Example 59-A. (±)-Ethyl 5-methyl-1-(6-(3-((2-methyl-4-(1-(pyridin-2-yl)piperidin-4-yl)phenyl)amino)-2,3-dihydro-1H-inden-4-yl)pyridin-2-yl)-1H-pyrazole-4-carboxylate

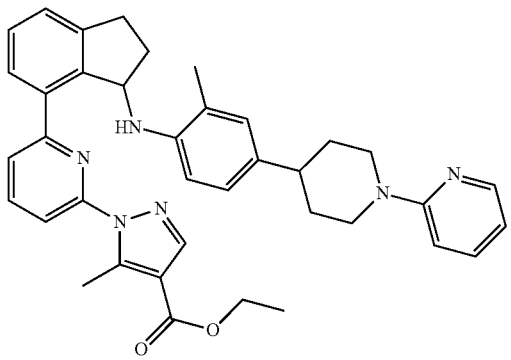 [SMILES: CCOC(=O)c1cnn(-c2cccc(-c3cccc4c3C(Nc3ccc(C5CCN(c6ccccn6)CC5)cc3C)CC4)n2)c1C]

Chloro-(2-dicyclohexylphosphino-2'8'-diisopropoxy-1,1'-biphenyl)[2-(2-aminoethyl)phenyl]palladium(II)-methyl-t-butyl ether adduct (CAS #1028206-60-1, 7.8 mg, 9.5 µmol) was added to a solution of (+)-ethyl 5-methyl-1-(6-(3-((2-methyl-4-(piperidin-4-yl)phenyl)amino)-2,3-dihydro-1H-inden-4-yl)pyridin-2-yl)-1H-pyrazole-4-carboxylate (Example 45-B) (102 mg, 0.190 mmol), sodium tert-butoxide (CAS #865-48-5, 26 mg, 0.267 mmol), and 2-chloropyridine (CAS #109-09-1, 17.7 µl, 0.189 mmol) in THF (1.9 mL). The resulting reaction mixture was stirred at 68° C. for 1 hour. The reaction mixture was diluted with EtOAc. The organic phase was then washed successively with water and brine, and then concentrated with onto Celite®. The resulting residue was purified by silica gel flash chromatography (0-50% EtOAc in heptane) to afford the title compound. MS (ESI+) m/z 613.6 (M+H).

Example 59. (±)-Methyl-16-(3-((2-methyl-4-(1-(pyridin-2-yl)piperidin-4-yl)phenyl)amino)-2,3-dihydro-1H-inden-4-yl)pyridin-2-yl)-1H-pyrazole-4-carboxylic Acid

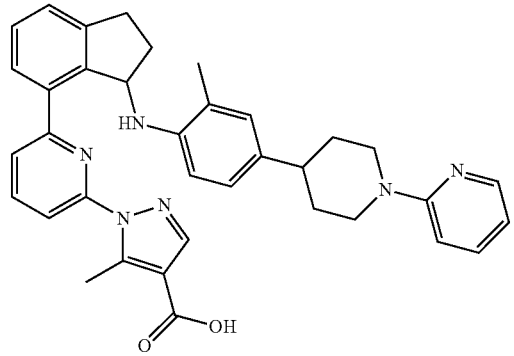 [SMILES: Cc1cc(C2CCN(c3ccccn3)CC2)ccc1NC1CCc2cccc(-c3cccc(-n4ncc(C(=O)O)c4C)n3)c21]

(±)-Ethyl 5-methyl-1-(6-(3-((2-methyl-4-(1-(pyridin-2-yl)piperidin-4-yl)phenyl)amino)-2,3-dihydro-1H-inden-4-yl)pyridin-2-yl)-1H-pyrazole-4-carboxylate was saponified as described for the preparation of Example 1. a) to give the title compound after RP-HPLC purification (HC-B). $^1$H NMR (400 MHz, Methanol-$d_4$) δ 8.08-8.04 (m, 1H), 7.90 (s, 1H), 7.86 (t, J=7.9 Hz, 1H), 7.71 (d, J=7.7 Hz, 1H), 7.59-7.51 (m, 3H), 7.45-7.38 (m, 2H), 6.86 (d, J=8.7 Hz, 1H), 6.81 (d, J=8.5 Hz, 1H), 6.72 (s, 1H), 6.65-6.60 (m, 1H), 6.56 (d, J=8.2 Hz, 1H), 5.35 (dd, J=7.1, 3.4 Hz, 1H), 4.34 (d, J=12.5 Hz, 2H), 3.24-3.15 (m, 1H), 3.01-2.86 (m, 3H), 2.63 (s, 3H), 2.61-2.53 (m, 1H), 2.53-2.41 (m, 1H), 2.14-2.04 (m, 1H), 1.85 (d, J=13.0 Hz, 2H), 1.70-1.57 (m, 5H). HRMS; calcd. for $C_{36}H_{37}N_6O_2$ (M+H) 585.2978, found 585.2985.

Example 60

Example 60-A. (±)-Ethyl 1-(6-(3-((4-(1-cyclopropylpiperidin-4-yl)-2-methylphenyl)amino)-2,3-dihydro-1H-inden-4-yl)pyridin-2-yl)-8-methyl-1H-pyrazole-4-carboxylate

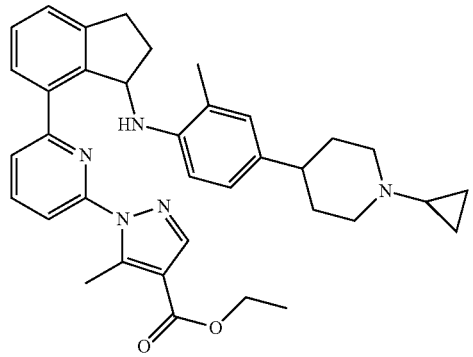 [SMILES: CCOC(=O)c1cnn(-c2cccc(-c3cccc4c3C(Nc3ccc(C5CCN(C6CC6)CC5)cc3C)CC4)n2)c1C]

(1-Ethoxycyclopropoxy)trimethylsilane (CAS #74-25-0; 35 µl, 0.174 mmol) was added to a solution of (±)-ethyl 5-methyl-1-(6-(3-((2-methyl-4-(piperidin-4-yl)phenyl)amino)-2,3-dihydro-1H-inden-4-yl)pyridin-2-yl)-1H-pyrazole-4-carboxylate (Example 45-B) (95 mg, 0.177 mmol), sodium cyanoborohydride (CAS #25895-60-7, 22.3 mg, 0.355 mmol), and acetic acid (1.0 µl, 0.018 mmol) in MeOH (1.8 mL) at room temperature. The resulting reaction mixture was heated to 50° C. for 24 h. The reaction mixture was cooled to room temperature, and then diluted with $CH_2Cl_2$ and saturated sodium bicarbonate. The organic layer was passed through an ISOLUTE® Phase Separator and the organic layer was concentrated to furnish the title compound. MS (ESI+) m/z 576.5 (M+H).

Example 60. (±)-1-(6-(3-(4-(1-Cyclopropylpiperidin-4-yl)-2-methylphenyl)amino)-2,3-dihydro-1H-inden-4-yl)pyridin-2-yl)-5-methyl-1H-pyrazole-4-carboxylic Acid

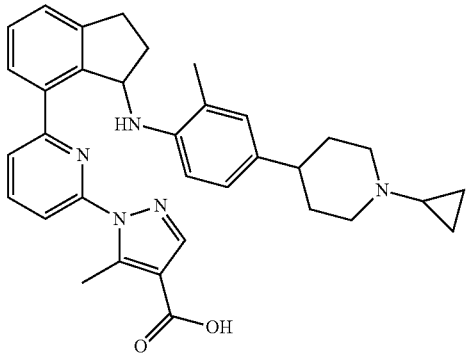 [SMILES: Cc1cc(C2CCN(C3CC3)CC2)ccc1NC1CCc2cccc(-c3cccc(-n4ncc(C(=O)O)c4C)n3)c21]

(±)-Ethyl 1-(6-(3-((4-(1-cyclopropylpiperidin-4-yl)-2-methylphenyl)amino)-2,3-dihydro-1H-inden-4-yl)pyridin-2-yl)-5-methyl-1H-pyrazole-4-carboxylate was saponified as described for the synthesis of Example 1. a) to give the title compound, after RP-HPLC purification (HC-C). $^1$H NMR (400 MHz, Methanol-$d_4$) δ 7.90 (t, J=7.9 Hz, 1H), 7.86 (s, 1H), 7.71 (dd, J=7.8, 0.9 Hz, 1H), 7.54 (dd, J=6.4, 2.4 Hz, 1H), 7.48 (dd, J=7.9, 0.8 Hz, 1H), 7.45-7.38 (m, 2H), 6.77 (dd, J=8.2, 2.2 Hz, 1H), 6.68 (d, J=2.2 Hz, 1H), 6.52 (d, J=8.3 Hz, 1H), 5.30 (dd, J=7.0, 3.3 Hz, 1H), 3.44-3.37 (m, 2H), 3.24-3.15 (m, 1H), 3.01-2.91 (m, 1H), 2.77 (t, J=12.2 Hz, 2H), 2.57-2.39 (m, 5H), 2.23 (s, 1H), 2.12-2.03 (m, 1H), 1.90 (d, J=13.9 Hz, 2H), 1.82-1.67 (m, 2H), 1.63 (s, 3H), 0.74 (d, J=7.7 Hz, 4H). HRMS; calcd. for $C_{34}H_{38}N_5O_2$(M+H) 548.3026, found 548.3041.

Example 61. a). (±)-1-(6-(3-(4-(1-(Cyclopropanecarbonyl)piperidin-4-yl)-2-(trifluoromethyl)phenoxy)-2,3-dihydro-1H-inden-4-yl)pyridin-2-yl)-5-(trifluoromethyl)-1H-pyrazole-4-carboxylic Acid

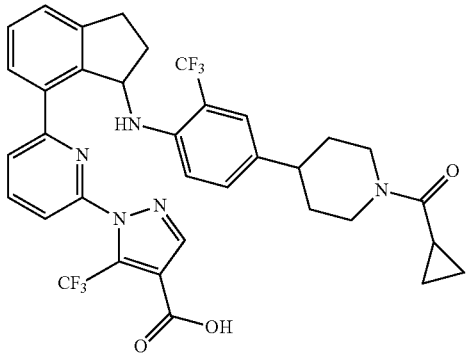 [SMILES: O=C(O)c1cnn(-c2cccc(-c3cccc4c3C(Nc3ccc(C5CCN(C(=O)C6CC6)CC5)cc3C(F)(F)F)CC4)n2)c1C(F)(F)F]

The title compound was synthesized by reaction of ethyl 1-(6-bromopyridin-2-yl)-5-(trifluoromethyl)-1H-pyrazole-4-carboxylate (Intermediate 1-1) with (±)-(4-(4-((7-bromo-2,3-dihydro-1H-inden-1-yl)oxy)-3-(trifluoromethyl)phenyl)piperidin-1-yl)(cyclopropyl)methanone (Intermediate 3-4-6) by the similar method as described for the synthesis of Example 3. $^1$H NMR (400 MHz, Methanol-$d_4$) δ 7.95 (dd, J=7.8, 8.0 Hz, 1H), 7.82-7.89 (m, 2H), 7.68 (d, J=7.5 Hz, 1H), 7.41-7.52 (m, 3H), 7.23 (d, J=2.2 Hz, 1H), 7.17 (dd, J=2.2, 8.6 Hz, 1H), 6.94 (d, J=8.6 Hz, 1H), 6.66 (dd, J=2.4, 6.6 Hz, 1H), 4.61-4.71 (m, 1H), 4.43-4.53 (m, 1H), 3.14-3.26 (m, 1H), 2.94-3.04 (m, 1H), 2.71-2.85 (m, 2H), 2.47-2.58 (m, 1H), 2.06-2.16 (m, 1H), 1.82-2.05 (m, 3H), 1.43-1.70 (m, 2H), 0.77-0.95 (m, 4H). HRMS; calcd $C_{35}H_{31}F_6N_4O_4$(M+H) 685.2249, found 685.2261.

Example 61. b). (+)- or (−)-1-(6-(3-(4-(1-(Cyclopropanecarbonyl)piperidin-4-yl)-2-(trifluoromethyl)phenoxy)-2,3-dihydro-1H-inden-4-yl)pyridin-2-yl)-5-(trifluoromethyl)-1H-pyrazole-4-carboxylic acid (Enantiomer-1) and (−)- or (+)-1-(6-(3-(4-(1-(cyclopropanecarbonyl)piperidin-4-yl)-2-(trifluoromethyl)phenoxy)-2,3-dihydro-1H-inden-4-yl)pyridin-2-yl)-5-(trifluoromethyl)-1H-pyrazole-4-carboxylic acid (Enantiomer-2)

Resolution of the enantiomers of (±)-1-(6-(3-(4-(1-(cyclopropanecarbonyl)piperidin-4-yl)-2-(trifluoromethyl)phenoxy)-2,3-dihydro-1H-inden-4-yl)pyridin-2-yl)-5-(trifluoromethyl)-1H-pyrazole-4-carboxylic acid was achieved by chiral SFC using CHIRALPAK® AD-H column with 25% IPA in $CO_2$ to give (+)- or (−)-1-(6-(3-(4-(1-(cyclopropanecarbonyl)piperidin-4-yl)-2-(trifluoromethyl)phenoxy)-2,3-dihydro-1H-inden-4-yl)pyridin-2-yl)-5-(trifluoromethyl)-1H-pyrazole-4-carboxylic acid (enantiomer-1, $t_r$=2.7 min) and (−)- or (+)-1-(6-(3-(4-(1-(cyclopropanecarbonyl)piperidin-4-yl)-2-(trifluoromethyl)phenoxy)-2,3-dihydro-1H-inden-4-yl)pyridin-2-yl)-5-(trifluoromethyl)-1H-pyrazole-4-carboxylic acid (enantiomer-2, $t_r$=3.9 min). $^1$H NMR and HRMS were substantially identical to (±)-1-(6-(3-(4-(1-(cyclopropanecarbonyl)piperidin-4-yl)-2-(trifluoromethyl)phenoxy)-2,3-dihydro-1H-inden-4-yl)pyridin-2-yl)-5-(trifluoromethyl)-1H-pyrazole-4-carboxylic acid.

Example 62

Example 62-A. (±)-Ethyl 1-(6-(3-((tert-butoxycarbonyl)amino)-2,3-dihydro-1H-inden-4-yl)pyridin-2-yl)-5-methyl-1H-pyrazole-4-carboxylate

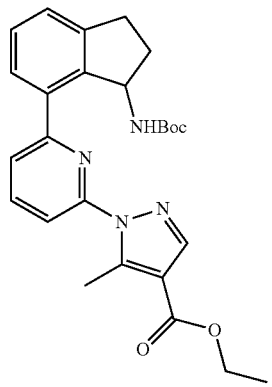 [SMILES: CCOC(=O)c1cnn(-c2cccc(-c3cccc4c3C(NC(=O)OC(C)(C)C)CC4)n2)c1C]

The title compound was synthesized by an analogous method as the preparation of Example 35-A but using tert-butyl (7-bromo-2,3-dihydro-1H-inden-1-yl)carbamate (ACS Med. Chem. Lett. 2011, 2, 565-570) instead of (±)-tert-butyl 4-(4-((4-bromo-2,3-dihydrobenzofuran-3-yl)amino)-3-methylphenyl)piperidine-1-carboxylate (Intermediate 3-11). (ESI+) m/z 463.3 (M+H).

Example 62-B. (±)-Ethyl 1-(6-(3-amino-2,3-dihydro-1H-inden-4-yl)pyridin-2-yl)-6-methyl-1H-pyrazole-4-carboxylate

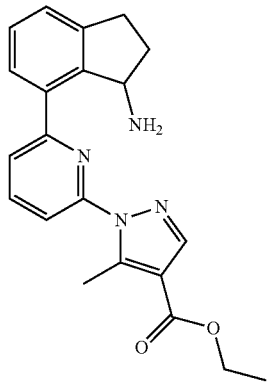 [SMILES: CCOC(=O)c1cnn(-c2cccc(-c3cccc4c3C(N)CC4)n2)c1C]

The title compound was synthesized by deprotection of (+)-ethyl 1-(6-(3-((tert-butoxycarbonyl)amino)-2,3-dihydro-1H-inden-4-yl)pyridin-2-yl)-5-methyl-1H-pyrazole-4-carboxylate by a similar method as described for the synthesis of Intermediate 6-1-E. MS (ESI+) m/z 363.0 (M+H).

Example 62-C. tert-Butyl 6-chloro-1-methyl-5',6'-dihydro-[3,4'-bipyridine]-1'(2'H)-carboxylate

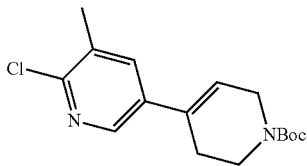 [SMILES: Cc1cc(C2=CCN(C(=O)OC(C)(C)C)CC2)cnc1Cl]

To a suspension of (6-chloro-5-methylpyridin-3-yl)boronic acid (CAS #1003043-40-0, 0.51 g, 2.98 mmol), tert-butyl 4-bromo-5,6-dihydropyridine-1 (2H)-carboxylate (CAS #159503-91-0, 0.975 g, 3.72 mmol) in toluene (7.4 ml) and MeOH (7.4 ml) was added potassium carbonate (2M in water: 3.7 ml, 7.4 mmol), followed by Pd(dppf)Cl$_2$·CH$_2$Cl$_2$ adduct (0.24 g, 0.3 mmol). The mixture was stirred at 90° C. for 0.75 h, and then cooled to room temperature. The reaction mixture was diluted with EtOAc. The mixture was then washed with H$_2$O, and then passed through an ISOLUTE® Phase Separator and concentrated. The residue was purified by silica gel flash column chromatography (0-50% EtOAc in heptane) to afford the title compound. MS (ESI+) m/z 309.2 (M+H).

Example 62-D. (6-Chloro-5-methyl-6',6'-dihydro-[3,4'-bipyridin]-1'(2'H)-yl)(cyclopropyl)methanone

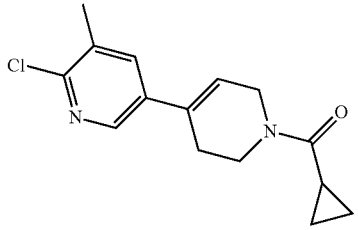 [SMILES: Cc1cc(C2=CCN(C(=O)C3CC3)CC2)cnc1Cl]

The title compound was synthesized in an analogous manner to the preparation of Intermediate 2-3. MS (ESI+) m/z 277.3 (M+H).

Example 62-E. (±)-Ethyl 1-(6-(3-((1'-cyclopropanecarbonyl)-5-methyl-1',2',3',6'-tetrahydro-[3,4'-bipyridin]-6-yl)amino)-2,3-dihydro-1H-inden-4-yl)pyridin-2-yl)-5-methyl-1H-pyrazole-4-carboxylate

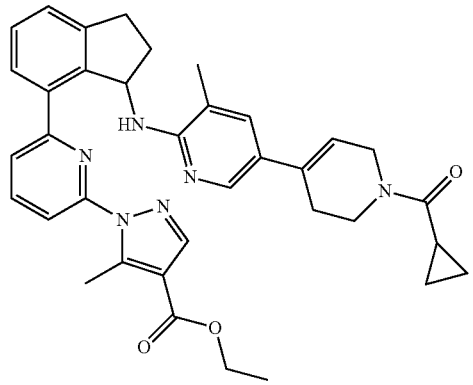 [SMILES: CCOC(=O)c1cnn(-c2cccc(-c3cccc4c3C(Nc3ncc(C5=CCN(C(=O)C6CC6)CC5)cc3C)CC4)n2)c1C]

To a suspension of ethyl 1-(6-(3-amino-2,3-dihydro-1H-inden-4-yl)pyridin-2-yl)-5-methyl-1H-pyrazole-4-carboxylate (Example 62-8) (50 mg, 0.138 mmol), sodium tert-butoxide (32 mg, 0.33 mmol), and (6-chloro-5-methyl-5',6'-dihydro-[3,4'-bipyridin]-1'(2'H)-yl)(cyclopropyl)methanone (Example 62-D) (38 mg, 0.138 mmol) in dioxane (1.4 mL) were added chloro-(2-dicyclohexylphosphino-2',6'-diisopropoxy-1,1'-biphenyl)[2-(2-aminoethyl)phenyl]palladium (II)-methyl-t-butyl ether adduct (CAS #1028206-60-1; 5.4 mg, 6.90 µmol) and 2-dicyclohexylphosphino-2',4',6'-triisopropylbiphenyl (CAS #564483-18-7, 3.3 mg, 6.90 µmol). The mixture was then stirred at 80° C. for 20 h. The reaction mixture was diluted with EtOAc and filtered through a plug of Celite®, and then the filtrate was concentrated onto Celite®. The residue was purified by silica gel flash column chromatography (0-50% EtOAc in heptane) to afford the title compound. MS (ESI+) m/z 603.2 (M+H).

Example 62-F. (±)-Ethyl 1-(6-(3-((5-(1-(cyclopropanecarbonyl)piperidin-4-yl)-3-methylpyridin-2-yl)amino)-2,3-dihydro-1H-inden-4-yl)pyridin-2-yl)-5-methyl-1H-pyrazole-4-carboxylate

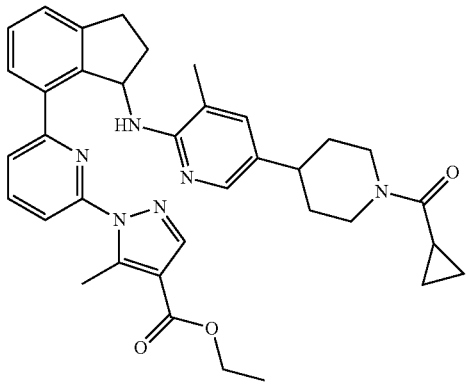 [SMILES: CCOC(=O)c1cnn(-c2cccc(-c3cccc4c3C(Nc3ncc(C5CCN(C(=O)C6CC6)CC5)cc3C)CC4)n2)c1C]

A mixture of (±)-ethyl 1-(6-(3-((1'-(cyclopropanecarbonyl)-5-methyl-1',2',3',6'-tetrahydro-[3,4'-bipyridin]-6-yl)amino)-2,3-dihydro-1H-inden-4-yl)pyridin-2-yl)-5-methyl-1H-pyrazole-4-carboxylate (30 mg, 0.05 mmol) and Pd/C (10%, 5 mg, 0.05 mmol) in EtOH (0.5 mL) was stirred under H$_2$ atmosphere at room temperature for 12 h. The mixture was filtered through a plug of Celite®, which was rinsed with MeOH. The filtrate was concentrated to furnish the title compound. MS (ESI+) m/z 605.5 (M+H).

Example 62. (±)-1-(6-(3-((5-(1-Cyclopropanecarbonyl)piperidin-4-yl)-3-methylpyridin-2-yl)amino)-2,3-dihydro-1H-inden-4-yl)pyridin-2-yl)-5-methyl-1H-pyrazole-4-carboxylic Acid

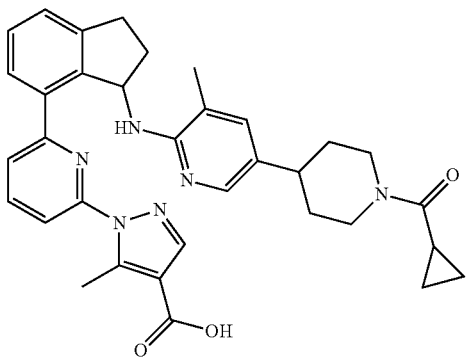 [SMILES: Cc1cc(C2CCN(C(=O)C3CC3)CC2)cnc1NC1CCc2cccc(-c3cccc(-n4ncc(C(=O)O)c4C)n3)c21]

The title compound was synthesized by saponification of (±)-ethyl 1-(6-(3-((5-(1-(cyclopropanecarbonyl)piperidin-4-yl)-3-methylpyridin-2-yl)amino)-2,3-dihydro-1H-inden-4-yl)pyridin-2-yl)-5-methyl-1H-pyrazole-4-carboxylate by a similar manner as described for the preparation of Example 7a. $^1$H NMR (400 MHz, Methanol-d$_4$) δ 7.87-7.80 (m, 2H), 7.60 (dd, J=7.7, 0.9 Hz, 1H), 7.54-7.49 (m, 2H), 7.46-7.39 (m, 2H), 7.34 (d, J=2.3 Hz, 1H), 7.16-7.10 (m, 1H), 5.95 (t, J=7.0 Hz, 1H), 4.64 (d, J=13.3 Hz, 1H), 4.47 (d, J=13.6 Hz, 1H), 3.27-3.22 (m, 1H), 3.21-3.11 (m, 1H), 3.06-2.94 (m, 1H), 2.79-2.60 (m, 6H), 2.06-1.76 (m, 4H), 1.62-1.40 (m, 5H), 0.95-0.86 (m, 2H), 0.86-0.78 (m, 2H). HRMS; calcd. for C$_{34}$H$_{37}$N$_6$O$_3$ (M+H) 577.2927, found 577.2922.

Example 63

Example 63-A. a). (+) Ethyl 1-(6-(3-((5-(1-(cyclopropanecarbonyl)piperidin-4-yl)-6-ethylpyridin-2-yl)amino)-2,3-dihydro-1H-inden-1-yl)pyridin-2-yl)-5-ethyl-1H-pyrazole-4-carboxylate

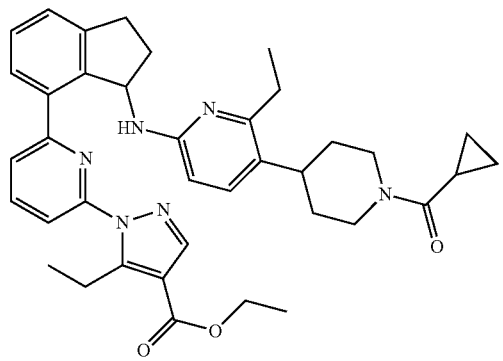 [SMILES: CCOC(=O)c1cnn(-c2cccc(-c3cccc4c3C(Nc3ccc(C5CCN(C(=O)C6CC6)CC5)c(CC)n3)CC4)n2)c1CC]

The title compound was synthesized by an analogous method as described for the synthesis of (±)-tert-butyl 4-(4-((7-(6-(4-(ethoxycarbonyl)-5-ethyl-1H-pyrazol-1-yl)pyridin-2-yl)-2,3-dihydro-1H-inden-1-yl)methyl)-2-ethylphenyl)piperidine-1-carboxylate (Example 39-A) but starting with ethyl 1-(6-bromopyridin-2-yl)-5-ethyl-1H-pyrazole-4-carboxylate (Intermediate 1-4-2) and (±)-tert-butyl 4-(6-((7-bromo-2,3-dihydro-1H-inden-1-yl)amino)-2-ethylpyridin-3-yl)piperidine-1-carboxylate (Intermediate 3-12). The resulting Boc protected compound can be reacted in accordance with the procedure described as Example 45-B, and the resulting amine can be reacted with cyclopropanecarboxylic acid in a fashion similar to the method used for Example 45-C. a). MS (ESI+) m/z 633.4 (M+H).

Example 63-A. b). Ethyl 1-(6-(3-((5-(1-(cyclopropanecarbonyl)piperidin-4-yl)-6-ethylpyridin-2-yl)amino)-2,3-dihydro-1H-inden-4-yl)pyridin-2-yl)-5-ethyl-1H-pyrazole-4-carboxylate (Enantiomer-1) and ethyl 1-(6-(3-((5-(1-(cyclopropanecarbonyl)piperidin-4-yl)-6-ethylpyridin-2-yl)amino)-2,3-dihydro-1H-inden-4-yl)pyridin-2-yl)-5-ethyl-1H-pyrazole-4-carboxylate (Enantiomer-2)

Resolution of the enantiomers of (±)-ethyl 1-(6-(3-((5-(1-(cyclopropanecarbonyl)piperidin-4-yl)-6-ethylpyridin-2-yl)amino)-2,3-dihydro-1H-inden-4-yl)pyridin-2-yl)-5-ethyl-1H-pyrazole-4-carboxylate was achieved by chiral SFC using CHIRALPAK® AD-H column with 5% to 55% MeOH gradient in CO$_2$ to give ethyl 1-(6-(3-((5-(1-(cyclopropanecarbonyl)piperidin-4-yl)-6-ethylpyridin-2-yl)amino)-2,3-dihydro-1H-inden-4-yl)pyridin-2-yl)-5-ethyl-1H-pyrazole-4-carboxylate (enantiomer-1, t$_r$=6.0 min) and (ethyl 1-(6-(3-(5-(1-(cyclopropanecarbonyl)piperidin-4-yl)-6-ethylpyridin-2-yl)amino)-2,3-dihydro-1H-inden-4-yl)pyridin-2-yl)-5-ethyl-1H-pyrazole-4-carboxylate (enantiomer-2, t$_r$=10.6 min).

Example 63a. (+)-1-(6-(3-((5-(1-(Cyclopropanecarbonyl) piperidin-4-yl)-6-ethylpyridin-2-yl)amino)-2,3-dihydro-1H-inden-4-yl)pyridin-2-yl)-5-ethyl-1H-pyrazole-4-carboxylic Acid

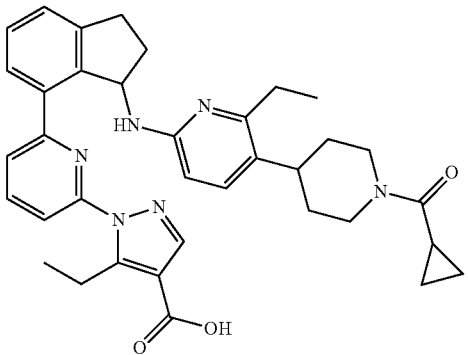 [SMILES: CCc1nc(NC2CCc3cccc(-c4cccc(-n5ncc(C(=O)O)c5CC)n4)c32)ccc1C1CCN(C(=O)C2CC2)CC1]

Saponification of ethyl 1-(6-(3-((5-(1-(cyclopropanecarbonyl)piperidin-4-yl)-6-ethylpyridin-2-yl)amino)-2,3-dihydro-1H-inden-4-yl)pyridin-2-yl)-5-ethyl-1H-pyrazole-4-carboxylate (enantiomer-2, $t_r$=3.9 min) similarly to the preparation of Example 7a afforded the title compound. $^1$H NMR (400 MHz, Methanol-$d_4$) δ 7.91 (s, 1H) 7.77-7.86 (m, 1H) 7.70 (d, J=7.7 Hz, 1H) 7.54-7.58 (m, 1H) 7.52 (d, J=8.08 Hz, 1H) 7.34-7.43 (m, 2H) 7.19 (d, J=8.97 Hz, 1H) 6.17 (t, J=8.02 Hz, 1H) 5.65-5.84 (m, 1H) 4.65 (d, J=13.14 Hz, 1H) 4.47 (d, J=14.02 Hz, 1H) 3.33-3.44 (m, 3H) 3.12-3.23 (m, 1H) 2.83-3.03 (m, 2H) 2.67-2.82 (m, 1H) 2.55-2.67 (m, 2H) 2.38-2.54 (m, 1H) 1.93-2.12 (m, 2H) 1.67-1.89 (m, 2H) 1.40-1.67 (m, 2H) 1.16 (t, J=7.52 Hz, 3H) 1.10 (t, J=7.26 Hz, 3H) 0.74-0.98 (m, 4H). HRMS; calcd. for $C_{36}H_{41}N_6O_3$ (M+H) 605.3235, found 605.3184.

Example 63b. (−)-1-(6-(3-((5-(1-(Cyclopropanecarbonyl) piperidin-4-yl)-6-ethylpyridin-2-yl)amino)-2,3-dihydro-1H-inden-4-yl)pyridin-2-yl)-5-ethyl-1H-pyrazole-4-carboxylic Acid The title compound was synthesized from ethyl 1-(6-(3-((5-(1-(cyclopropanecarbonyl)piperidin-4-yl)-6-ethylpyridin-2-yl)amino)-2,3-dihydro-1H-inden-4-yl)pyridin-2-yl)-5-ethyl-1H-pyrazole-4-carboxylate (enantiomer-1, $t_r$=3.7 min) by a similar manner as described for the synthesis of Example 7a. $^1$H NMR and HRMS data were substantially identical to Example 63a.

Example 64

The following compounds were synthesized by the similar method as outlined for the synthesis of Example 29 but using either a chloroformate or a sulfonyl chloride as outlined in the table below instead of using ethyl chloroformate as in Example 29-C.

| Example | Chemical structure $^1$HNMR and HRMS data | IUPAC name chloroformate or sulfonyl chloride |
|---|---|---|
| 64-1 | [structure] $^1$H NMR (400 MHz, Methanol-$d_4$) δ 7.86-7.95 (m, 2 H) 7.72 (dd, J = 7.8, 0.8 Hz, 1 H) 7.57-7.63 (m, 2 H) 7.41-7.51 (m, 2 H) 7.36-7.39 (m, 3 H) 7.29-7.36 (m, 1 H) 6.94 (d, J = 8.5 Hz, 1 H) 6.53 (dd, J = 8.5, 2.7 Hz, 1 H) 6.48 (d, J = 2.7 Hz, 1 H) 6.17 (dd, J = 6.1, 2.5 Hz, 1 H) 5.14 (s, 2 H) 4.27 (d, J = 11.4 Hz, 2 H) 3.12-3.28 (m, 3 H) 2.82-3.03 (m, 4 H) 2.52-2.61 (m, 2 H) 2.39-2.50 (m, 1 H) 2.17-2.26 (m, 1 H) 1.64-1.73 (m, 2 H) 1.50-1.63 (m, 2 H) 1.35-1.40 (m, 1 H) 1.08-1.16 (m, 6 H). HRMS; calcd. for $C_{41}H_{43}N_4O_5$ (M + H) 671.3233, found 671.3233. | (S)-1-(6-(3-(4-(1-((Benzyloxy)carbonyl)pipendin-4-yl)-3-ethylphenoxy)-2,3-dihydro-1H-inden-4-yl)pyridin-2-yl)-5-ethyl-1H-pyrazole-4-carboxylic acid<br>Benzyl chloroformate |

-continued

| Example | Chemical structure<br>¹HNMR and HRMS data | IUPAC name<br>chloroformate or sulfonyl chloride |
|---|---|---|
| 64-2 | | (S)-5-Ethyl-1-(6-(3-(3-ethyl-4-(1-(isobutoxycarbonyl)piperidin-4-yl)phenoxy)-2,3-dihydro-1H-inden-4-yl)pyridin-2-yl)-1H-pyrazole-4-carboxylic acid<br>isobutyl chloroformate |

¹H NMR (400 MHz, Methanol-d₄) δ 7.86-7.96 (m, 2 H) 7.72 (dd, J = 7.8, 0.8 Hz, 1 H) 7.57-7.64 (m, 2 H) 7.40-7.51 (m, 2 H) 6.95 (d, J = 8.6 Hz, 1 H) 6.53 (dd, J = 8.5, 2.7 Hz, 1 H) 6.49 (d, J = 2.7 Hz, 1 H) 6.17 (dd, J = 6.2, 2.4 Hz, 1 H) 4.25 (dd, J = 13.2, 1.7 Hz, 2 H) 3.88 (d, J = 6.6 Hz, 2 H) 3.16-3.28 (m, 3 H) 2.82-3.03 (m, 4 H) 2.52-2.62 (m, 2 H) 2.45 (td, J = 14.0, 8.1 Hz, 1 H) 2.25-2.18 (m, 1 H) 1.89-2.01 (m, 1 H) 1.65-1.74 (m, 2 H) 1.49-1.64 (m, 2 H) 1.12 (t, J = 7.5 Hz, 6 H) 0.94-1.00 (m, 6 H). HRMS; calcd. for C₃₈H₄₅N₄O₅ (M + H) 637.3390, found 637.3389.

| 64-3 | | (S)-5-Ethyl-1-(6-(3-(3-ethyl-4-(1-(isopropoxycarbonyl)piperidin-4-yl)-phenoxy)-2,3-dihydro-1H-inden-4-yl)-pyridin-2-yl)-1H-pyrazole-4-carboxylic acid<br>isopropyl chloroformate |

¹H NMR (400 MHz, Methanol-d₄) δ 7.86-7.96 (m, 2 H) 7.72 (dd, J = 7.7, 0.8 Hz, 1 H) 7.56-7.64 (m, 2 H) 7.40-7.51 (m, 2 H) 6.95 (d, J = 8.6 Hz, 1 H) 6.54 (dd, J = 8.5, 2.7 Hz, 1 H) 6.49 (d, J = 2.7 Hz, 1 H) 6.17 (dd, J = 6.1, 2.21 Hz, 1 H) 4.86-4.94 (m, 2 H) 4.24 (d, J = 12.3 Hz, 2 H) 3.16-3.26 (m, 2 H) 2.81-3.03(m, 4 H) 2.53-2.63 (m, 2 H) 2.39-2.51 (m, 1 H) 2.16-2.27 (m, 1 H) 1.64-1.73 (m, 2 H) 1.47-1.62 (m, 2 H) 1.24-1.31 (m, 6 H) 1.07-1.16 (m, 6 H). HRMS; calcd. for C₃₇H₄₃N₄O₅ (M + H) 623.3233, found 623.3240

| 64-4 | | (S)-5-Ethyl-1-(6-(3-(3-ethyl-4-(1-(propoxycarbonyl)piperidin-4-yl)phenoxy)-2,3-dihydro-1H-inden-4-yl)pyridin-2-yl)-1H-pyrazole-4-carboxylic acid<br>propyl chloroformate |

¹H NMR (400 MHz, Methanol-d₄) δ 7.91 (s, 1 H) 7.81-7.88 (m, 1 H) 7.68 (dd, J = 7.8, 0.8 Hz, 1 H) 7.54-7.63 (m, 2 H) 7.45 (dt, J = 14.8, 7.3 Hz, 2 H) 6.98 (d, J = 8.6 Hz, 1 H) 6.57 (dd, J = 8.5, 2.6 Hz, 1 H) 6.53 (d, J = 2.7 Hz, 1 H) 6.16 (dd, J = 6.0, 2.1 Hz, 1 H) 4.25 (d, J = 11.4 Hz, 2 H) 4.05 (t, J = 6.6 Hz, 2 H) 3.36-3.41 (m, 2 H) 3.21 (dt, J = 16.0, 7.9 Hz, 1 H) 2.81-3.02 (m, 4 H) 2.54-2.63 (m, 2 H) 2.36-2.48 (m, 1 H) 2.18-2.29 (m, 1 H) 1.50-1.75 (m, 6 H) 1.07-1.17 (m, 6 H) 0.98 (t, J = 7.5 Hz, 3 H). HRMS; calcd. for C₃₇H₄₃N₄O₅ (M + H) 623.3233, found 623.3248

-continued

| Example | Chemical structure<br>¹HNMR and HRMS data | IUPAC name<br>chloroformate or sulfonyl chloride |
|---|---|---|
| 64-5 | | (S)-1-(6-(3-(4-(1-((Allyloxy)carbonyl)-piperidin-4-yl)-3-ethylphenoxy)-2,3-dihydro-1H-inden-4-yl)pyridin-2-yl)-5-ethyl-1H-pyrazole-4-carboxylic acid<br>allyl chloroformate |

¹H NMR (400 MHz, Methanol-d₄) δ 7.84-7.96 (m, 2 H) 7.72 (dd, J = 7.7, 0.8 Hz, 1 H) 7.57-7.63 (m, 2 H) 7.39-7.51 (m, 2 H) 6.96 (d, J = 8.6 Hz, 1 H) 6.54 (dd, J = 8.6, 2.78 Hz, 1 H) 6.49 (d, J = 2.7 Hz, 1 H) 6.17 (dd, J = 6.1, 2.3 Hz, 1 H) 5.92-6.04 (m, 1 H) 5.29-5.36 (m, 1 H) 5.18-5.25 (m, 1 H) 4.60 (dt, J =5.4, 1.5 Hz, 2 H) 4.26 (d, J = 11.8 Hz, 2 H) 3.16-3.28 (m, 2 H) 2.82-3.03 (m, 5 H) 2.57 (dd, J = 7.5, 2.02 Hz, 2 H) 2.45 (d, J = 8.6 Hz; 1 H) 2.17-2.27 (m, 1 H) 1.56-1.74 (m, 2 H) 1.57 (d, J = 12.8 Hz, 2 H) 1.08-1.16 (m, 6 H). HRMS; calcd. for $C_{37}H_{41}N_4O_5$ (M + H) 621.3077, found 621.3074.

| 64-6 | | (S)-1-(6-(3-(4-(1-((Cyclopropyl-methoxy)carbonyl)piperidin-4-yl)-3-ethylphenoxy)-2,3-dihydro-1H-inden-4-yl)pyridin-2-yl)-5-ethyl-1H-pyrazole-4-carboxylic acid<br>Cyclopropylmethyl chloroformate |

¹H NMR (400 MHz, Methanol-d₄) δ 7.93 (s, 1 H) 7.86-7.91 (m, 1 H) 7.71 (dd, J = 7.8, 0.7 Hz, 1 H) 7.60 (dd, J = 8.0, 0.7 Hz, 2 H) 7.40-7.51 (m, 2 H) 6.96 (d, J = 8.6 Hz, 1 H) 6.54 (dd, J = 8.6, 2.7 Hz, 1 H) 6.50 (d, J = 2.8 Hz, 1 H) 6.17 (dd, J = 6.0, 2.3 Hz, 1 H) 4.26 (d, J = 12.1 Hz, 2 H) 3.93 (d, J = 7.2 Hz, 2 H) 3.15-3.28 (m, 3 H) 2.81-3.03 (m, 5 H) 2.54-2.61 (m, 2 H) 2.39-2.49 (m, 1 H) 2.18-2.27 (m, 1 H) 1.64-1.74 (m, 2 H) 1.50-1.64 (m, 2 H) 1.12 (td, J = 7.4, 1.5 Hz, 6 H) 0.53-0.61 (m, 2 H) 0.27-0.34 (m, 2 H). HRMS; calcd. for $C_{38}H_{43}N_4O_5$ (M + H) 635.3233, found 635.3216.

| 64-7 | | (S)-5-Ethyl-1-(6-(3-(3-ethyl-4-(1-(methoxycarbonyl)piperidin-4-yl)phenoxy)-2,3-dihydro-1H-inden-4-yl)pyridin-2-yl)-1H-pyrazole-4-carboxylic acid<br>Methyl chloroformate |

¹H NMR (400 MHz, Methanol-d₄) δ 7.91 (s, 1 H) 7.85 (dd, J = 8.0, 7.7 Hz, 1 H) 7.68 (dd, J = 7.7, 0.7 Hz, 1 H) 7.59-7.62 (m, 1 H) 7.57 (dd, J = 8.0, 0.8 Hz, 1 H) 7.44-7.50 (m, 1 H) 7.40-7.44 (m, 1 H) 6.98 (d, J = 8.6 Hz, 1 H) 6.55-6.61 (m, 1 H) 6.53 (d, J = 2.2 Hz, 1 H) 6.16 (dd, J = 6.0, 2.2 Hz, 1 H) 4.17-4.29 (m, 2 H) 3.70 (s, 3 H) 3.34-3.43 (m, 2 H) 3.16-3.26 (m, 2 H) 2.82-3.02 (m, 4 H) 2.52-2.63 (m, 2 H) 2.36-2.48 (m, 1 H) 2.19-2.28 (m, 1 H) 1.65-1.73 (m, 2 H) 1.50-1.64 (m, 2 H) 1.08-1.16 (m, 6 H). HRMS: calcd. for $C_{35}H_{39}N_4O_5$ (M + H) 595.2920, found 595.2915.

| Example | Chemical structure<br>¹HNMR and HRMS data | IUPAC name<br>chloroformate or sulfonyl chloride |
|---|---|---|
| 64-8 | 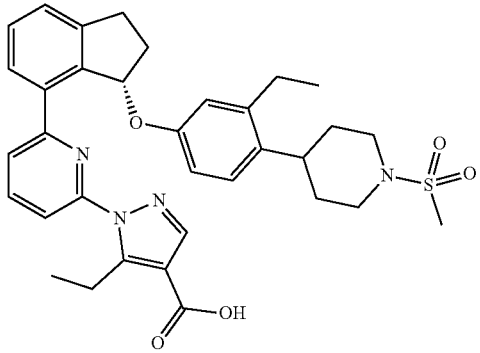 [SMILES: CCc1cc(O[C@H]2CCc3cccc(-c4cccc(-n5ncc(C(=O)O)c5CC)n4)c32)ccc1C1CCN(S(C)(=O)=O)CC1]<br>¹H NMR (400 MHz, Methanol-d₄) δ 7.91 (s, 1 H) 7.85 (dd, J = 8.0, 7.8 Hz, 1 H) 7.67 (dd, J = 7.7, 0.7 Hz, 1 H) 7.58-7.63 (m, 1 H) 7.57 (dd, J = 8.0, 0.7 Hz, 1 H) 7.39-7.50 (m, 2 H) 7.03 (d, J = 8.6 Hz, 1 H) 6.59 (dd, J = 8.5, 2.8 Hz, 1 H) 6.53 (d, J = 2.7 Hz, 1 H) 6.15-6.22 (m, 1 H) 3.78-3.88 (m, 2 H) 3.33-3.44 (m, 2 H) 3.16-3.27 (m, 1 H) 2.94-3.04 (m, 1 H) 2.74-2.91 (m, 6 H) 2.51-2.64 (m, 2 H) 2.36-2.49 (m, 1 H) 2.17-2.29 (m, 1 H) 1.67-1.87 (m, 4 H) 1.05-1.18 (m, 6 H). HRMS; calcd. for C₃₄H₃₉N₄O₅S (M + H) 615.2641, found 615.2631 | (S)-5-Ethyl-1-(6-(3-(3-ethyl-4-(1-(methylsulfonyl)piperidin-4-yl)-phenoxy)-2,3-dihydro-1H-inden-4-yl)pyridin-2-yl)-1H-pyrazole-4-carboxylic acid<br>Methanesulfonyl chloride |

Example 65

Example 65-A. (S)-tert-Butyl 4-(4-((7-(6-(4-(ethoxycarbonyl)-6-isopropyl-1H-pyrazol-1-yl)pyridin-2-yl)-2,3-dihydro-1H-inden-1-yl)oxy)-2-ethyl-phenyl)piperidine-1-carboxylate Example 65-B. (S)-Ethyl 1-(6-(3-(3-ethyl-4-(piperidin-4-yl)phenoxy)-2,3-dihydro-1H-inden-4-yl)pyridin-2-yl)-5-isopropyl-1H-pyrazole-4-carboxylate

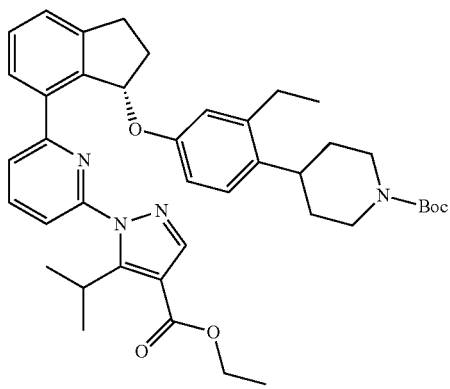 [SMILES: CCOC(=O)c1cnn(-c2cccc(-c3cccc4c3[C@@H](Oc3ccc(C5CCN(C(=O)OC(C)(C)C)CC5)c(CC)c3)CC4)n2)c1C(C)C]

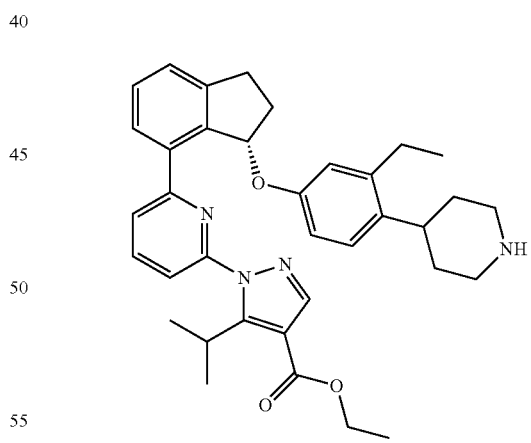

The title compound was synthesized by reaction of ethyl 1-(6-bromopyridin-2-yl)-5-isopropyl-1H-pyrazole-4-carboxylate (Intermediate 1-4-7) with (S)-tert-butyl 4-(4-((7-bromo-2,3-dihydro-1H-inden-1-yl)oxy)-2-ethylphenyl)piperidine-1-carboxylate (Intermediate 34-5) by a similar method as described for the synthesis of Example 29-A. MS (ESI+) m/z 665.5 (M+H).

The title compound was synthesized by deprotection of S-tert-butyl 4-(4-((7-(6-(4-(ethoxycarbonyl)-5-isopropyl-1H-pyrazol-1-yl)pyridin-2-yl)-2,3-dihydro-1H-inden-1-yl)oxy)-2-ethylphenyl)piperidine-1-carboxylate by a similar method as described for the synthesis of Example 29-8. MS (ESI+) m/z 579.5 (M+H).

Example 65-C. (S)-Ethyl 1-(6-(3-(4-(1-(cyclopropanecarbonyl)piperidin-4-yl)-3-ethylphenoxy)-2,3-dihydro-1H-inden-4-yl)pyridin-2-yl)-5-isopropyl-1H-pyrazole-4-carboxylate

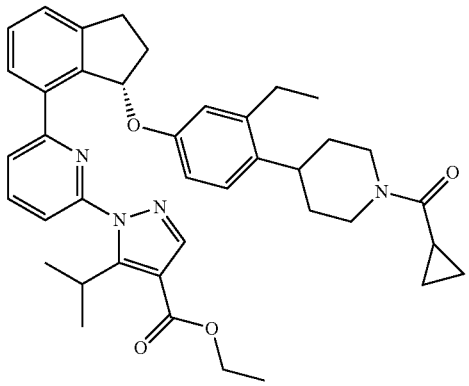 [SMILES: CCOC(=O)c1cnn(-c2cccc(-c3cccc4c3[C@@H](Oc3ccc(C5CCN(C(=O)C6CC6)CC5)c(CC)c3)CC4)n2)c1C(C)C]

The title compound was synthesized by reaction of (S)-ethyl 1-(6-(3-(3-ethyl-4-(piperidin-4-yl)phenoxy)-2,3-dihydro-1H-inden-4-yl)pyridin-2-yl)-5-isopropyl-1H-pyrazole-4-carboxylate with cyclopropanecarboxylic acid by a similar manner as described for the synthesis of Example 30-A. MS (ESI+) m/z 647.5 (M+H).

Example 65. (S)-1-(6-(3-(4-(1-(Cyclopropanecarbonyl)piperidin-4-yl)-3-ethylphenoxy)-2,3-dihydro-1H-inden-4-yl)pyridin-2-yl)-6-isopropyl-1H-pyrazole-4-carboxylic Acid

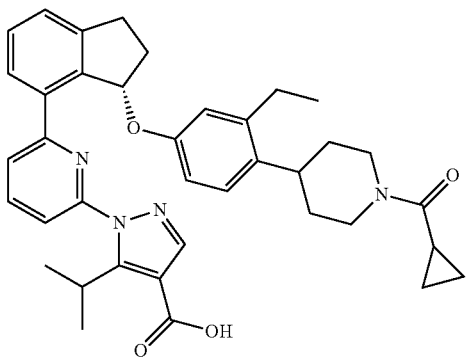 [SMILES: CCc1cc(O[C@H]2CCc3cccc(-c4cccc(-n5ncc(C(=O)O)c5C(C)C)n4)c32)ccc1C1CCN(C(=O)C2CC2)CC1]

The title compound was synthesized by saponification of (S)-ethyl 1-(6-(3-(4-(1-(cyclopropanecarbonyl)piperidin-4-yl)-3-ethylphenoxy)-2,3-dihydro-1H-inden-4-yl)pyridin-2-yl)-5-isopropyl-1H-pyrazole-4-carboxylate by a similar method as described for the synthesis of Example 7a. $^1$H NMR (400 MHz, Methanol-$d_4$) δ 7.90-7.96 (m, 2H), 7.80 (dd, J=0.7, 7.8 Hz, 1H), 7.60 (d, J=7.2 Hz, 1H), 7.41-7.51 (m, 3H), 6.98 (d, J=8.4 Hz, 1H), 6.52-6.57 (m, 1H), 6.50 (d, J=2.6 Hz, 1H), 6.22 (d, J=5.6 Hz, 1H), 4.61-4.70 (m, 1H), 4.42-4.52 (m, 1H), 3.71 (quin, J=6.9 Hz, 1H), 3.15-325 (m, 2H), 2.92-3.05 (m, 2H), 2.70-2.81 (m, 1H), 2.53-2.68 (m, 2H), 2.37-2.48 (m, 1H), 2.17-2.27 (m, 1H), 1.97-2.05 (m, 1H), 1.50-1.86 (m, 4H), 1.26-1.35 (m, 6H), 1.14 (t, J=7.5 Hz, 3H), 0.77-0.95 (m, 4H). HRMS; calcd. for $C_{38}H_{43}N_4O_4$ (M+H) 619.3284, found 619.3295.

Biological Example 1. CHO Cellular Assay

Chinese hamster ovary (CHO) cells overexpressing soluble guanylate cyclase were generated to test the effect of sGC activators in a cellular context. Human cDNAs for GUCYA3 (RefSeq: NM_000856.3) and GUCYB3 (RefSeq: NM_000857.1) were amplified by PCR from a HUVEC (Human Umbilical Vein Endothelial Cells) cDNA library and cloned into mammalian expression vectors. CHO K1 cells (ATCC CCL-61) were transfected using Lipofectamine 2000 following manufacturer's instructions and stably expressing clones were identified by antibiotic selection. CHO GUCY clone 8E10 was used for subsequent experiments.

Cells were seeded at a density of 3000 cells/well in white 384-well proxyplates (Perkin Elmer) and incubated overnight, then the medium was removed and cells were washed with assay buffer (HBSS, 0.1% BSA. 1 mM IBMX, 20 uM ODQ). sGC activators were serially diluted in DMSO, then diluted in assay buffer prior to adding to cells (10 ul/well, final DMSO concentration 0.5%). Cells were incubated with compounds for 1 h room temperature, then assayed for cGMP production using Cisbio cGMP HTRF kit (62GM2PEC) according to manufacturer's instructions. The EC50s are calculated based on the amount of cGMP interpolated from the standard curve, using a 4-parameter sigmoidal dose-response.

Compounds of invention are active on sGC activation. Data on Table 1 collected using the assay of Biological Example 1. The minimum $EC_{50}$ quantification limit of the assay is 0.5 nM, therefore any compound listed as having an $EC_{50}$ value of 0.5 nM has an $EC_{50}$ of ≤0.5 nM.

TABLE 1

| Example number | $EC_{50}$ (nM) | Example number | $EC_{50}$ (nM) |
|---|---|---|---|
| (−)-1. b) | 10 | 7a | 0.5 |
| (+)-1. b) | 0.5 | 7b | 2.4 |
| 2 | 1 | (−)-8. b) | 53 |
| 3a | 1 | (+)-8. b) | 0.5 |
| 3b | 6.9 | 9. b). (−) | 184 |
| 4a | 2.4 | 9. b). (+) | 0.5 |
| 4b | 116 | 10a | 0.5 |
| 5-1 | 39 | 10b | 49 |
| 5-2 | 1 | 11-1 | 1 |
| 5-3 | 0.5 | 11-2 | 1 |
| 5-4 | 2 | 11-3 | 1.4 |
| 5-5 | 2.4 | 11-4 | 0.5 |
| 5-6 | 0.5 | 12 | 1 |
| 5-7 | 0.5 | 13 | 0.5 |
| 5-8 | 1 | 14 | 0.5 |
| 5-9 | 0.5 | 15 | 1.5 |
| 6. b). (+) | 0.5 | 16 | 3.5 |
| 6. b). (−) | 24 | 45a | 0.5 |
| 5-10 | 0.5 | 45b | 3.5 |
| 17a | 0.5 | (+)-46-1 | 0.5 |
| 17b | 0.5 | (−)-46-1 | 100 |
| 18 | 1.4 | (+)-46-2 | 1 |
| 19a | 0.5 | (−)-46-2 | 160 |
| 19b | 0.5 | (+)-46-3 | 1 |
| (+)-20-1 | 0.5 | (−)-46-3 | 303 |
| (−)-20-1 | 0.5 | (+) or (−)-46-4 | 1.4 |
| (+)-20-2 | 9.9 | (−) or (+)-46-4 | 136 |
| (−)-20-2 | 1 | (+)-46-5 | 1 |
| (+)-20-3 | 0.5 | (−)-46-5 | 681 |
| (−)-20-3 | 0.5 | (+)-46-6 | 0.5 |
| 21-1 | 0.5 | 47a | 0.5 |
| 21-2 | 0.5 | 47b | 27 |
| 22a | 1 | 48a | 0.5 |
| 22b | 4.5 | 48b | 11 |
| 23 | 2 | 49a | 0.5 |
| 24 | 7.9 | 49b | 20 |
| 25 | 2.4 | 50a | 0.5 |
| 26 | 21 | 50b | 12 |
| 27 | 0.5 | 51a | 0.5 |
| 28 | 4.5 | 51b | 3 |
| 29 | 1 | (−)-52-1 | 19 |
| 30 | 0.5 | (+)-52-1 | 0.5 |

TABLE 1-continued

| Example number | EC$_{50}$ (nM) | Example number | EC$_{50}$ (nM) |
|---|---|---|---|
| 31-1 | 0.5 | (−)-52-2 | 1 |
| 31-2 | 0.5 | (+)-52-2 | 0.5 |
| 31-3 | 0.5 | (−)-52-3 | 3 |
| 31-4 | 0.5 | (+)-52-3 | 0.5 |
| 32a | 0.5 | 52-4 | 0.5 |
| 32b | 0.5 | 52-5 | 1 |
| 33 | 0.5 | 52-6 | 1.4 |
| 34a | 0.5 | (−)-53-1 | 21 |
| 34b | 3.9 | (+)-53-1 | 0.5 |
| 35a | 0.5 | (−)-53-2 | Not determined |
| 35b | 17 | (+)-53-2 | 1 |
| (+)-36-1 | 0.5 | (+)-53-3 | 3.5 |
| (−)-36-1 | 20 | (−)-53-3 | 59 |
| (+)-36-2 | 0.5 | (+)-53-4 | 0.5 |
| (−)-36-2 | 1 | (−)-53-4 | 24 |
| 37. b). (+) | 0.5 | 54. b). (−) | 168 |
| 37. b). (−) | 6.3 | 54. b). (+) | 1 |
| 38-1 (−) | 17 | 55-1 (−) | 15 |
| 38-1 (+) | 0.5 | 55-1 (+) | 0.5 |
| 38-2 (−) | 9 | 55-2 | 0.5 |
| 38-2 (+) | 0.5 | 56 | 1 |
| 38-3 (+) | 0.5 | 57 | 1 |
| 38-3 (−) | 33 | 58. b). (−) | 3.2 |
| 39. b). (−) | 1 | 58. b). (+) | 0.5 |
| 39. b). (+) | 0.5 | 59 | 1 |
| 40-1 (−) | 15 | 60 | 5.3 |
| 40-1 (+) | 0.5 | 61. b). (enantiomer-1) | 15 |
| 40-2 (−) | 25 | 61. b). (enantiomer-2) | 2 |
| 40-2 (+) | 0.5 | 62 | 6 |
| 40-3 (−) | 49 | 63a | 2 |
| 40-3 (+) | 0.5 | 63b | 60 |
| 41. b). (−) | 18 | 64-1 | 2 |
| 41. b). (+) | 0.5 | 64-2 | 3 |
| 42. b). (−) | 93 | 64-3 | 1 |
| 42. b). (+) | 0.5 | 64-4 | 0.5 |
| 43 (+) | 1 | 64-5 | 0.5 |
| 43 (−) | 23 | 64-6 | 1.4 |
| 44 (+) | 0.5 | 64-7 | 0.5 |
| 44 (−) | 9.9 | 64-8 | 0.5 |

What is claimed is:

1. A compound according to Formula (I)

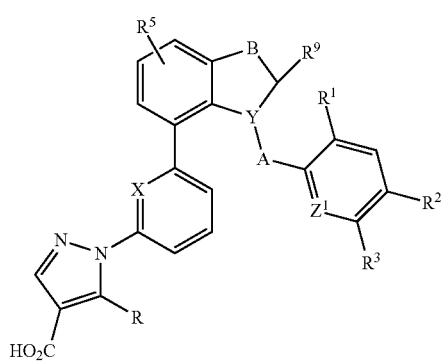

or a pharmaceutically acceptable salt thereof, wherein
X is N;
Y is N;
A is CH$_2$;
B is CR$^7$R$^8$;
Z$^1$ is CR$^4$;
R is hydrogen, C$_1$-C$_4$alkyl, monofluoromethyl, difluoromethyl or trifluoromethyl;
R$^1$ is hydrogen, halogen, C$_1$-C$_4$alkyl or trifluoromethyl
R$^2$ is piperidinyl which is N-substituted with C$_1$-C$_4$alkyl, C$_3$-C$_6$cycloalkyl, haloC$_1$-C$_4$alkyl, C(O)C$_1$-C$_4$alkyl, S(O)$_2$C$_1$-C$_4$alkyl, C(O)C$_3$-C$_6$cycloalkyl, C(O)haloC$_1$-C$_4$alkyl, C(O)C$_1$-C$_4$alkoxy, C(O)C$_1$-C$_4$alkenoxy or CO(O)$_2$benzyl, wherein each cycloalkyl is optionally substituted by hydroxy and each alkyl or alkoxy is optionally substituted by hydroxyl, C$_1$-C$_4$alkoxy or C$_3$-C$_6$cycloalkyl;
R$^3$ is hydrogen, halogen or C$_1$-C$_4$alkyl;
R$^4$ is hydrogen or C$_1$-C$_4$alkyl;
R$^5$ is hydrogen, halogen, C$_1$-C$_4$alkyl or C$_3$-C$_6$cycloalkyl;
R$^7$ is hydrogen or C$_1$-C$_4$alkyl; or
R$^8$ is hydrogen or C$_1$-C$_4$alkyl; and
R$^9$ is hydrogen or C$_1$-C$_4$alkyl.

2. A compound according to Formula (Ia)

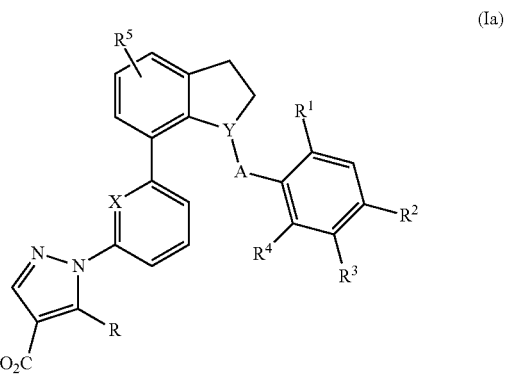

or a pharmaceutically acceptable salt thereof, wherein
X is N;
Y is N;
A is CH$_2$;
R is hydrogen, C$_1$-C$_4$alkyl or trifluoromethyl;
R$^1$ is hydrogen, halogen or C$_1$-C$_4$alkyl;
R$^2$ is piperidinyl which is N-substituted with C$_1$-C$_4$alkyl, C$_3$-C$_6$cycloalkyl, haloC$_1$-C$_4$alkyl, C(O)C$_1$-C$_4$alkyl, C(O)C$_3$-C$_6$cycloalkyl, C(O)haloC$_1$-C$_4$alkyl or C(O)C$_1$-C$_4$alkoxy;
R$^3$ is hydrogen or C$_1$-C$_4$alkyl;
R$^4$ is hydrogen or C$_1$-C$_4$alkyl and
R$^5$ is hydrogen, halogen, C$_1$-C$_4$alkyl or C$_3$-C$_6$cycloalkyl.

3. The compound of claim 2 which is represented by the formula (Ib):

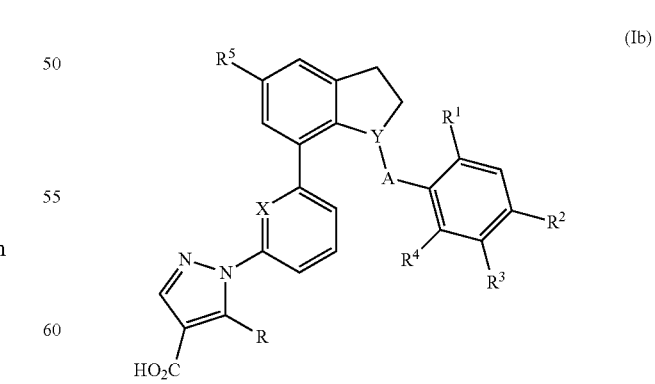

or a pharmaceutically acceptable salt thereof.

4. The compound of claim 2, wherein R$^2$ is N-substituted piperidin-4-yl wherein the N-substituent is 2,2,2-trifluoroethyl, C(O)cyclopropyl or C(O)C$_1$-C$_4$alkyl.

5. The compound of claim 2, wherein $R^1$ is hydrogen or methyl;
$R^3$ is hydrogen, methyl or ethyl, wherein at least one of $R^1$ or $R^3$ is hydrogen; and
$R^4$ is hydrogen.

6. The compound of claim 2, wherein $R^1$ is methyl; and $R^3$ and $R^4$ are hydrogen.

7. The compound of claim 2, wherein $R^1$ and $R^4$ are hydrogen and $R^3$ is ethyl.

8. The compound of claim 2, wherein R is trifluoromethyl, methyl or ethyl.

9. The compound of claim 2, wherein R is trifluoromethyl.

10. The compound of claim 2, wherein R is methyl or ethyl.

11. The compound of claim 2, wherein the compound is a compound according to Formula (IV):

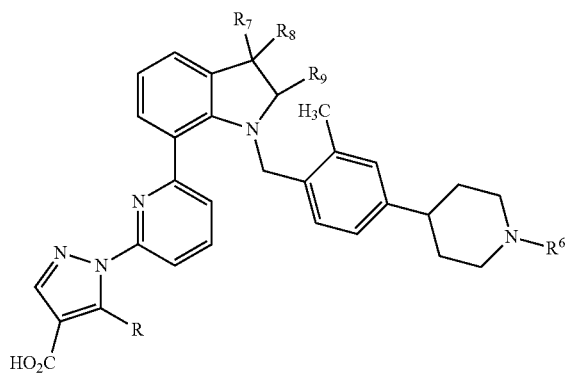

(IV)

Wherein
R is methyl, ethyl or trifluoromethyl;
$R^6$ is 2,2,2-trifluoroethyl, C(O)cyclopropyl or C(O)$C_1$-$C_4$alkyl; and
Each of $R^7$, $R^8$ and $R^9$ is independently selected from hydrogen and methyl; or a pharmaceutically acceptable salt thereof.

12. The compound of claim 11, wherein R is methyl or ethyl; and $R^6$ is 2,2,2-trifluoroethyl.

13. The compound of claim 2, wherein the compound is a compound according to Formula (V):

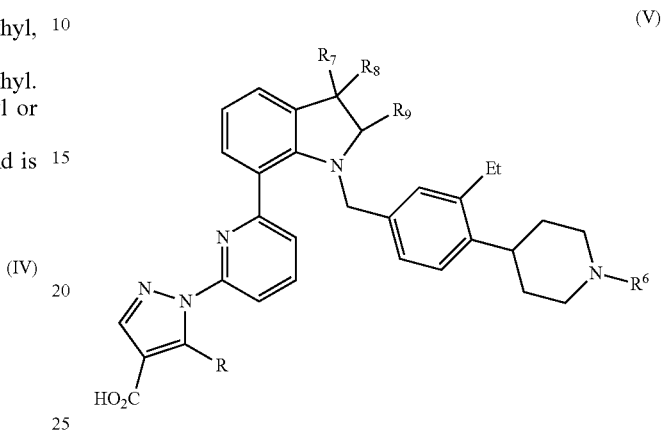

(V)

Wherein
R is methyl, ethyl or trifluoromethyl;
$R^6$ is 2,2,2-trifluoroethyl, C(O)cyclopropyl or C(O)$C_1$-$C_4$alkyl; and
each of $R^7$, $R^8$ and $R^9$ is independently selected from hydrogen and methyl; or a pharmaceutically acceptable salt thereof.

14. The compound of claim 13, wherein R is methyl or ethyl; and $R^6$ is C 2,2,2-trifluoroethyl.

15. A pharmaceutical composition comprising a compound of claim 2, or a pharmaceutically acceptable salt thereof, and a pharmaceutically acceptable excipient.

* * * * *